US007314940B2

United States Patent
Graczyk et al.

(10) Patent No.: US 7,314,940 B2
(45) Date of Patent: Jan. 1, 2008

(54) JUN KINASE INHIBITORS

(75) Inventors: Piotr Graczyk, London (GB); Hirotoshi Numata, London (GB); Afzal Khan, London (GB); Vanessa Palmer, London (GB); Darren Peter Medland, London (GB); Hitoshi Oinuma, Tokyo (JP); Gurpreet Bhatia, London (GB)

(73) Assignee: Eisai Co., Ltd., Tokyo (JP)

( * ) Notice: Subject to any disclaimer, the term of this patent is extended or adjusted under 35 U.S.C. 154(b) by 194 days.

(21) Appl. No.: 10/473,578

(22) PCT Filed: Apr. 4, 2002

(86) PCT No.: PCT/GB02/01598

§ 371 (c)(1),
(2), (4) Date: Apr. 23, 2004

(87) PCT Pub. No.: WO02/081475

PCT Pub. Date: Oct. 17, 2002

(65) Prior Publication Data

US 2004/0235864 A1 Nov. 25, 2004

(30) Foreign Application Priority Data

Apr. 6, 2001 (GB) .................. 0108770.9

(51) Int. Cl.
*A61K 31/4184* (2006.01)
*A61K 31/4188* (2006.01)
*C07D 235/02* (2006.01)
*C07D 519/00* (2006.01)
*C07D 487/04* (2006.01)

(52) U.S. Cl. .................. 548/302.7; 514/299; 514/300; 514/393; 546/118; 546/121

(58) Field of Classification Search .............. 548/302.7
See application file for complete search history.

(56) References Cited

U.S. PATENT DOCUMENTS 4,719,218 A * 1/1988 Bender et al. .............. 514/300

FOREIGN PATENT DOCUMENTS

| EP | 0 737 685 | 10/1996 |
|---|---|---|
| EP | 1 106 621 | 6/2001 |
| WO | WO 92/10498 A1 * | 6/1992 |
| WO | WO 92/10499 A1 * | 6/1992 |
| WO | WO 99/21859 | 5/1999 |
| WO | WO 00/35909 | 6/2000 |
| WO | WO 00/35921 | 6/2000 |
| WO | WO 00/56710 | 9/2000 |
| WO | WO 01/12609 | 2/2001 |
| WO | WO 01/47922 | 7/2001 |
| WO | WO 01/49288 | 7/2001 |
| WO | WO 02/16359 | 2/2002 |
| WO | WO 02/081475 | 10/2002 |
| WO | WO 03/082869 | 10/2003 |

OTHER PUBLICATIONS

Golub et al., Science, vol. 286, Oct. 15, 1999, pp. 531-537.*
Ham et al, Neuron, 14(5):927-939 (1995).
Watson et al, J. Neurosci., 18(2):751-762 (1998).
Eilers et al, J. Neurosci., 18(5):1713-1724 (1998).
Eilers et al, J. Neurochem., 76(5):1439-1454 (2001).
Young et al, J. Biol. Chem., 272(18):12116-12121 (1997).
Lisnock et al, Biochemistry, 39(11):3141-3148 (2000).
Cao et al, J. Biol. Chem., 279(34):35903-35913 (2004).
Henry et al, Bioorg. Med. Chem. Lett. 1998, 8, 3335-3340.
Adams et al., Bioorg. Med. Chem. Lett. 2001, 11, 2867-2870.
Harper and LoGasso, *Drugs of the Future* 2001, 26, 957-973.

* cited by examiner

*Primary Examiner*—Laura L. Stockton
(74) *Attorney, Agent, or Firm*—Wilmer Cutler Pickering Hale and Dorr LLP

(57) ABSTRACT

The present invention provides novel compounds of formula I and their use in the inhibition of c-Jun N-terminal kinases. The present invention further provides the use of these compounds in medicine, in particular in the prevention and/or treatment of neurodegenerative disorders related to apoptosis and/or inflammation.

12 Claims, No Drawings

JUN KINASE INHIBITORS

RELATED APPLICATIONS

This application is a § 371 of PCT/GB02/01598 filed Apr. 4, 2002, which claims priority to GB 0108770.9 filed Apr. 6, 2001.

FIELD OF THE INVENTION

The present invention relates to novel compounds, their use in the inhibition of c-Jun N-terminal kinases, their use in medicine and particularly in the prevention and/or treatment of neurodegenerative disorders related to apoptosis and/or inflammation. The invention also provides processes for manufacture of said compounds, compositions containing them and processes for manufacturing such compositions.

BACKGROUND OF THE INVENTION c-Jun N-terminal kinases (hereinafter referred to as "JNKs") are members of the mitogen-activated protein kinase (MAPK) family. JNKs are involved in response to various stimuli, including proinflammatory cytokines and environmental stress. JNKs, and JNK3 in particular, play an important role during apoptotic death of cells and therefore have been implicated in various disorders including stroke, traumatic brain injury and other neurodegenerative diseases such as Parkinson disease, Alzheimer disease and others. Since JNK activity is a physiological regulator of AP-1 transcriptional activity, JNK inhibitors are expected to reduce inflammatory response.

Apoptosis is a form of cell death in which the cell actively participates in its own destruction in a process involving a characteristic series of biochemical and morphological changes which are regulated by specific cell death genes. The apoptotic cell death is a process that has been observed in the developing mammalian nervous system. In mice, the inactivation by homologous recombination of genes that encode proteins that promote apoptosis, such as the caspase-3 or the Bax protein, prevents developmental neuronal cell death. The destruction of genes that encode cell death suppressors such as Bcl-x, leads to enhanced neuronal cell death. There is increasing evidence that apoptosis plays an important role in the pathology of acute and chronic neurodegenerative diseases. For example, in transgenic mice overexpressing the anti-apoptotic Bcl-2 protein in the nervous system there is a decrease in infarct volume following cerebral ischemia. Similarly, injection of the caspase inhibitor BAF reduces neuronal cell death following hypoxia/ischaemia in neonatal rats. Another example is spinal muscular atrophy (a motor neurondisease) where loss of function mutations in the SMN gene is associated with the disease. Recent data has shown that the wild type SMN protein binds to Bcl-2 and co-operates with it to inhibit apoptosis. These results suggest that inhibitors of neuronal apoptosis could be beneficial in the treatment of human neurodegenerative diseases. There is increasing evidence that neuronal apoptosis is an important pathological feature of stroke, traumatic brain injury and other neurodegenerative diseases. Therefore, pharmacotherapy using inhibitors of neuronal apoptosis may provide a therapeutic benefit in neurodegenerative conditions.

A number of groups have studied the mechanisms of neuronal cell death using in vitro cell culture systems and the results suggest that in some systems the transcription factor c-Jun is activated by the removal of survival signals and promotes cell death.

Antibodies specific for c-Jun protected NGF-deprived rat sympathetic neurones from apoptosis. Analogous neuroprotection due to expression of a c-Jun dominant negative mutant has been demonstrated, whereas overexpression of wild type c-Jun protein was sufficient to induce apoptosis in the presence of NGF. Estus and co-workers recently showed that an increase in c-Jun RNA levels occurs in cortical neurones undergoing apoptosis after treatment with β-amyloid peptide. It has also been shown that c-Jun is required for apoptosis in cerebellar granule neurones deprived of survival signals.

c-Jun is activated by JNKs, which phosphorylate its transcriptional activation domain. In humans there are three JNK genes: JNK1, JNK2 and JNK3. The RNAs encoding JNK1 and JNK2 are expressed in many tissues, including the brain, but JNK3 is restricted to the nervous system and to a smaller extent the heart and testes.

JNKs are strongly activated in cellular responses to various stresses such as UV radiation, heat shock, osmotic shock, DNA-damaging agents, and proinflammatory cytokines such as TNFα, IL-1β and others. Upstream regulators of the JNK pathway include kinases such as SEK1, MKK7 and MEKK1. There is evidence that Jun kinase activity is required for neuronal apoptosis in vitro. Overexpression of MEKK1 in sympathetic neurones increased c-Jun protein levels and phosphorylation and induced apoptosis in the presence of NGF indicating that activation of the Jun kinase pathway can trigger neuronal cell death. The Jun kinase pathway has been shown to be necessary for the death of differentiated PC12 cells deprived of NGF. Furthermore, compound CEP-1347, which inhibits the c-Jun pathway (upstream of Jun kinase), protects motor neurones against cell death induced by survival factor withdrawal.

In JNK3 homozygous (-/-) knockout mice, epileptic seizures and death of hippocampal CA3 neurones induced by injection of kainic acid is blocked. This indicates that JNK3 is involved in certain forms of neuronal cell death in vivo. It is also a critical component of GluR6-mediated excitotoxicity. Furthermore, JNK3 (-/-) mice appear to develop normally and are viable suggesting that JNK3 is not essential for development or viability.

Strong nuclear JNK3 immunoreactivity in the brain CA1 neurones of patients with acute hypoxia suggests that JNK3 is involved in hypoxia-related neurodegeneration. Transient hypoxia, may also trigger apoptosis through JNK signaling pathway in developing brain neurones.

Furthermore, JNK3 immunoreactivity is colocalized with Alzheimer disease-affected neurones. Moreover JNK3 is related to neurofibrillary pathology of Alzheimer disease. In particular, JNK3 induces robust phosphorylation of amyloid precursor protein (APP) thus affecting its metabolism in disease state.

DETAILED DESCRIPTION OF THE INVENTION

The present inventors have provided compounds which are inhibitors of c-Jun N-terminal kinases.

The first aspect of the invention therefore relates to a compound of formula I as illustrated below:

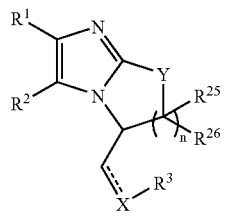

wherein Y is CH$_2$ or NH,
R$^{25}$ and R$^{26}$ are both hydrogen or R$^{25}$ and R$^{26}$ together are carbonyl;
n is 1 or 2;
the bond C⋯X is a single or a double bond;
R$^1$ is aryl, substituted aryl, heterocyclyl or substituted heterocyclyl wherein the optionally substituted aryl or heterocyclyl groups is optionally fused to a partially unsaturated or fully saturated five to seven membered ring containing zero to three heteroatoms, and each substitutable carbon atom in R$^1$, including the optional fused ring, is optionally and independently substituted by one or more of halogen, C$_{1-4}$ alkyl, haloalkyl, OR, SR, OH, NO$_2$, CN, NH$_2$, NHR, NR$_2$, NHCOR, NHCONHR, NHCONR$_2$, NRCOR, NHCO$_2$R, CO$_2$R, CO$_2$H, COR, CONHR, CONR$_2$, S(O)$_2$R, SONH$_2$, S(O)R, SO$_2$NHR, or NHS(O)$_2$R; and each saturated carbon in the optional fused ring is further optionally and independently substituted by =O, =S, =NNHR, NNR$_2$, =N—OR, =NNHCOR, =NNHCO$_2$R, =NNSO$_2$R, or =NR; and each substitutable nitrogen atom in R$^1$ is optionally substituted by R, COR, SO$_2$R or CO$_2$R; wherein R is H, C$_{1-4}$ alkyl or haloalkyl;
R$^2$ is an optionally substituted heterocyclic group;
X is CHR$^{16}$, CR$^{16}$, NR$^{16}$, C=O, NR$^{16}$CO, O, S S(O) or S(O)$_2$, wherein R$^{16}$ is hydrogen, C$_{1-4}$ alkyl optionally substituted with one or more of OR$^{20}$, NR$^{20}$R$^{21}$ or aryl, where R$^{20}$ and R$^{21}$ are independently H, aryl or C$_{1-4}$ alkyl;
R$^3$ is H, optionally substituted C$_{1-10}$ alkyl, optionally substituted alkylaryl, aryl, substituted aryl, optionally substituted alkylheterocyclyl, heterocyclyl wherein the groups are optionally substituted by one or more of C$_{1-4}$ alkyl, aryl, heterocycyl, alkylaryl, halogen, haloalkyl, OR$^{15}$, SR$^{15}$, NO$_2$, CN, NR$^{15}$$_2$, NHR$^{15}$, NHCOR$^{15}$, NR$^{15}$COR$^{15}$, NR$^{15}$CONR$^{15}$$_2$, NHCO$_2$R$^{15}$, CO$_2$R$^{15}$, COR$^{15}$, CONR$^{15}$$_2$, SOR$^{15}$, SO$_2$R$^{15}$, SONR$^{15}$$_2$ NHS(O)$_2$R$^{15}$;or substituted heterocyclyl wherein the optionally substituted aryl or heterocyclyl group is optionally fused to one or more partially unsaturated or fully saturated five to seven membered ring containing zero to three heteroatoms and wherein each substitutable carbon atom including the optional fused ring, is optionally and independently substituted by one or more of H, C$_{1-4}$ alkyl, aryl, heterocyclyl, alkylaryl, halogen, haloalkyl, OR$^{15}$, SR$^{15}$, OH, NO$_2$, CN, NH$_2$, NHR$^{15}$, NR$^{15}$$_2$, NHCOR$^{15}$, NHCONHR$^{15}$, NHCONR$^{15}$$_2$, NR$^{15}$COR$^{15}$, NHCO$_2$R$^{15}$, CO$_2$R$^{15}$, CO$_2$H, COR$^{15}$, CONHR$^{15}$, CONR$^{15}$$_2$, S(O)$_2$R$^{15}$, SONH$_2$, S(O)R$^5$, SO$_2$NHR$^{15}$, or NHS(O)$_2$R$^{15}$ and wherein each saturated carbon in the fused ring is further optionally and independently substituted by =O, =S, =NNHR$^{15}$, NNR$^{15}$$_2$, =N—OR$^{15}$, =NNHCOR$^{15}$, =NNHCO$_2$R$^{15}$, =NNSO$_2$R$^{15}$, or =NR$^{15}$; wherein each substitutable nitrogen atom is optionally substituted by H, or C$_{1-4}$ alkyl, COR$^{15}$, SO$_2$R$^{15}$ or CO$_2$R$^{15}$, wherein R$^{15}$ is H, C$_{1-4}$ alkyl, haloalkyl, or optionally substituted alkylaryl;
or a pharmaceutically acceptable salt thereof.

Where a group contains two or more R$^{15}$ moieties, each of the R$^{15}$ moieties is independently H, C$_{1-4}$ alkyl, haloalkyl, or optionally substituted alkylaryl.

Preferably the heterocyclic group of R$^3$ is pyridinyl, pyrimidinyl, pyrazinyl, pyridazinyl, quinolyl, isoquinolyl, quinazolinyl, imidazolyl, isoamyl, benzimidazolyl, furyl, thiophenyl, pyridyl, phenanthrolinyl. Preferably the aryl group of R$^3$ is phenyl or naphthyl.

If X is NR$^{16}$, R$^{16}$ and R$^3$ can together form a fully saturated, partially unsaturated and unsaturated four to seven membered ring, aryl, substituted aryl, heterocyclyl or substituted heterocyclyl ring containing up to three heteroatoms, wherein the ring structure is optionally fused to a partially unsaturated or fully saturated five to seven membered ring containing zero to three heteroatoms, and wherein each substitutable carbon atom in the ring including the optional fused ring, is optionally and independently substituted by C$_{1-4}$ alkyl, aryl, alkylaryl, halogen, OR$^{22}$, SR$^{22}$, OH, CO, NO$_2$, CN, NH$_2$, NHR$^{22}$, NR$^{22}$$_2$, NHCOR$^{22}$, NHCONHR$^{22}$, NHCONR$^{22}$$_2$, NRCOR$^{22}$, NHCO$_2$R$^{22}$, CO$_2$R$^{22}$, CO$_2$H, COR$^{22}$, CONHR$^{22}$, CONR$^{22}$$_2$, S(O)$_2$R$^{22}$, SONH$_2$, S(O)R$^{22}$, SO$_2$NHR$^{22}$, or NHS(O)$_2$R$^{22}$ and wherein each saturated carbon in the fused ring is further optionally and independently substituted by =O, =S, =NNHR$^{22}$, NNR$^{22}$$_2$, =N—OR$^{22}$, =NNHCOR$^{22}$, =NNHCO$_2$R$^{22}$, =NNSO$_2$R$^{22}$, or =NR$^{22}$; wherein each substitutable nitrogen atom in the ring structure is optionally substituted by R$^{22}$, COR$^{22}$, SO$_2$R$^{22}$ or CO$_2$R$^{22}$, where R$^{22}$ is hydrogen or C$_{1-4}$ alkyl.

If X is CHR$^{16}$ or CR$^{16}$, R$^{16}$ and R$^3$ can together form a fully saturated, partially unsaturated and unsaturated four to seven membered ring, aryl, substituted aryl, heterocyclyl or substituted heterocyclyl ring containing up to three heteroatoms, wherein the ring structure is optionally fused to a partially unsaturated or fully saturated five to seven membered ring containing zero to three heteroatoms, and wherein each substitutable carbon atom in the ring including the optional fused ring, is optionally and independently substituted by C$_{1-4}$ alkyl, aryl, alkylaryl, halogen, OR$^{22}$, SR$^{22}$, OH, CO, NO$_2$, CN, NH$_2$, NHR$^{22}$, NR$^{22}$$_2$, NHCOR$^{22}$, NHCONHR$^{22}$, NHCONR$^{22}$$_2$, NRCOR$^{22}$, NHCO$_2$R$^{22}$, CO$_2$R$^{22}$, CO$_2$H, COR$^{22}$, CONHR$^{22}$, CONR$^{22}$$_2$, S(O)$_2$R$^{22}$, SONH$_2$, S(O)R$^{22}$, SO$_2$NHR$^{22}$, or NHS(O)$_2$R$^{22}$ and wherein each saturated carbon in the fused ring is further optionally and independently substituted by =O, =S, =NNHR$^{22}$, NNR$^{22}$$_2$, =N—OR$^{22}$, =NNHCOR$^{22}$, =NNHCO$_2$R$^{22}$, =NNSO$_2$R$^{22}$, or =NR$^{22}$; wherein each substitutable nitrogen atom in the ring structure is optionally substituted by R$^{22}$, COR$^{22}$, SO$_2$R$^{22}$ or CO$_2$R$^{22}$, where R$^{22}$ is hydrogen or C$_{1-4}$ alkyl.

Preferably, the heterocyclic group of R$^2$ is 4-pyridinyl, pyrimidinyl, quinolyl, isoquinolinyl, quinazolin-4-yl, 1-imidazolyl, isoamyl or benzimidazolyl, the heterocyclyl is optionally substituted with one or more of NHR$^4$, NR$^4$R$^5$, SR$^4$, S(O)R$^4$, S(O)$_2$R$^4$, or OR$^4$ wherein R$^4$ and R$^5$ are independently H, optionally substituted C$_{1-10}$ alkyl, optionally substituted alkylaryl, or optionally substituted alkylheterocyclyl; wherein the substituents are OR$^6$ or NR$^6$R$^7$ where R$^6$ and R$^7$ are independently H or C$_{1-4}$ alkyl; and the alkyl group is methyl, ethyl, n-propyl, i-propyl, cyclopropyl, substituted cyclopropyl for example CH$_2$-cyclopropyl, n-butyl, i-butyl, s-butyl, t-butyl, cyclobutyl, substituted cyclobutyl, pentyl, cyclopentyl, substituted cyclopentyl, hexyl, cyclohexyl, substituted cyclohexyl, heptyl, cycloheptyl, substituted cycloheptyl, octyl, cyclooctyl, or substituted cyclooctyl wherein the optionally substituted cycloalkyl group is optionally fused to a partially unsaturated or fully saturated five to seven membered ring containing zero to three heteroatoms.

For the purposes of this invention, alkyl relates to both straight chain and branched alkyl radicals of 1 to 10 carbon atoms, preferably 1 to 8 carbon atoms and most preferably 1 to 4 carbon atoms including but not limited to methyl, ethyl, n-propyl, isopropyl, n-butyl, sec-butyl, isobutyl, tert-butyl n-pentyl, n-hexyl, n-heptyl, n-octyl. The term alkyl also encompasses cycloalkyl radicals including but not limited to cyclopropyl, cyclobutyl, $CH_2$-cyclopropyl or $CH_2$-cyclobutyl. Cycloalkyl groups may be optionally substituted or fused to one or more aryl, heterocyclyl or cycloalkyl group. Haloalkyl relates to an alkyl radical preferably having 1 to 4 carbon atoms substituted with one or more halide atoms for example $CH_2CH_2Br$, $CF_3$ or $CCl_3$.

Aryl relates to an aromatic hydrocarbon including but not limited to phenyl, napthyl, anthracenyl or phenanthracenyl. Heterocyclyl relates to a 5-10 membered ring system containing one or more heteroatoms selected from N, O or S. The heterocyclyl system can be fully saturated, partially saturated or unsaturated and includes but is not limited to pyridine, furan, pyrimidine, pyridazine, pyrazine, thiazole, thiophene, oxazole, thiadiazole, quinoline, isoquinoline, triazole, imidazole, quinazoline, morpholine or benzimidazole. Halogen relates to F, Cl, Br or I.

Preferably a compound according the first aspect of the invention is a compound of formula II or III

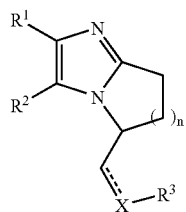

II

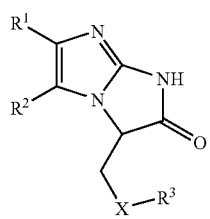

III wherein n is 1 or 2 and $R^1$, $R^2$, $R^3$ and X are as described above for formula I.

Preferably, $R^1$ is aryl or heterocyclyl, optionally substituted with one or more of alkyl, haloalkyl, halogen, OR, SR, SOR, $NR_2$, wherein R is independently selected from hydrogen, $C_{1-4}$ alkyl or haloalkyl.

More preferably the aryl group is phenyl or napthyl, most preferably phenyl; the heterocyclyl group is preferably furanyl, thiophenyl, pyridyl or quinolinyl.

The halogen is preferably F, Cl or Br, more preferably F; the haloalkyl group is preferably $CF_3$, the alkyl group is preferably methyl, ethyl or propyl.

Most preferably, $R^1$ is 4-fluorophenyl.

Preferably $R^2$ is selected from 4-pyridyl, 4-pyrimidinyl, 4-quinolyl, 6-isoquinolyl, 4-quinazolinyl, 1-imidazolyl, 1-benzimidazolyl and 6-benzimidazolyl, each of which is optionally substituted with $SR^4$, $S(O)R^4$, $S(O)_2R^4$, $OR^4$, $NHR^4$, $NR^4R^5$, wherein $R^4$ and $R^5$ are independently hydrogen, optionally subsituted $C_{1-8}$ alkyl, optionally substituted $C_{1-6}$alkylaryl or optionally substituted $C_{1-6}$alkylheterocyclyl, wherein the optional substitutents are one or more of $OR^6$ or $NR^6R^7$, wherein $R^6$ and $R^7$ are independently hydrogen or $C_{1-4}$ alkyl.

More preferably $R^2$ is optionally substituted 4-pyridyl or 4-pyrimidinyl, most preferably optionally substituted 4-pyrimidinyl.

Preferably the alkyl group for $R^2$ is methyl, ethyl, n-propyl, i-propyl, cyclopropyl, substituted cyclopropyl for example $CH_2$-cyclopropyl, n-butyl, i-butyl, s-butyl, t-butyl, cyclobutyl, substituted cyclobutyl, n-pentyl, n-hexyl, n-heptyl, n-octyl; aryl is preferably phenyl and heterocyclyl is preferably pyridinyl or morpholinyl.

Preferably X is $CHR^{16}$, $CR^{16}$, O, S or $NR^{16}$

Where X is O, $R^3$ is preferably $C_{1-8}$ alkyl, alkylaryl, alkylheterocyclyl, aryl, heterocyclyl or cycloalkyl optionally substituted with one or more of $C_{1-4}$ alkyl, halogen, haloalkyl, aryl, alkylaryl, $NO_2$, $NH_2$, $OR^{15}$ Preferably aryl is phenyl or napthyl; alkylaryl is preferably methyl or ethyl carrying one or more phenyl groups (for example —$CH_2Ph$, —$CHPh_2$ or —$C(Ph)_3$) wherein the aryl group may be substituted by any of the substituents discussed above e.g. methoxy; heterocyclyl is preferably 2-pyridyl, 4-pyridyl, 2-quinolinyl, 2-pyrimidinyl, pyrazinyl, 2-quinoxalinyl, 1-isoquinolinyl or 4-quinolinyl, pyridazinyl, more preferably 2-pyridyl or 4-pyridyl, the cycloalkyl group is a 3, 4, 5, 6 or 7 membered ring and can be fused to one or more aryl, heterocyclyl or cycloalkyl group.

Preferably phenyl groups are substituted with halogen, alkyl, haloalkyl, aryl alkylaryl, $NO_2$, $NH_2$ or OR; preferably naphthyl groups are optionally substituted with alkyl more preferably with methyl; preferably heterocyclyl groups are optionally substituted with halogen, haloalkyl, aryl, $NO_2$, alkyl, CN or $OR^{15}$.

Preferably halogen is F, Cl or Br; alkyl is preferably methyl, ethyl, propyl or butyl, pentyl, hexyl, heptyl or octyl; haloalkyl is preferably $CF_3$; $R^{15}$ is preferably methyl.

Where X is $NR^{16}$, $R^{16}$ is preferably hydrogen, or $C_{1-4}$ alkyl optionally substituted with $OR^{20}$ or $NR^{20}R^{21}$ or heterocyclyl, wherein alkyl is more preferably methyl, ethyl, n-propyl, i-propyl or butyl, $R^{20}$ and $R^{21}$ are independently hydrogen, aryl, preferably phenyl, or $C_{1-4}$ alkyl, preferably methyl, wherein heterocyclyl is preferably pyridinyl, quinolinyl or isoquinolinyl;

$R^3$ is preferably alkylaryl optionally substituted with $OR^{15}$, alkyl or halogen, wherein the alkyl group is methyl, ethyl, propyl or butyl more preferably methyl or ethyl, halogen is F, Cl or Br, $R^{15}$ is alkyl preferably methyl or ethyl and aryl is preferably phenyl.

When X is $NR^{16}$ and $R^{16}$ and $R^3$ can together form a fully saturated, partially saturated or unsaturated four to seven membered ring, $R^{16}$ and $R^3$ preferably form morpholinyl, tetrahydroquinolinyl, pyridinyl, quinolinyl, isoquinolinyl, pyrrolidinyl, pyrroyl, pyrazoyl, succinimidyl, tetrahydroisoquinolinyl, indolinyl or indolyl optionally substituted with one or more of aryl, alkylaryl, halogen or $OR^{22}$ where $R^{22}$ is $C_{1-4}$ alkyl, preferably methyl or ethyl, aryl is preferably phenyl, halogen is F, Cl or Br.

When X is $CR^{16}$, $R^3$ is preferably heterocyclyl such as pyridinyl, thiophenyl, or furanyl;

When X is $CHR^{16}$, $R^3$ is preferably cycloalkyl, heterocylcyl or aryl;

When X is $CR^{16}$ or $CHR^{16}$, $R^{16}$ and $R^3$ can together form a fully saturated, partially saturated or unsaturated four to seven membered ring, $R^{16}$ and $R^3$ preferably form cyclopentyl, phenyl, cyclohexyl; optionally substituted with one or more of aryl, alkylaryl, halogen or $OR^{22}$ wherein $R^{22}$ is $C_{1-4}$ alkyl preferably methyl or ethyl, aryl is preferably phenyl, halogen is preferably F, Cl or Br.

When X is $SO_2$ or S, $R^3$ is preferably aryl or alkylaryl such as phenyl or benzyl optionally substituted with $OR^{22}$ or halogen.

For the purposes of this invention, any of $R^1$, $R^2$, $R^3$ and X can be present in combination with any other $R^1$, $R^2$, $R^3$ or X group.

Representative compounds according to the first aspect of the invention are illustrated below.

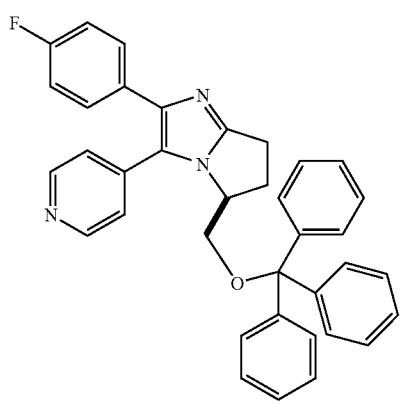

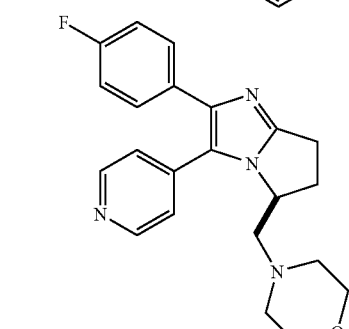

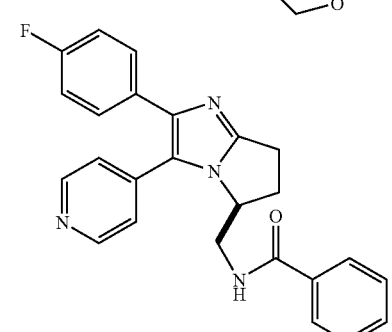

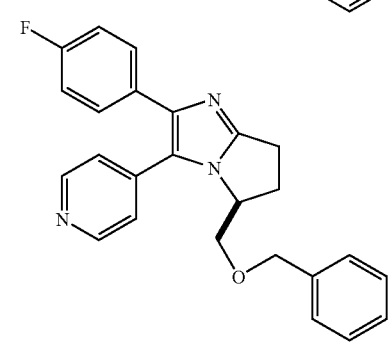

-continued

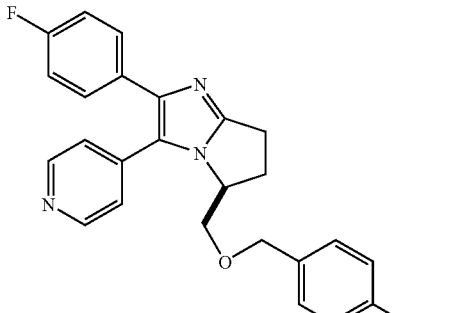

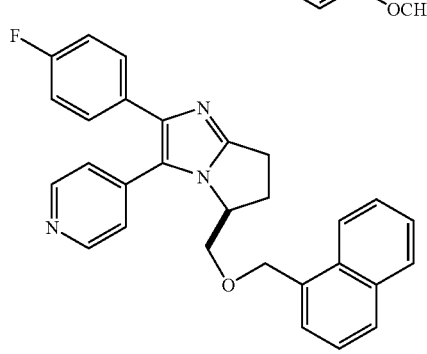

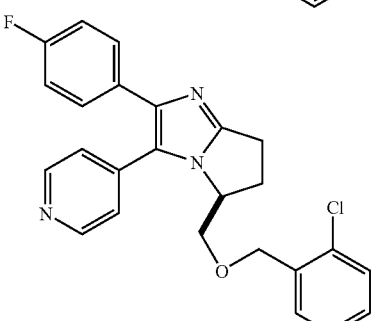

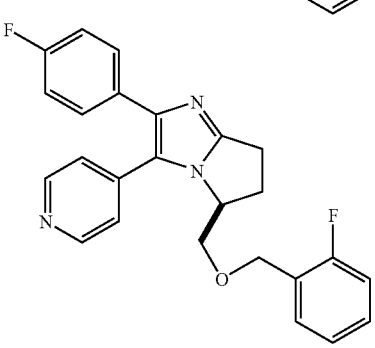

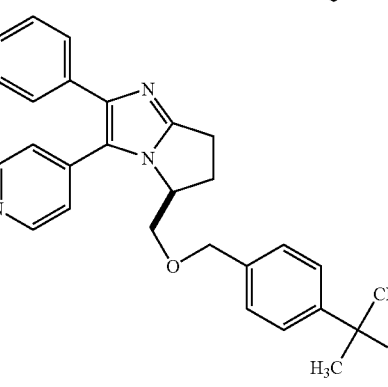

-continued
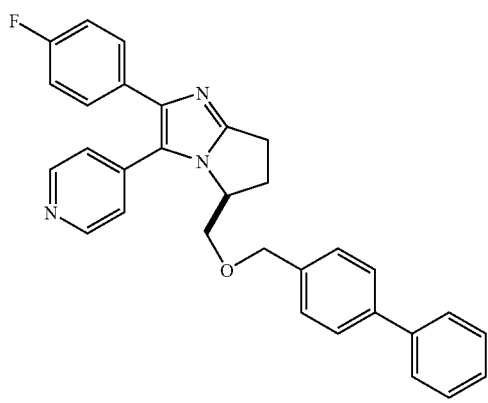
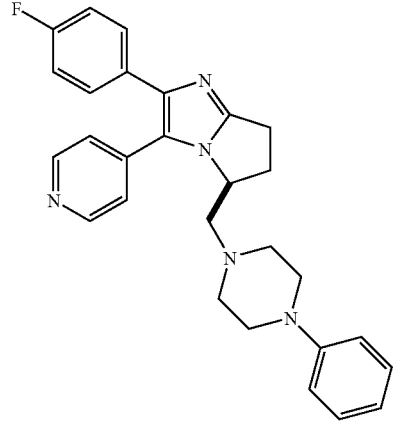
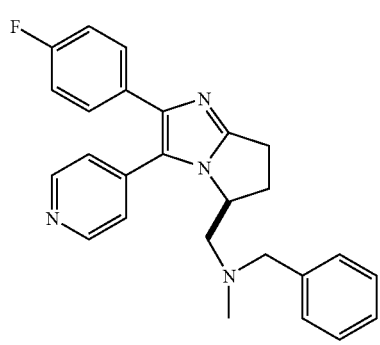
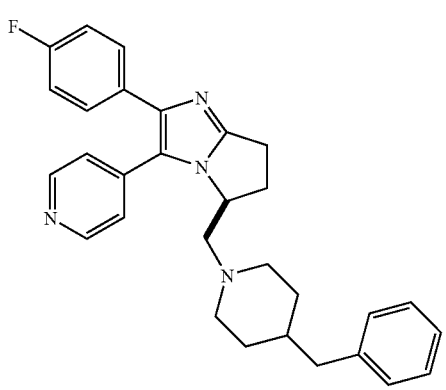
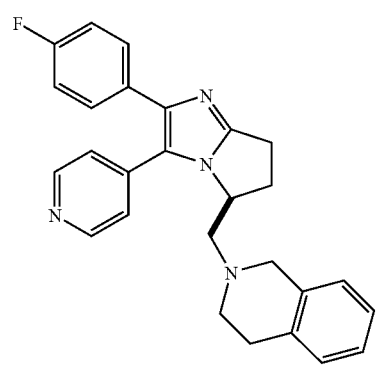
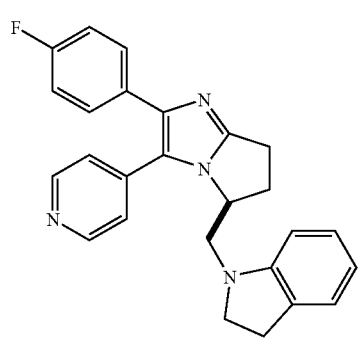
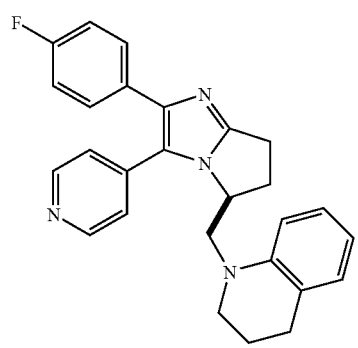
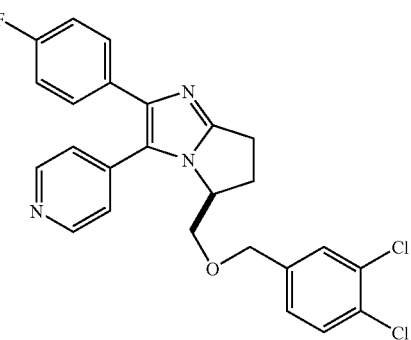

-continued
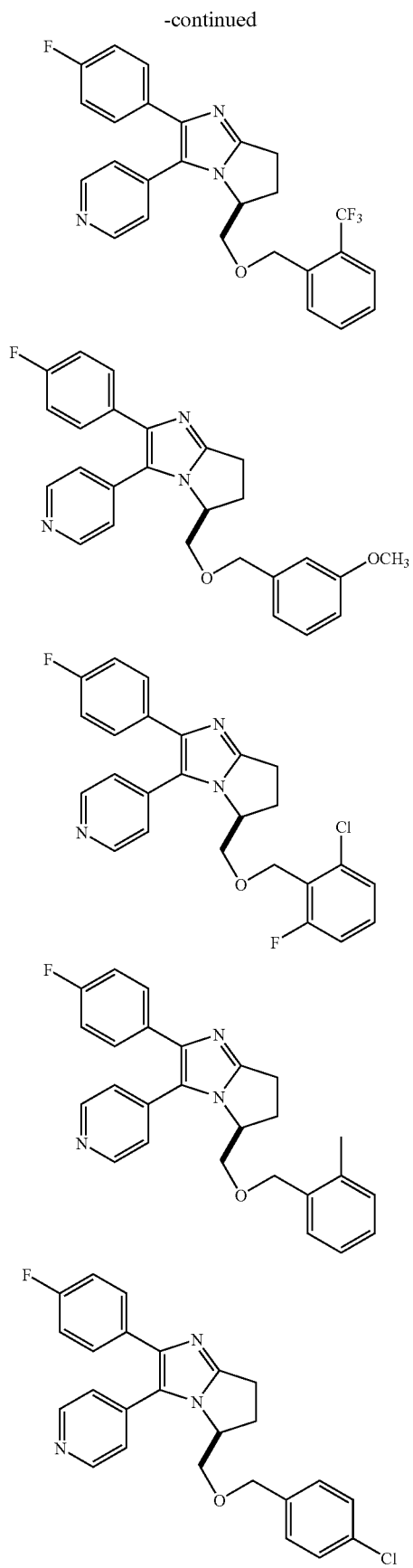
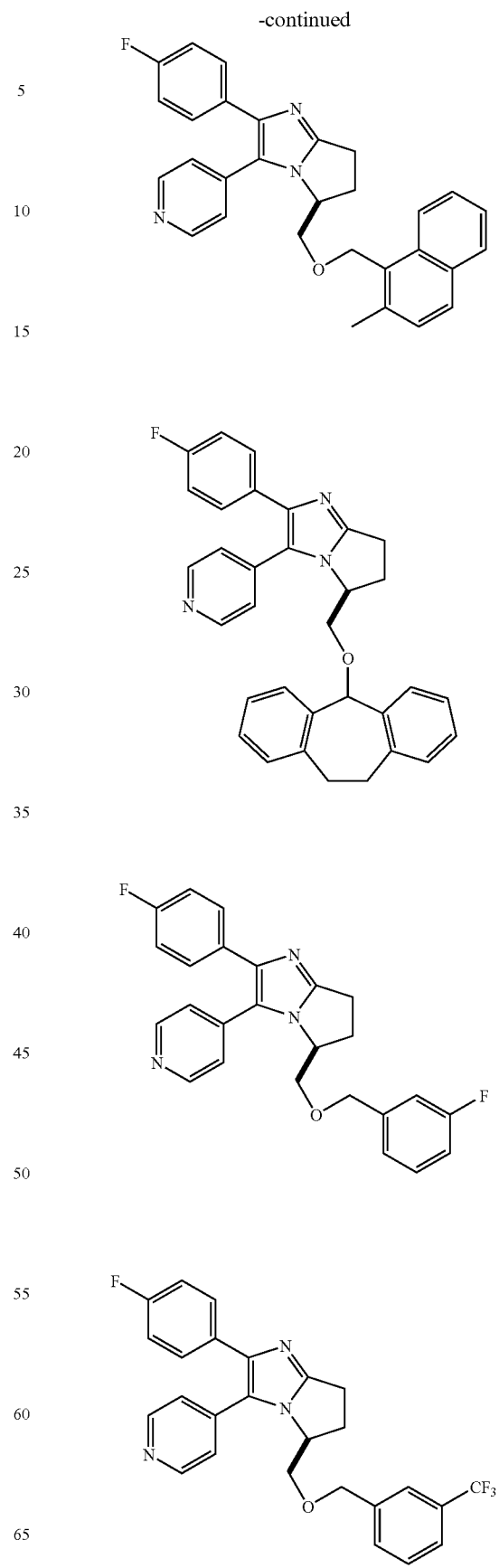

-continued
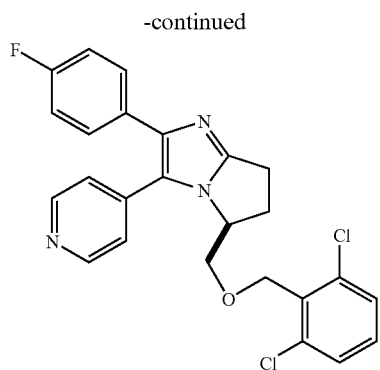
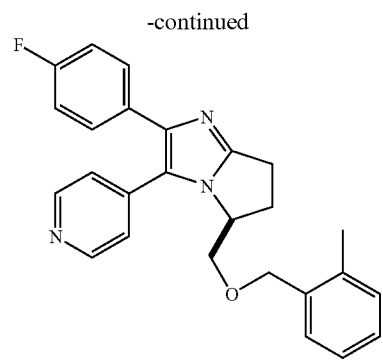
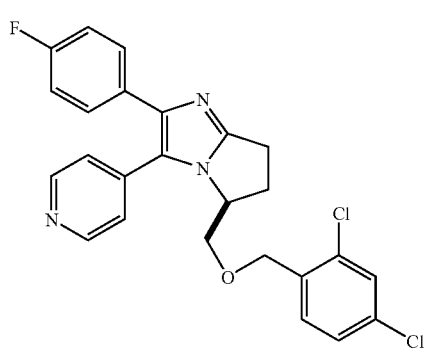
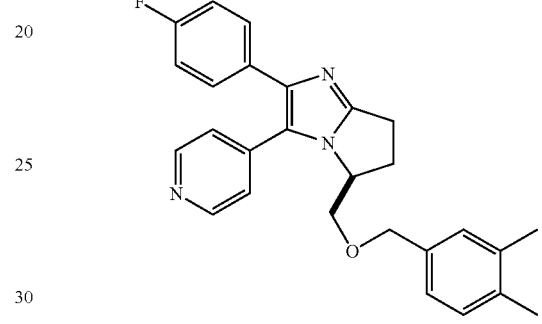
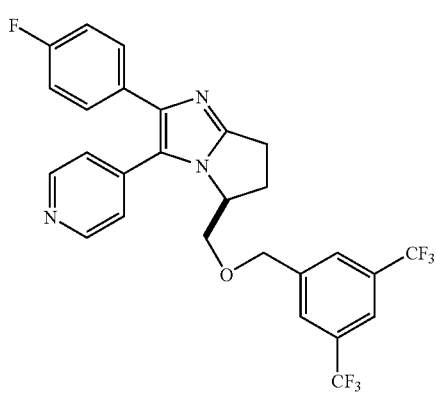
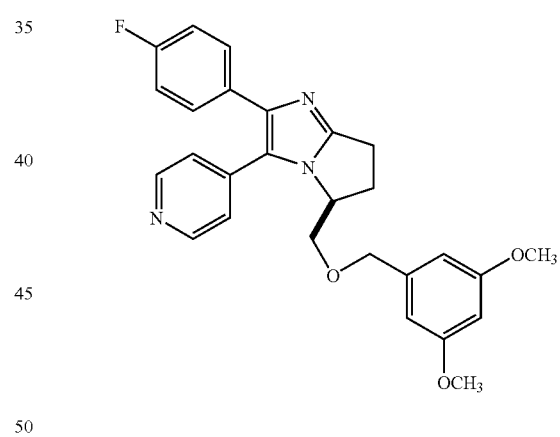
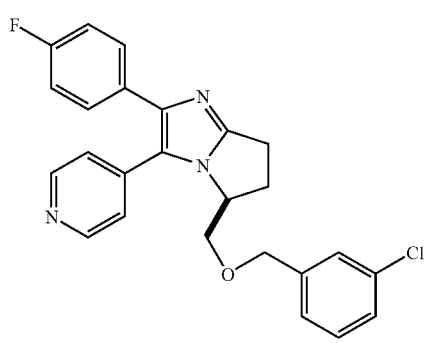
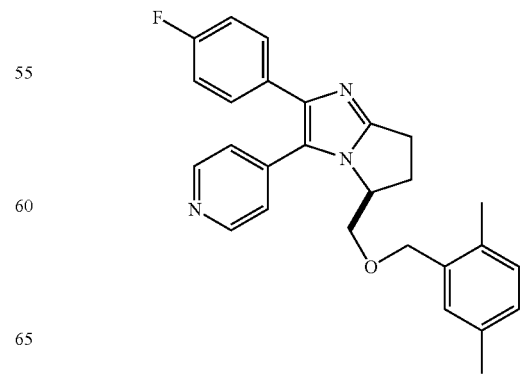

-continued
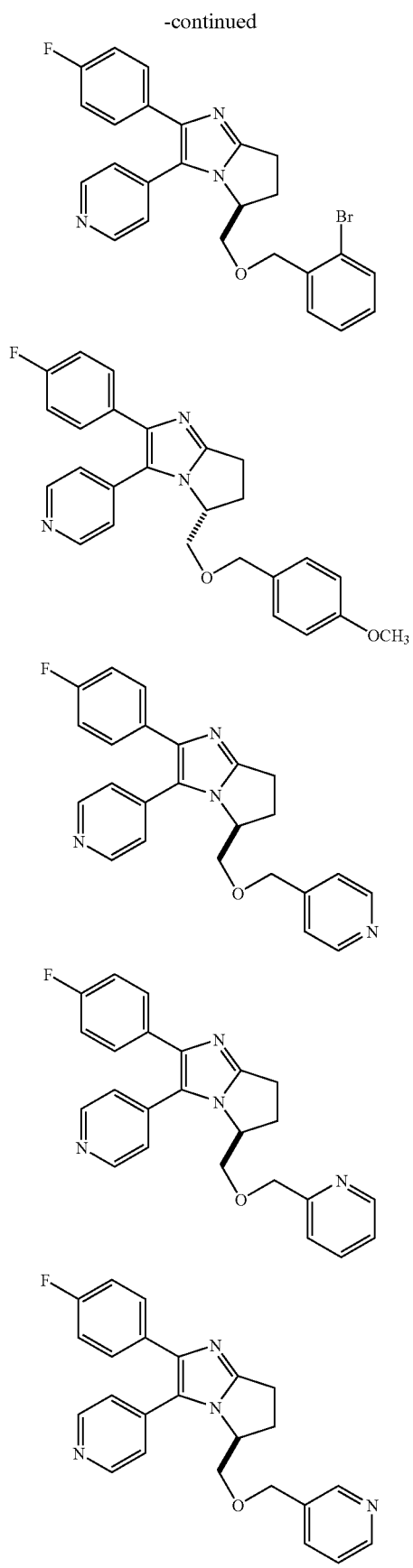
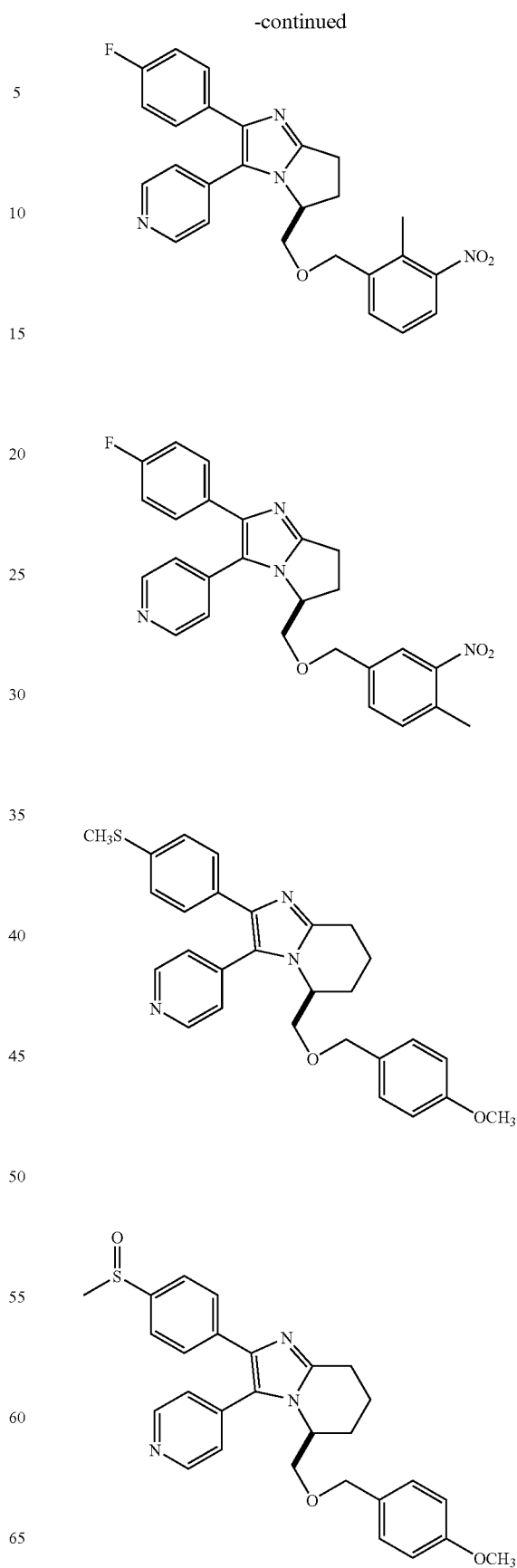

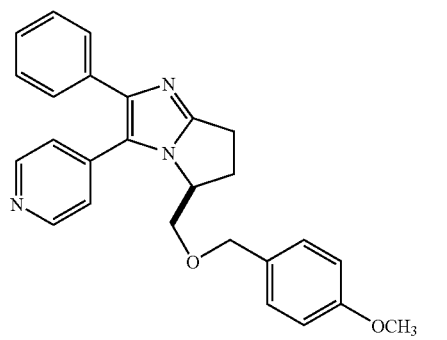
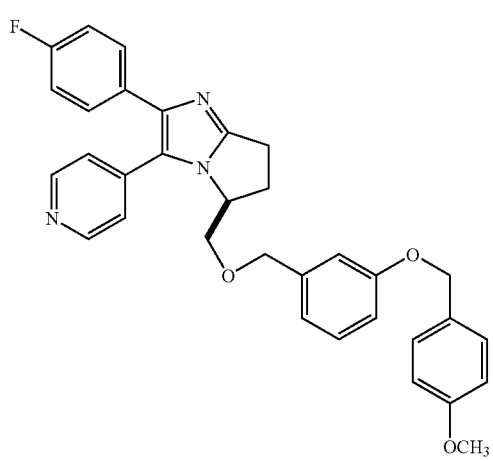
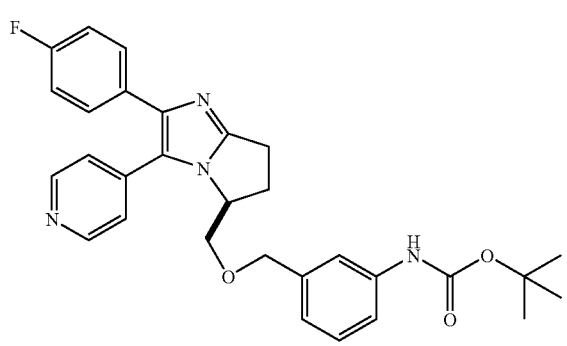
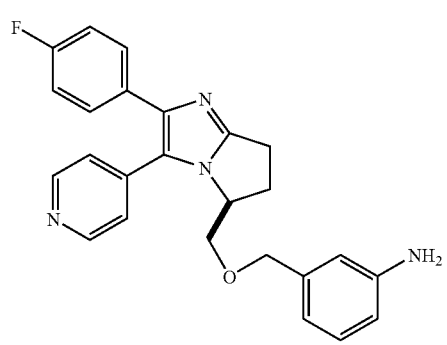
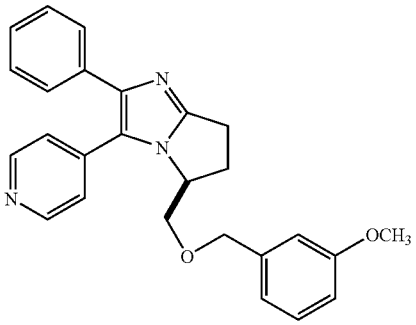
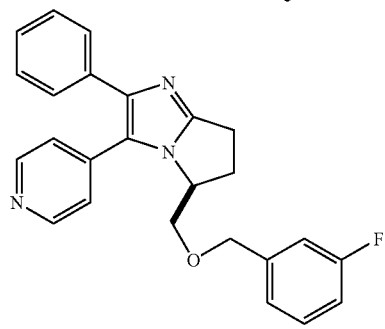
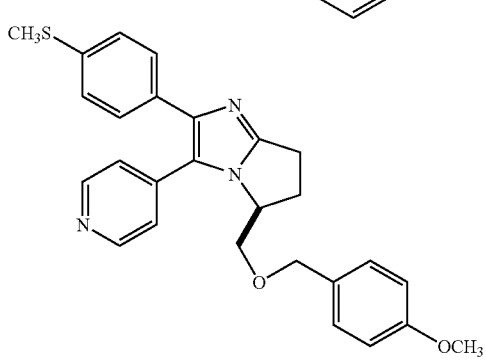
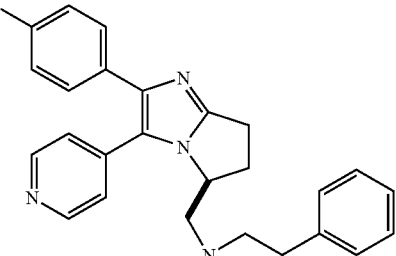
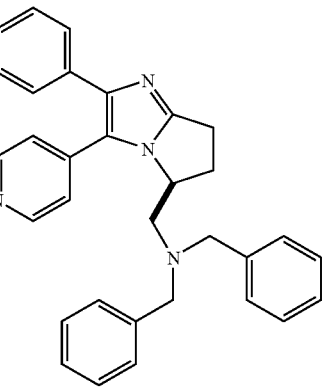

-continued
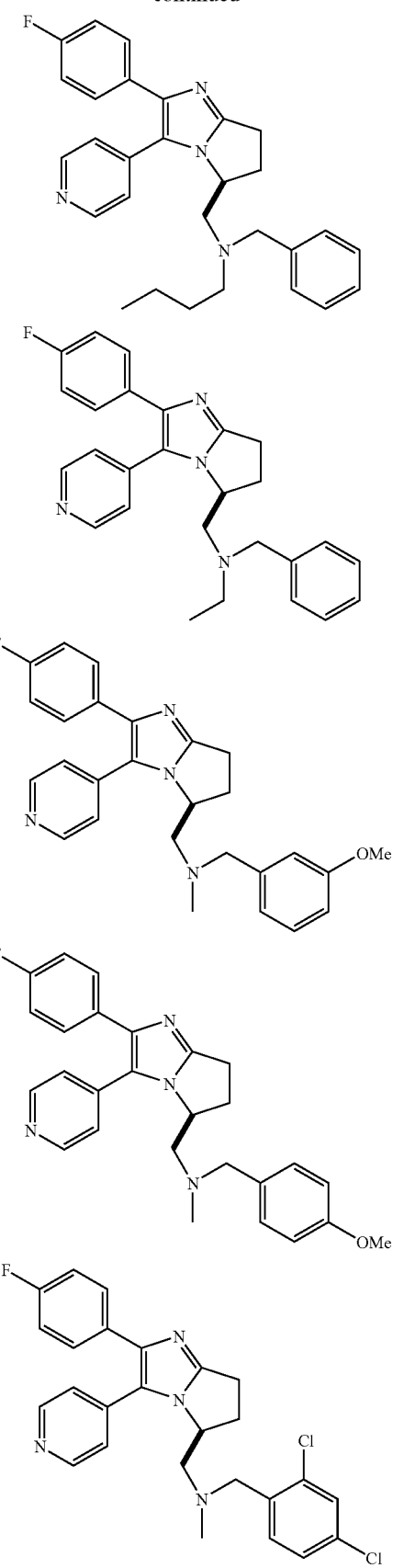
-continued
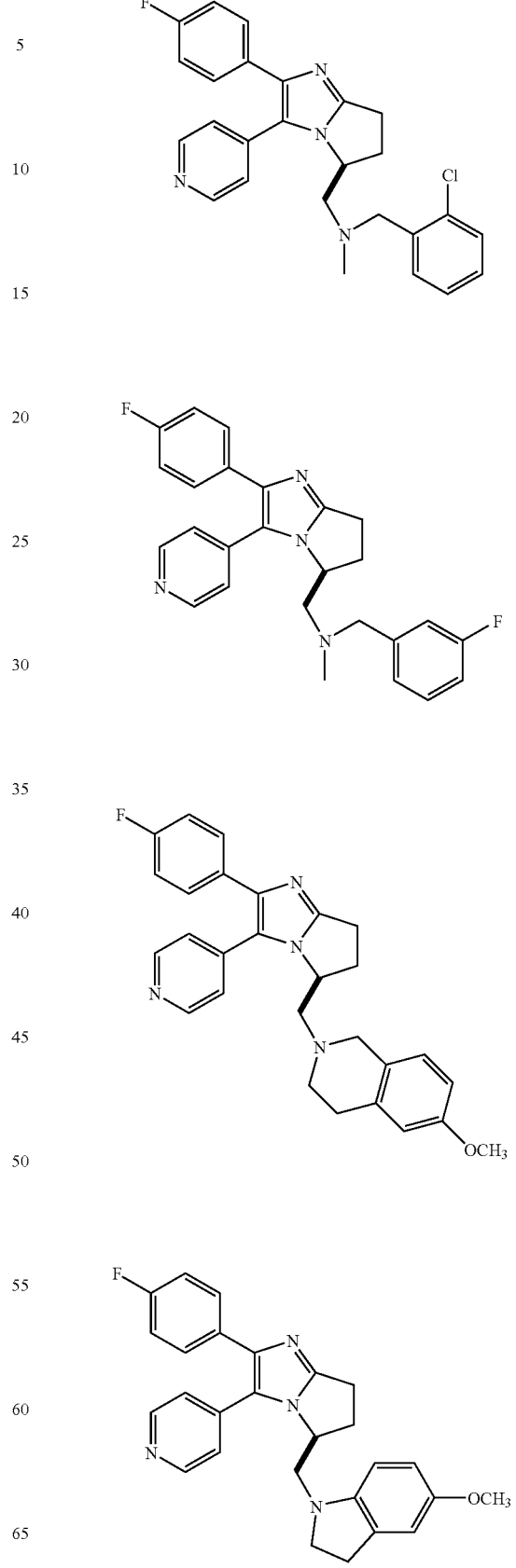

-continued
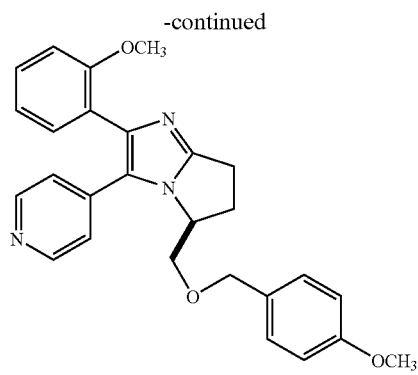
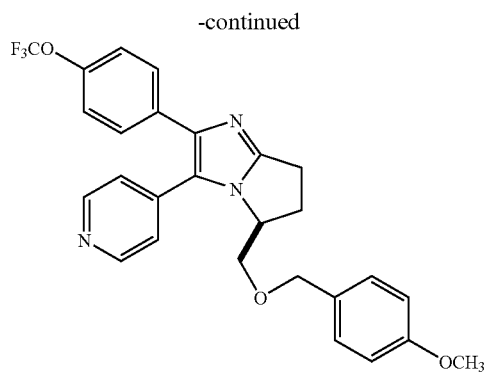
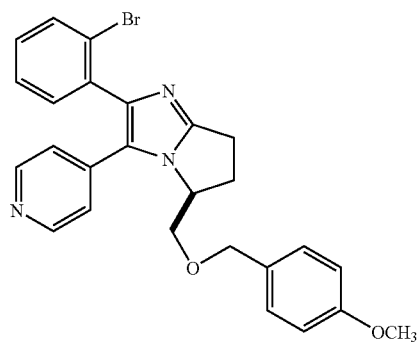
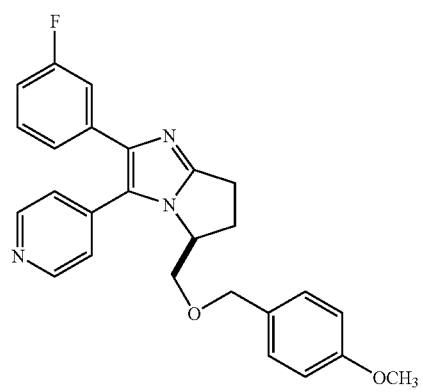
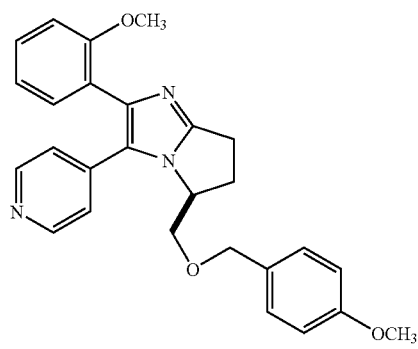
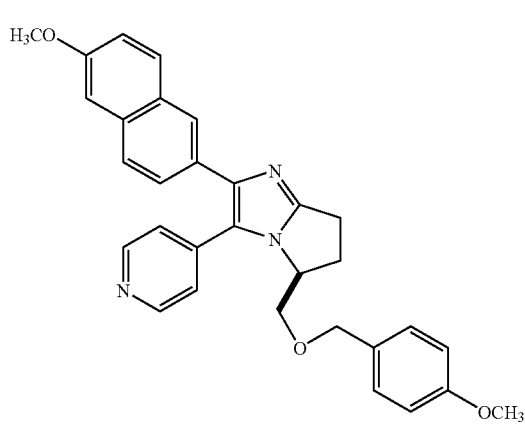
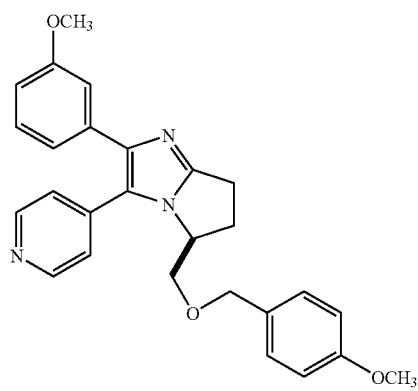
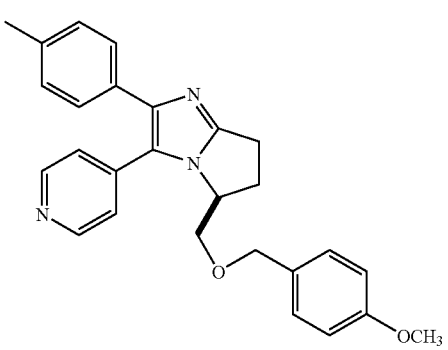

-continued
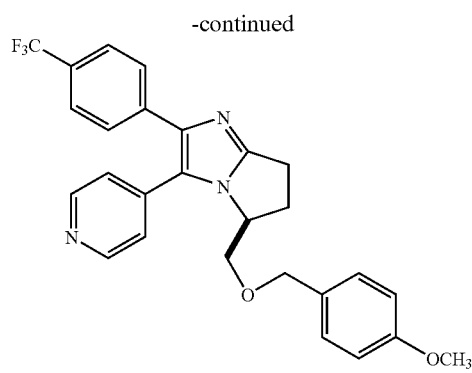
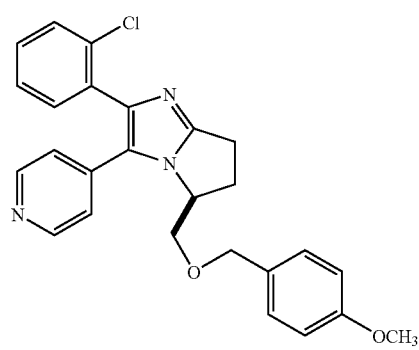
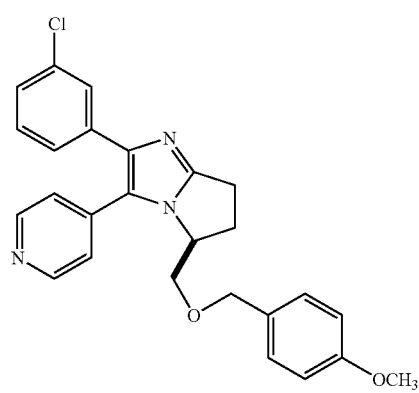
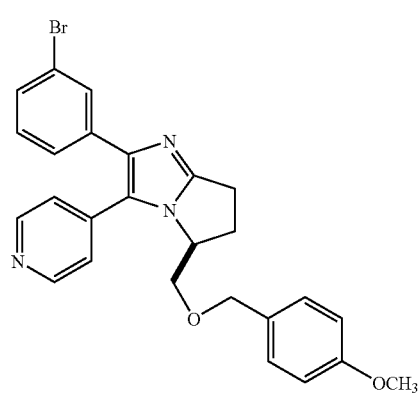
-continued
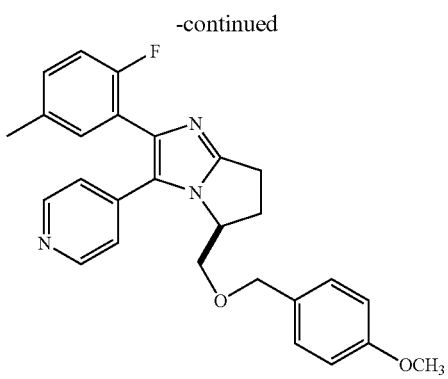
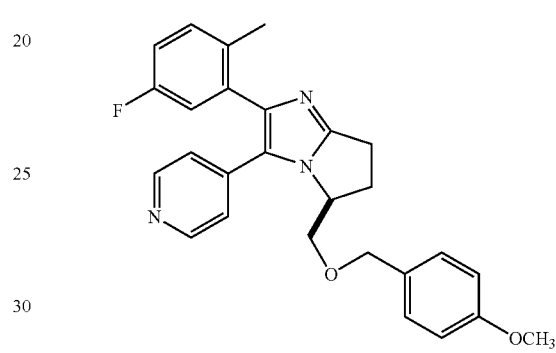
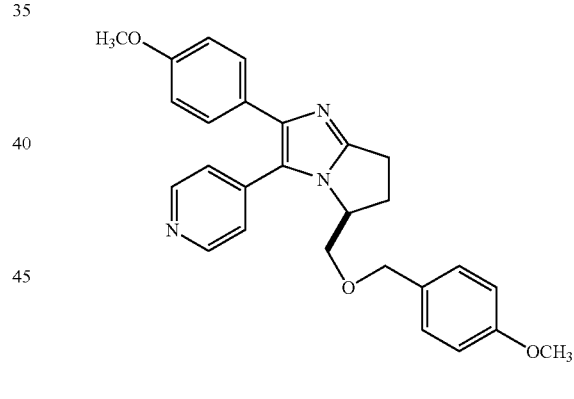
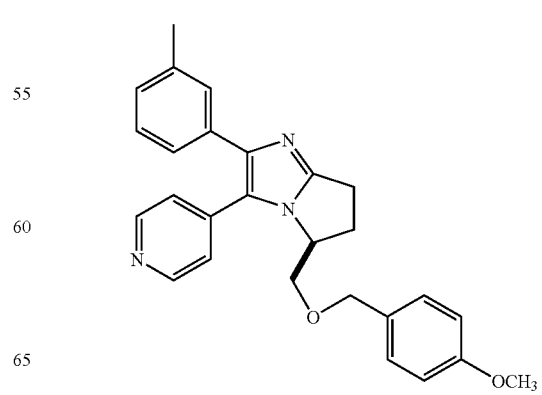

-continued
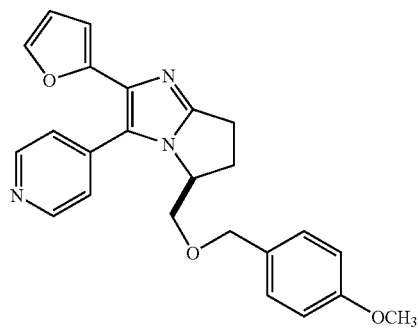
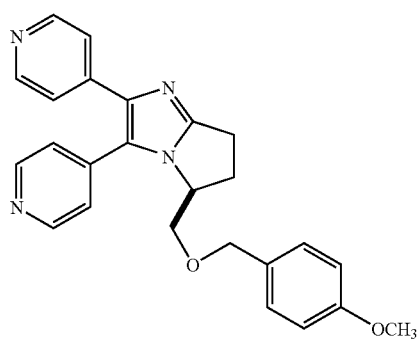
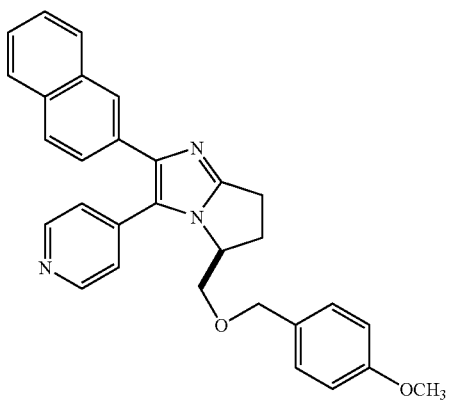
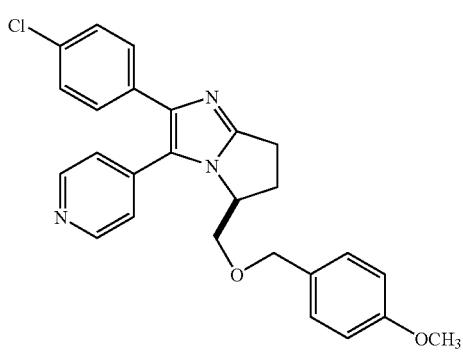
-continued
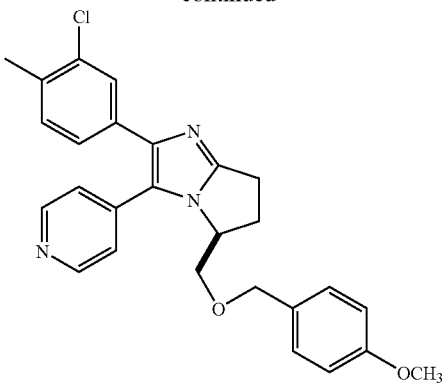
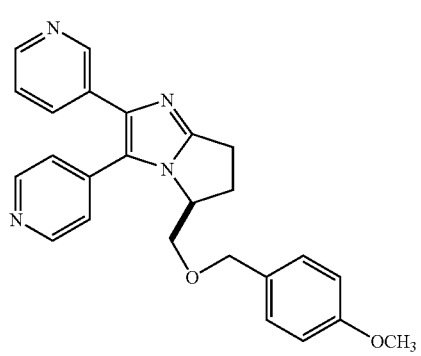
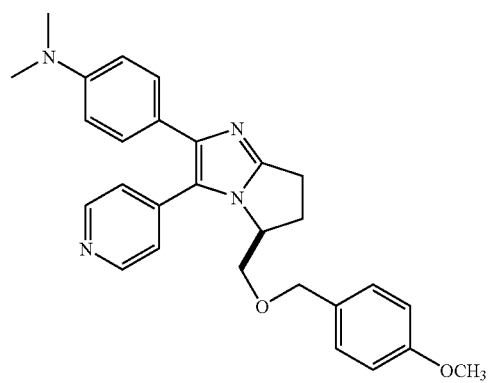
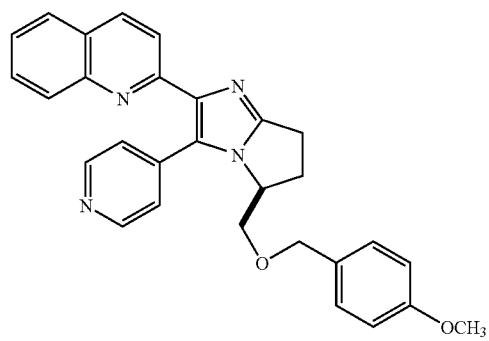

-continued
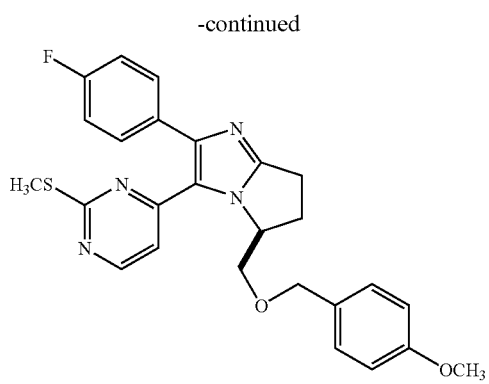
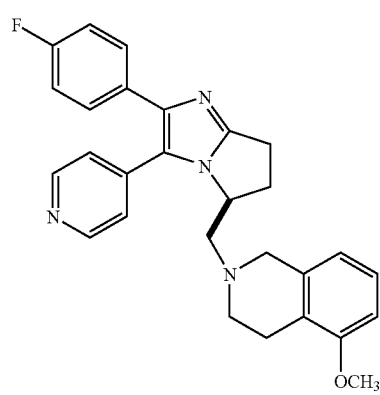
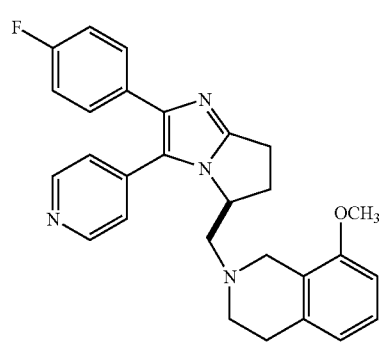
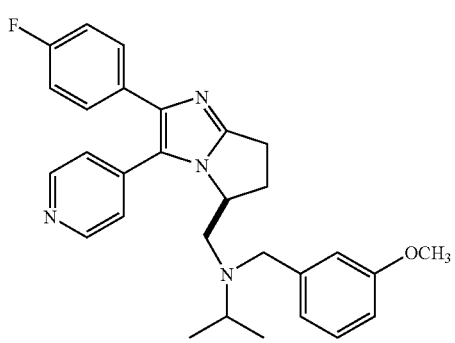
-continued
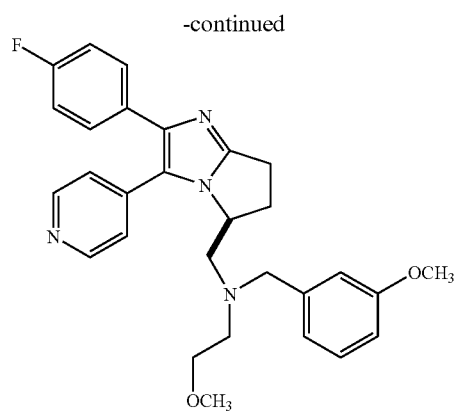
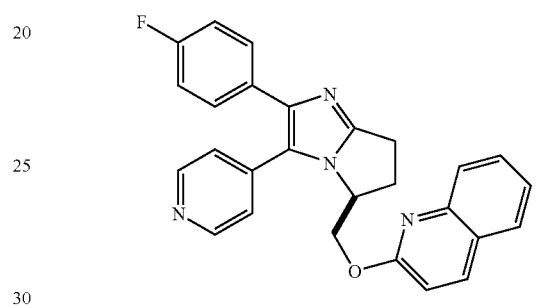
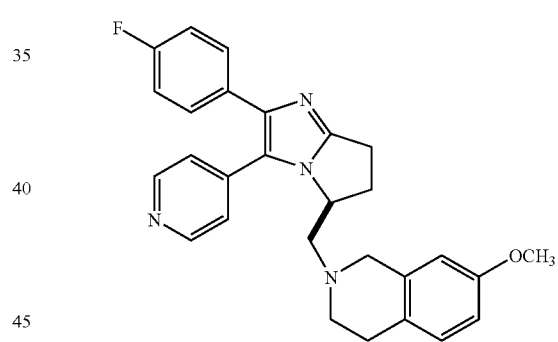
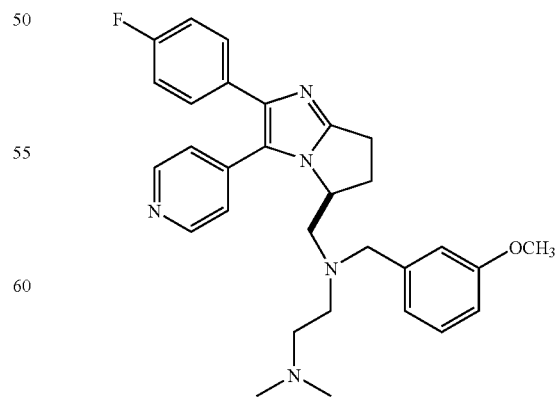

-continued
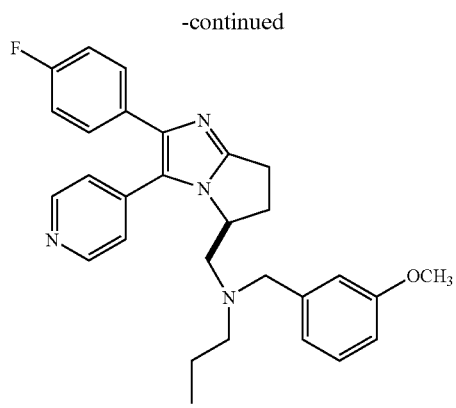
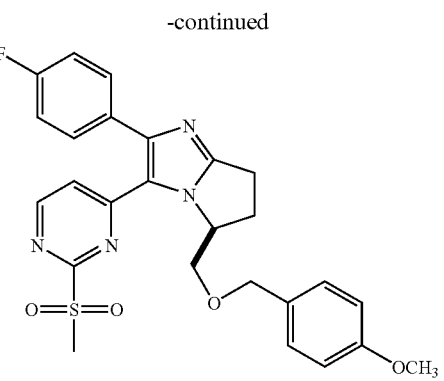
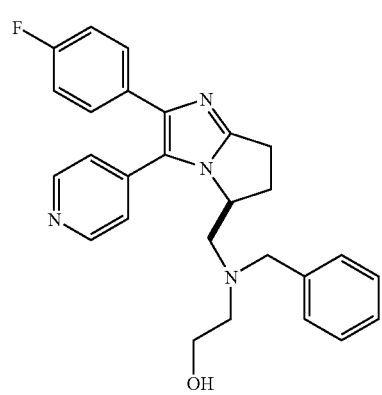
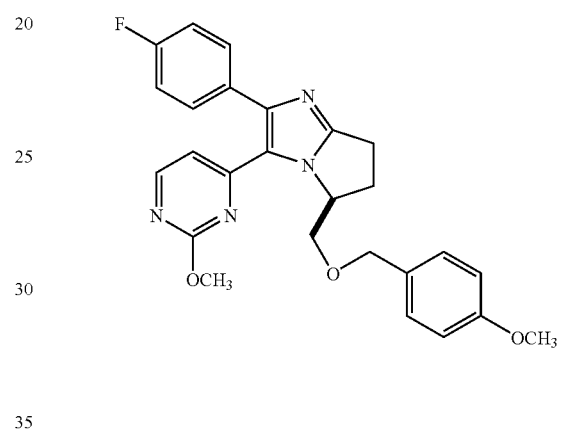
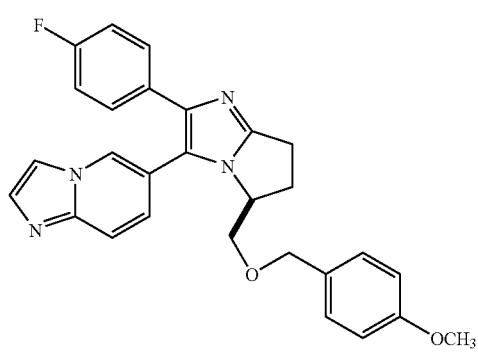
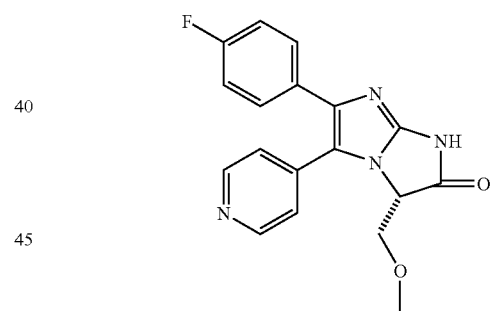
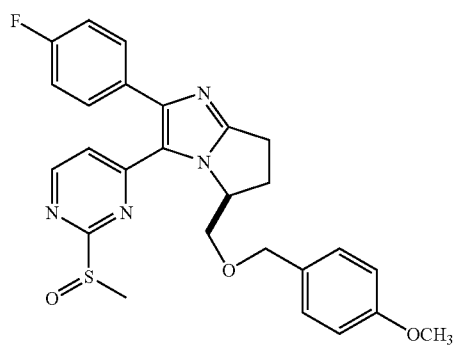
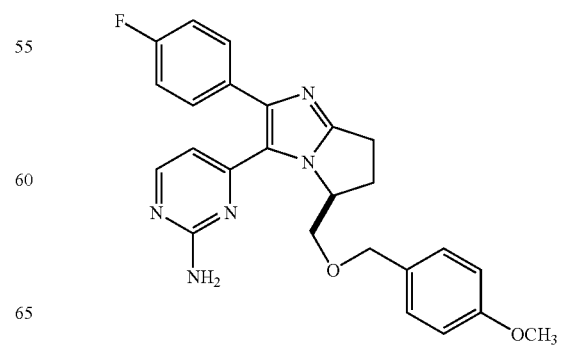

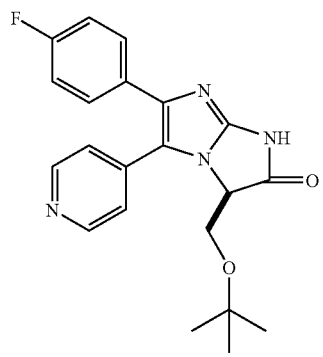
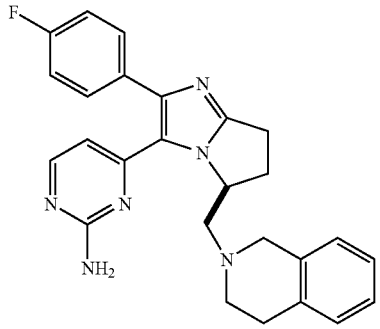
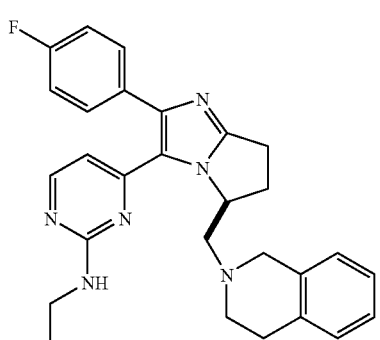
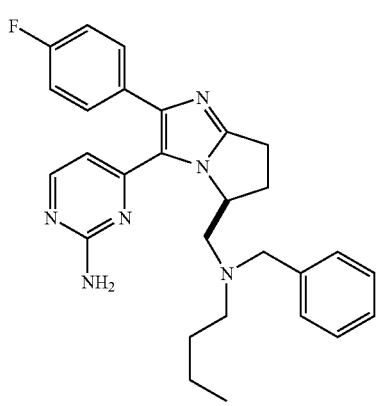

-continued
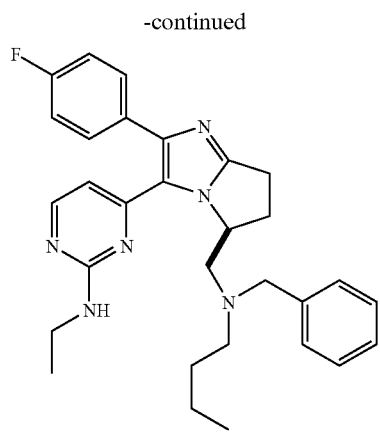
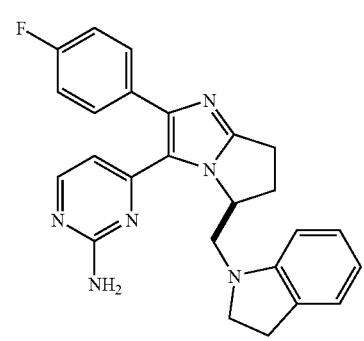
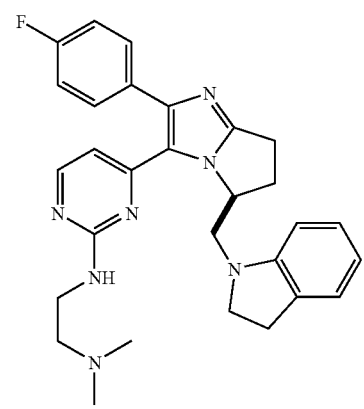
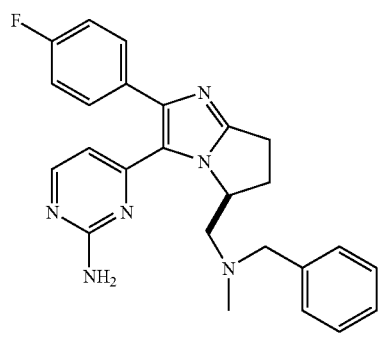
-continued
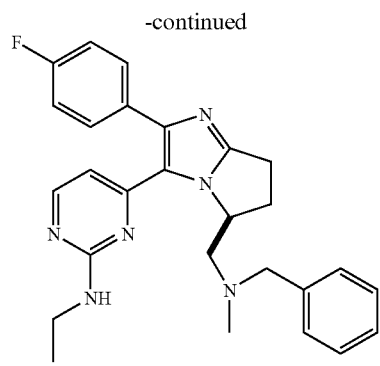
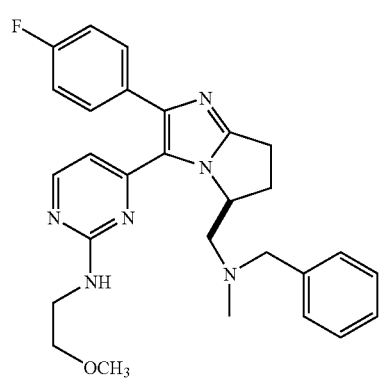
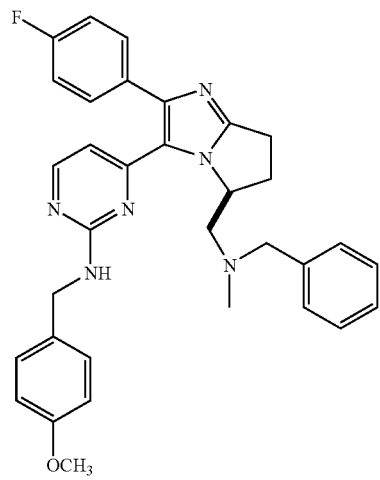
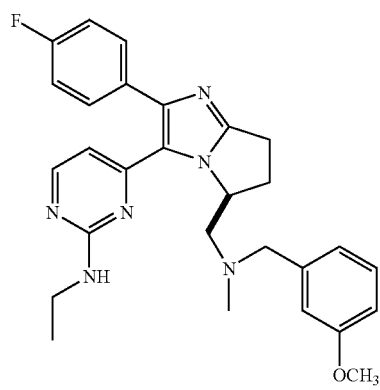

-continued
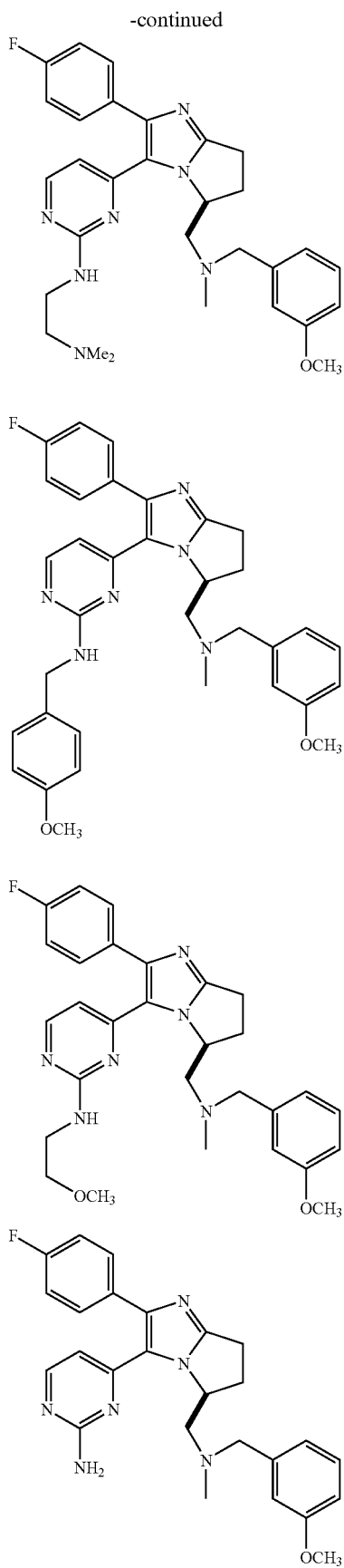
-continued
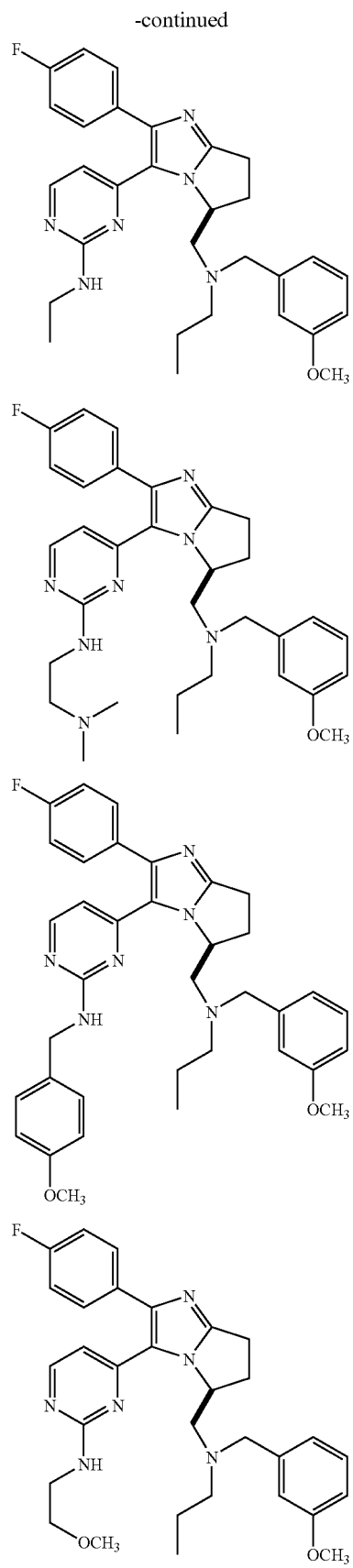

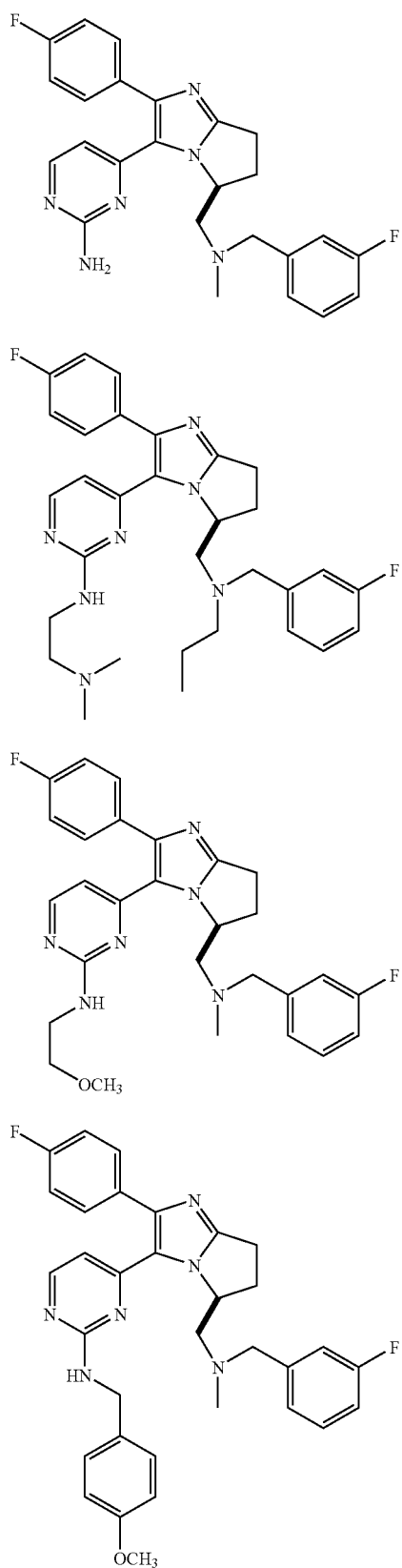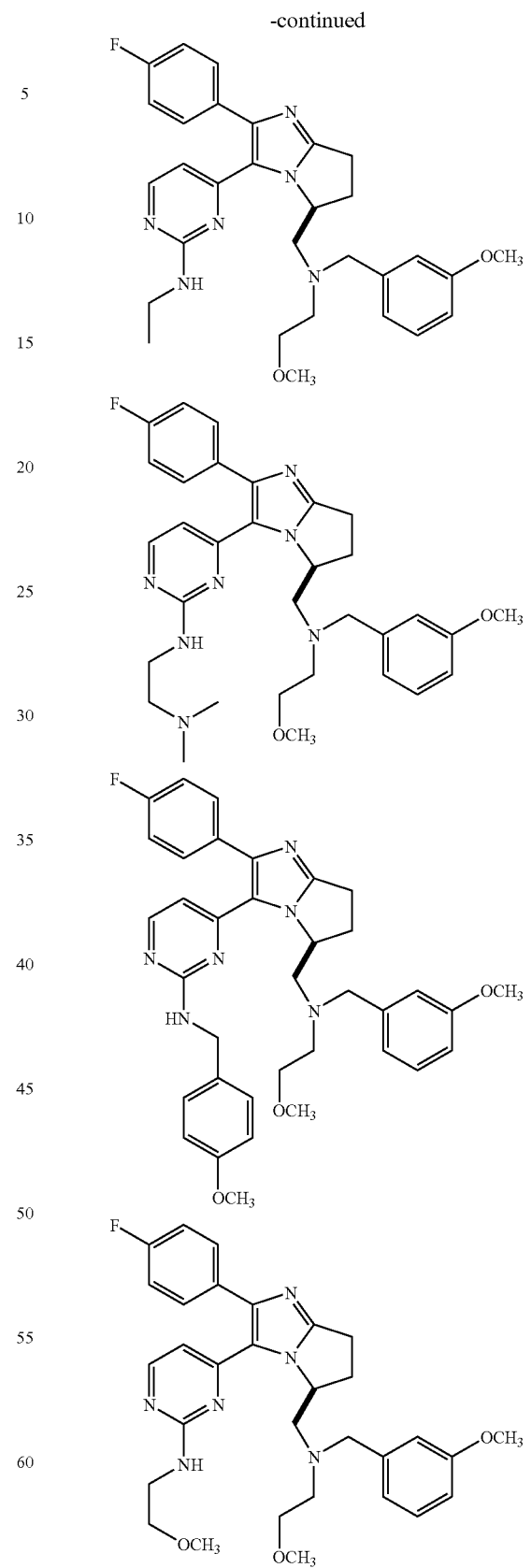

-continued
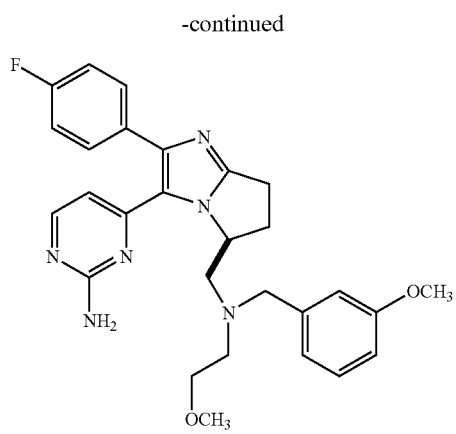
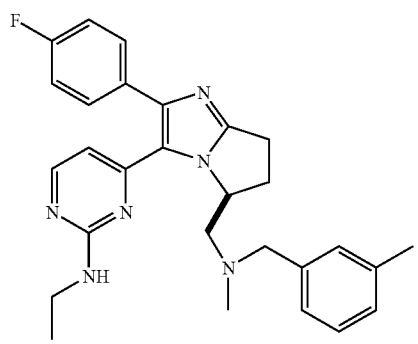
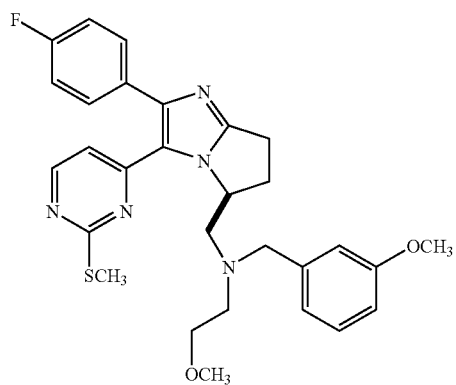
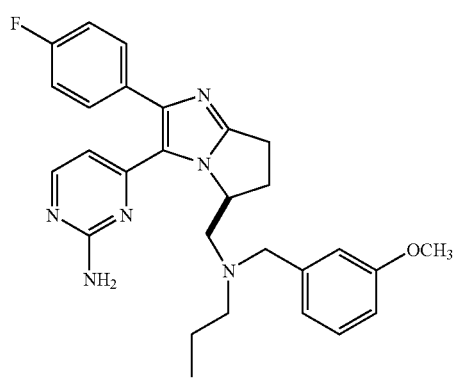
-continued
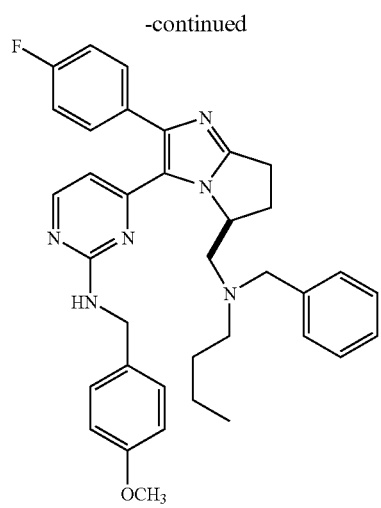
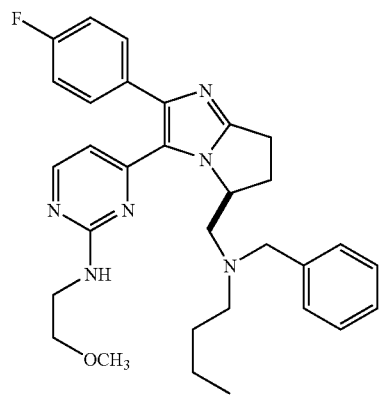
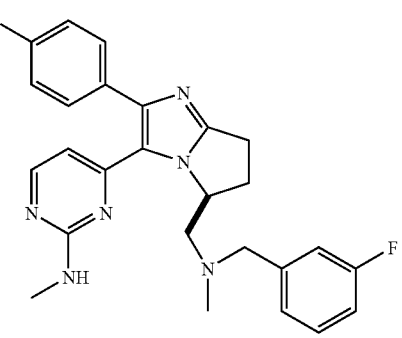
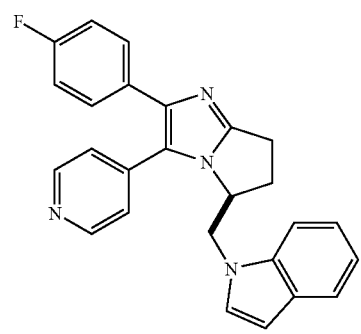

-continued
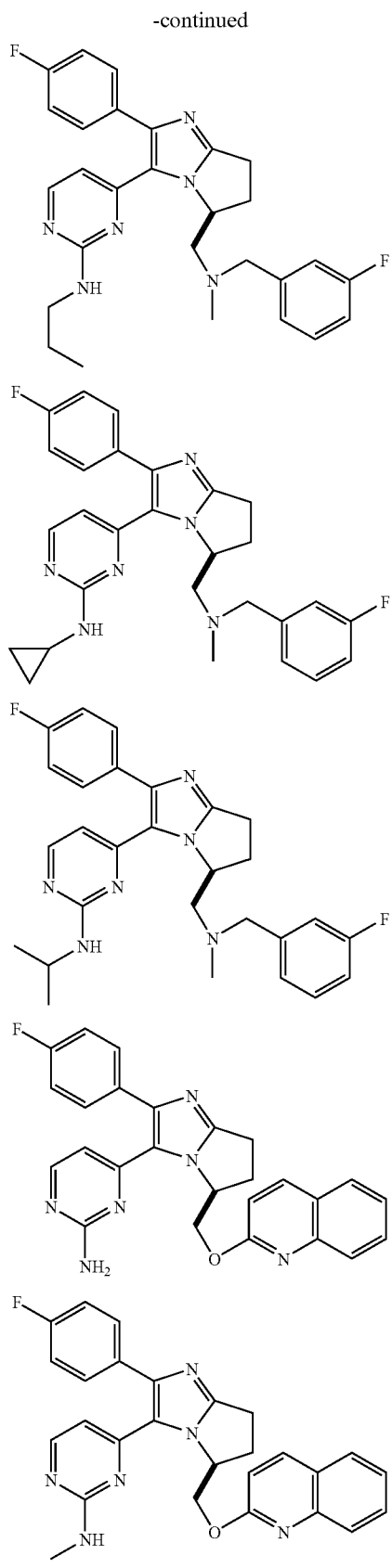
-continued
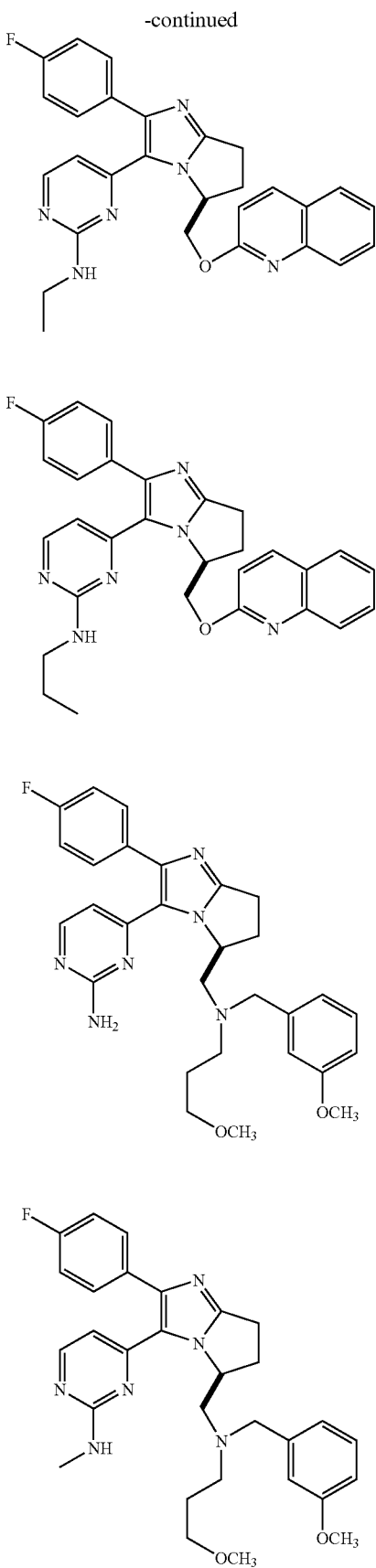

-continued
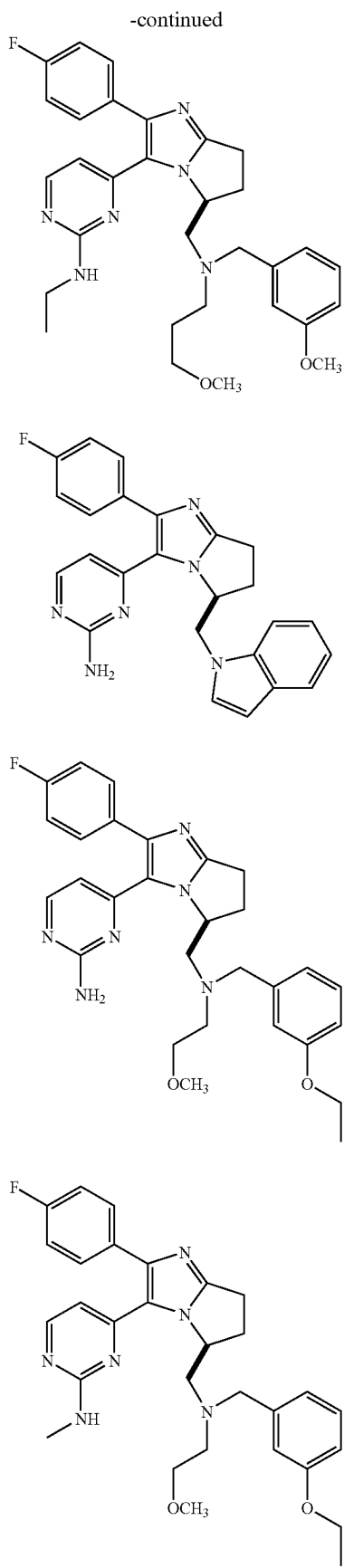
-continued
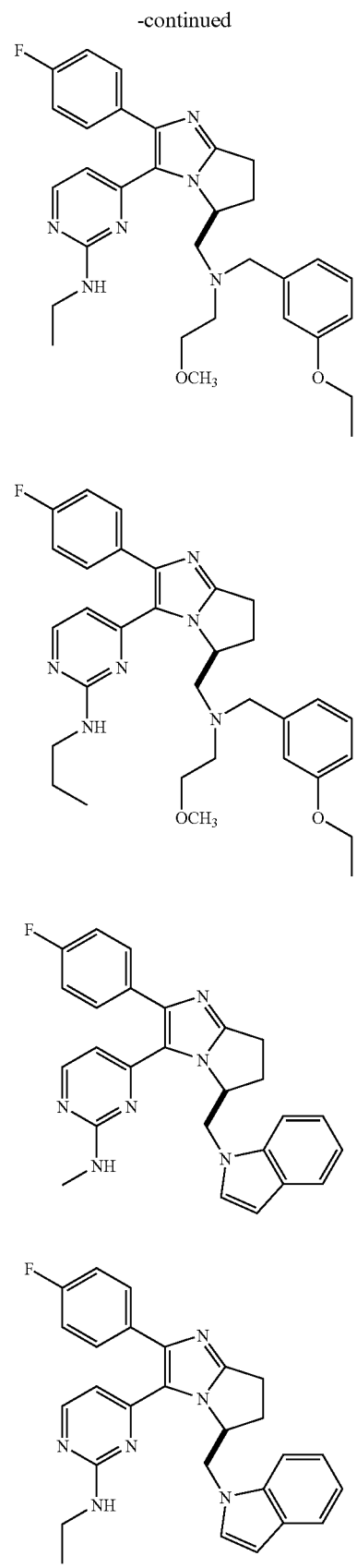

-continued
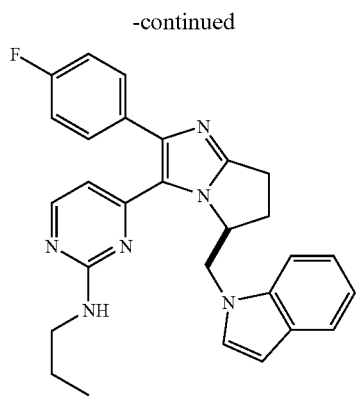
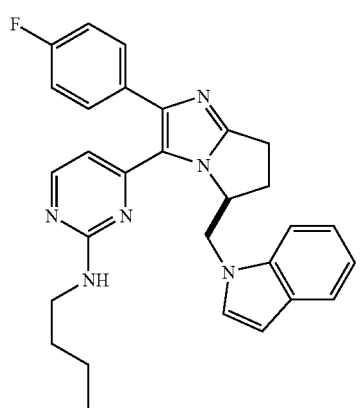
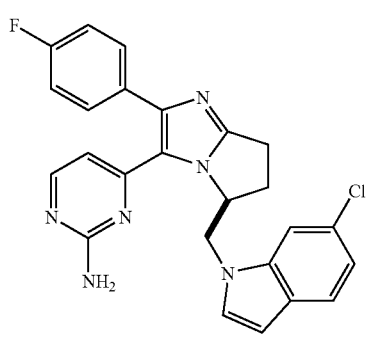
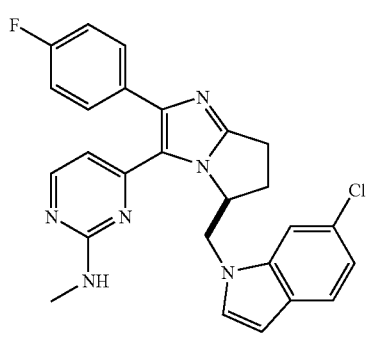
-continued
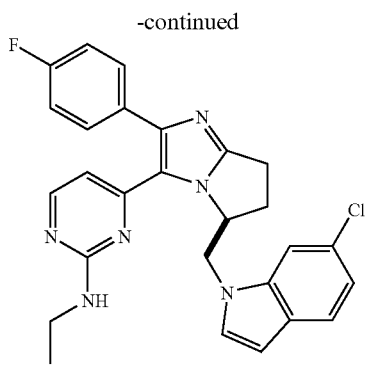
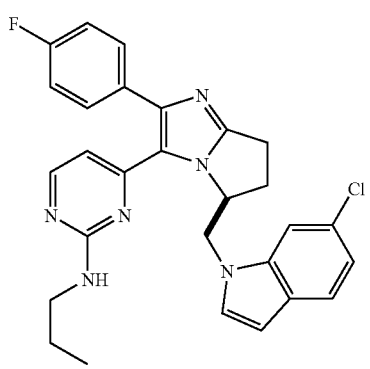
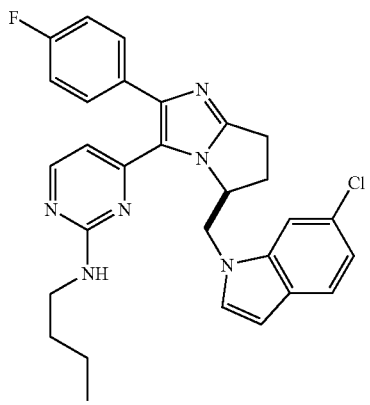
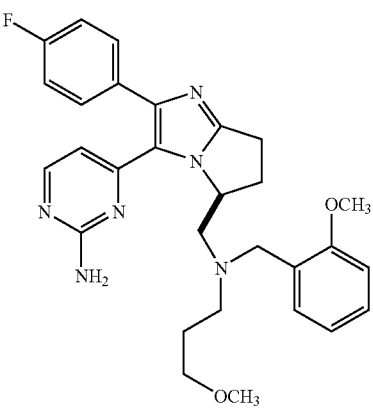

-continued
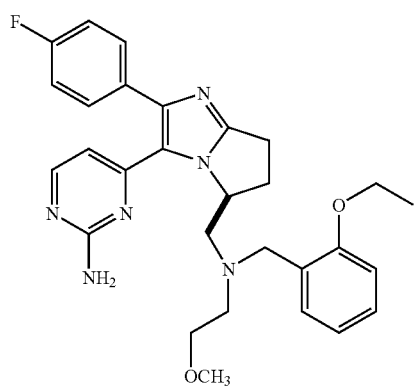
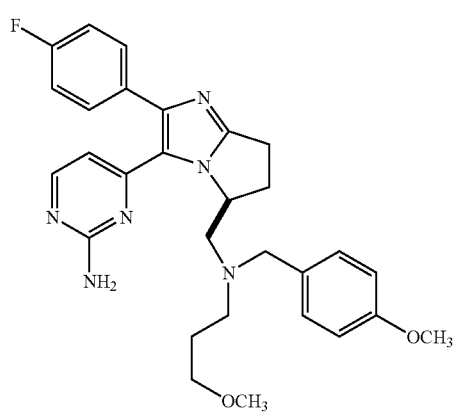
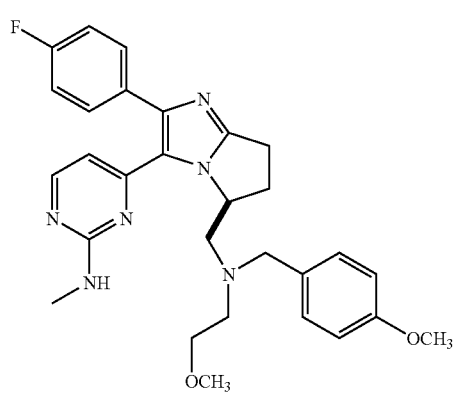
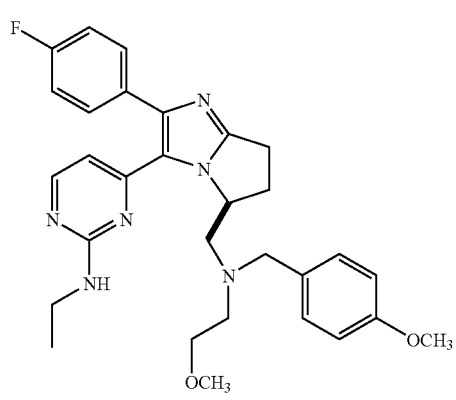
-continued
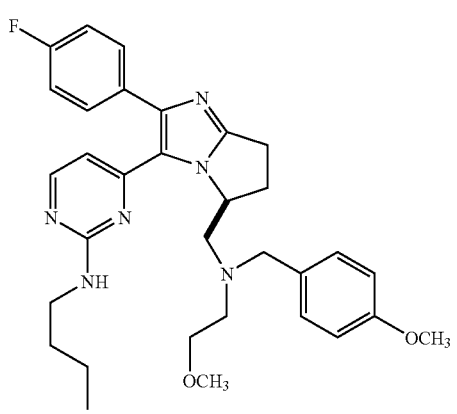
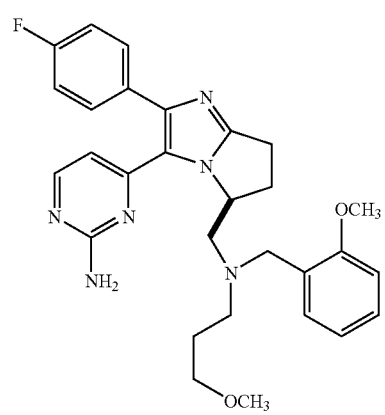
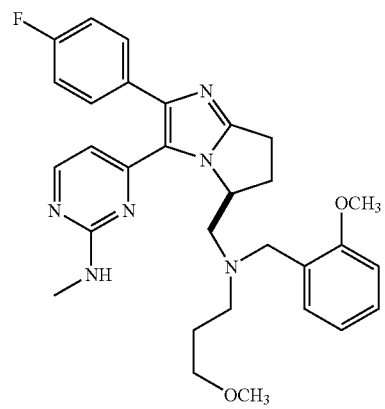

-continued
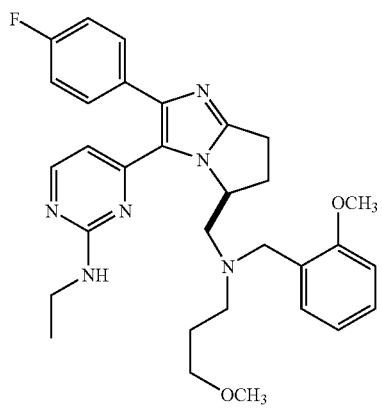
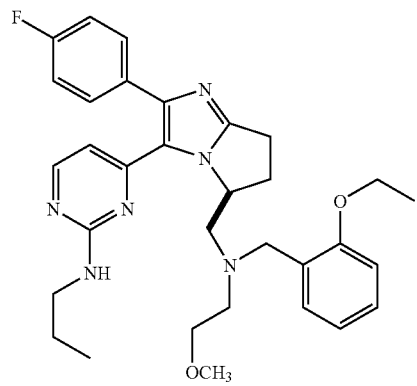
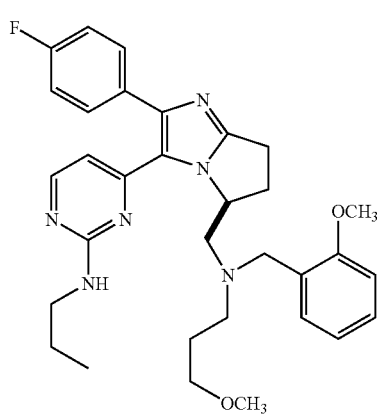
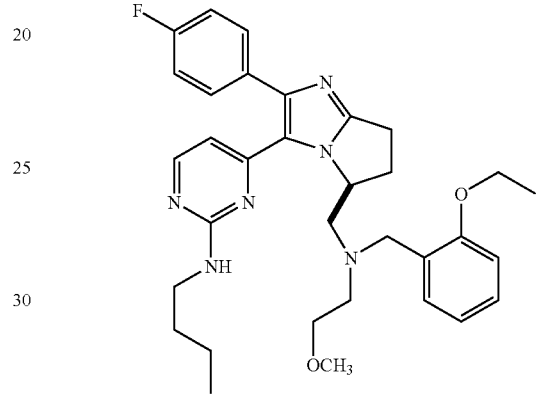
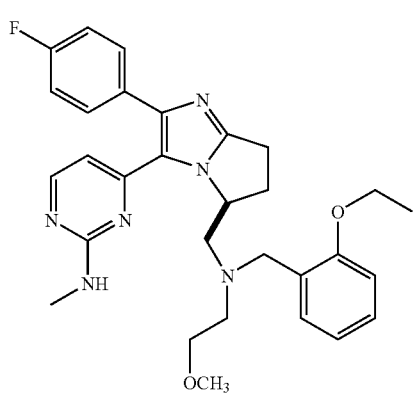
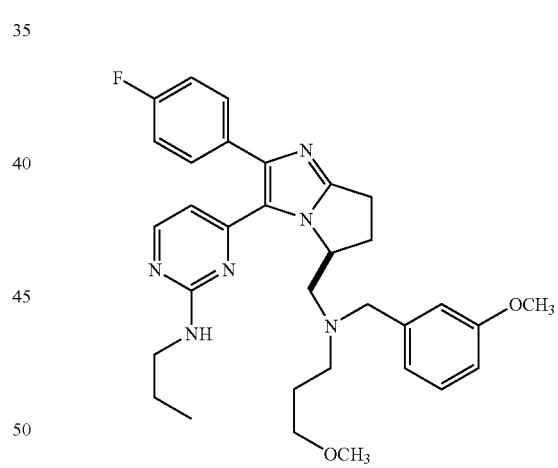
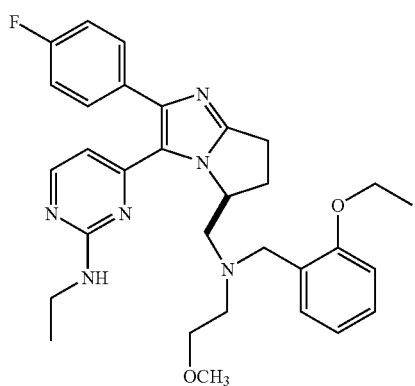
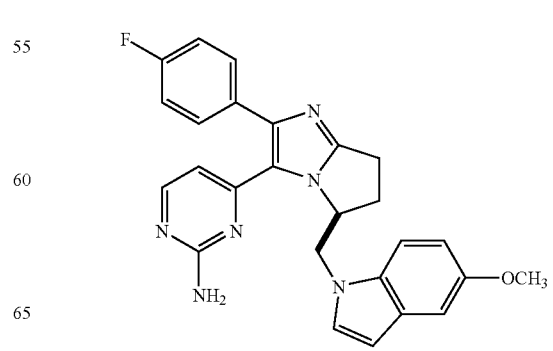

51
-continued
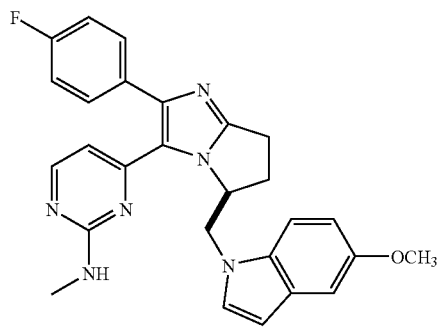
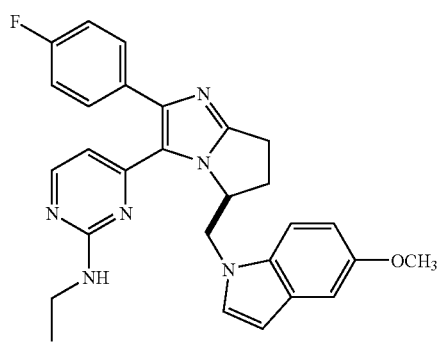
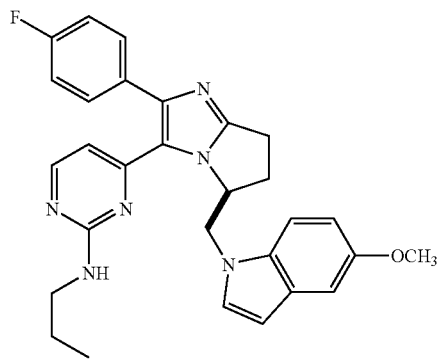
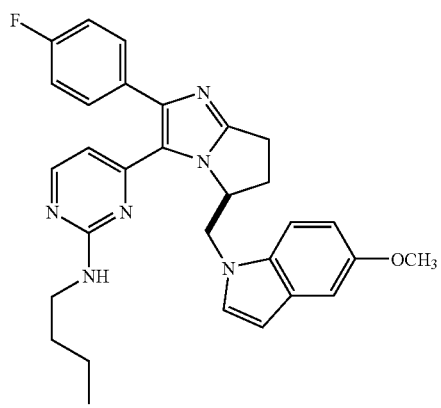
52
-continued
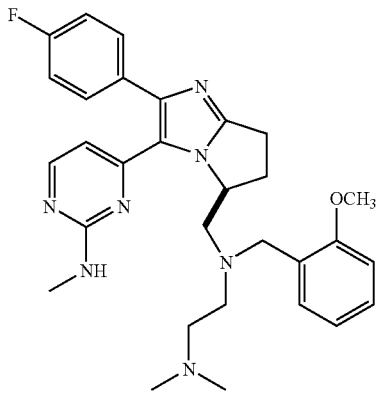
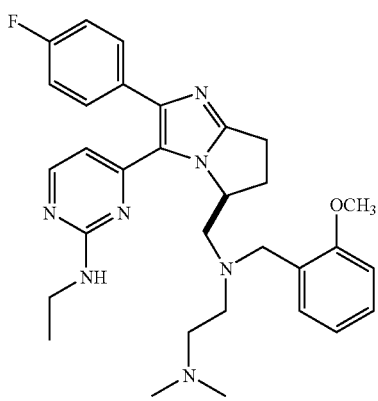
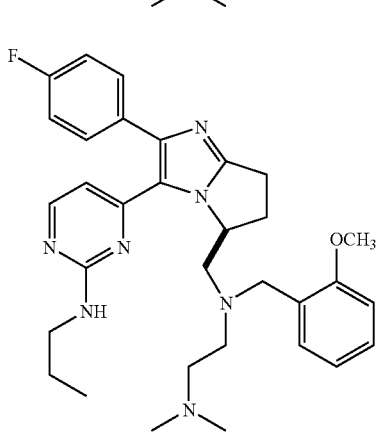
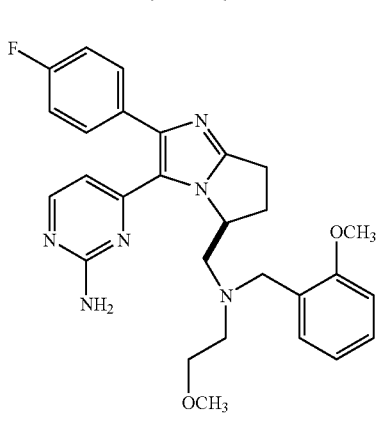

-continued
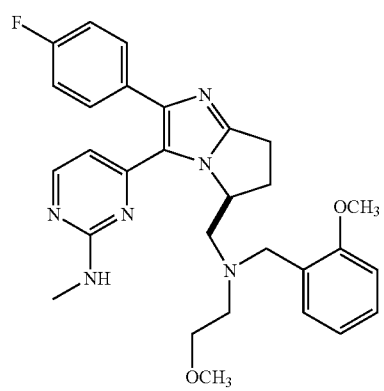
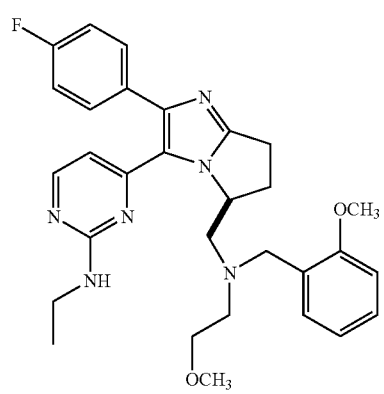
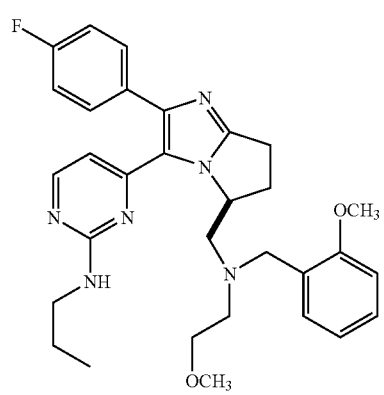
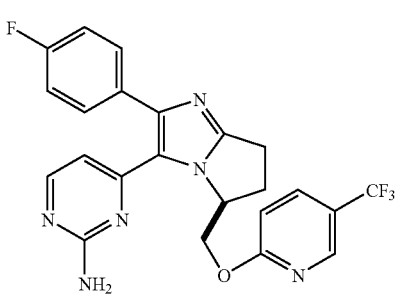
-continued
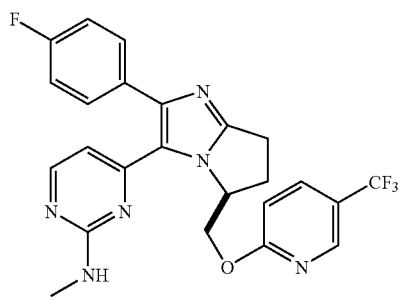
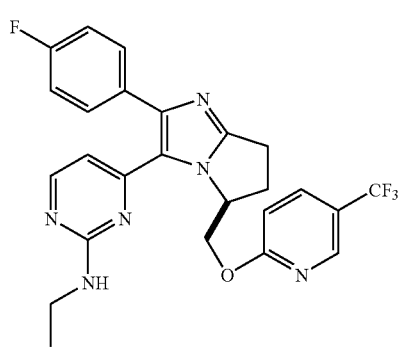
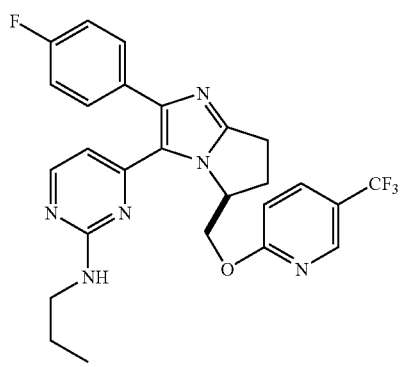
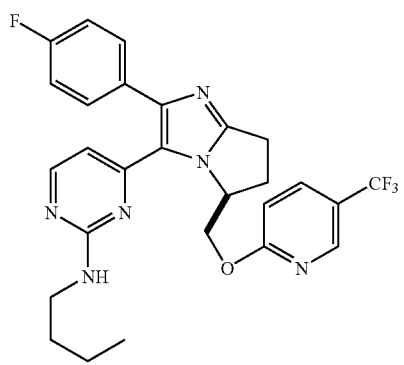

-continued
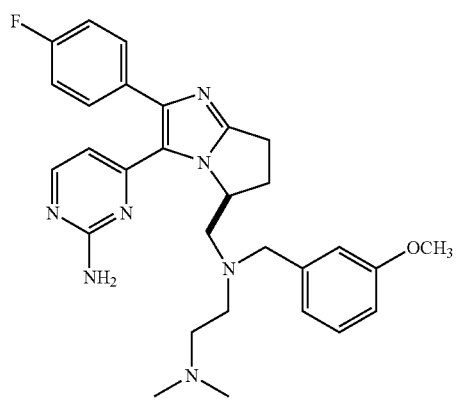
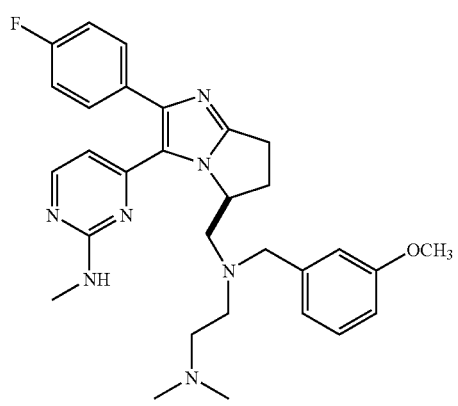
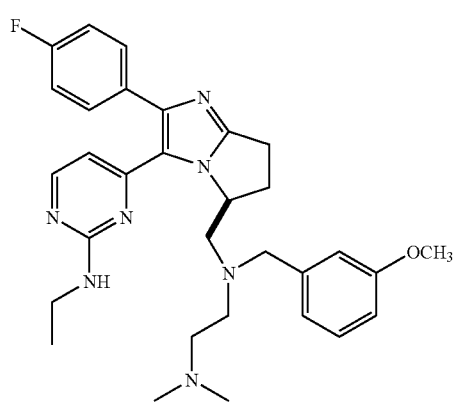
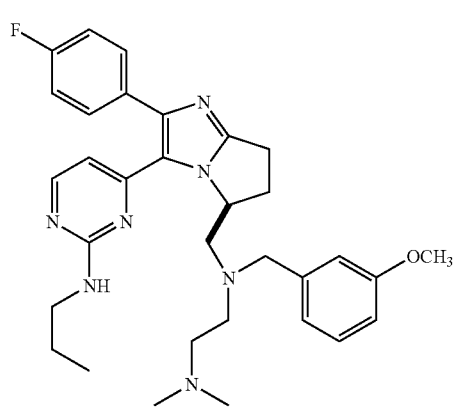
-continued
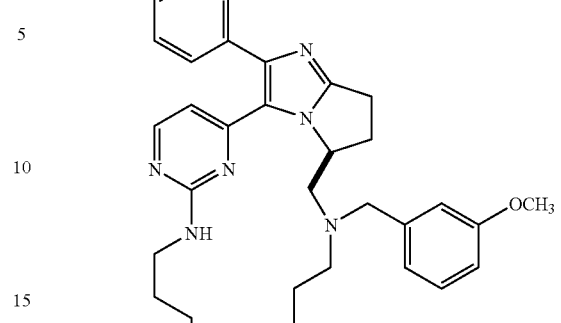
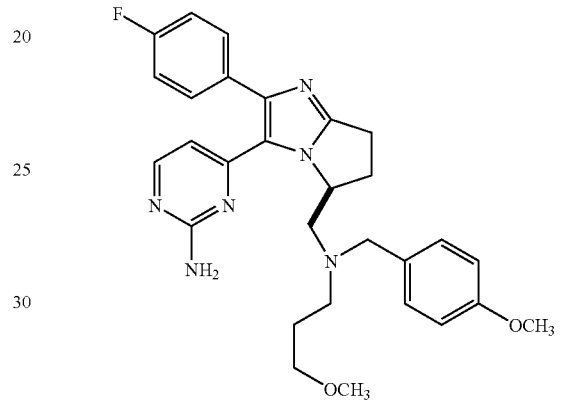
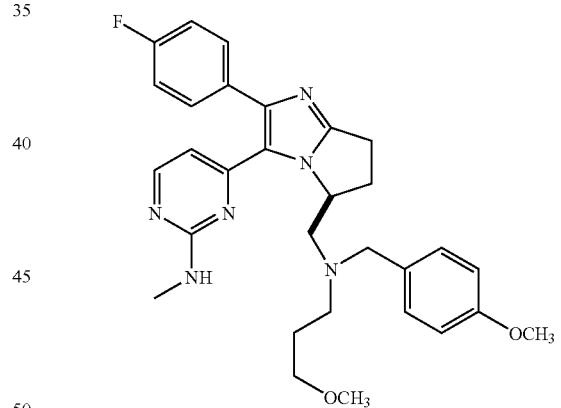
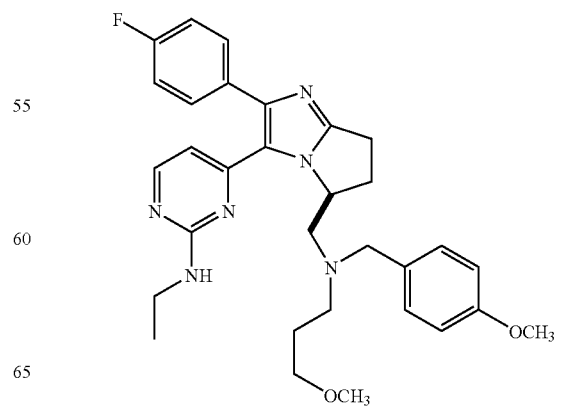

-continued
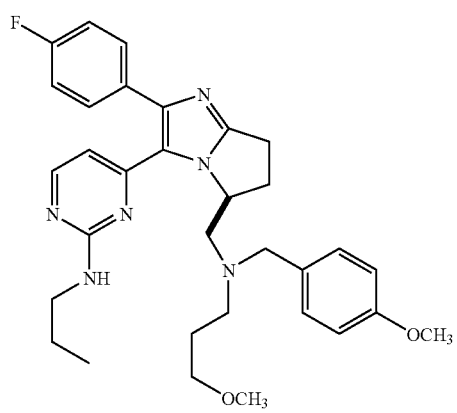
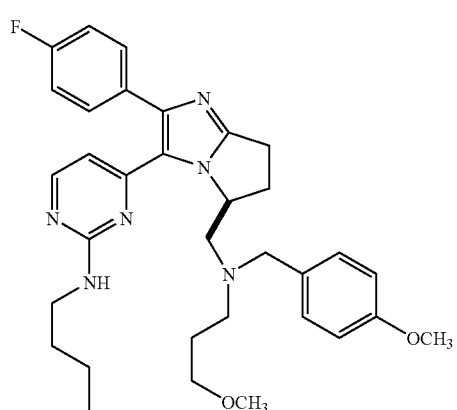
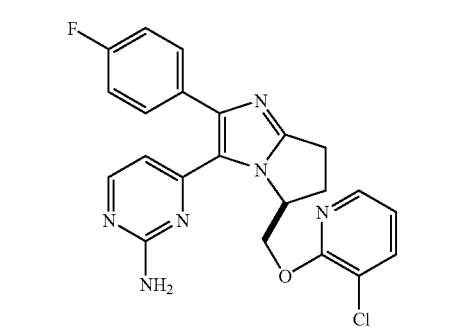
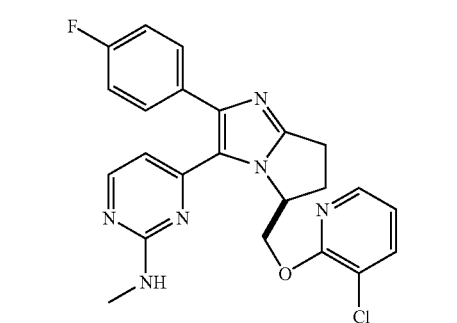
-continued
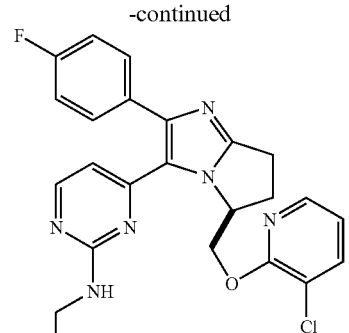
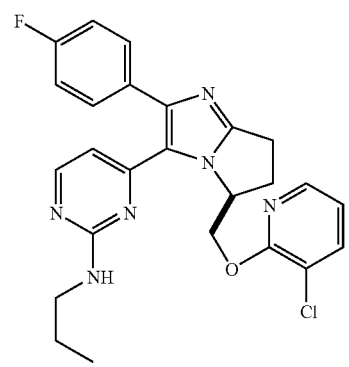
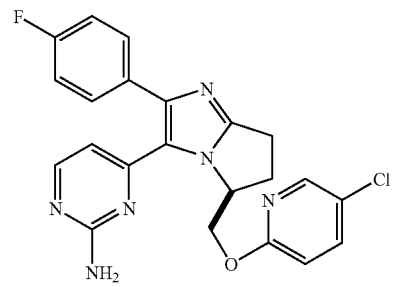
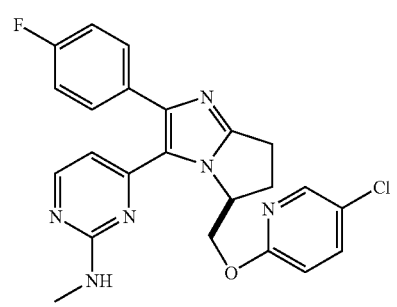
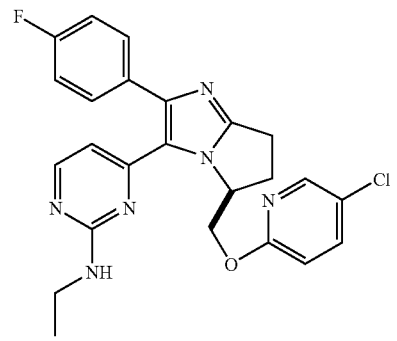

-continued
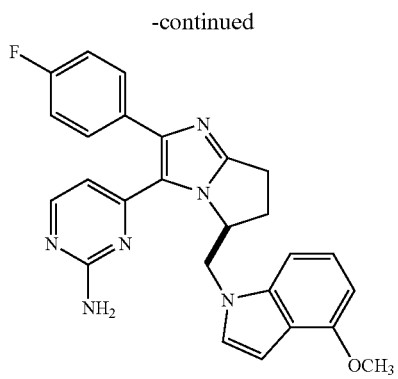
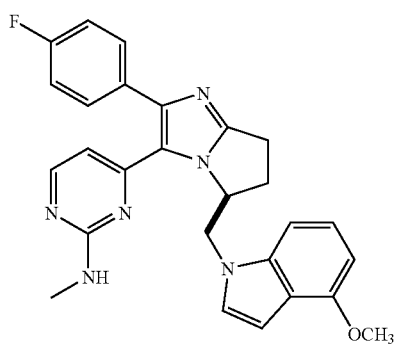
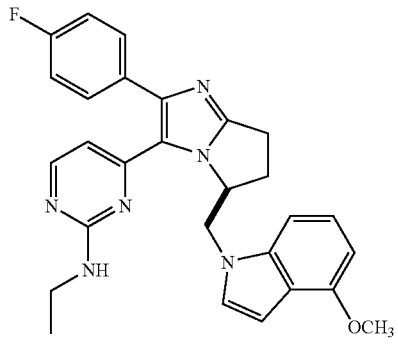
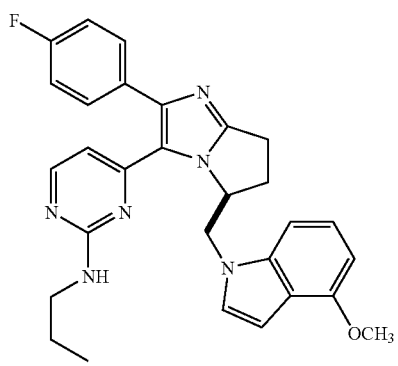
-continued
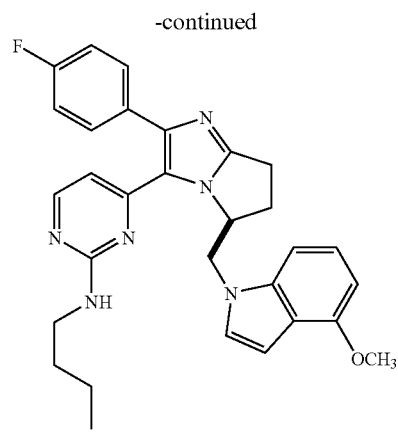
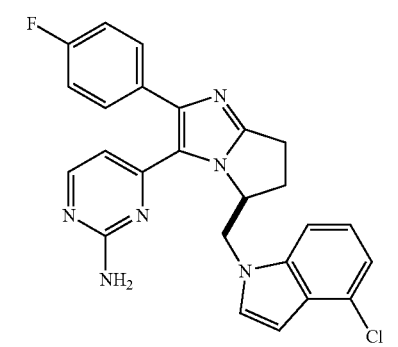
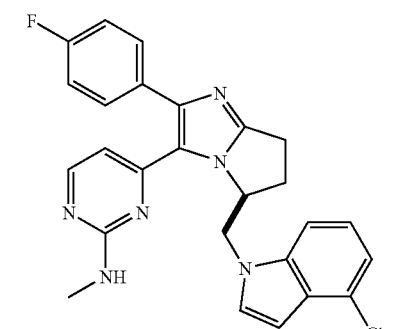
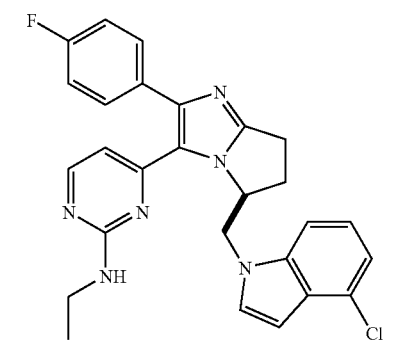

-continued
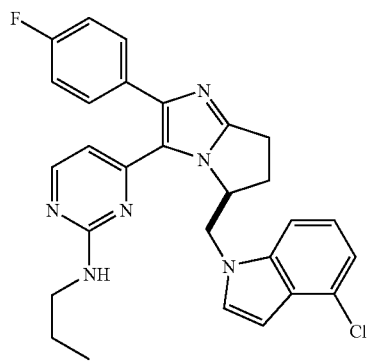
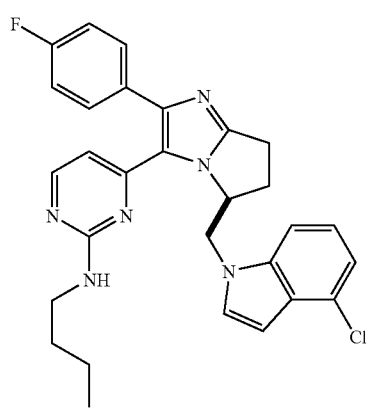
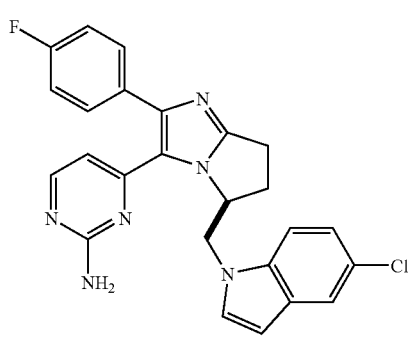
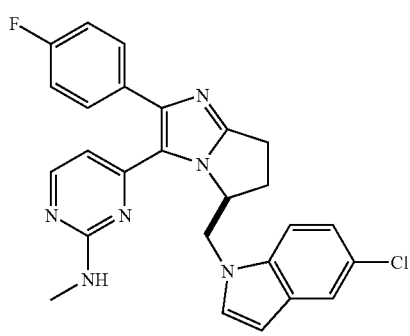
-continued
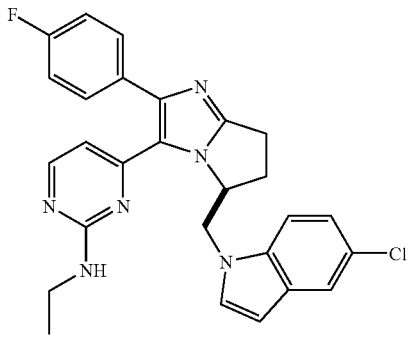
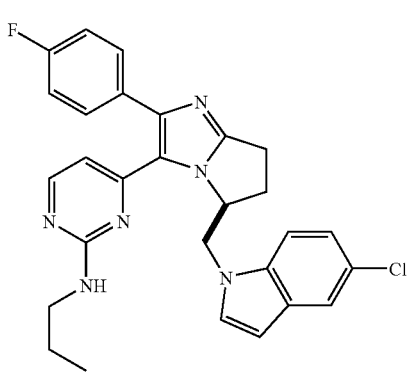
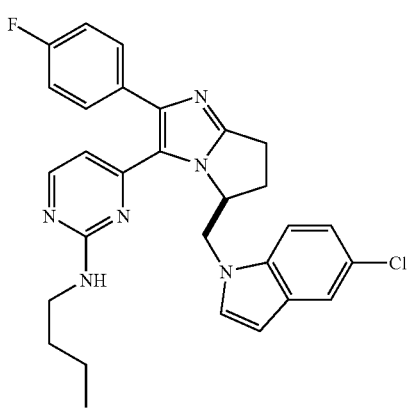
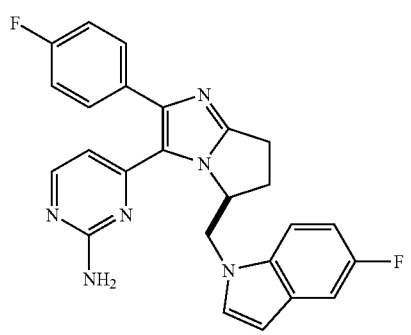

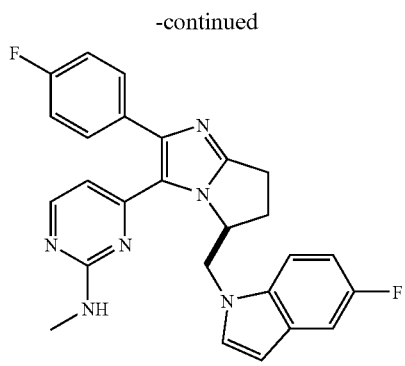
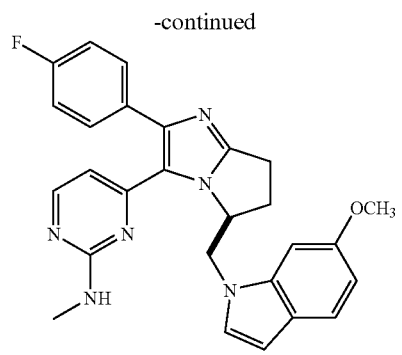
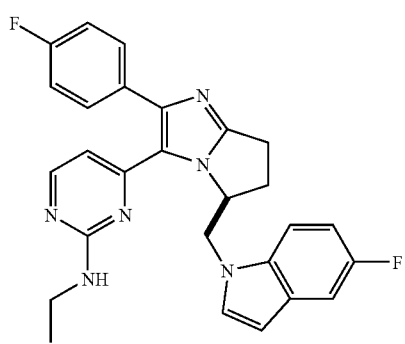
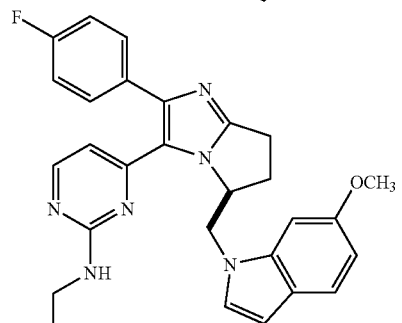
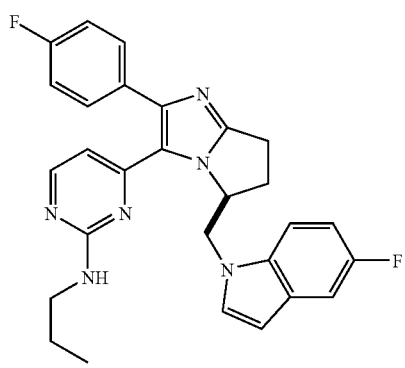
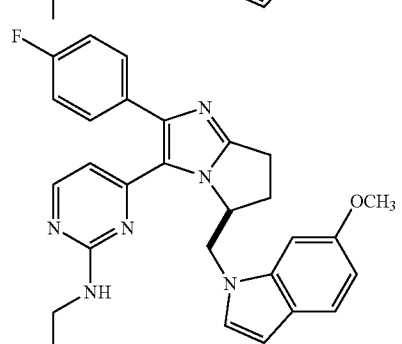
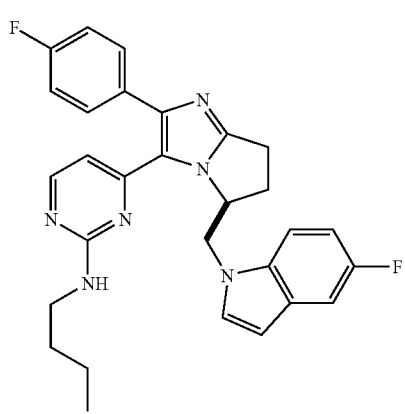
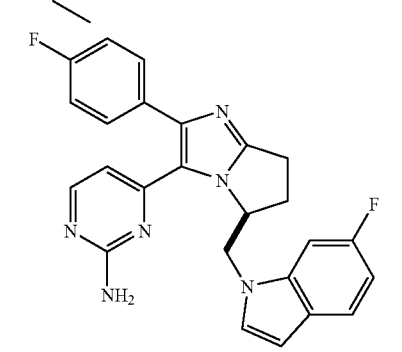
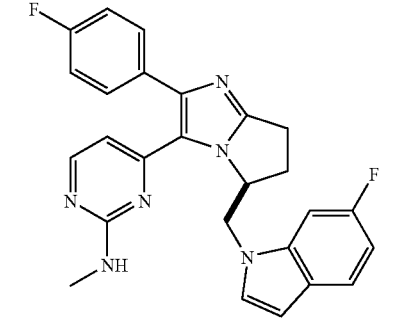

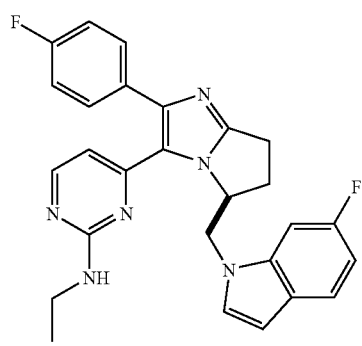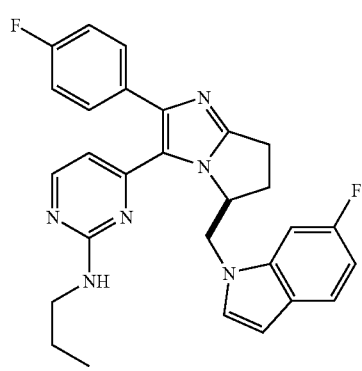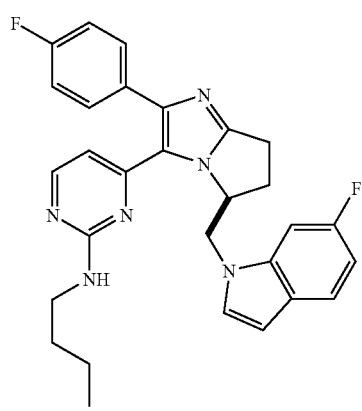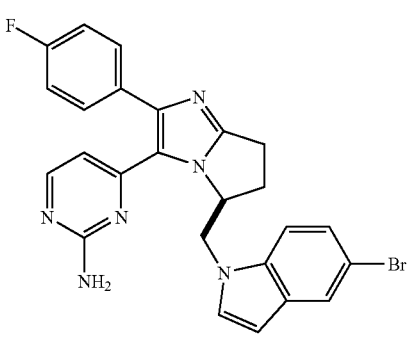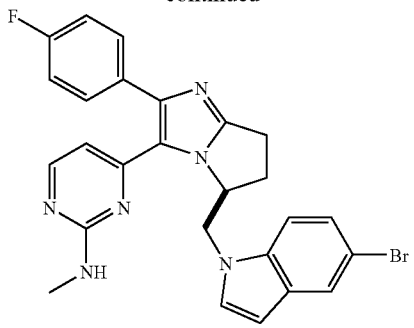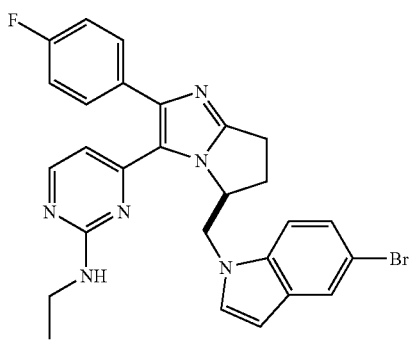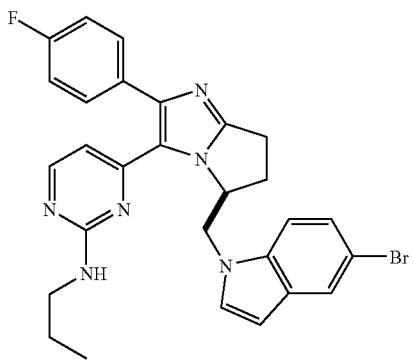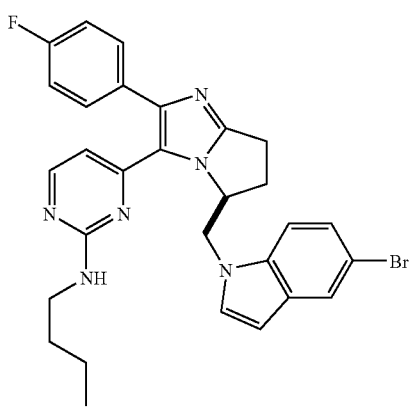

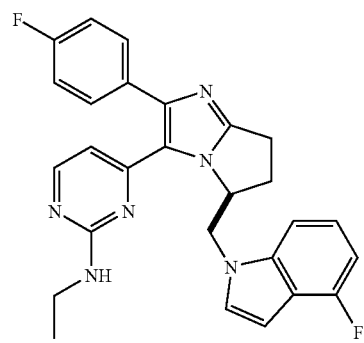
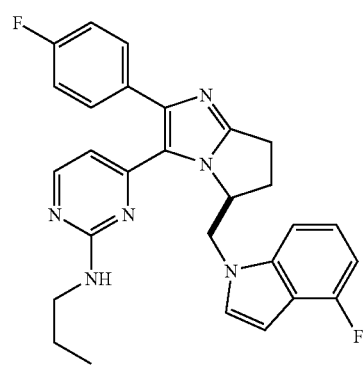
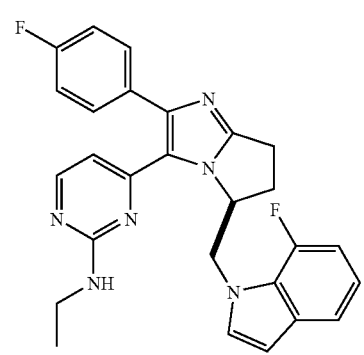
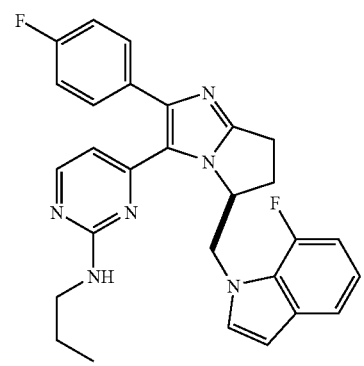
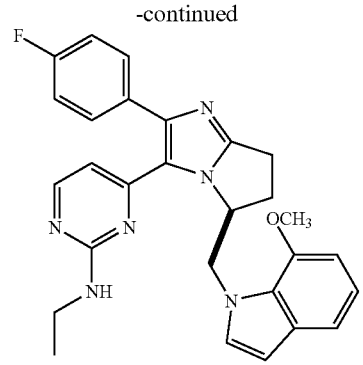
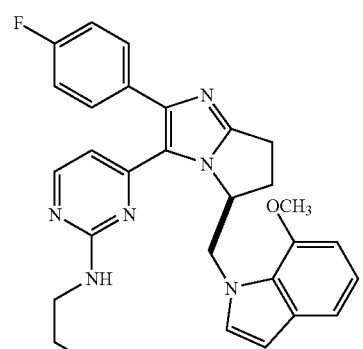
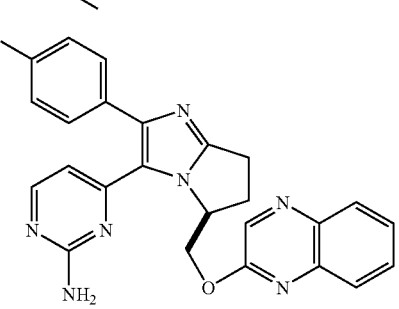
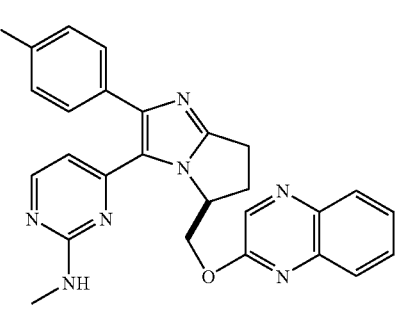
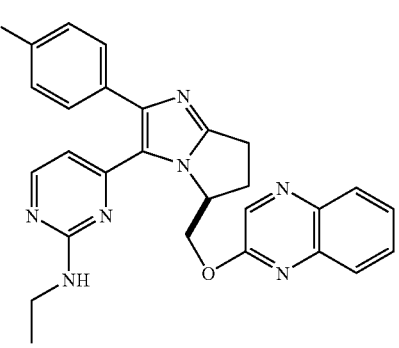

-continued
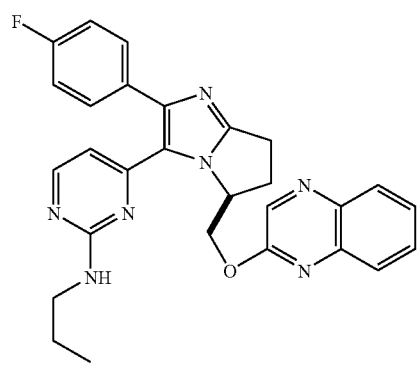
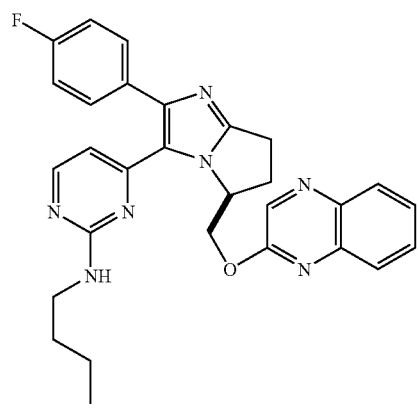
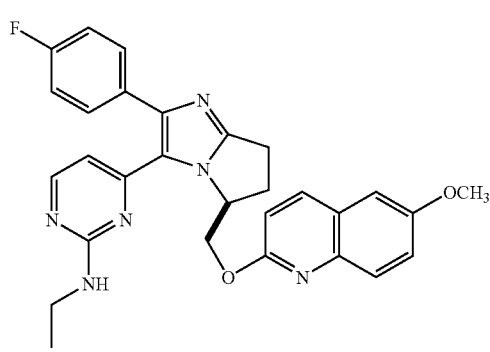
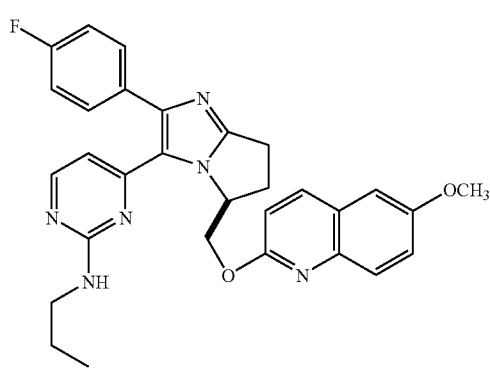
-continued
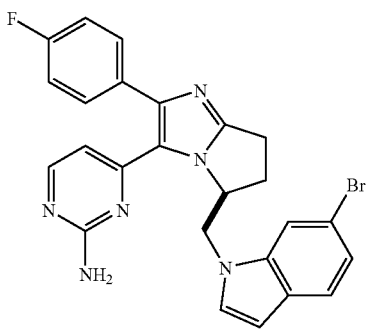
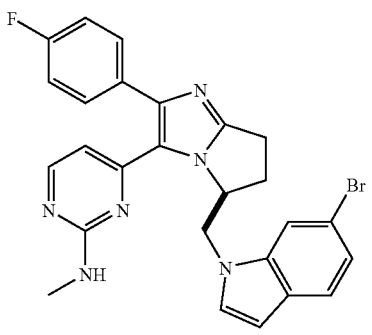
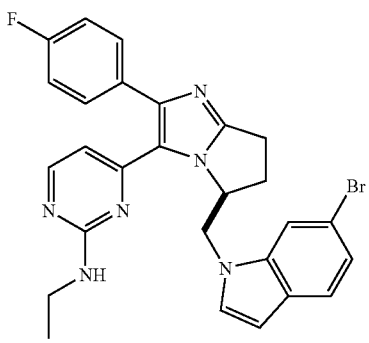
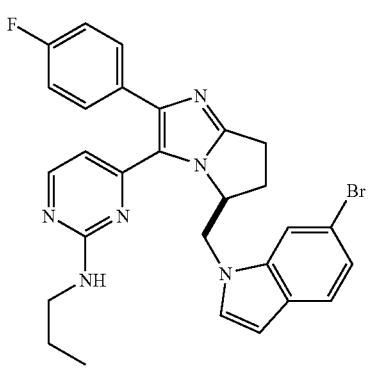

-continued
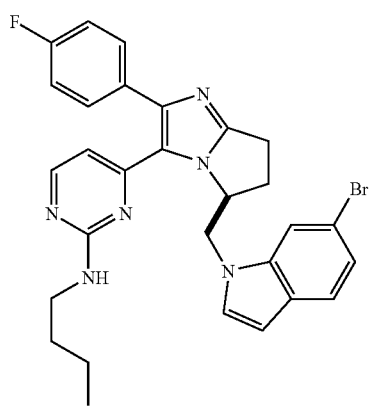
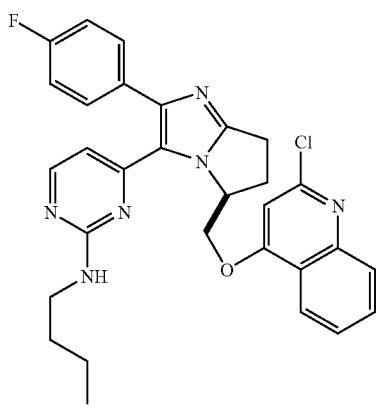
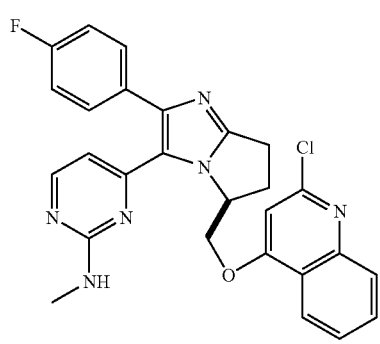
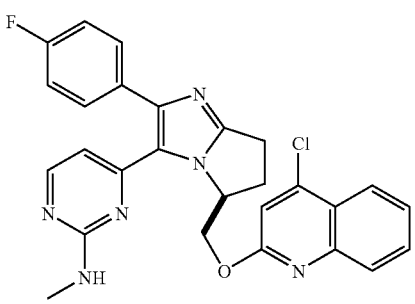
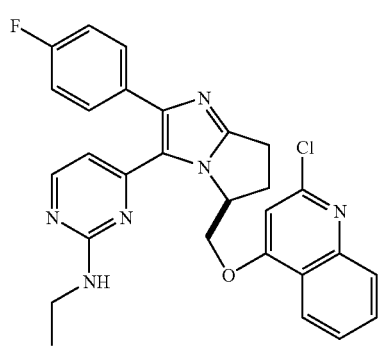
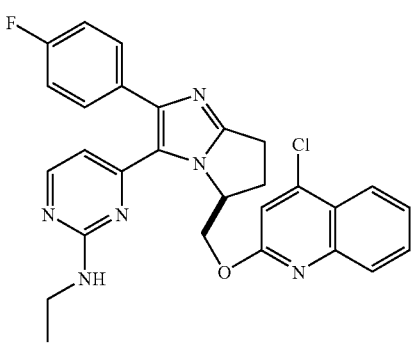
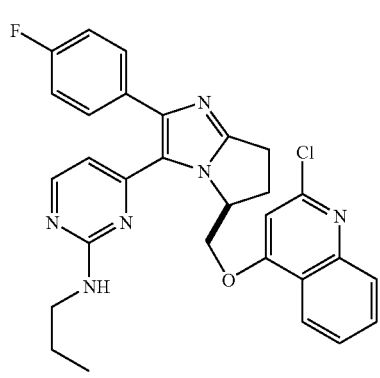
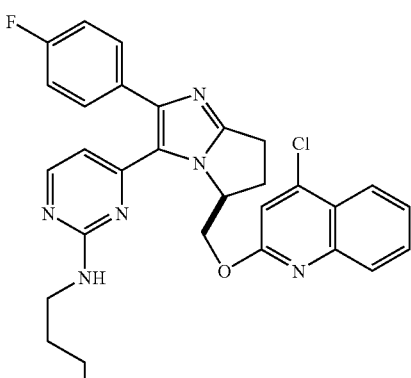

-continued
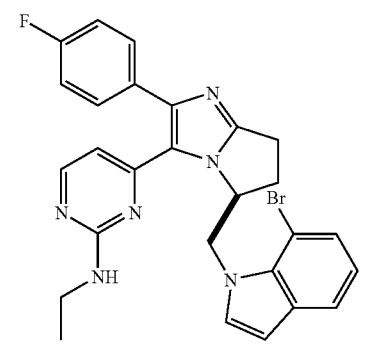
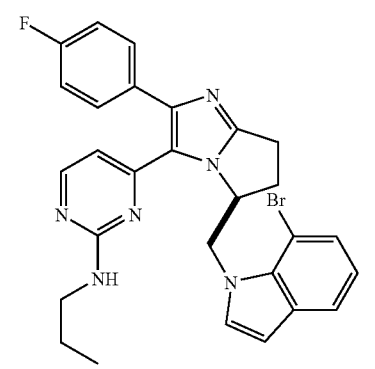
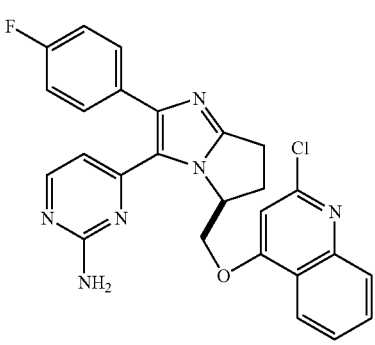
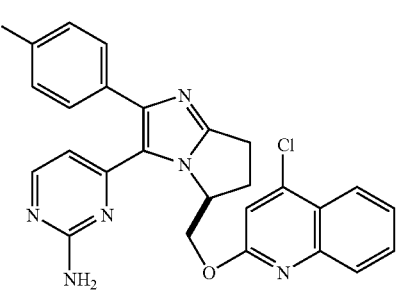
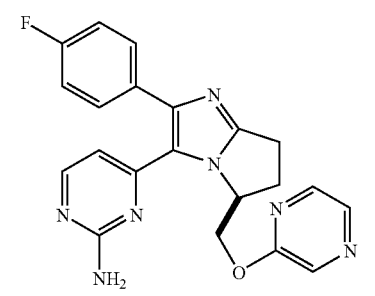
-continued
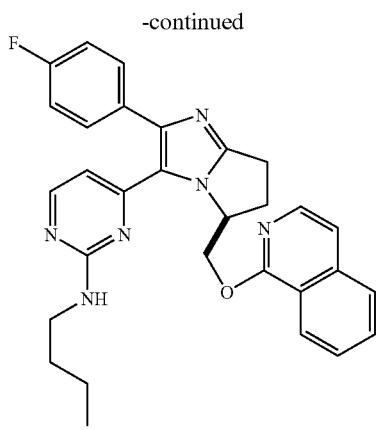
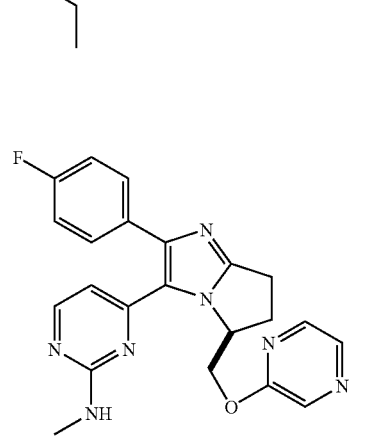
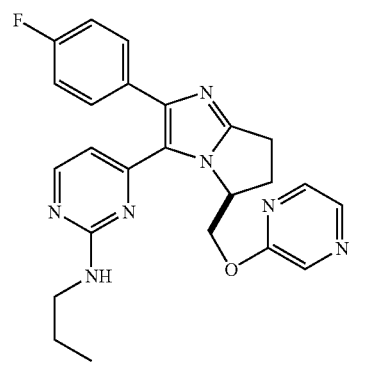
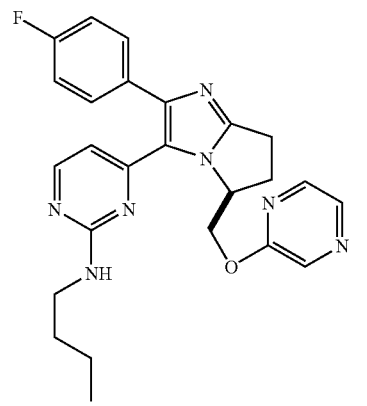

-continued
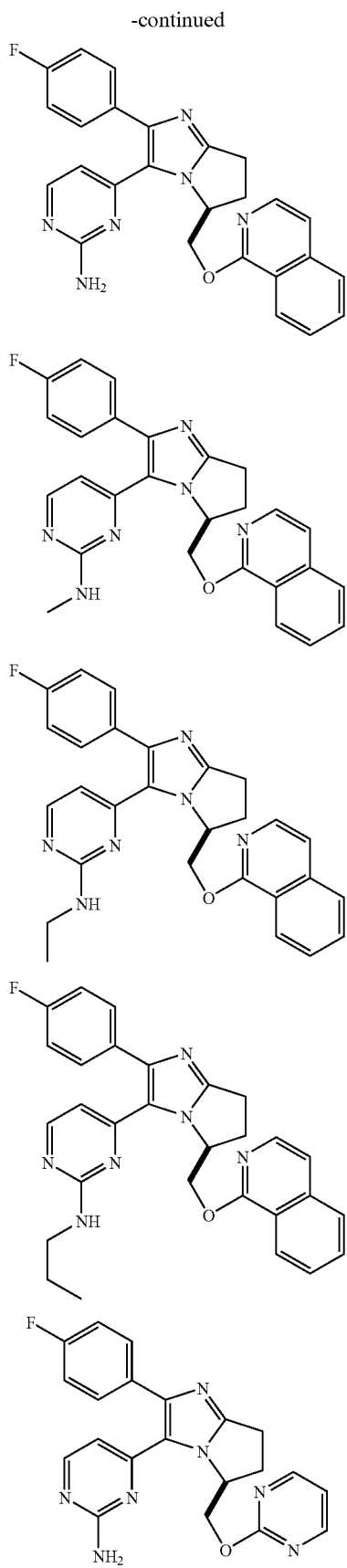
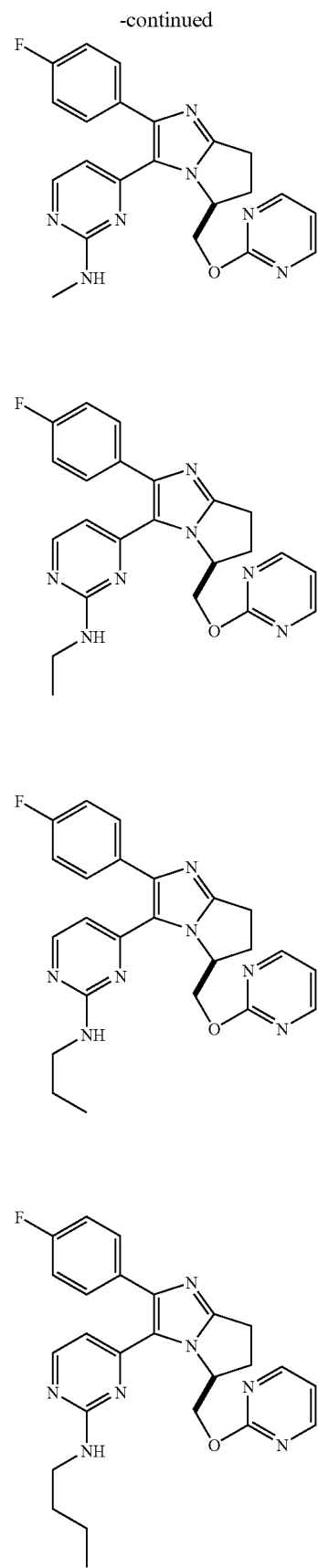

-continued
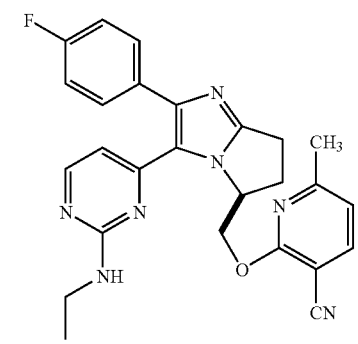
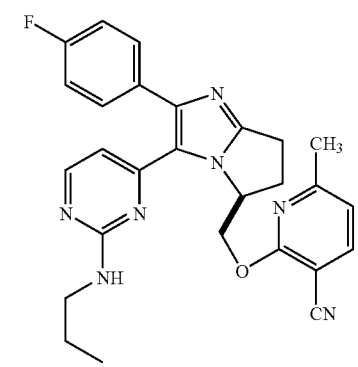
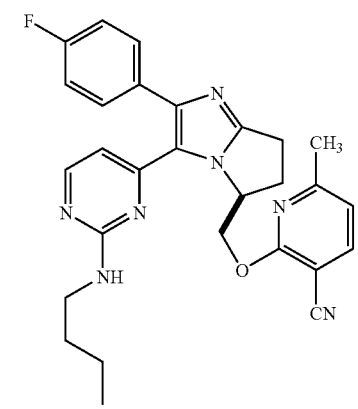
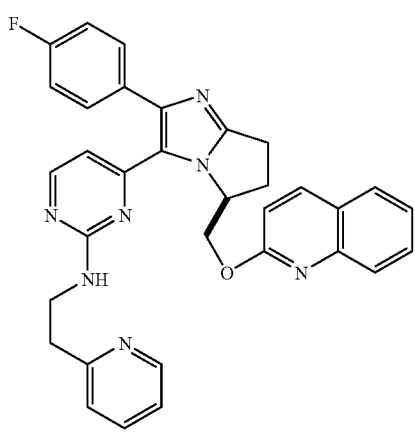
-continued
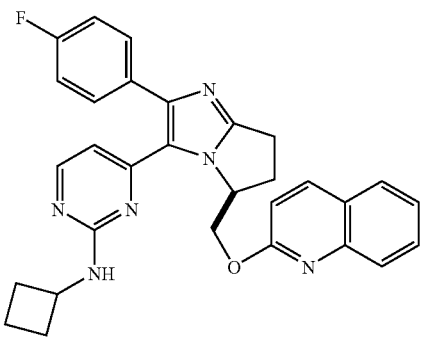
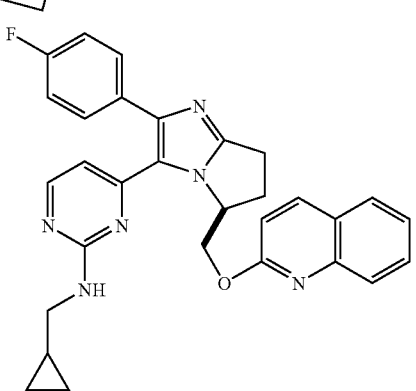
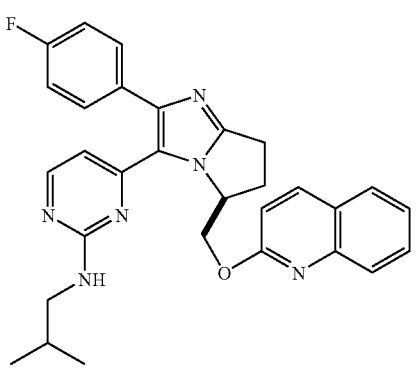
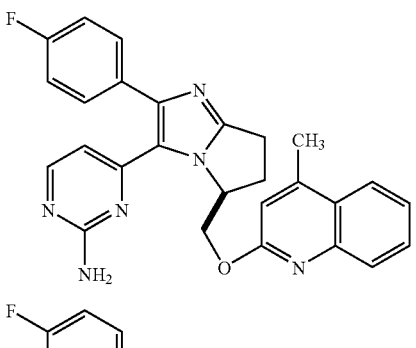
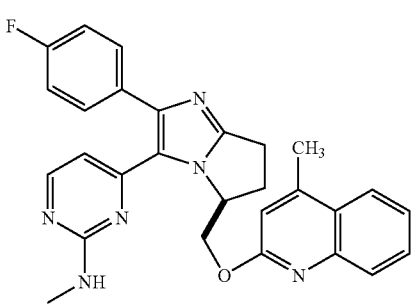

-continued
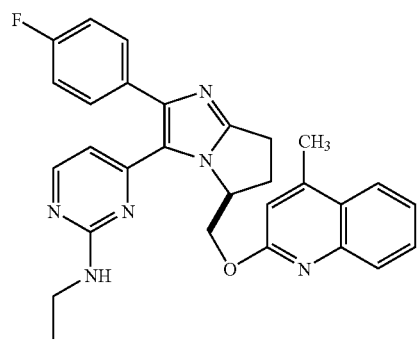
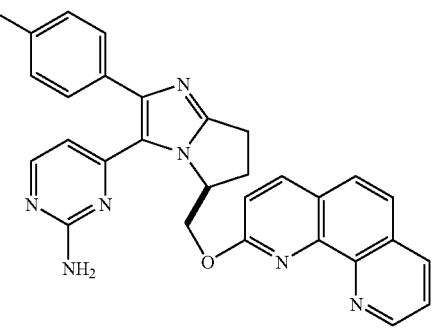
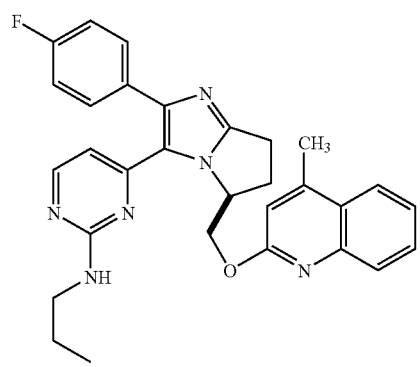
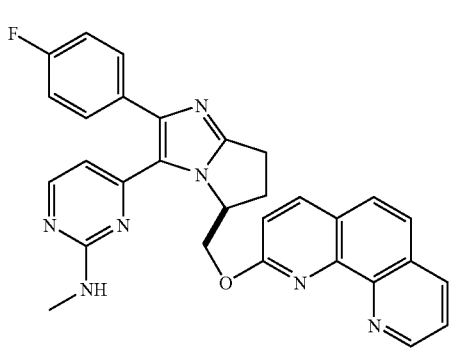
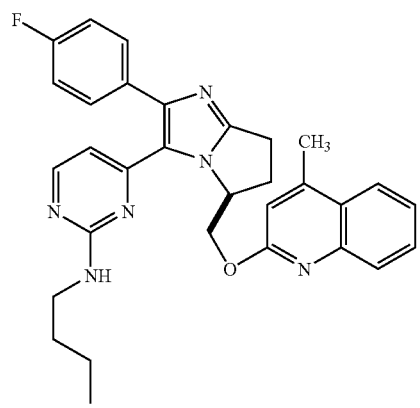
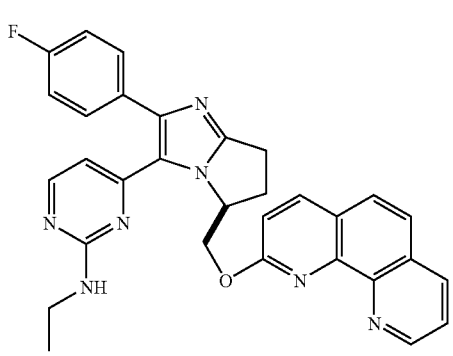
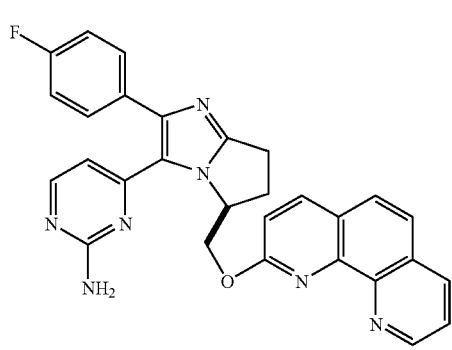
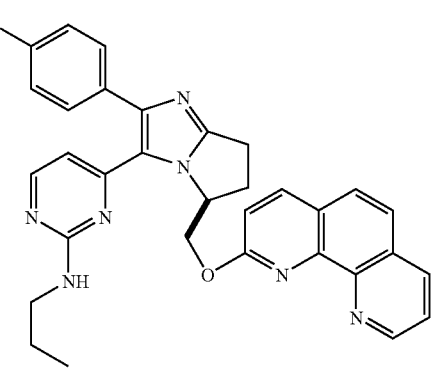

-continued
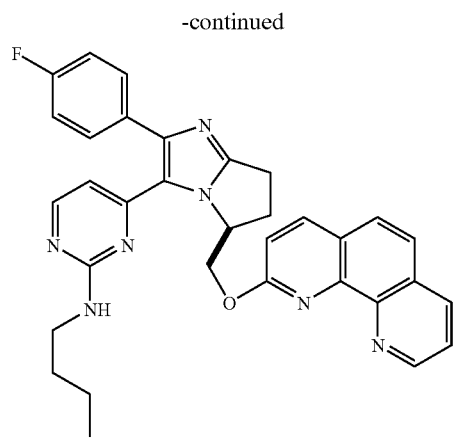
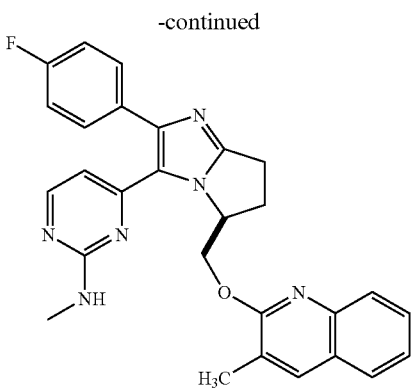
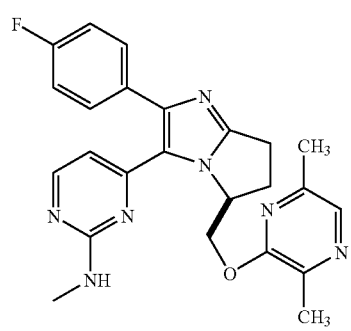
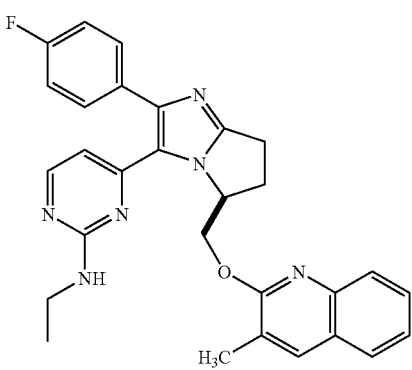
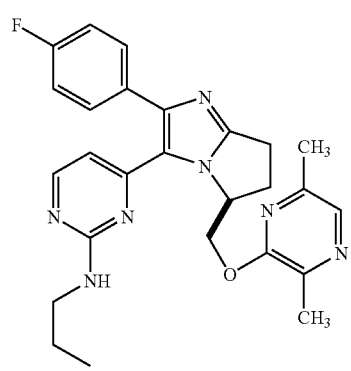
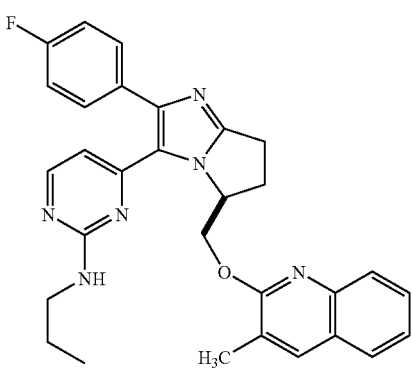
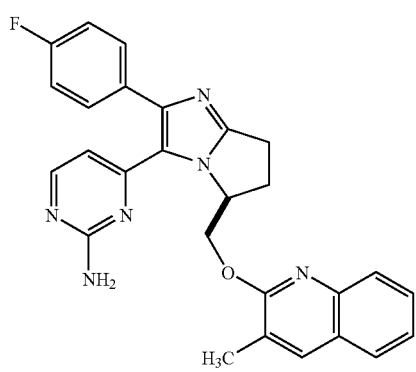
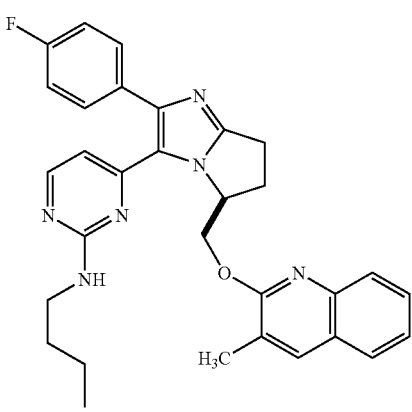

-continued
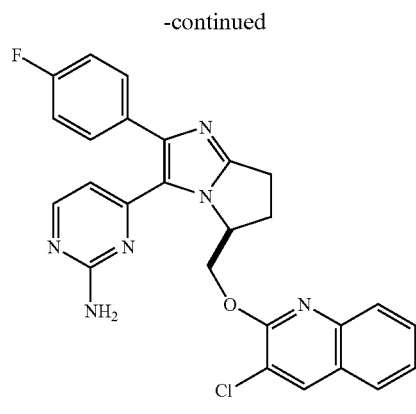
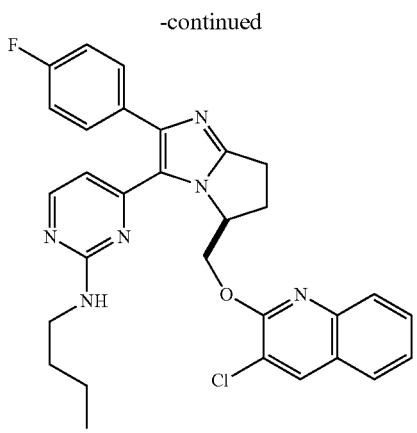
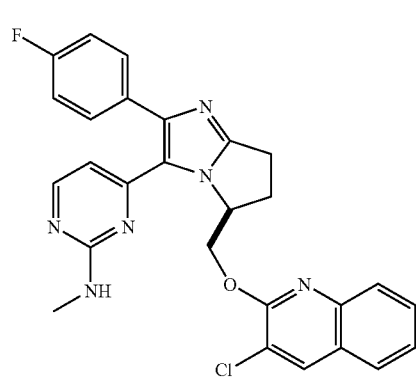
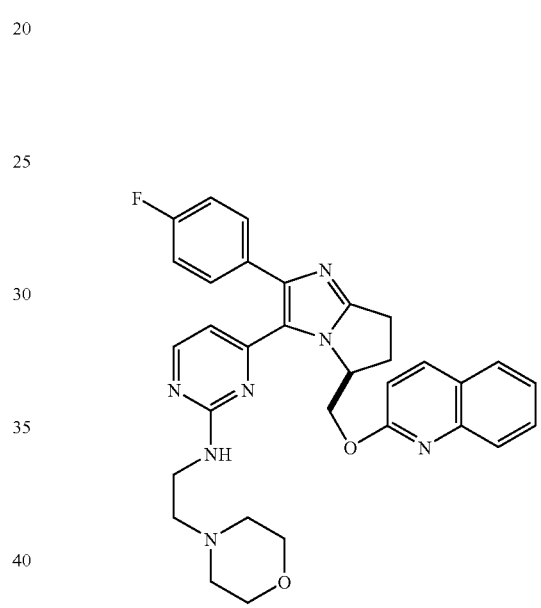
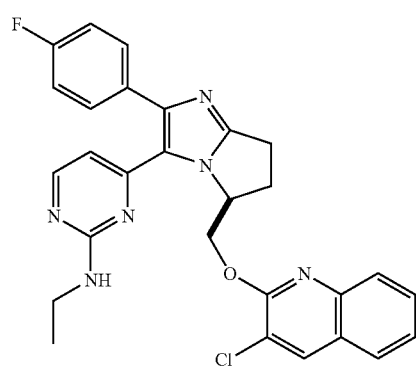
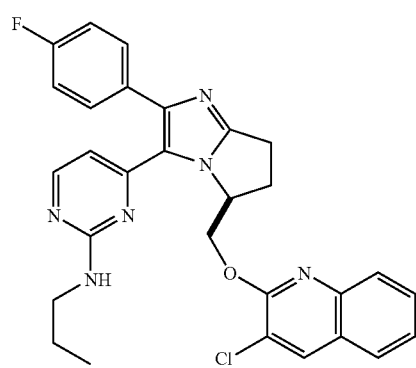
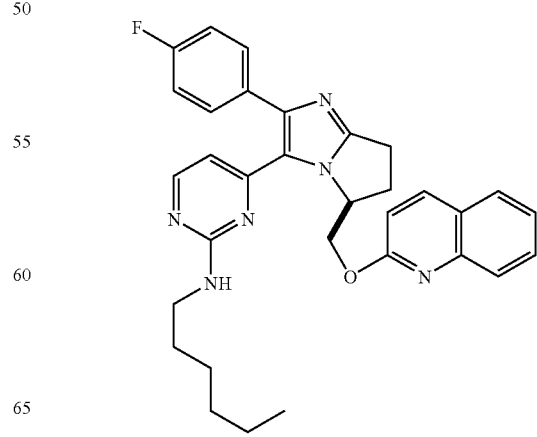

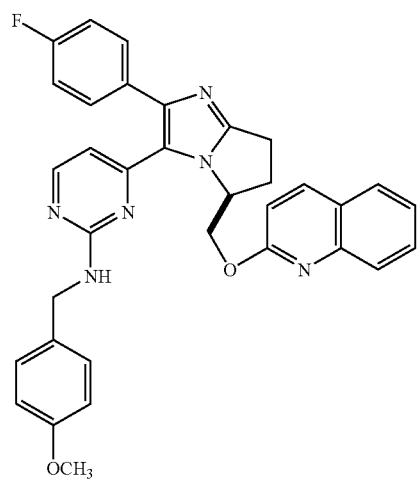
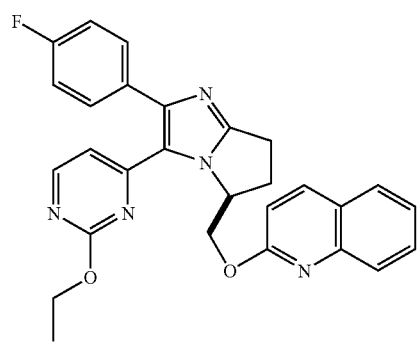
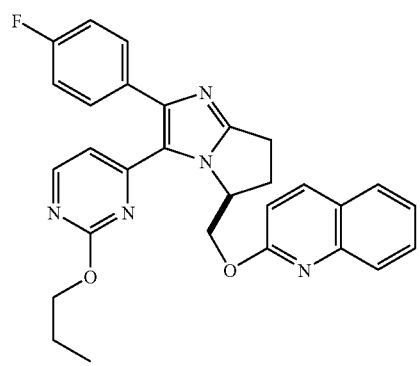
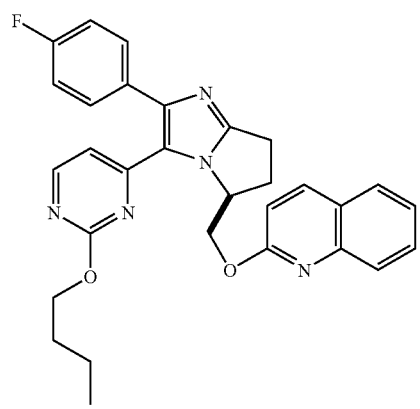
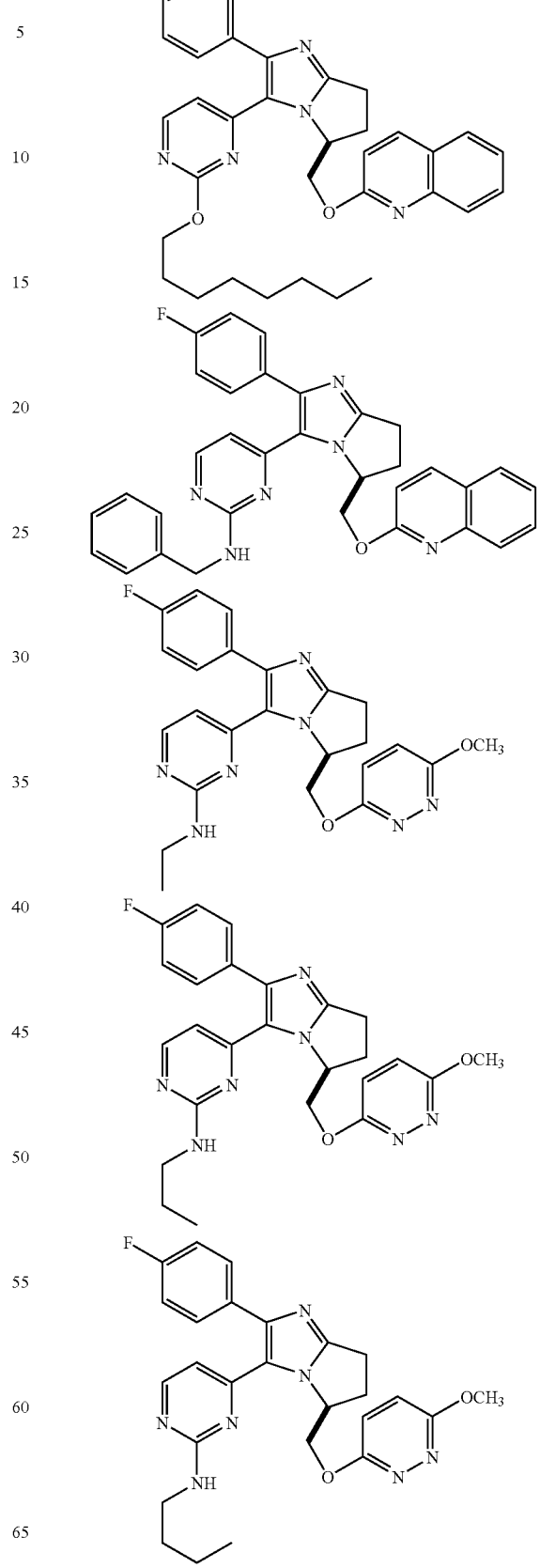

87
-continued
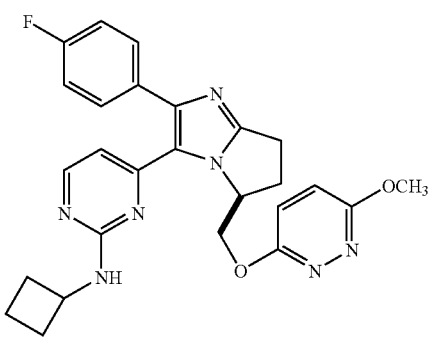
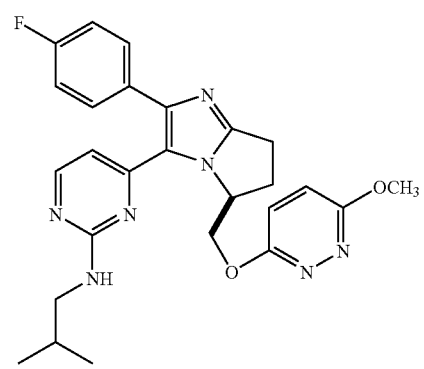
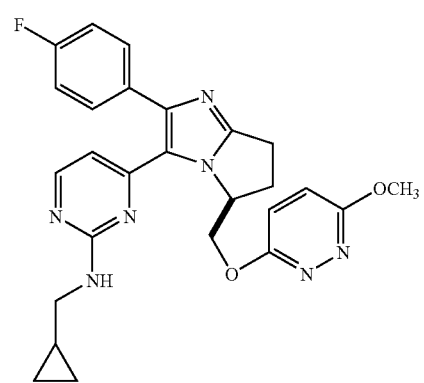
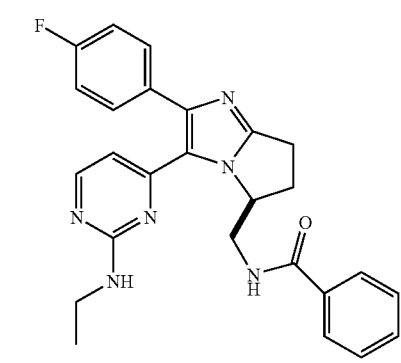
88
-continued
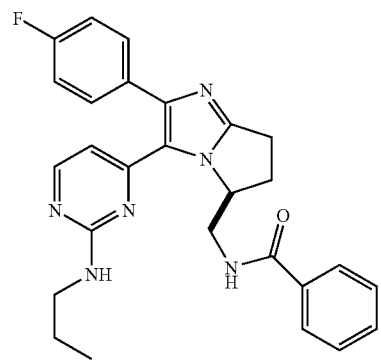
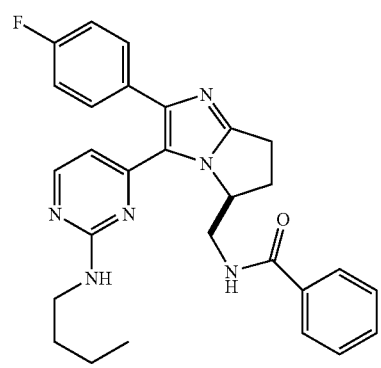
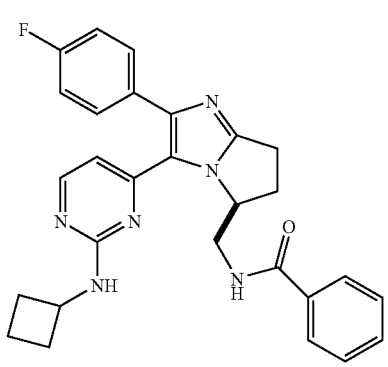
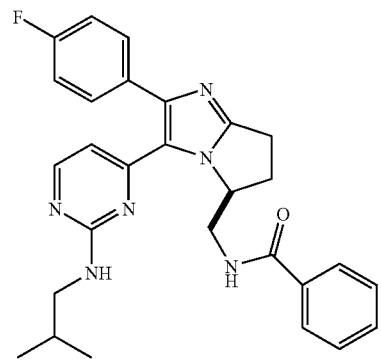

-continued
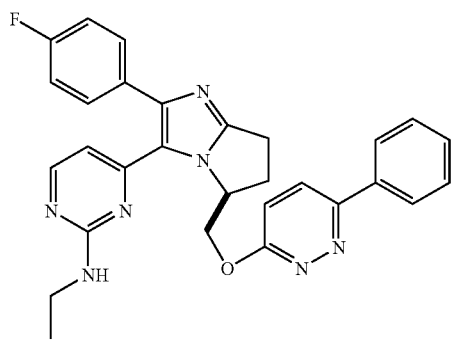
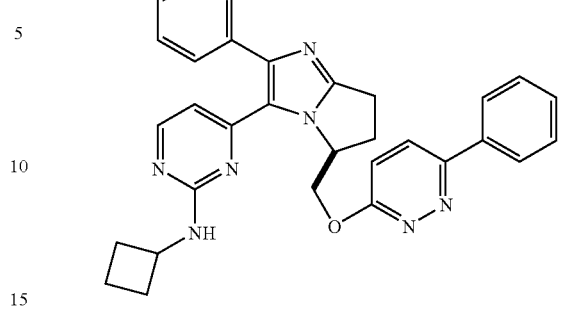
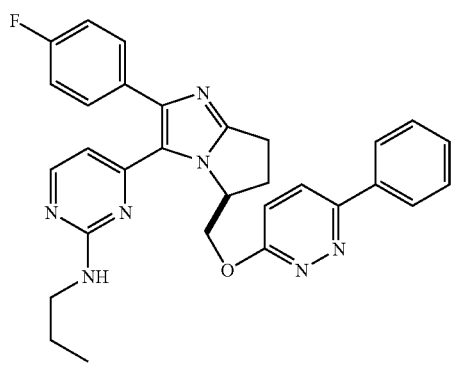
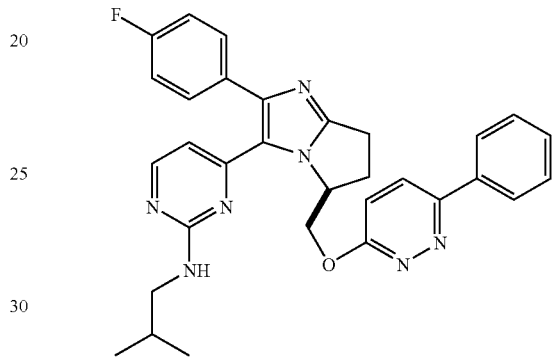
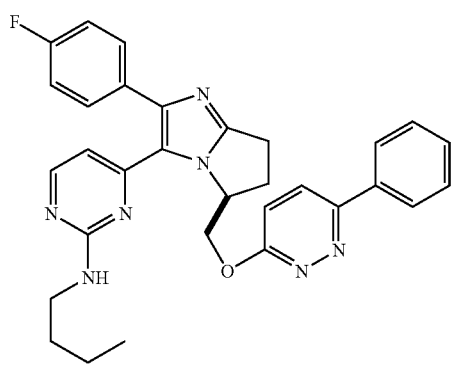
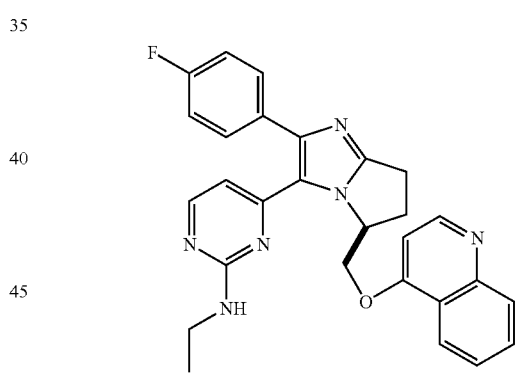
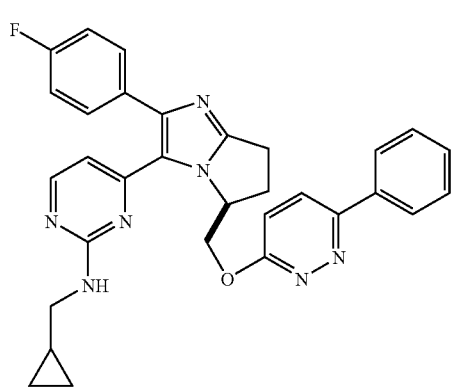
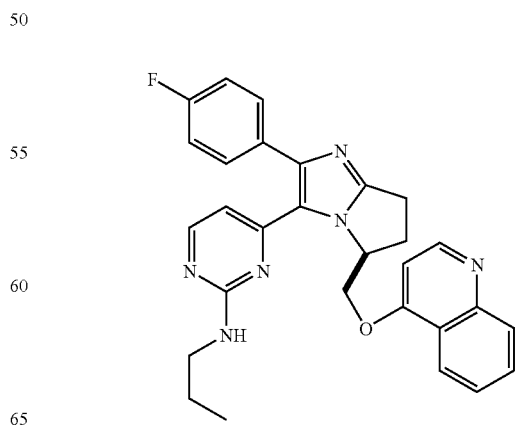

-continued
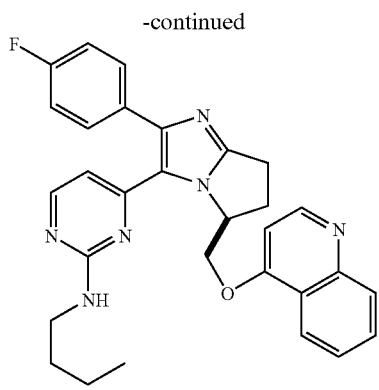
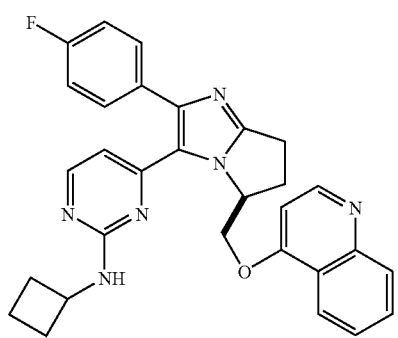
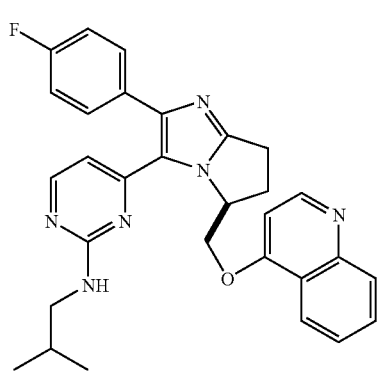
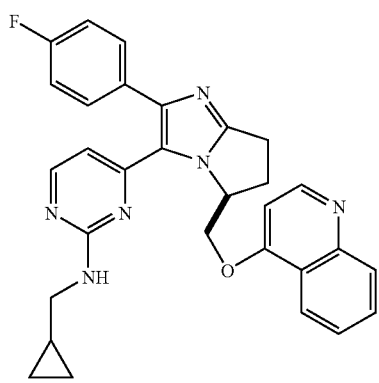
-continued
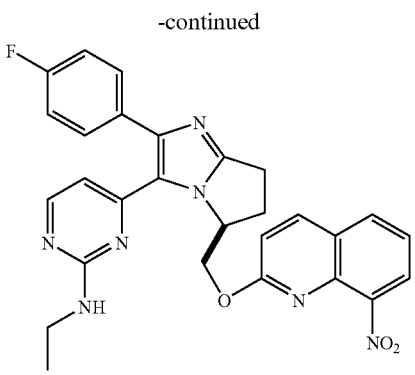
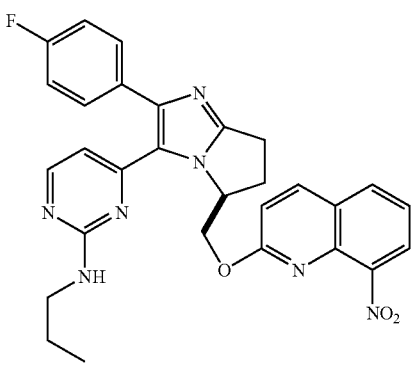
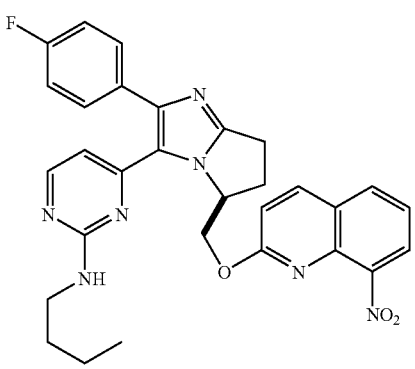
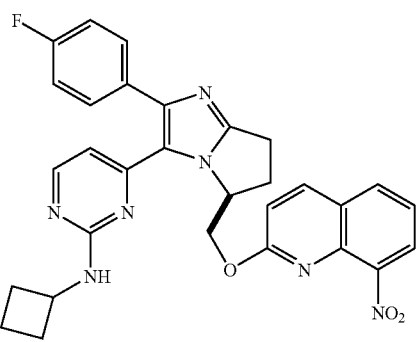

93
-continued
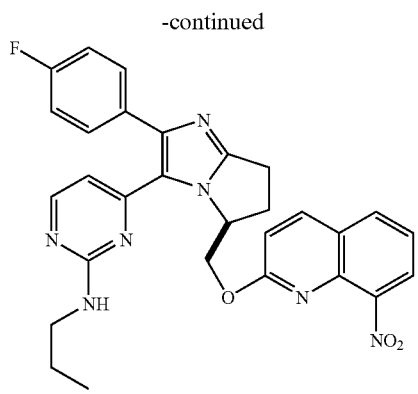
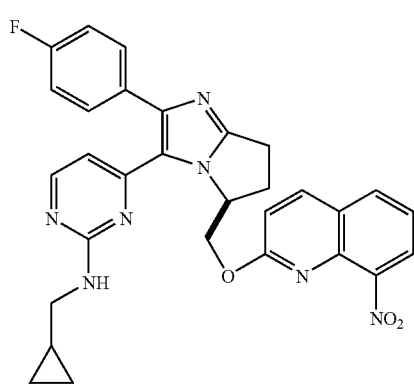
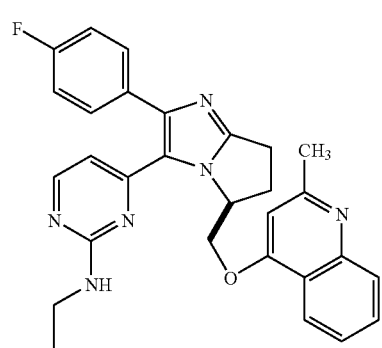
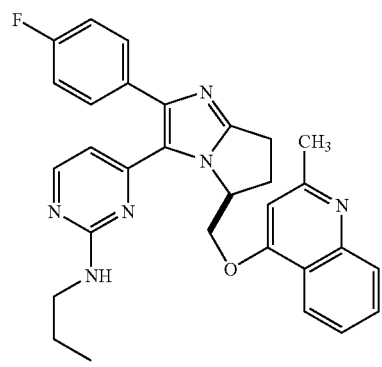
94
-continued
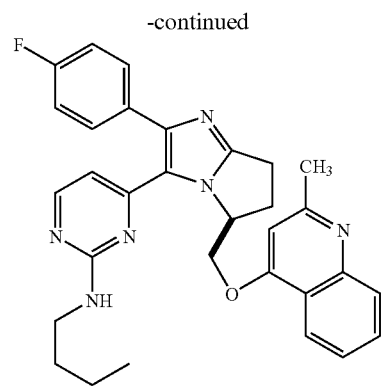
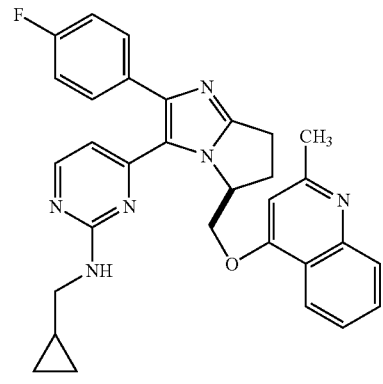
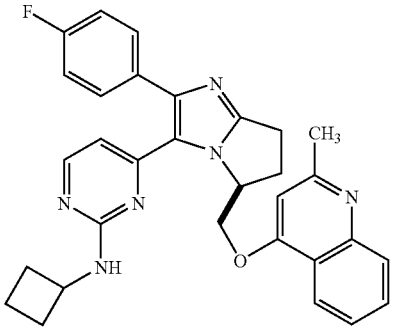
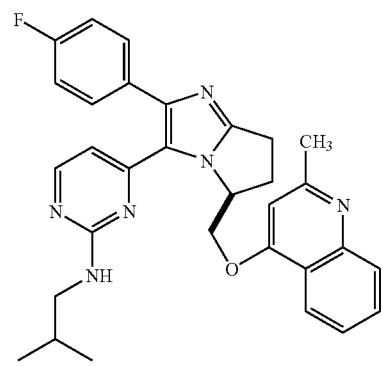

95
-continued
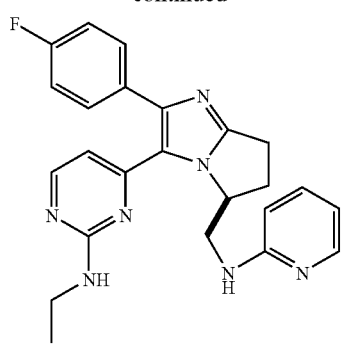
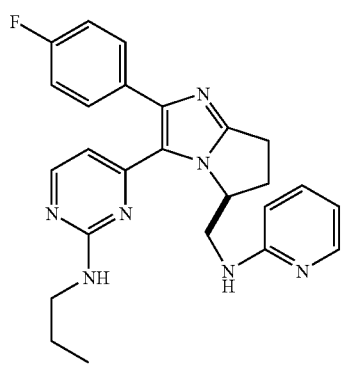
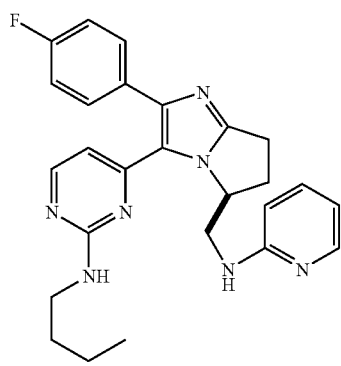
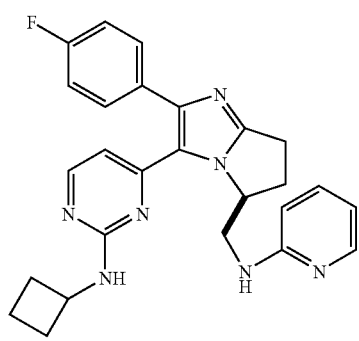
96
-continued
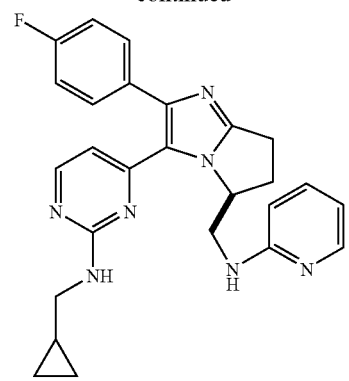
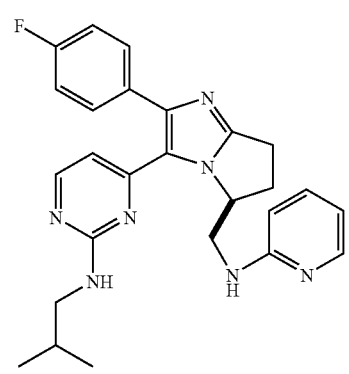
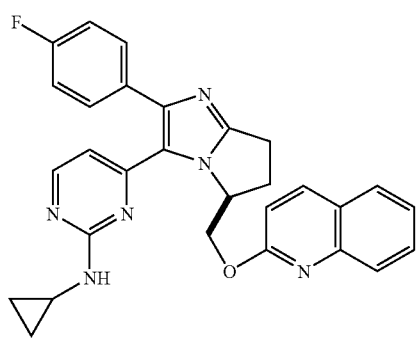
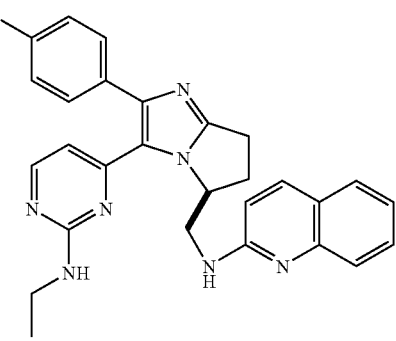

-continued
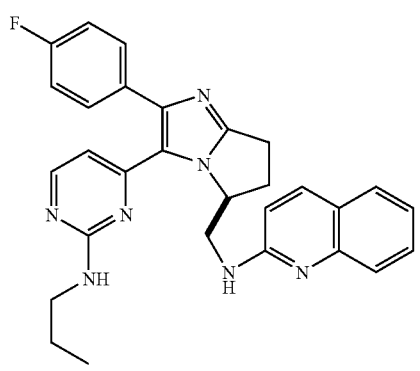
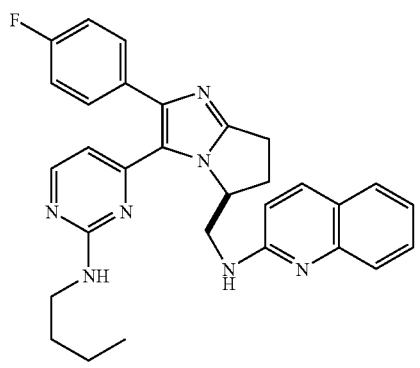
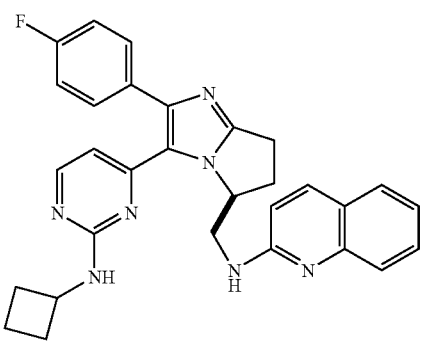
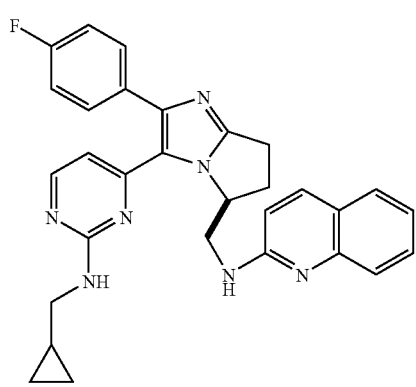
-continued
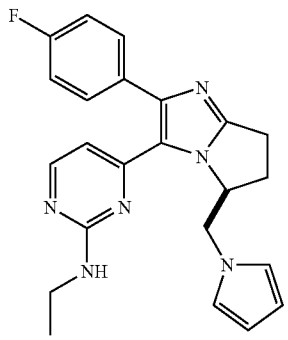
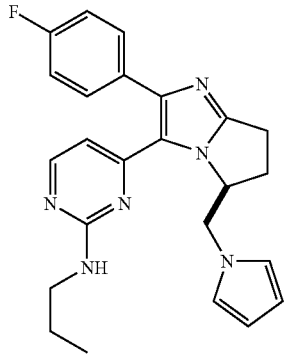
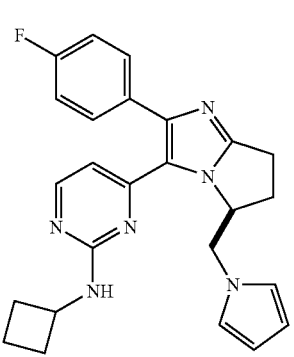
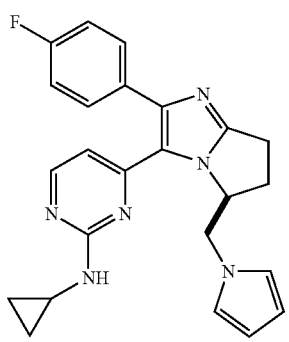

-continued
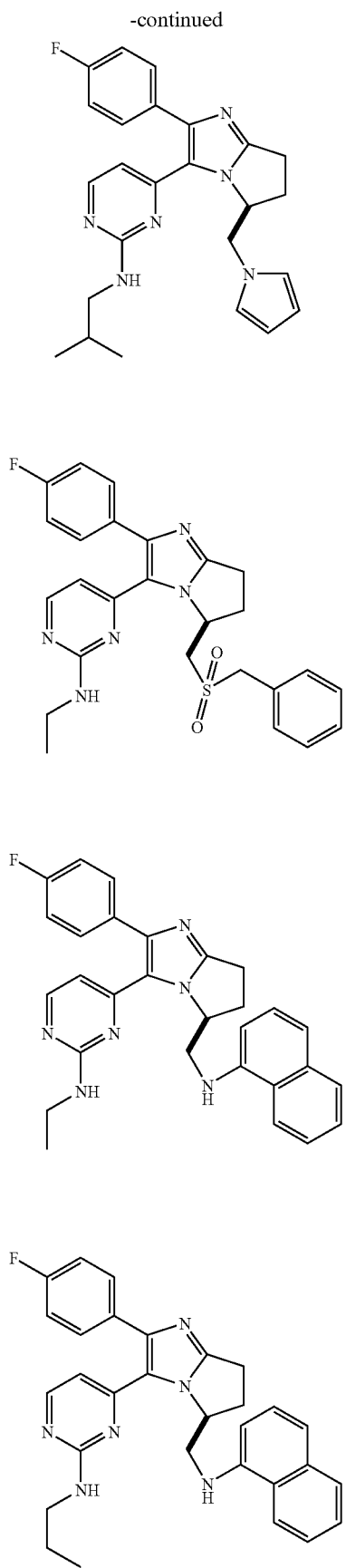
-continued
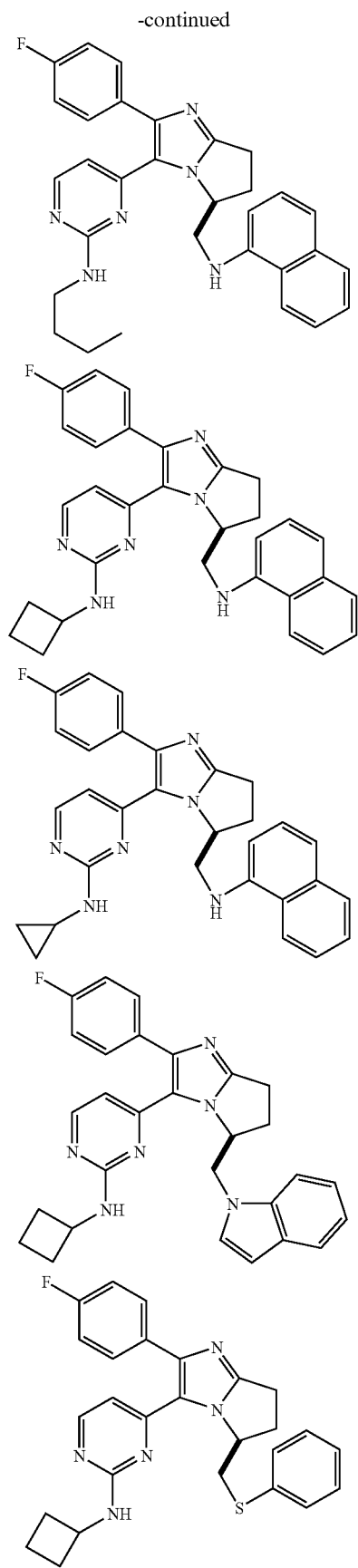

-continued
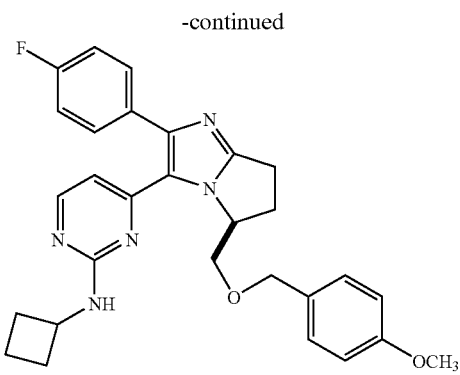
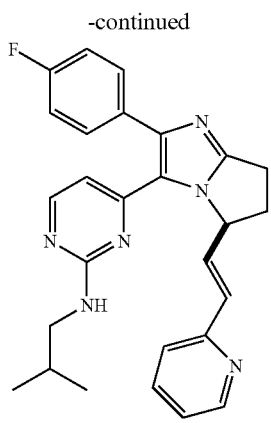
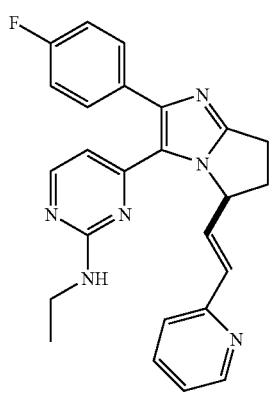
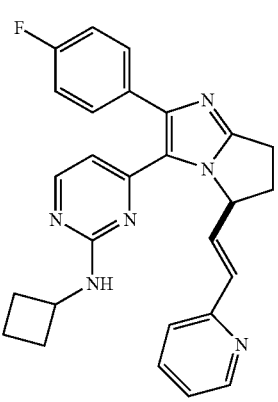
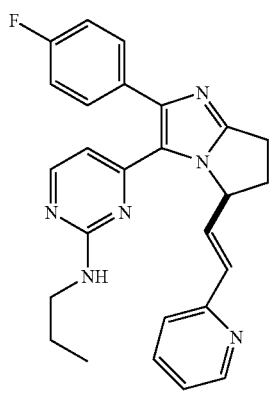
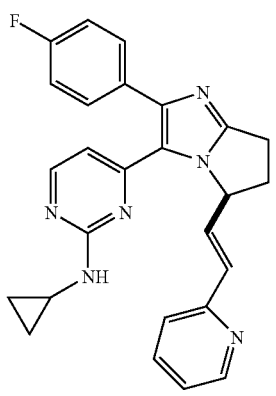
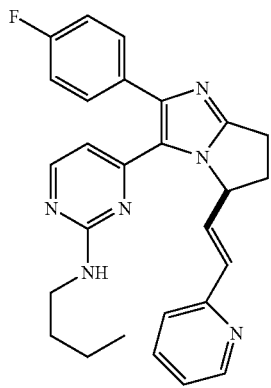
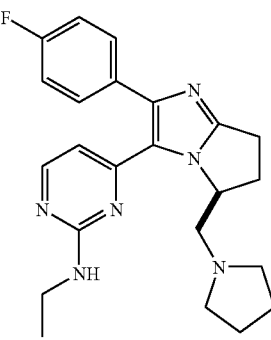

103
-continued
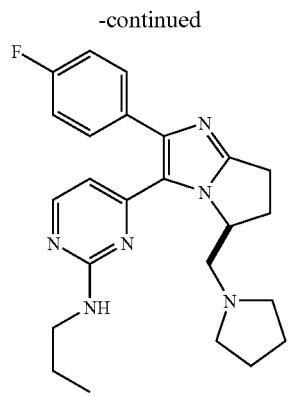
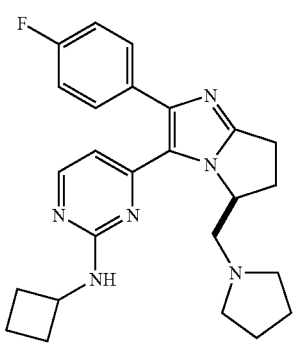
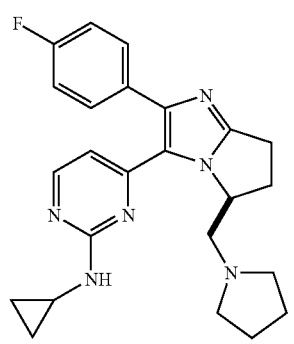
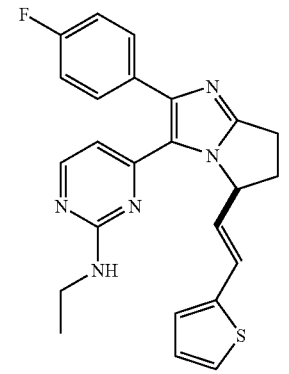
104
-continued
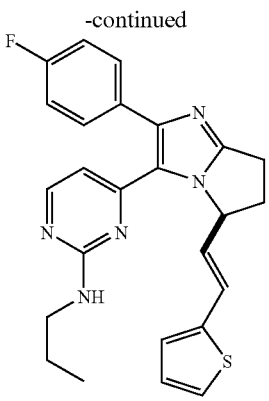
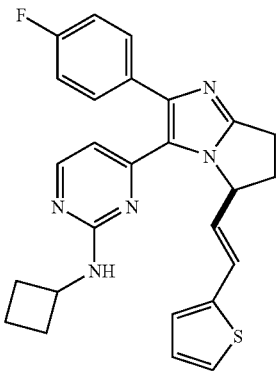
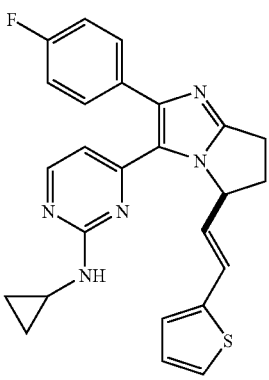
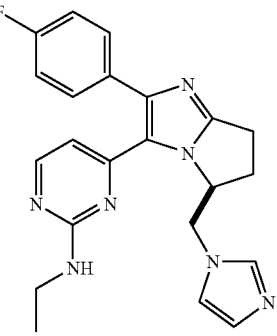

-continued
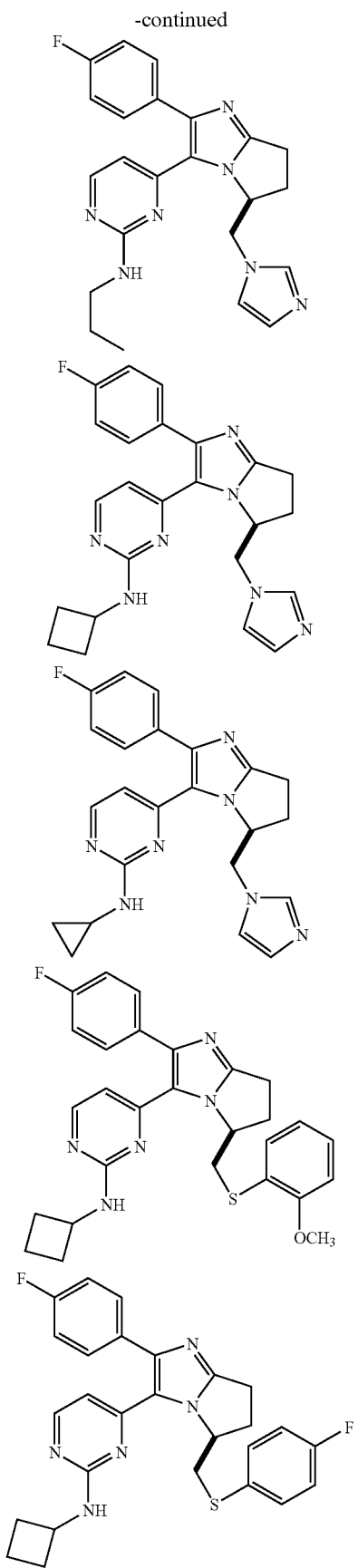
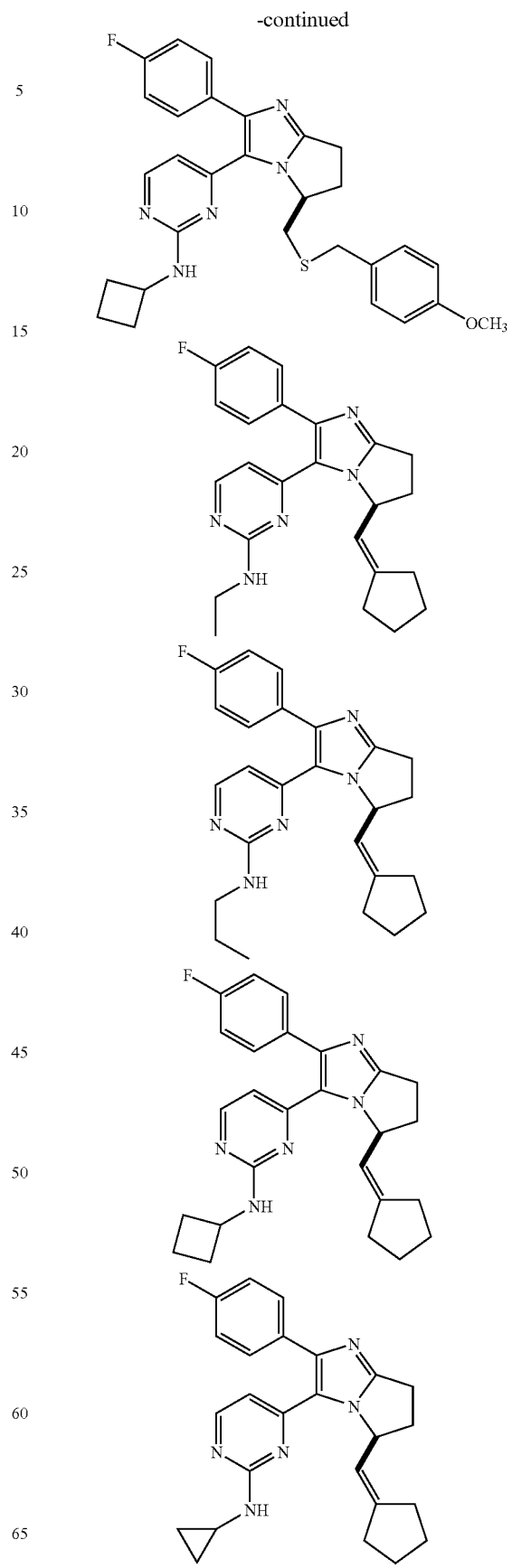

-continued
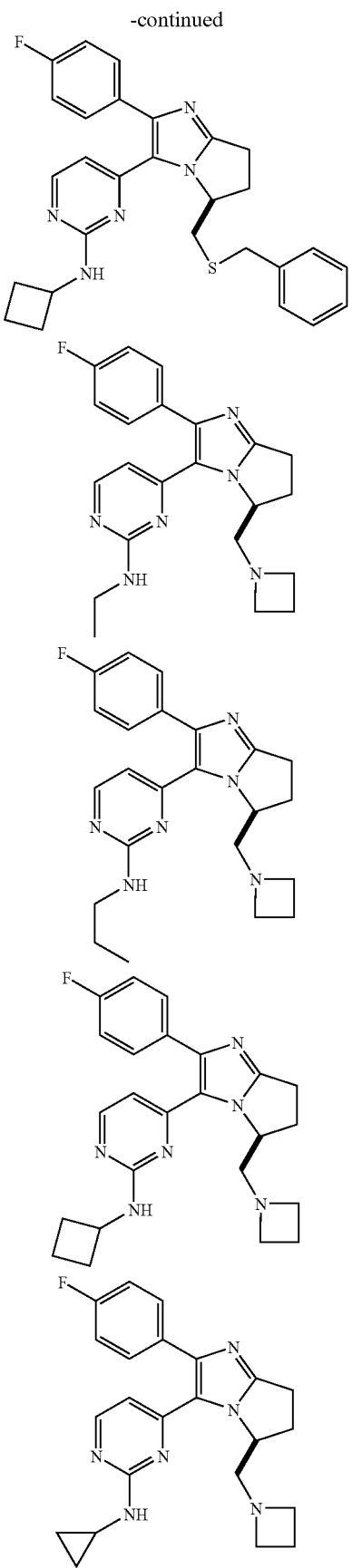
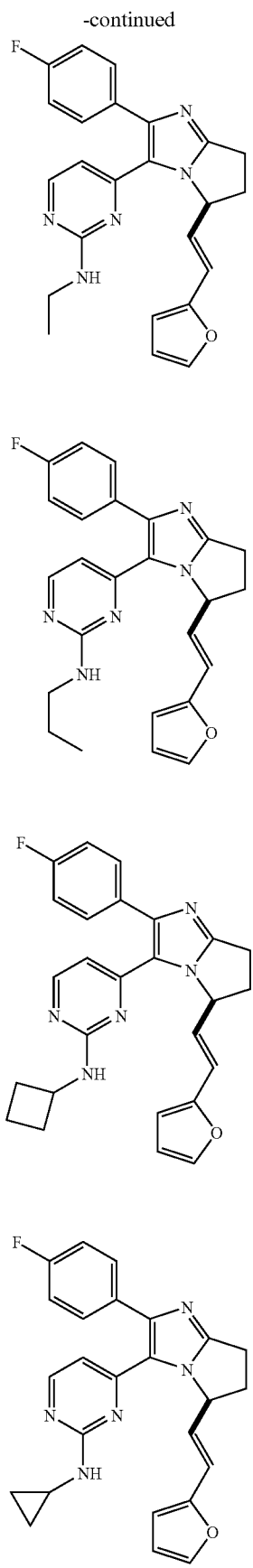

109
-continued
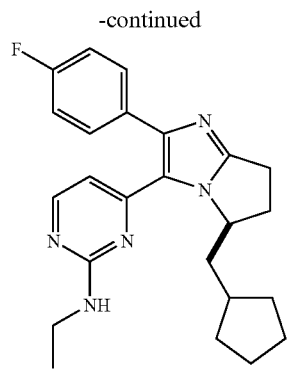
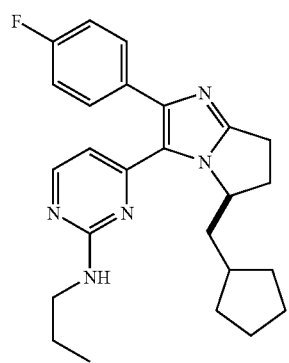
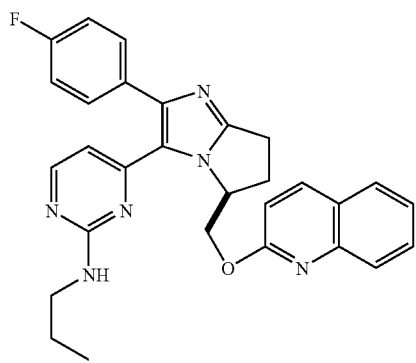
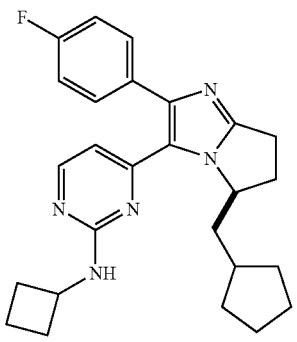
110
-continued
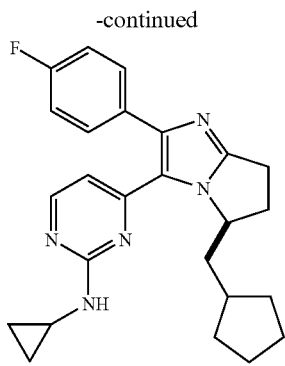
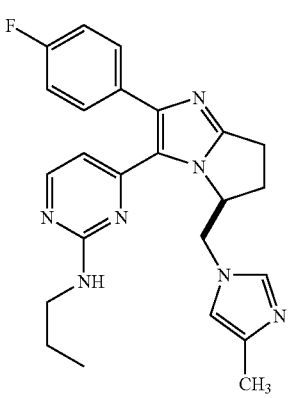
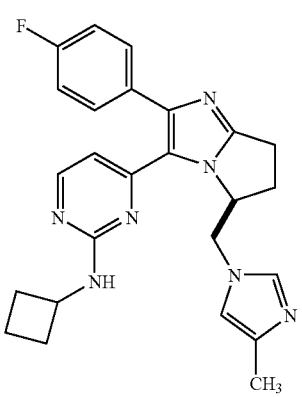
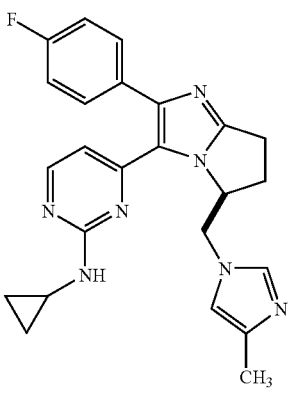

111
-continued
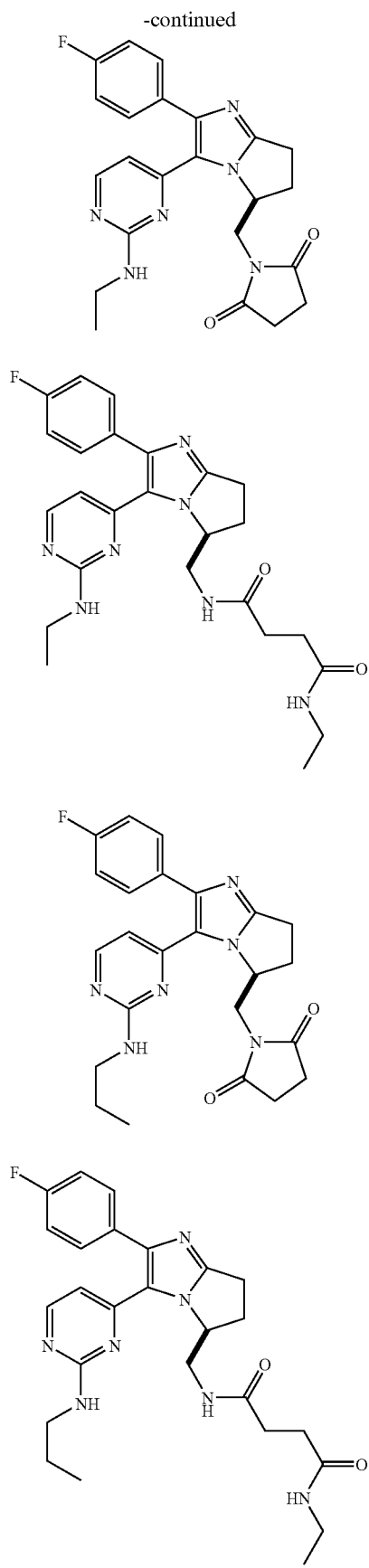
112
-continued
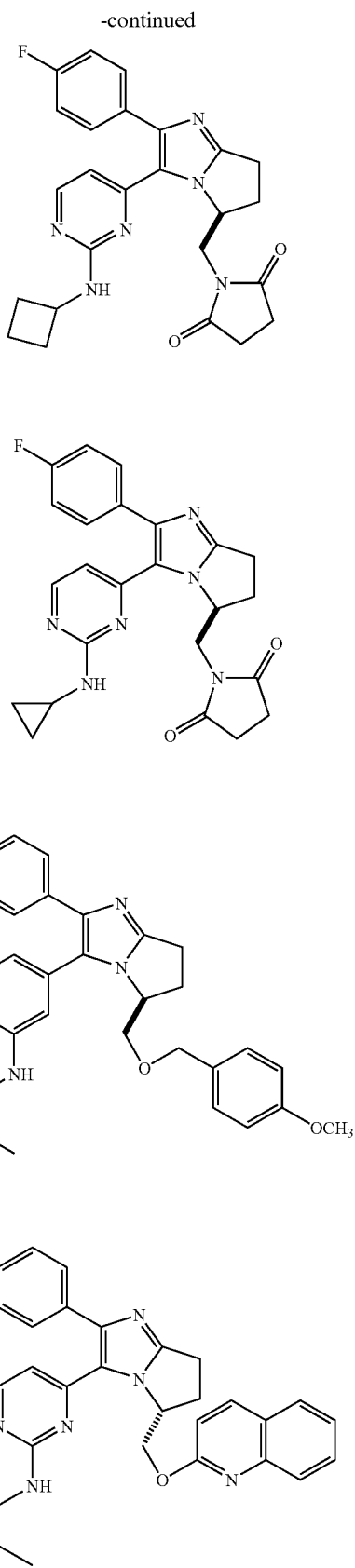

113
-continued
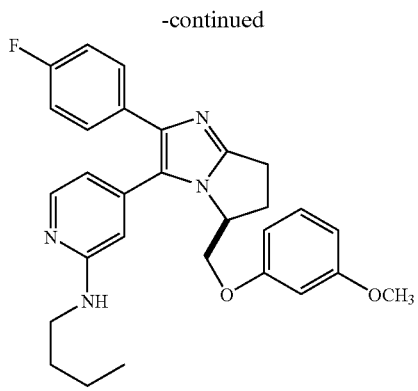
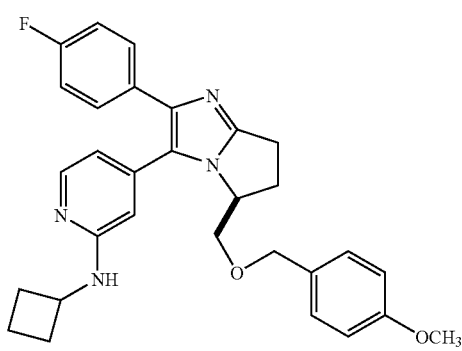
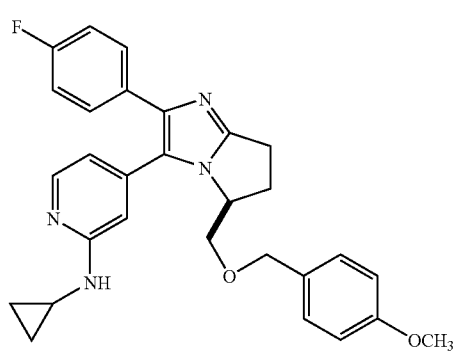
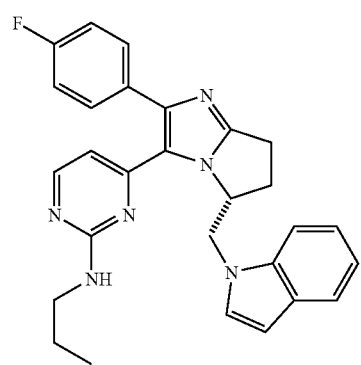
114
-continued
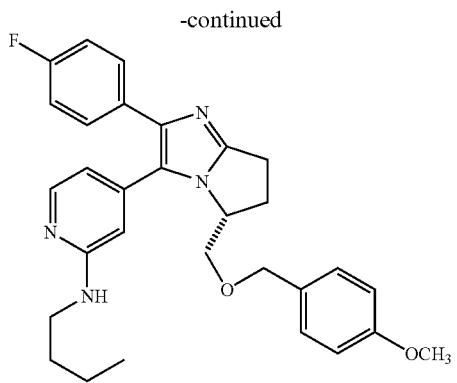
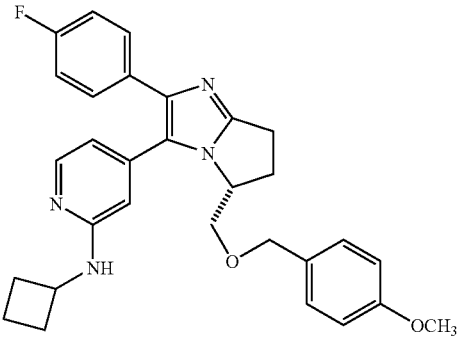
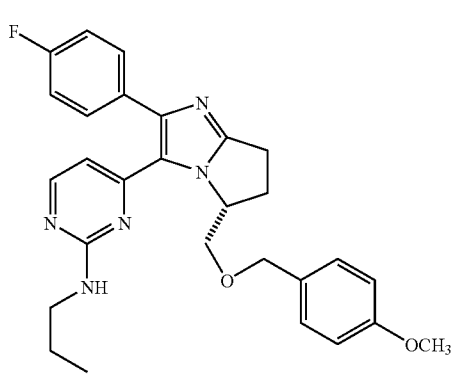

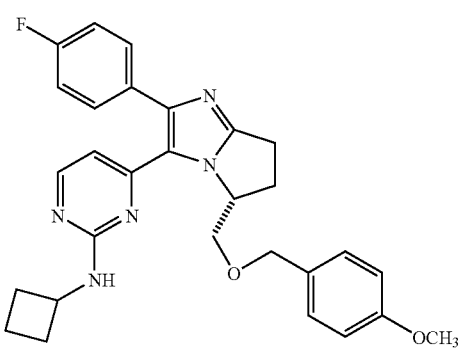

The compounds of the first aspect may be provided as a salt, preferably as a pharmaceutically acceptable salt of compounds of formula I, II or III. Examples of pharmaceutically acceptable salts of these compounds include those derived from organic acids such as acetic acid, malic acid, tartaric acid, citric acid, lactic acid, oxalic acid, succinic acid, fumaric acid, maleic acid, benzoic acid, salicylic acid, phenylacetic acid, mandelic acid, methanesulphonic acid, benzenesulphonic acid and p-toluenesulphonic acid, mineral acids such as hydrochloric and sulphuric acid and the like, giving methanesulphonate, benzenesulphonate, p-toluenesulphonate, hydrochloride and sulphate, and the like, respectively or those derived from bases such as organic and inorganic bases. Examples of suitable inorganic bases for the formation of salts of compounds for this invention include the hydroxides, carbonates, and bicarbonates of ammonia, lithium, sodium, calcium, potassium, aluminium, iron, magnesium, zinc and the like. Salts can also be formed with suitable organic bases. Such bases suitable for the formation of pharmaceutically acceptable base addition salts with compounds of the present invention include organic bases which are nontoxic and strong enough to form salts. Such organic bases are already well known in the art and may include amino acids such as arginine and lysine, mono-, di-, or trihydroxyalkylamines such as mono-, di-, and triethanolamine, choline, mono-, di-, and trialkylamines, such as methylamine, dimethylamine, and trimethylamine, guanidine; N-methylglucosamine; N-methylpiperazine; morpholine; ethylenediamine; N-benzylphenethylamine; tris(hydroxymethyl) aminomethane; and the like.

Salts may be prepared in a conventional manner using methods well known in the art. Acid addition salts of said basic compounds may be prepared by dissolving the free base compounds according to the first or second aspects of the invention in aqueous or aqueous alcohol solution or other suitable solvents containing the required acid. Where a compound of the invention contains an acidic function, a base salt of said compound may be prepared by reacting said compound with a suitable base. The acid or base salt may separate directly or can be obtained by concentrating the solution e.g. by evaporation. The compounds of this invention may also exist in solvated or hydrated forms.

The invention also extends to a prodrug of the aforementioned compounds such as an ester or amide thereof. A prodrug is any compound that may be converted under physiological conditions or by solvolysis to any of the compounds of the invention or to a pharmaceutically acceptable salt of the compounds of the invention. A prodrug may be inactive when administered to a subject but is converted in vivo to an active compound of the invention.

The compounds of the invention may contain one or more asymmetric carbon atoms and may exist in racemic and optically active forms. Furthermore, for compounds of the invention where X is CR$^{16}$, the compounds may exist in trans or cis form. The first aspect of the invention covers all of these compounds.

In the second aspect of the invention, there is provided a process for the manufacture of any one or more of the compounds according to the first aspect of the invention. Thus, the present invention provides a process for the preparation of a novel compound of formula I, II or III by converting an intermediate alcohol into a compound of formula I, II or III.

Intermediate Alcohol

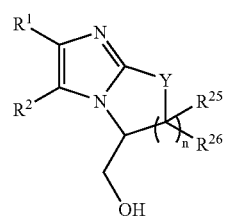

The intermediate alcohol can be converted to a compound of the invention using methodology known in the art. Examples of the conversion of intermediate alcohol into compounds of the invention are shown below.

where the group R$^3$ contains an amine functionality, the group may be introduced as a Boc-protected derivative and subsequently deprotected.

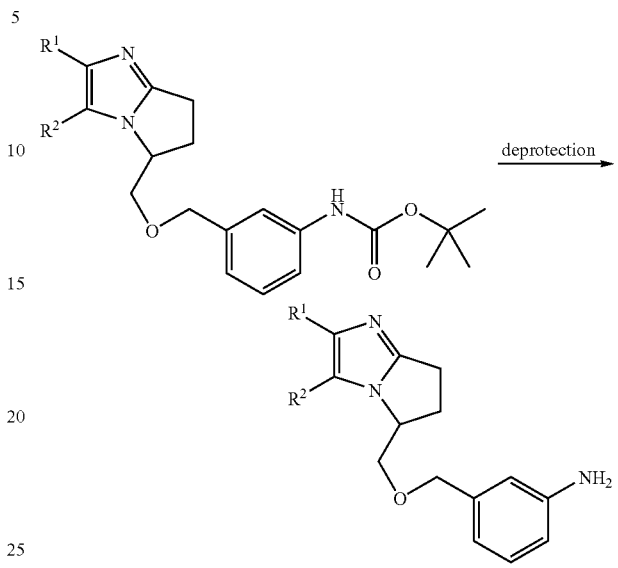

The intermediate alcohol may also be alkylated to give a compound of the present invention using a suitable alkylating or arylating agent such as an alkyl halide for example,

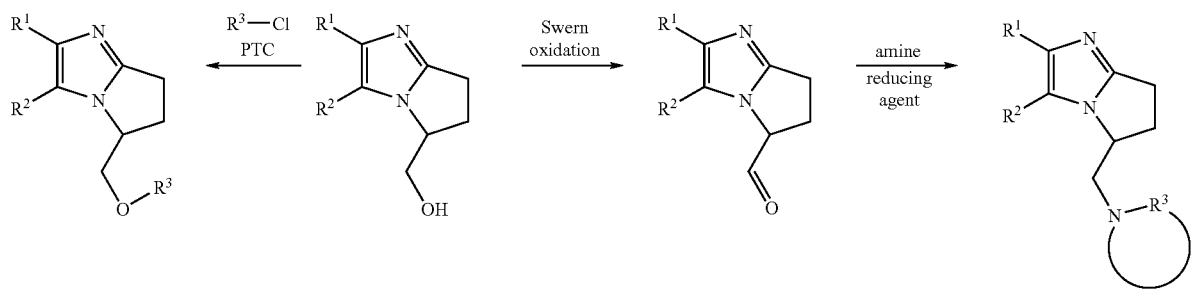

"Swern oxidation" means any oxidation using a sulphoxide and an activator. One may give an example of dimethyl sulphoxide, triethylamine and pyridine-SO$_3$ complex. Another example would involve dimethylsulphoxide, triethylamine and oxalyl chloride.

"amine" means ammonia, primary amine or secondary amine and their salts such as hydrochloride, hydrobromide, etc.

"reducing agent" means any agent suitable to effect reductive amination, for instance NaBH$_4$, NaBH$_3$CN, NaBH(OAc)$_3$, etc.

The group R$^3$ may be introduced into the compound of the first aspect in a protected form. In particular, where the group R$^3$ contains one or more reactive functionalities e.g. amine, alcohol, carboxylic acid, NO$_2$, CN, aldehyde, ketone, SO$_2$R$^{15}$, SR$^{15}$, SOR$^{15}$, the group R can be introduced into the compound of the invention in a protected form and optionally deprotected in a subsequent step. For example, p-methoxybenzyl chloride, benzyl chloride, or an aryl halide or a heterocyclyl halide, for example 2-chloroquinoline, 2-chloropyridine, 4-chloroquinoline, 4-chloropyridine, 2-chloropyrimidine or chloropyrazine.

The intermediate alcohol can be activated, for instance by formation of sulfonate, which then can be reacted with various nucleophiles (Nu-H), for example, thiols, cyanides, secondary amines, anions generated from heterocycles with the help of a base, as shown below.

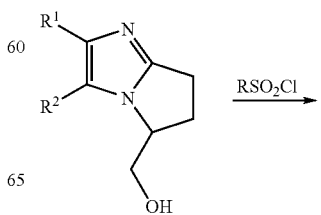

-continued

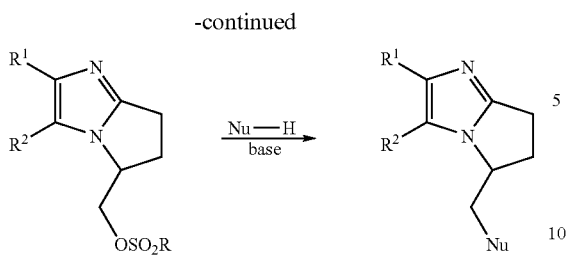

Another example of activation using phosphine-disulfide system is presented below:

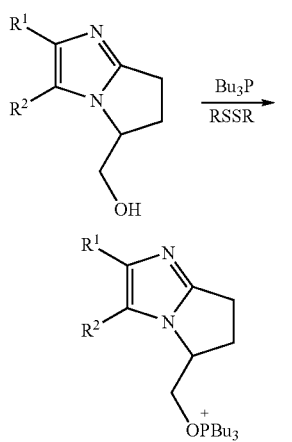

The intermediate alcohol can be converted into the corresponding aldehyde by an oxidation reaction (e.g. a Swern oxidation as illustrated above). The aldehyde intermediate can then be converted into a compound of formula I, II and III. For example, the obtained aldehyde can be reacted with an amine using reductive amination conditions or, in the case of indoline, converted further to the relevant indole derivative as shown below.

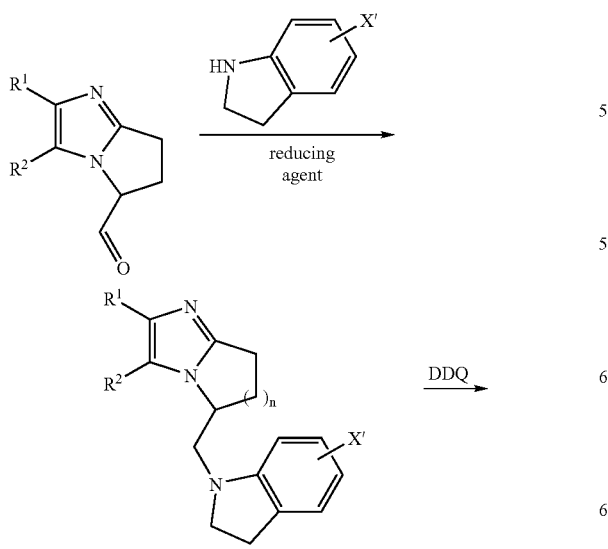

-continued

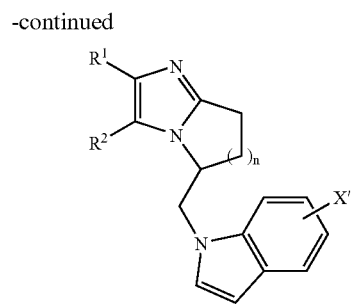

"reducing agent" means any agent suitable to effect reductive amination, for instance $NaBH_4$, $NaBH_3CN$, $NaBH(OAc)_3$, etc.

"X" is a substituent on the heterocyclyl group as previously defined for the compound of the first aspect.

Another example involves the Wittig reaction between the aldehyde and an ylide. The formed alkene can be reduced as shown below:

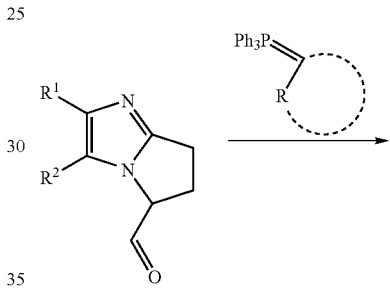

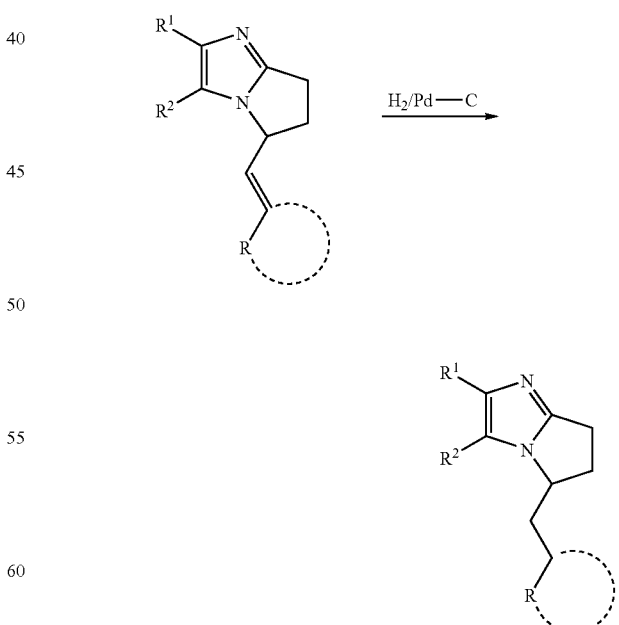

The alcohol can also be converted into the relevant aminomethyl derivative, which can undergo further transformations as shown below

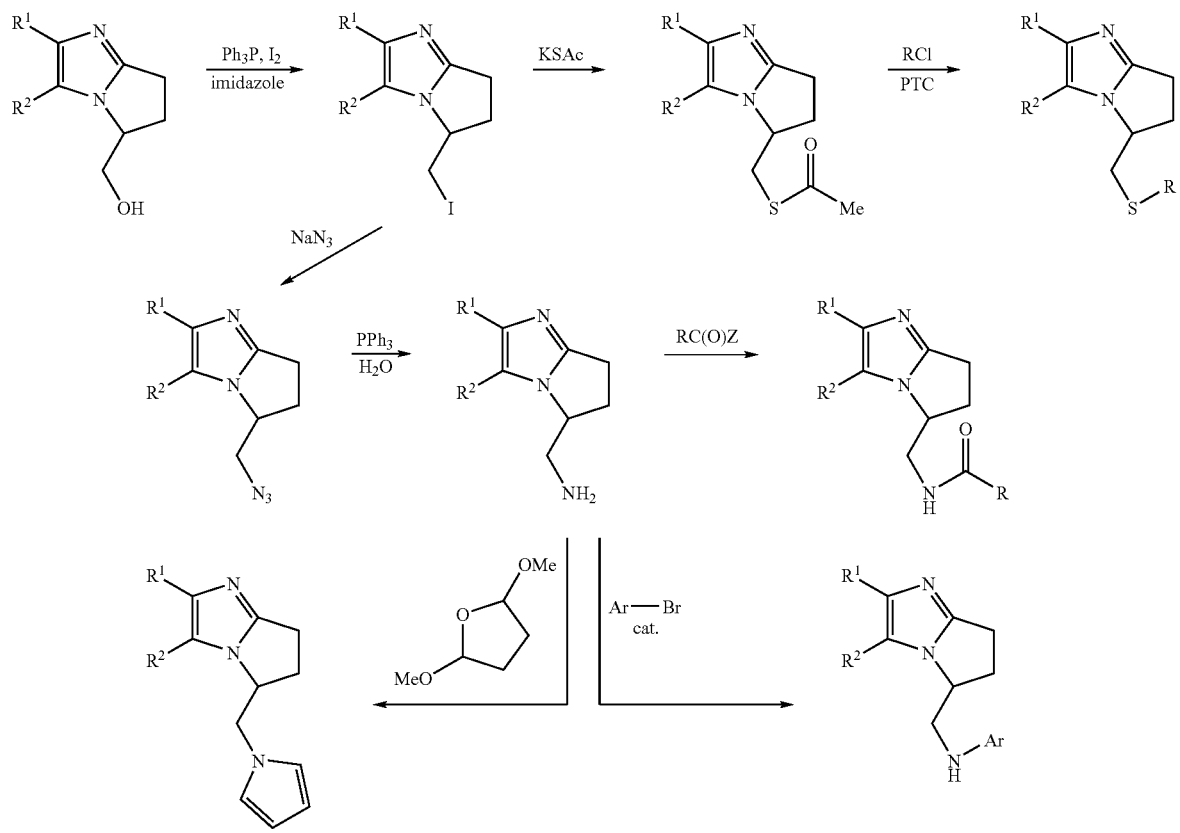

"PTC" means phase transfer catalysis conditions, which can be run in many ways and using various catalysts. One may give an example of using an aqueous solution of sodium hydroxide and an ammonium salt as a catalyst, for instance tetrabutylammonium hydrogen sulphate, etc.

Ar-Br/cat. means palladium-catalysed amination of aryl (heteroaryl) bromides.

A compound of formula I, II or III may undergo one or more further reactions to provide a different compound of formula I, II or III. For example, a compound may undergo a reduction, oxidation, elimination, substitution and/or addition reaction.

For example, compounds containing a thio group may be elaborated further as shown below.

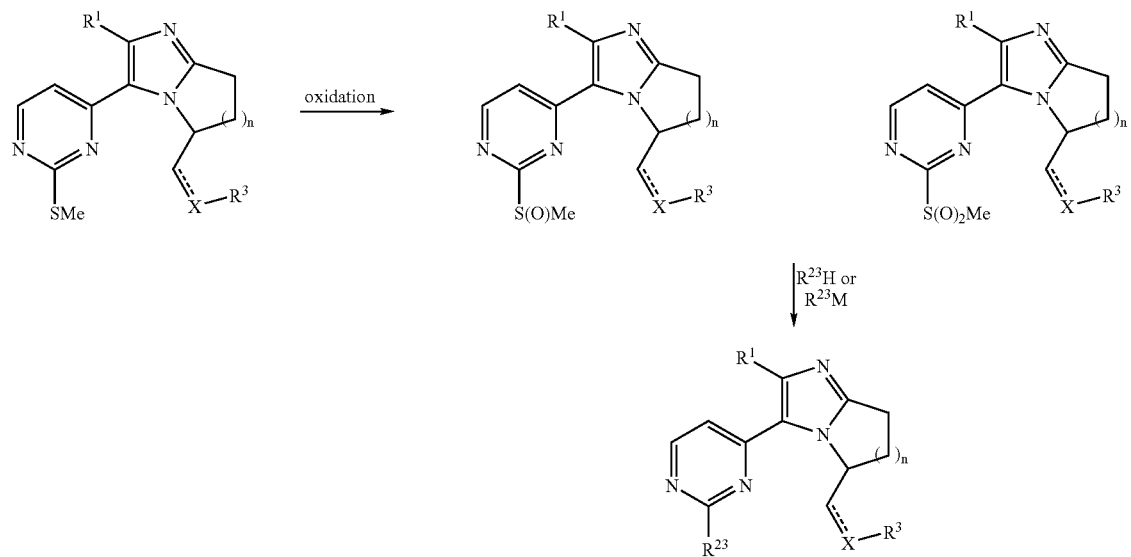

"oxidation" means oxidation using any agent known to oxidise sulphide into sulphoxide and/or sulphone, for example hydrogen peroxide or oxone. "$R^{23}$ H" means $R^4R^5NH$, $R^4NH_2$, $R^4OH$, $R^4SH$ while "$R^{23}M$" their respective metal salts.

The intermediate alcohol can be prepared by a number of different methods. The preparation of the intermediate alcohol from a lactam is illustrated below as an example of one such method.

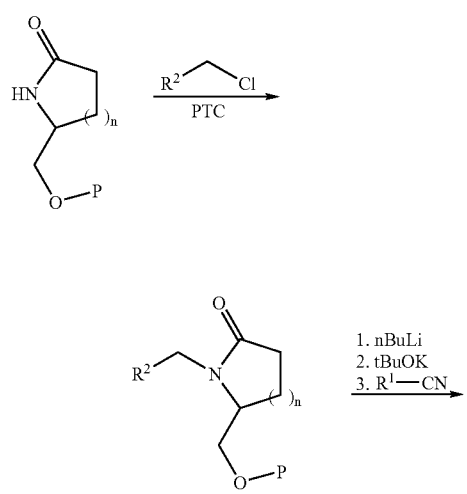

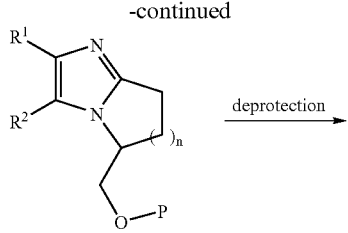

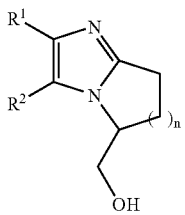

"n" means 1 or 2

"P" means any alcohol protecting group suitable to use under basic conditions, for instance trityl, benzyl, silyl, etc.

"PTC" means phase transfer catalysis conditions, which can be run in many ways and using various catalysts. One may give an example of using an aqueous solution of sodium hydroxide and an ammonium salt as a catalyst, for instance tetrabutylammonium hydrogen sulphate, etc.

"acid" means any mineral acid, preferably hydrochloric acid.

An alternative method for the synthesis of the intermediate alcohol from a lactam is presented in the scheme below:

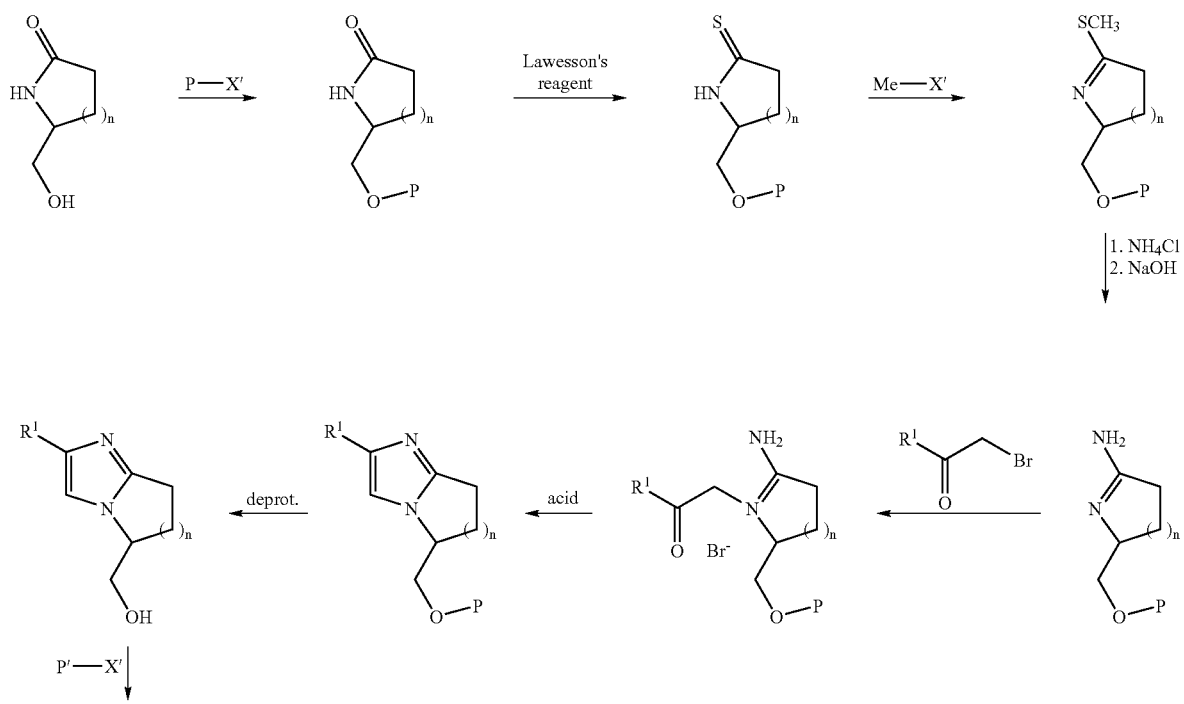

-continued

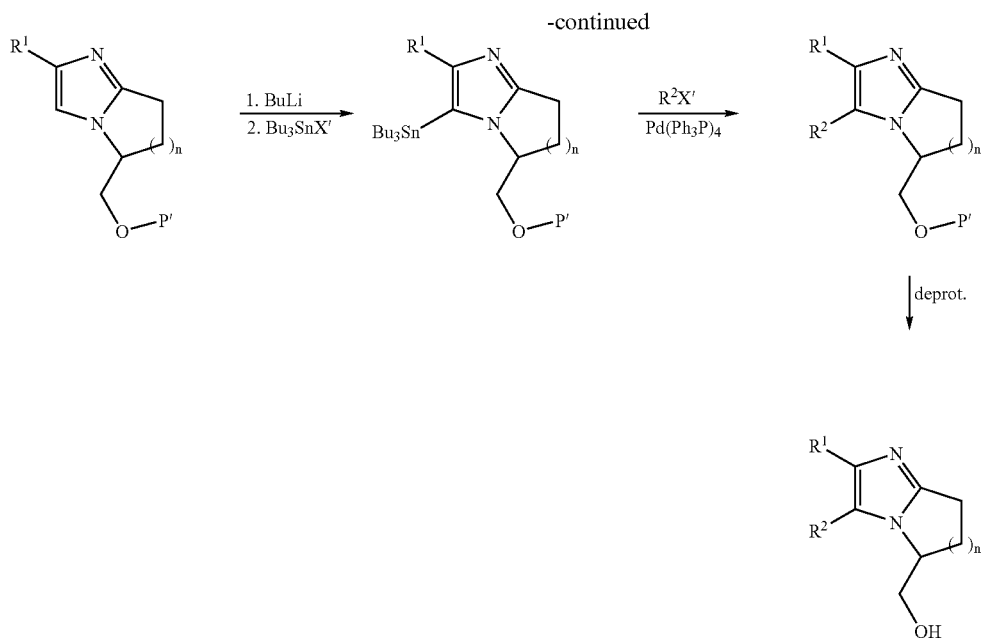

P-X' means any silyl or benzyl-type derivative (X'=Cl, Br, I, sulphonate) suitable for protection of the hydroxyl group. For example one may give tert-butyldiphenylchlorosilane and tert-butyldimethylchlorosilane.

P'—X' means another silyl or benzyl-type derivative (X'=Cl, Br, I, sulphonate) suitable for protection of the hydroxyl group. For example one may give p-methoxybenzyl chloride.

Starting lactam is available from commercial sources or synthesised by analogy to methodology known in the art (Yoshifuji et al. *Chem. Pharm. Bull.* 1987, 35, 2994, Hermitage and Maloney *Tetrahedron Asymmetry* 1994, 5, 1463).

A representative example is shown below

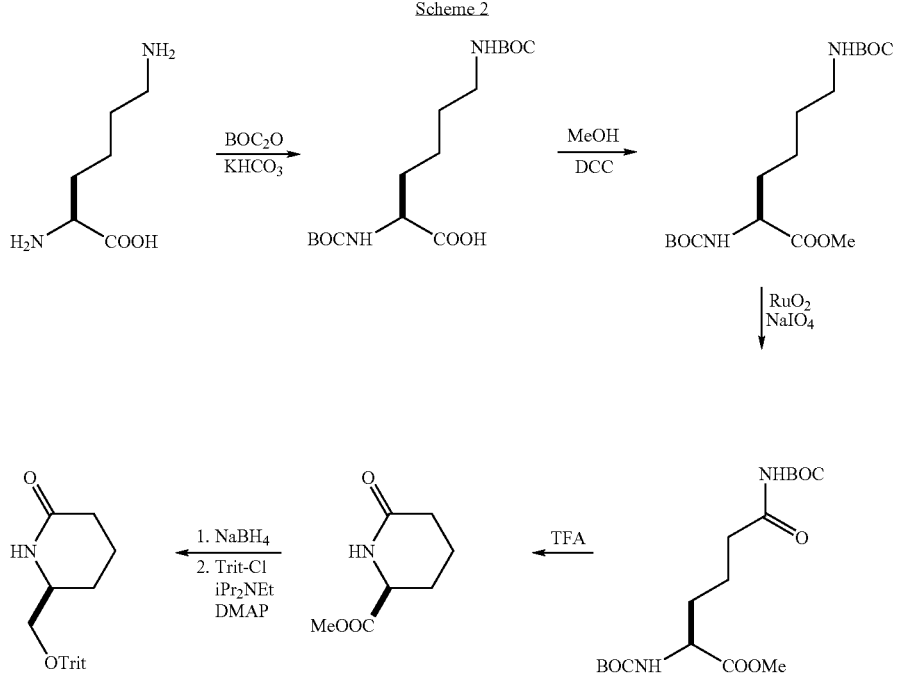

Scheme 2

Alternatively, the compounds of the invention may be synthesised from an intermediate lactam as illustrated below.

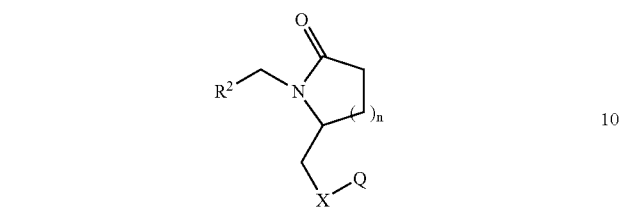

Where X-Q is the group X-R³, the reaction of the intermediate lactam with a nitrile derivative R¹-CN under basic conditions leads to a compound of the invention as illustrated below.

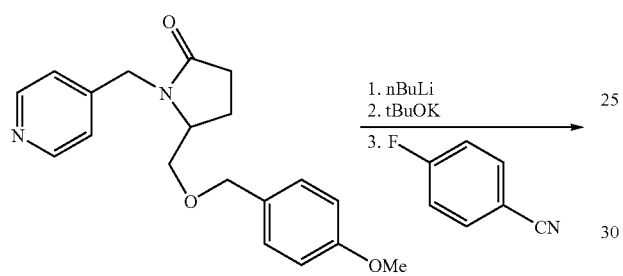

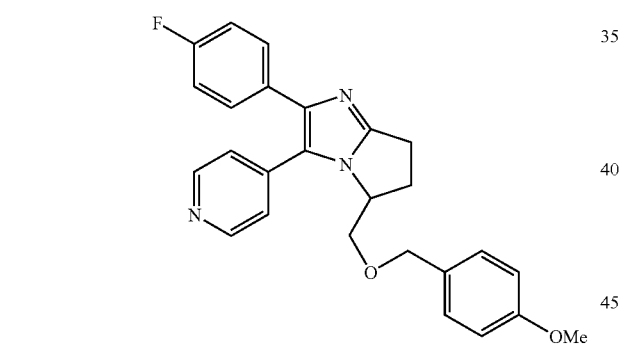

Where X-Q is a protected or deprotected alcohol (i.e Q is a protecting group or hydrogen), reaction with R¹-CN provides an intermediate alcohol which can undergo further reaction (e.g. alkylation with a group R³-Cl) as previously discussed to produce a compound of the first aspect.

The scheme below shows the preparation of compounds represented by general formula III Scheme 7

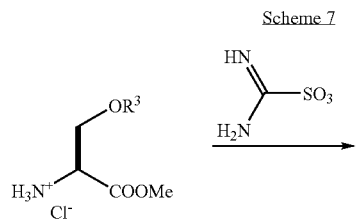

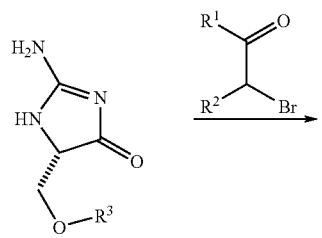

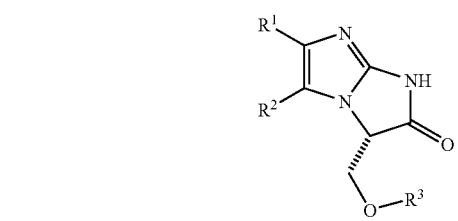

The starting material for this example is a derivative of serine which can provided as a pure enantiomer (l or d) or a mixture of enantiomers.

The third aspect of the invention provides an intermediate of the compounds of the first aspect of the invention. Preferably, the intermediate is of formula IV.

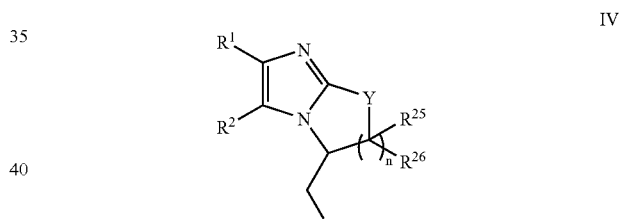

wherein $R^1$ and $R^2$ are as defined for the first aspect of the invention and Z is a group OH, =O, $N_3$, $NH_2$, $OSO_2R^{30}$, $SCOR^{30}$, CN or I wherein $R^{30}$ is an alkyl group, preferably methyl or ethyl.

Examples of intermediates of the third aspect are illustrated below.

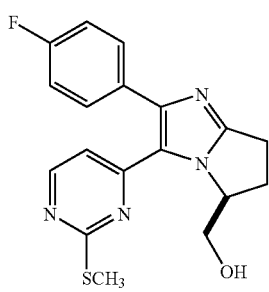

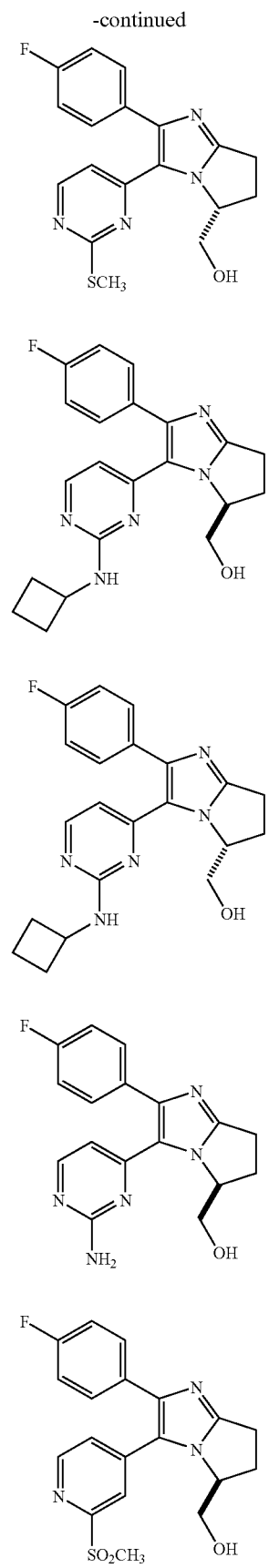
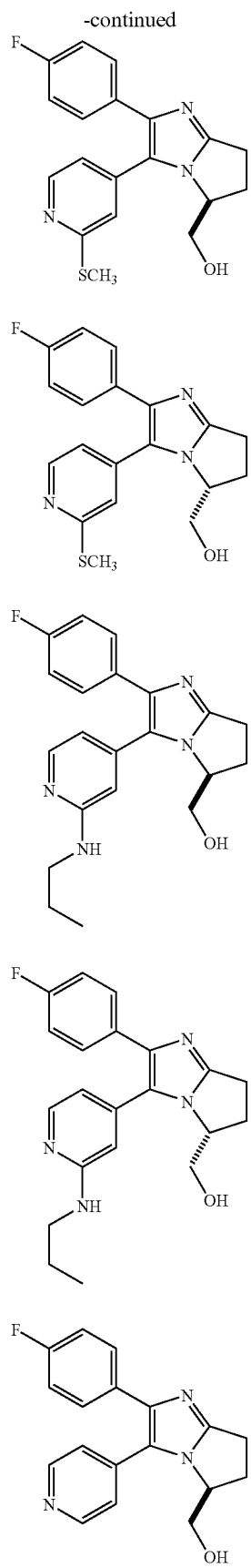

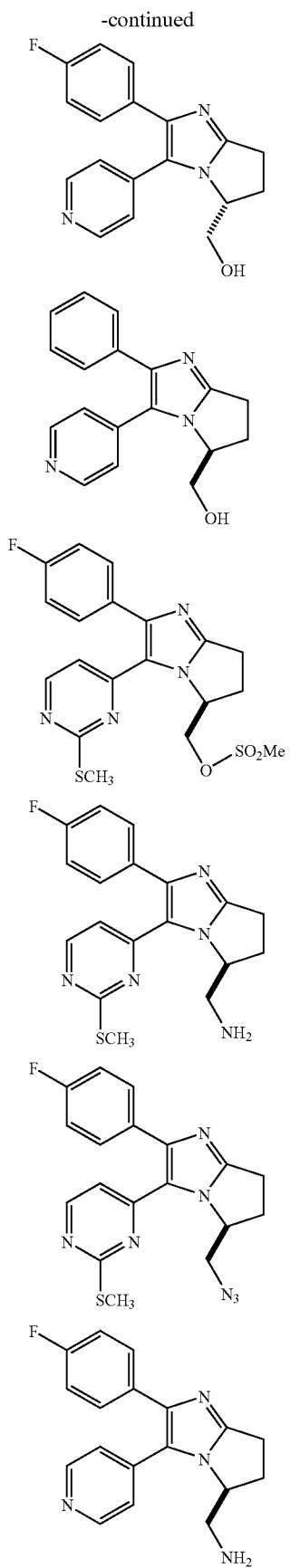
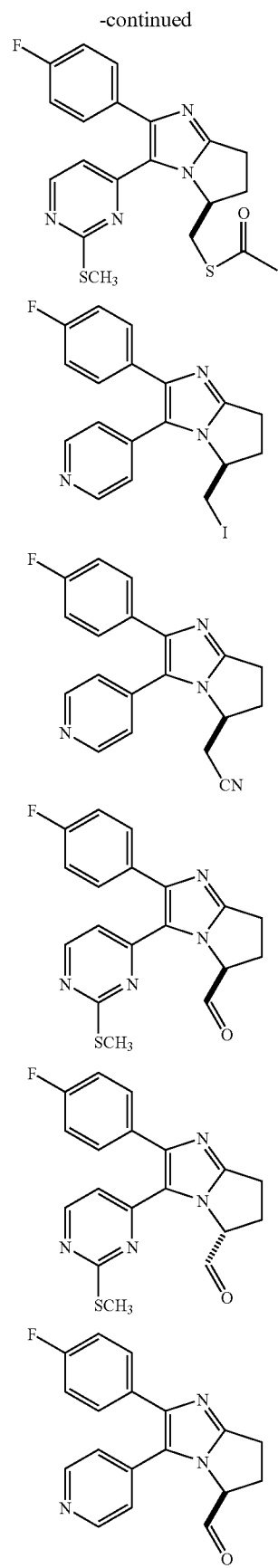

-continued

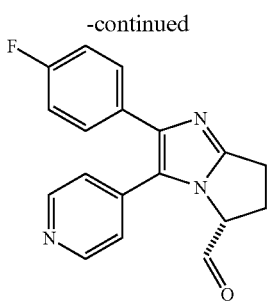

An intermediate of the third aspect of the invention may be converted into another intermediate of the third aspect. For example, an intermediate compound may undergo a reduction, oxidation, elimination, substitution and/or addition reaction. Several examples of such transformations have already been presented above. A further example scheme is shown below.

The composition may also comprise one or more additional active agent, such as an anti-inflammatory agent (for example a p38 inhibitor, glutamate receptor antagonist, or a calcium channel antagonist), a chemotherapeutic agent and/or an antiproliferative agent.

Suitable carriers and/or diluents are well known in the art and include pharmaceutical grade starch, mannitol, lactose, magnesium stearate, sodium saccharin, talcum, cellulose, glucose, sucrose, (or other sugar), magnesium carbonate, gelatin, oil, alcohol, detergents, emulsifiers or water (preferably sterile). The composition may be a mixed preparation of a composition or may be a combined preparation for simultaneous, separate or sequential use (including administration).

The composition according to the invention for use in the aforementioned indications may be administered by any convenient method, for example by oral (including by inhalation), parenteral, mucosal (e.g. buccal, sublingual, nasal), rectal or transdermal administration and the compositions adapted accordingly.

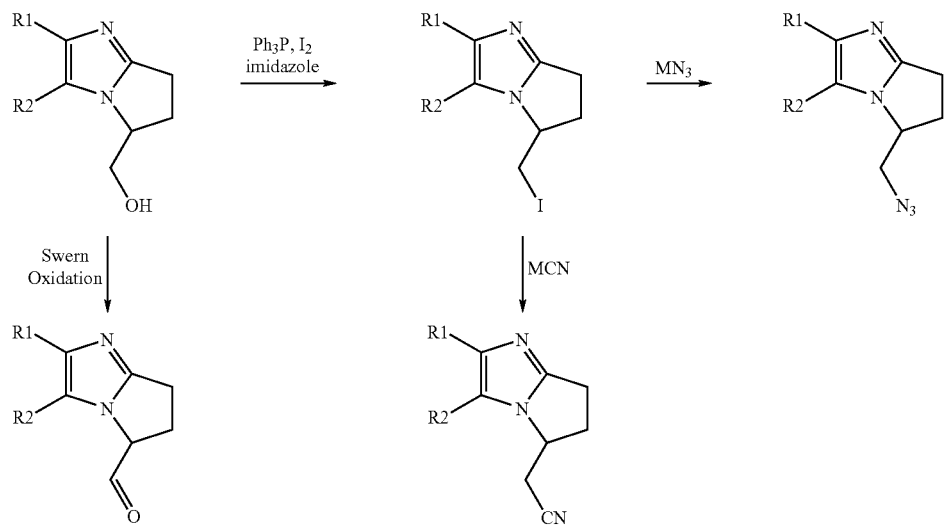

"MCN" means a metal cyanide such as for example NaCN, KCN, etc.

"$MN_3$" means a metal azide such as for example $NaN_3$ or $KN_3$, etc.

The present invention also encompasses a process for manufacturing a compound of the first aspect, the process comprising providing a starting material, which is commercially available or can be produced by a method known in the art, converting the starting material to form an intermediate compound of the third aspect using a process as described above or a process known in the art (and optionally converting the intermediate compound so formed into another intermediate compound) and then converting the intermediate compound into a compound of the first aspect using a process as described above or a process known in the art (and optionally converting the compound of the first aspect so formed into another compound of the first aspect).

The fourth aspect of the invention provides a composition comprising a compound according to the first aspect of the invention in combination with a pharmaceutically acceptable carrier, diluent or excipient.

For oral administration, the composition can be formulated as liquids or solids, for example solutions, syrups, suspensions or emulsions, tablets, capsules and lozenges.

A liquid formulation will generally consist of a suspension or solution of the compound or physiologically acceptable salt in a suitable aqueous or non-aqueous liquid carrier(s) for example water, ethanol, glycerine, polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and microcrystalline cellulose.

A composition in the form of a capsule can be prepared using routine encapsulation procedures. For example, powders, granules or pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Compositions for oral administration may be designed to protect the active ingredient against degradation as it passes through the alimentary tract, for example by an outer coating of the formulation on a tablet or capsule.

Typical parenteral compositions consist of a solution or suspension of the compound or physiologically acceptable salt in a sterile aqueous or non-aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal or oral administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a pharmaceutically acceptable propellant. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal or vaginal administration are conveniently in the form of suppositories (containing a conventional suppository base such as cocoa butter), pessaries, vaginal tabs, foams or enemas.

Compositions suitable for transdermal administration include ointments, gels, patches and injections including powder injections.

Conveniently the composition is in unit dose form such as a tablet, capsule or ampoule.

The fifth aspect of the invention provides a process for the manufacture of a composition according to the fourth aspect of the invention. The manufacture can be carried out by standard techniques well known in the art and involves combining a compound according to the first aspect of the invention and the pharmaceutically acceptable carrier or diluent. The composition may be in any form including a tablet, a liquid, a capsule, and a powder or in the form of a food product, e.g. a functional food. In the latter case the food product itself may act as the pharmaceutically acceptable carrier.

The sixth aspect of the present invention relates to a compound of the first aspect, or a composition of the fourth aspect, for use in medicine.

The compounds of the present invention are inhibitors of JNK, such as JNK1, JNK2, or JNK3. In particular, the compounds of the present invention are inhibitors of JNK3. Preferably, the compounds of the present invention inhibit JNK3 selectively (i.e. the compounds of the invention preferably show greater activity against JNK3 than JNK1 and 2). For the purpose of this invention, an inhibitor is any compound which reduces or prevents the activity of the JNK enzyme.

The compounds are therefore useful for conditions for which inhibition of JNK activity is beneficial. Thus, preferably, this aspect provides a compound of the first aspect, or a composition of the fourth aspect of the present invention, for the prevention or treatment of a JNK-mediated disorder. The compounds of the first aspect of the invention may thus be used for the inhibition of JNK, more preferably for the inhibition of JNK3.

A "JNK-mediated disorder" is any disease or deleterious condition in which JNK plays a role. Examples include neurodegenerative disorder (including dementia), inflammatory disease, a disorder linked to apoptosis, particularly neuronal apoptosis, autoimmune disease, destructive bone disorder, proliferative disorder, cancer, infectious disease, allergy, ischemia reperfusion injury, heart attack, angiogenic disorder, organ hypoxia, vascular hyperplasia, cardiac hypertrophy, thrombin induced platelet aggregation and any condition associated with prostaglandin endoperoxidase synthase-2. The compounds of the present invention may be used for any of these JNK-mediated disorders.

The compounds of the present invention are particularly useful for the prevention or treatment of a neurodegenerative disorder. In particular, the neurodegenerative disorder results from apoptosis and/or inflammation. Examples of neurodegenerative disorders are: dementia; Alzheimer's disease; Parkinson's disease; Amyotrophic Lateral Sclerosis; Huntington's disease; senile chorea; Sydenham's chorea; hypoglycemia; head and spinal cord trauma including traumatic head injury; acute and chronic pain; epilepsy and seizures; olivopontocerebellar dementia; neuronal cell death; hypoxia-related neurodegeneration; acute hypoxia; glutamate toxicity including glutamate neurotoxicity; cerebral ischemia; dementia linked to meningitis and/or neurosis; cerebrovascular dementia; or dementia in an HIV-infected patient.

The neurodegenerative disorder may be a peripheral neuropathy, including mononeuropathy, multiple mononeuropathy or polyneuropathy. Examples of peripheral neuropathy may be found in diabetes mellitus, Lyme disease or uremia; peripheral neuropathy caused by a toxic agent; demyelinating disease such as acute or chronic inflammatory polyneuropathy, leukodystrophies, or Guillain-Barré syndrome; multiple mononeuropathy secondary to a collagen vascular disorder (e.g. polyarteritis nodosa, SLE, Sjögren's syndrome); multiple mononeuropathy secondary to sarcoidosis; multiple mononeuropathy secondary to a metabolic disease (e.g. diabetes or amyloidosis); or multiple mononeuropathy secondary to an infectious disease (e.g Lyme disease or HIV infection).

The compounds of the invention can also be used to prevent or treat disorders resulting from inflammation. These include, for example, inflammatory bowel disorder, bronchitis, asthma, acute pancreatitis, chronic pancreatitis, allergies of various types, and possibly Alzheimer's disease. Autoimmune diseases which may also be treated or prevented by the compounds of the present invention include rheumatoid arthritis, systemic lupus erythematosus, glumerulonephritis, scleroderma, chronic thyroiditis, Graves's disease, autoimmune gastritis, diabetes, autoimmune haemolytis anaemia, autoimmune neutropaenia, thrombocytopenia, atopic dermatitis, chronic active hepatitis, myasthenia gravis, multiple sclerosis, ulcerative colitis, Crohn's disease, psoriasis or graft vs host disease.

A compound of the present invention may be administered simultaneously, subsequently or sequentially with one or more other active agent, such as an anti-inflammatory agent e.g. p38 inhibitor, glutamate receptor antagonist, calcium channel antagonist, a chemotherapeutic agent or an antiproliferative agent. For example, for acute treatment, a p38 inhibitor may be administered to a patient prior to administering a compound of the present invention.

The compounds of the invention will normally be administered in a daily dosage regimen (for an adult patient) of, for example, an oral dose of between 1 mg and 2000 mg, preferably between 30 mg and 1000 mg, e.g. between 10 and 250 mg or an intravenous, subcutaneous, or intramuscular dose of between 0.1 mg and 100 mg, preferably between 0.1 mg and 50 mg, e.g. between 1 and 25 mg of the compound of the formula (I) or a physiologically acceptable salt thereof calculated as the free base, the compound being administered 1 to 4 times per day. Suitably the compounds will be administered for a period of continuous therapy, for example for a week or more.

The seventh aspect of the invention relates to a method of treating or preventing a JNK-mediated disorder in an individual, which method comprises administering to said individual a compound of the first aspect or a composition of the fourth aspect. The active compound is preferably administered in a cumulative effective amount. The individual may be in need of the treatment or prevention. Any of the JNK-mediated disorders listed above in relation to the sixth aspect may be the subject of treatment or prevention according to the seventh aspect. One or more other active agent may be administered to the individual simultaneously, subsequently or sequentially to administering the compound. The other active agent may be an anti-inflammatory agent such as a p38 inhibitor, glutamate receptor antagonist, calcium channel antagonist, a chemotherapeutic agent or an antiproliferative agent, but is preferably p38 inhibitor for acute treatment.

The eighth aspect of the present invention provides the use of a compound of the first aspect in the manufacture of a medicament for the prevention or treatment of a JNK-mediated disorder. The medicament may be used for treatment or prevention of any of the JNK-mediated disorders listed above in relation to the sixth aspect. Again, the compound of the present invention may be administered simultaneously, subsequently or sequentially with one or more other active agent, preferably a p38 inhibitor for acute treatment.

In the ninth aspect of the invention, there is provided an assay for determining the activity of the compounds of the present invention, comprising providing a system for assaying the activity and assaying the activity of the compound. Preferably the assay is for the JNK inhibiting activity of the compound, more preferably it is for the JNK3-specific inhibiting activity of the compounds. The compounds of the invention may be assayed in vitro, in vivo, in silico, or in a primary cell culture or a cell line. In vitro assays include assays that determine inhibition of either the kinase activity or ATPase activity of activated JNK. Alternatively, in vitro assays may quantitate the ability of a compound to bind JNK and may be measured either by radiolabelling the compound prior to binding, then isolating the inhibitor/JNK complex and determining the amount of the radiolabel bound or by running a competition experiment where new inhibitors are incubated with JNK bound to known radioligands. An example of an assay which may be used is Scintillation Proximity Assay (SPA), preferably using radiolabelled ATP. Another example is ELISA. Any type or isoform of JNK may be used in these assays.

In the tenth aspect, there is provided a method of inhibiting the activity or function of a JNK, particularly JNK3, which method comprises exposing a JNK to a compound or a composition of the first or fourth aspect of the present invention. The method may be performed in a research model, in vitro, in silico, or in vivo such as in an animal model. A suitable animal model may be a kainic acid model in rat or mice, traumatic brain injury model in rat, or MPTP in mice.

All features of each of the aspects apply to all other aspects mutatis mutandis.

Below, the present invention is illustrated using non-limiting examples.

EXAMPLES

Synthetic Preparation of Alcohol (S)-13 (Scheme 1)

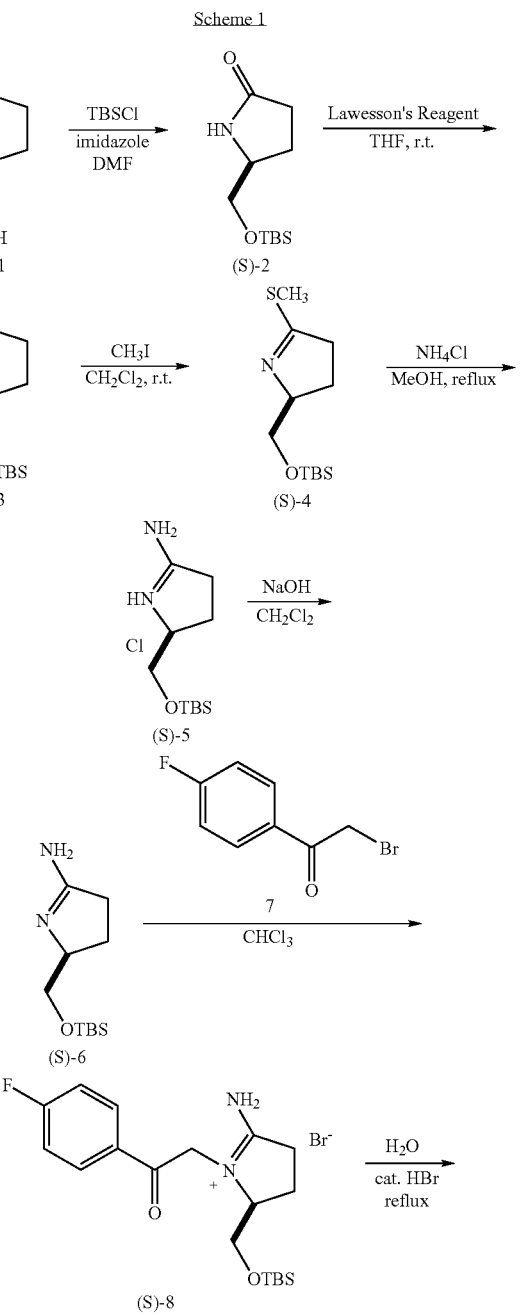

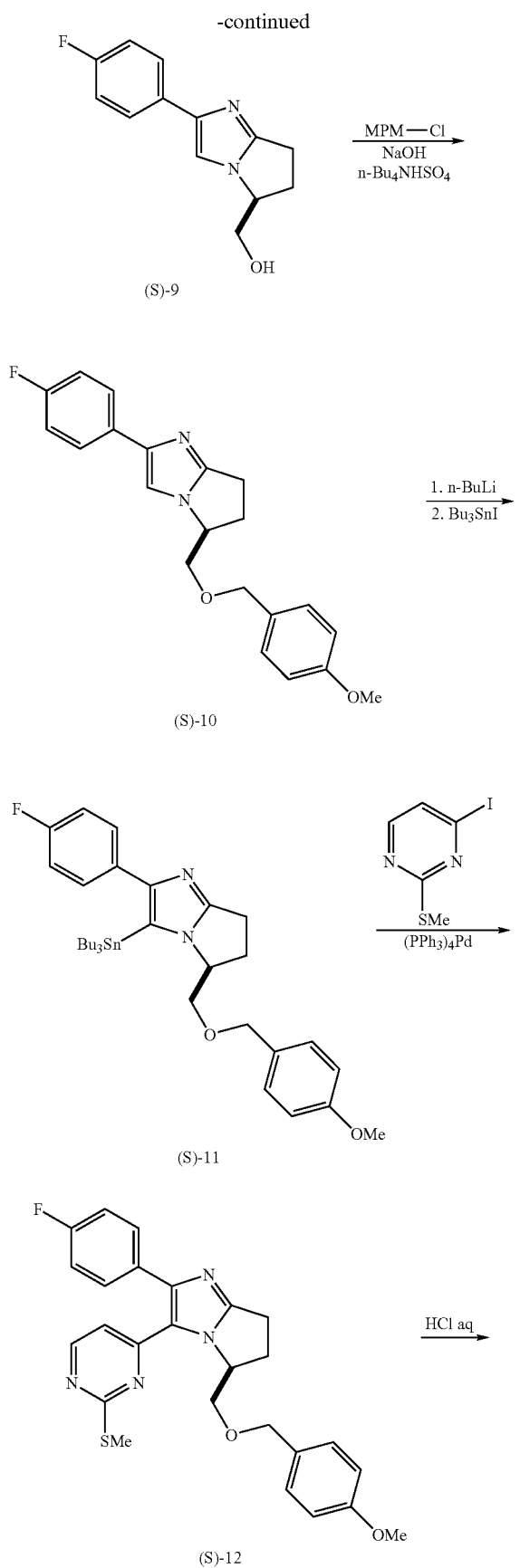

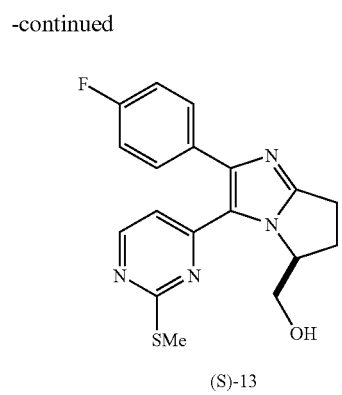

References Relevant to the Preparation Shown in Scheme 1.
Conversion 1→5: Leutenegger, U. et al. *Tetrahedron* 1992, 48(11), 2143-2156
Conversion 6→9: *Chemistry of Heterocyclic Compounds* 1997, 33(10)
Conversion 9→10: *Synth. Commun.* 1992, 22(18), 2659

(S)-5-[(tert-Butyl)dimethylsilyloxy]methyl-2-pyrrolidinone; (S)-2

A mixture of (S)-1 (100 g, 0.869 mol), TBS-Cl (262 g, 1.74 mol), and imidazole (237 g, 3.47 mol) in DMF (686 mL) was stirred for 72 h at room temperature. Water was added and the product was extracted three times with benzene/AcOEt (1:1, v/v). The extracts were washed with brine, dried over MgSO$_4$, and concentrated. The residue was evaporated four times with p-xylene (250 mL). The product was isolated by silicagel chromatography (SGC, Merck silicagel 60, 230-400 mesh, 1.2 kg) with gradient elution (hexane to AcOEt) to give (S)-2 (186 g, 93%) as colorless oil.

Instead of chromatographic purification we also successfully used filtration of a solution of the crude product (after evaporation with p-xylene) in CH$_2$Cl$_2$ through a plug of silicagel (1 L) with final elution using 5% MeOH in CH$_2$Cl$_2$.

(S)-5-[(tert-Butyl)dimethylsilyloxy]methyl-2-thiopyrrolidinone; (S)-3

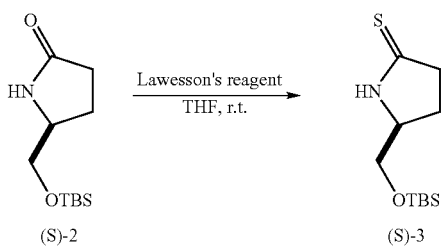

A mixture of (S)-2 (194.25 g, 0.85 mol) (dried before the reaction by 3× evaporation with p-xylene) and Lawesson's reagent (181.53 g, 0.53 mol) in THF (1.8 L) was stirred for 2 h at room temperature. After removal of the solvent, the residue was concentrated, dissolved in CH$_2$Cl$_2$ and filtered through a plug of silicagel (250 mL). Final elution was done with hexane:AcOEt=1:1. The filtrate was concentrated to afford 130.93 g (63%) of (S)-3 as oil, which was used in the next step.

(S)-2-(tert-Butyl-dimethyl-silanyloxymethyl)-5-methylsulfanyl-3,4-dihydro-2H-pyrrole; (S)-4

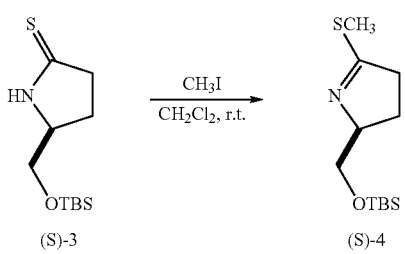

To a solution of (S)-3 (86 g, 0.35 mol) in CH$_2$Cl$_2$ (368 mL) was added at r.t. CH$_3$I (308 mL). After stirring at room temperature for 2 h under N$_2$, further 15 ML of CH$_3$I was added. The reaction mixture was stirred for additional 2 h. Solution colour changed to slightly brown then insoluble material appeared. The reaction mixture was concentrated under reduced pressure then in vacuo. The product was dissolved in dichloromethane and washed with saturated aqueous NaHCO$_3$ solution. Organic layer was filtered through cotton wool and concentrated to give (S)-4 (91 g, 100%) as colourless oil, which partially solidified on standing

(S)-5-(tert-Butyl-dimethyl-silanyloxymethyl)-4,5-dihydro-3H-pyrrol-2-ylamine hydrochloride; (S)-5

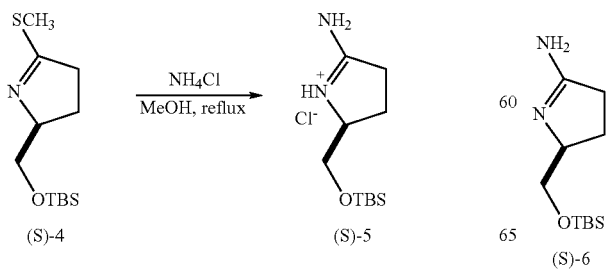

A mixture of (S)-4 (57 g, 0.22 mol) and NH$_4$Cl (20.3 g, 0.23 mmol) in anhydrous MeOH (406 mL) was refluxed for 3 h under N$_2$. The solvent was evaporated and the residue was dissolved in CH$_2$Cl$_2$. The solution was filtered through cotton wool and filtrate was concentrated in vacuo to give white solid, which was washed with cold hexane. The solid residue was dried to afford (S)-5 (37 g, 66%) as a white powder.

(S)-5-(tert-Butyl-dimethyl-silanyloxymethyl)-4,5-dihydro-3H-pyrrol-2-ylamine; (S)-6

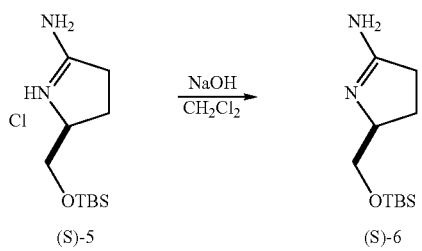

Procedure 1

To a suspension of (S)-5 (5.0 g, 18.9 mmol) in CH$_2$Cl$_2$ (29 mL) was added 6.0 M aqueous solution of NaOH (3.15 mL, 18.9 mmol) under vigorous stirring at room temperature. Reaction mixture was stirred for 5 min until the mixture became clear solution. The reaction mixture was poured into CH$_2$Cl$_2$ and washed with small amount of water. The organic extract was dried over MgSO$_4$ and concentrated to give (S)-6 (4.03 g, 93%) as semisolid.

Procedure 2

Salt (S)-5 (8 g, 30.5 mmol) was added portionwise at room temperature to a stirred mixture of AcOEt and saturated aqueous NaHCO$_3$ (1:1, total of 240 mL). The mixture was then stirred for 30 min. Organic layer was separated and the aqueous phase was extracted with AcOEt containing 1% MeOH (3×200 mL). Combined organic solutions were dried over MgSO$_4$ then concentrated to afford (S)-6 (6.3 g, 90%) as waxy oil.

(S)-2-[2-Amino-5-(tert-butyl-dimethyl-silanyloxymethyl)-pyrrolidin-1-yl]-1-(4-fluoro-phenyl)-ethanone hydrobromide; (S)-8

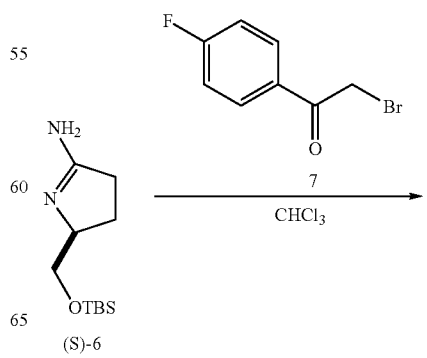

-continued

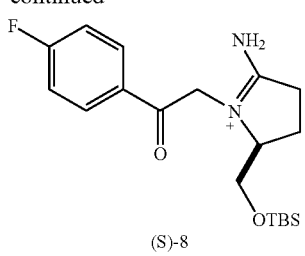
(S)-8

To a stirred solution of (S)-6 (4.02 g, 17.6 mmol) in chloroform (37 mL) was added dropwise at room temperature a solution of bromomethylketone 7 (4.0 g, 18.4 mmol) in chloroform (29 mL) over a period of 1 h. After stirring at room temperature for additional 1.5 h, solvent was removed under reduced pressure to give viscous oil, which was washed with hexane with the help of sonication (2×). Hexane extracts were discarded and the residue was dried in vacuum to afford (S)-8, which was used directly in the next step.

(S)-[2-(4-Fluoro-phenyl)-6,7-dihydro-5H-pyrrolo[1,2-a]imidazol-5-yl]-methanol; (S)-9

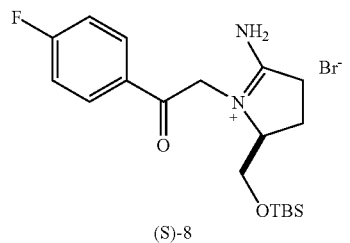 

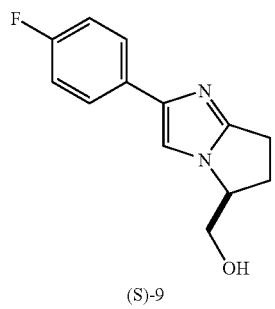
(S)-9

A 30% solution of HBr in AcOH (4 drops) was added to a solution of salt (S)-8 in water containing 30% of EtOH (total of 200 mL) and the mixture was refluxed for 5.5 h. After cooling, the mixture was neutralized with sat. aq. NaHCO₃ and extracted with AcOEt (2×). Organic extracts were combined and washed with water and brine, dried over MgSO₄ then concentrated. The residue was purified by SGC using a gradient elution with CH₂Cl₂ as a nonpolar component and MeOH containing 10% NH₄OH as the polar one. The product eluted at 5% MeOH/NH₄OH in CH₂Cl₂. Yield 1.31 g (32%) of (S)-9 as a pale brown solid.

(S)-2-(4-Fluoro-phenyl)-5-(4-methoxy-benzyloxymethyl)-6,7-dihydro-5H-pyrrolo[1,2-a]imidazole; (S)-10

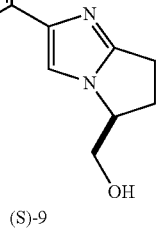 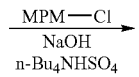
(S)-9

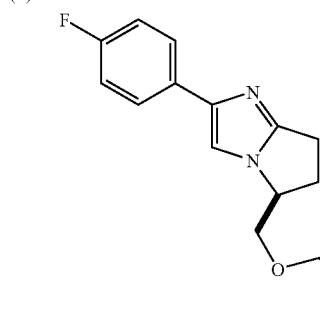
(S)-10

A mixture of alcohol (S)-9 (50.0 g, 0.215 mol), p-methoxybenzyl chloride (35.1 mL, 40.5 g, 0.259 mol), n-Bu₄NHSO₄ (7.25 g, 21.4 mmol) and 50% aqueous NaOH (37.8 mL, 0.72 mol) in benzene (500 mL) was stirred at r.t. overnight. The organic phase was separated and the residue was extracted with benzene (3×100 mL). Combined organic solutions were washed with brine, dried (MgSO₄) and concentrated. The residual oil was separated by means of SGC to afford the MPM derivative (S)-10 (72.18 g, 95%) as pale yellow oil, which crystallised on standing in a refrigerator.

Stannyl Derivative (S)-11

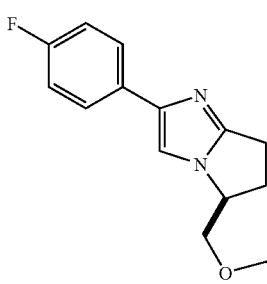 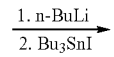
(S)-10

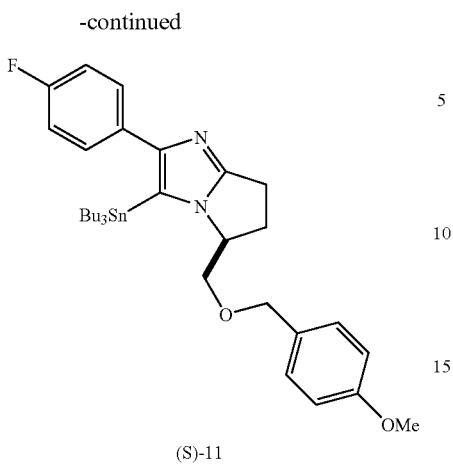

(S)-11

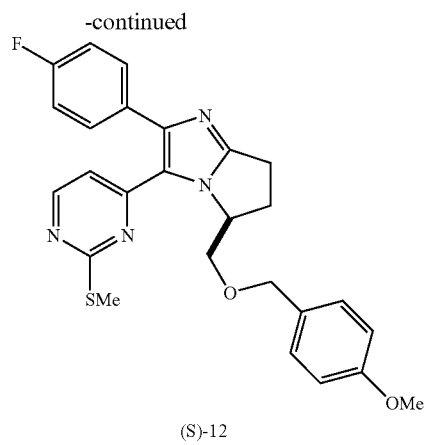

(S)-12

To a stirred and cooled (−78° C.) solution of imidazole derivative (S)-10 (70.85 g, 0.201 mol) in THF (580 mL), 2.5 M solution of n-BuLi in hexanes (100 mL, 0.25 mol) was added over 4 min period. After the addition was completed the mixture was stirred at −78° C. for 35 min. Then, 90% $Bu_3SnI$ (77.7 mL, 0.245 mol) was added rapidly. The dark red colour of the mixture disappeared and the temperature increased to −50° C. After stirring in a cooling bath (−78° C.) for 1 h, the reaction was quenched by the addition of saturated aqueous $NaHCO_3$ (300 mL). The mixture was allowed to warm up to r.t. Organic layer was separated and the aqueous phase was extracted with AcOEt (3×700 mL). Combined organic solutions were washed with brine, dried over $MgSO_4$ and concentrated in vacuum to afford (S)-11 as dark brown oil (178 g). The crude product (S)-11 was evaporated with toluene (3×500 mL) and used in the next step without additional purification.

(S)-2-(4-Fluoro-phenyl)-5-(4-methoxy-benzyloxymethyl)-3-(2-methylsulfanyl-pyrimidin-4-yl)-6,7-dihydro-5H-pyrrolo[1,2-a]imidazole; (S)-12

The crude product (S)-11, prepared in the previous step, was reacted with 4-iodo-2-methylthiopyrimidine (75.4 g, 0.299 mol), $(Ph_3P)_4Pd$ (76.6 g, 66.3 mmol) in DMF (1.5 L) at 78-83° C. over a period of 4 days. The mixture was cooled to r.t. and solvent was evaporated in vacuum. The residue was separated between water-AcOEt. The organic layer was washed with water, brine, dried ($MgSO_4$), filtered, and concentrated. The residue was separated by means of SGC with hexane-AcOEt as eluent (in gradient) to afford (S)-12 (77 g, 80% from (S)-10).

(S)-[2-(4-Fluoro-phenyl)-3-(2-methylsulfanyl-pyrimidin-4-yl)-6,7-dihydro-5H-pyrrolo[1,2-a]imidazol-5-yl]-methanol; (S)-13

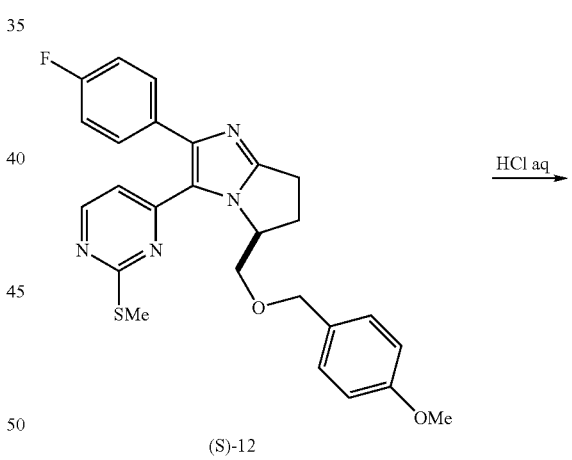

(S)-12

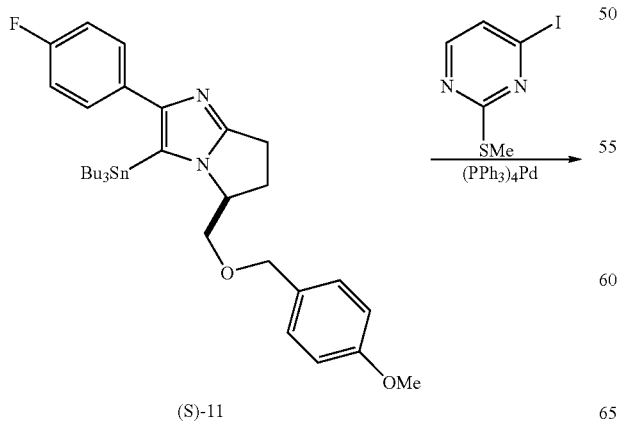

(S)-11

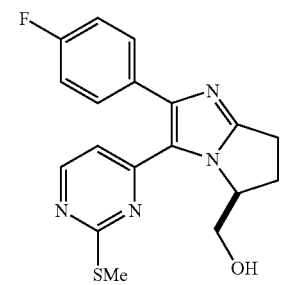

(S)-13

A solution of MPM ether (S)-12 (55 g, 0.115 mol) in MeOH (200 mL): 6N HCl (1 L) was refluxed for 1 h, cooled to r.t. and poured into a cooled (external ice bath) mixture of NaOH (240 g, 6.0 mol), water (1.5 L) and dichloromethane (1 L). The white solid was filtered off. The filtrate was extracted with 10% MeOH in CH₂Cl₂ (4×). The extracts were concentrated to afford additional portion of the solid. The combined solids were purified by means of SGC to afford (S)-13 (14.5 g, 35%) as a white solid.

2-Bromo-1-(4-fluoro-phenyl)-ethanone (7)

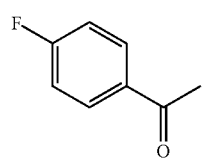

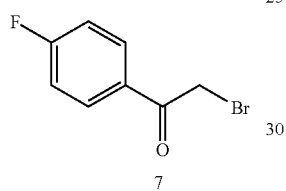

7

A solution of 1-(4-fluorophenyl)-ethanone (20.0 g, 144.7 mmol) in CHCl₃ (320 mL) was added to a refluxing mixture of CuBr₂ (64.8 g, 290.11 mmol) in AcOEt (640 mL). The mixture was then refluxed for 5 h. Solvent was evaporated and the remaining solid was boiled in 350 mL of EtOH and filtered while hot through Celite. The ethanolic solution was concentrated, dissolved in CH₂Cl₂ and filtered through a short column of silicagel, initially with hexane; with final elution with hexane:ethyl acetate=1:1. The residue crystallized from hexane at −20° C. to give white crystals of 7 (22.98 g, 73%).

Synthetic Preparation of Alcohol (S)-15 (Scheme 2; Method 1)

Scheme 2

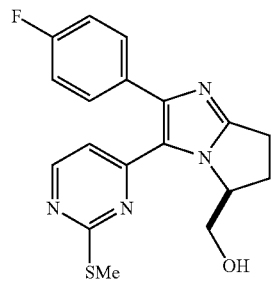

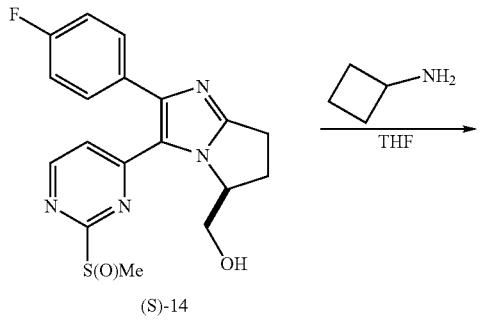

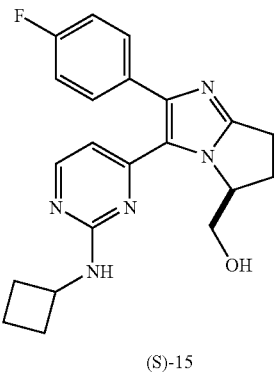

(S)-[2-(4-Fluoro-phenyl)-3-(2-methanesulfinyl-pyrimidin-4-yl)-6,7-dihydro-5H-pyrrolo[1,2-a]imidazol-5-yl]-methanol; (S)-14

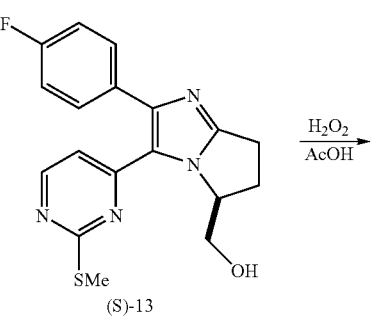

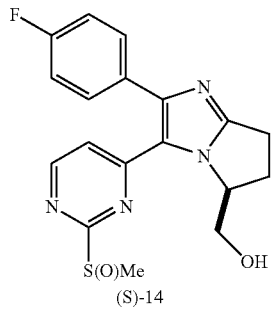

Glacial acetic acid (4.5 mL) and 30% $H_2O_2$ (318 µL, 2.808 mmol) were added to alcohol (S)-13. The mixture was allowed to stir at r.t. overnight, evaporated to dryness with toluene to give crude sulphoxide (S)-14 as a white solid which was used directly in the next reaction.

(S)-[3-(2-Cyclobutylamino-pyrimidin-4-yl)-2-(4-fluoro-phenyl)-6,7-dihydro-5H-pyrrolo[1,2-a]imidazol-5-yl]-methanol; (S)-15

Synthetic Preparation of Alcohol (S)-15 (Scheme 3; Method 2)

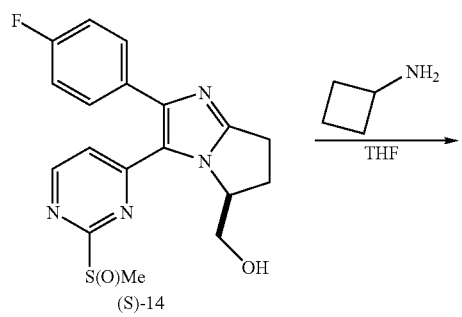

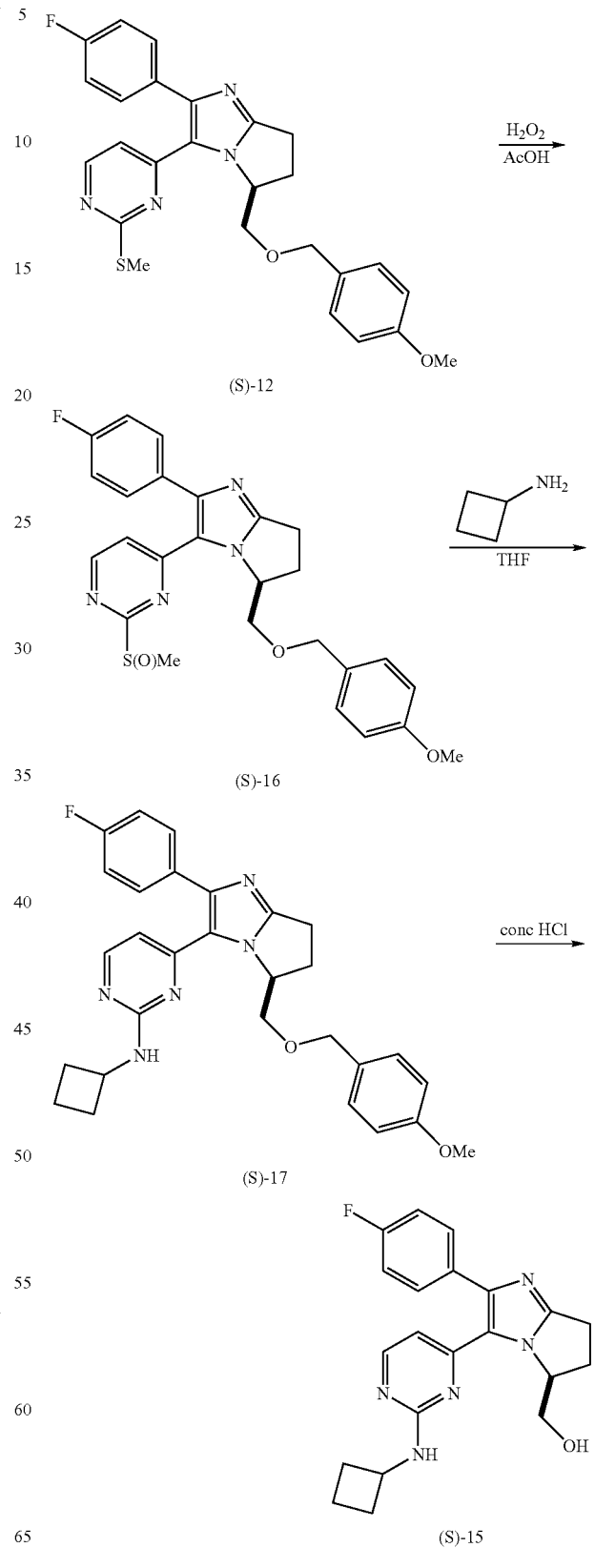

Cyclobutylamine (1.20 mL, 14.04 mmol) was added to a solution of sulphoxide (S)-14 (522 mg, 1.40 mmol) in dry THF (0.8 mL) and the mixture left to stir at r.t. overnight. The excess amine and THF were removed by evaporation. Purification by SGC using $CH_2Cl_2$:MeOH as eluent in gradient afforded alcohol (S)-15 (208.8 mg, 39%) as a yellow oil.

$^1$H NMR (400 MHz, $CDCl_3$) δ 1.66-1.82 (m, 2H), 1.84-1.98 (m, 2H), 2.33-2.47 (m, 3H), 2.68-2.90 (m, 2H), 2.97-3.10 (m, 1H), 3.77 (dd, J=11.2, 7.3 Hz, 1H), 3.91 (dd, J=11.2, 3.6 Hz, 1H), 4.37-4.48 (m, 1H), 4.90 (bs, 1H), 5.41 (d, J=8.3 Hz, 1H), 6.38 (d, J=5.3 Hz, 1H), 7.03 (t, J=8.6 Hz, 2H), 7.50 (dd, J=8.6, 5.5 Hz, 2H), 8.01 (d, J=5.3 Hz, 1H); MS (ESP+) m/e 380 (M+H).

(S)-2-(4-Fluoro-phenyl)-3-(2-methanesulfinyl-pyrimidin-4-yl)-5-(4-methoxy-benzyloxymethyl)-6,7-dihydro-5H-pyrrolo[1,2-a]imidazole; (S)-16

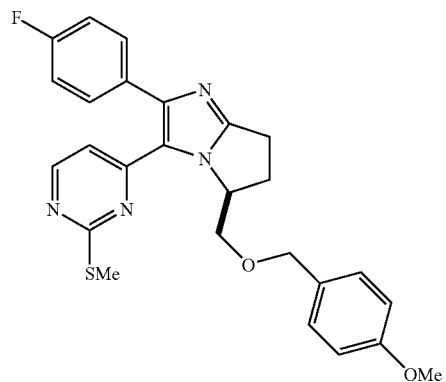

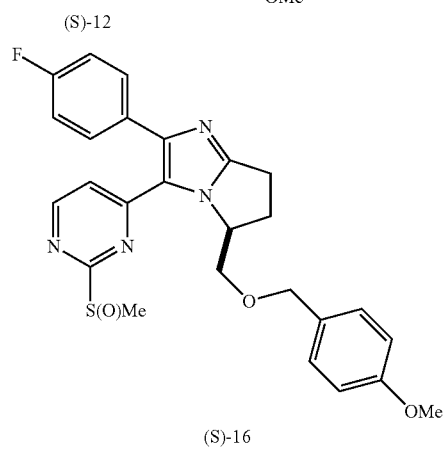

A solution of thioether (S)-12 (1.20 g, 2.54 mmol) in glacial AcOH (1.5 mL) and 30% H₂O₂ (770 μL, 6.79 mmol) was left to stir at r.t. overnight. The reaction mixture was evaporated to dryness with toluene to afford crude sulfoxide (S)-16 (1.66 g) as a white solid which was used directly in the next reaction.

(S)-Cyclobutyl-[4-[2-(4-fluoro-phenyl)-5-(4-methoxy-benzyloxymethyl)-6,7-dihydro-5H-pyrrolo[1,2-a]imidazol-3-yl]-pyrimidin-2-yl]-amine; (S)-17

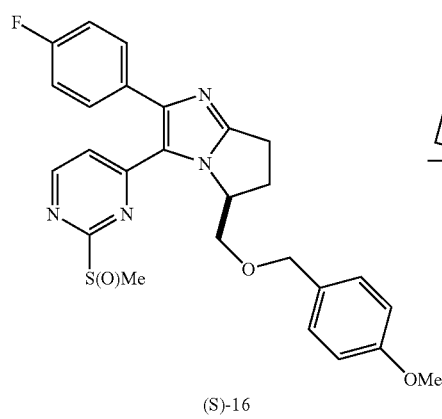

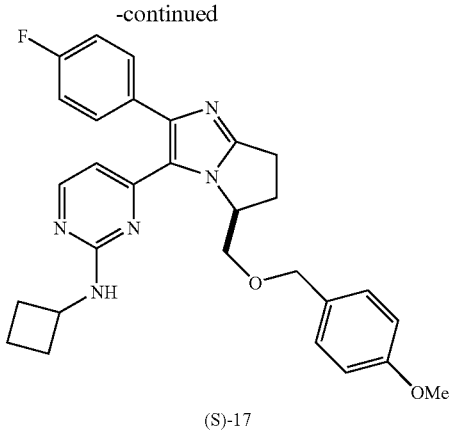

Cyclobutylamine (1.44 mL, 16.854 mmol) was added to a solution of sulfoxide (S)-16 (1.66 g, 3.370 mmol) in dry THF (6.0 mL) and stirred at r.t. overnight. The mixture was concentrated in vacuo and separated by SGC with AcOEt:hexane as eluent to afford amine (S)-17 (255.12 mg, 15%) as a yellow foam.

(S)-[3-(2-Cyclobutylamino-pyrimidin-4-yl)-2-(4-fluoro-phenyl)-6,7-dihydro-5H-pyrrolo[1,2-a]imidazol-5-yl]-methanol; (S)-15

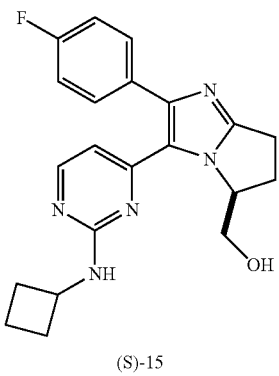

Amine (S)-17 (248 mg, 0.496 mmol) was dissolved in conc. HCl (2.0 mL) and was allowed to stir for two hours at r.t. The mixture was carefully transferred into a mixture of saturated aqueous NaHCO₃ and AcOEt. The organic layer was separated. The aqueous layer was extracted with AcOEt. The organic solutions were combined, dried over MgSO$_4$, concentrated and purified by SGC using CH$_2$Cl$_2$:MeOH as eluent in gradient afforded alcohol (S)-15 (175.6 mg, 93%) as a yellow oil. Analytical data—see Method 1.
Synthetic Preparation of Alcohol (R)-13 (Scheme 4)
Scheme 4
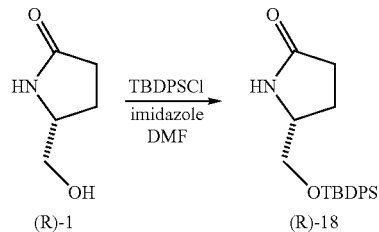
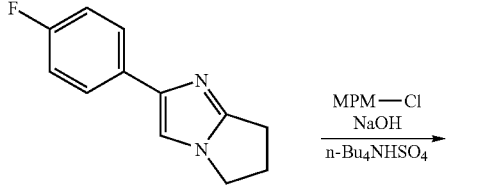
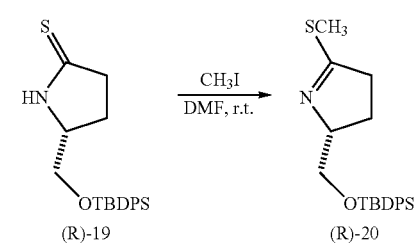
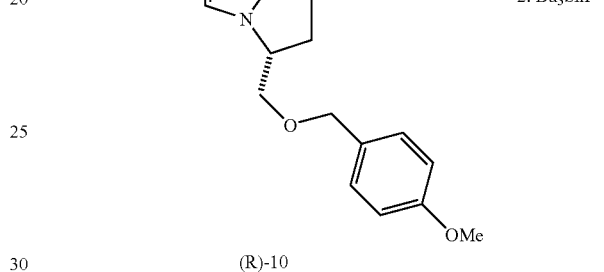
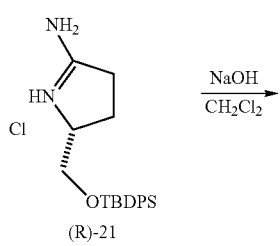
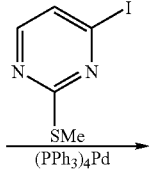
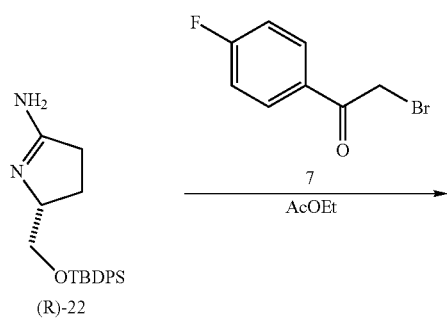
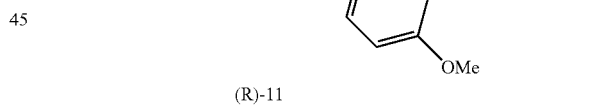
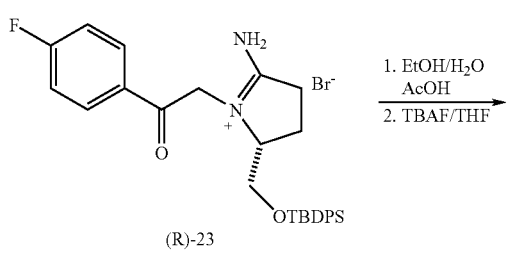
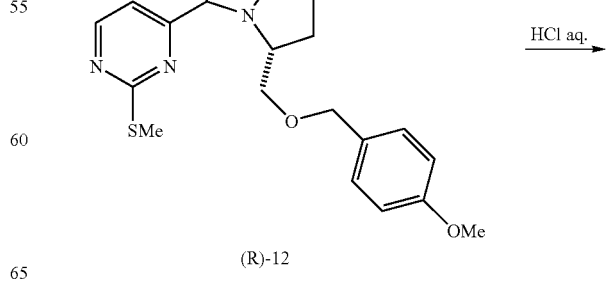

-continued

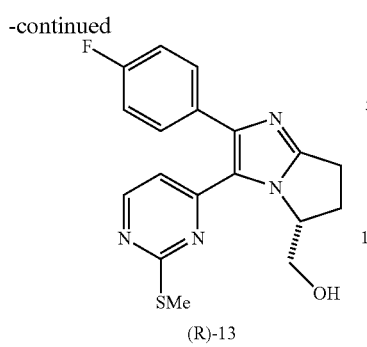

(R)-13

(R)-5-[(tert-Butyl)dimethylsilyloxy]methyl-2-pyrrolidinone; (R)-18

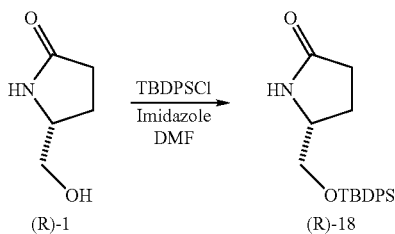

A mixture of (R)-1 (20 g, 174 mmol), tert-butyldiphenylchlorosilane (49.7 mL, 191 mmol), and imidazole (14.9 g, 217 mmol) in DMF (78 mL) was stirred for 2.5 h at r.t. Solvent was removed under reduced pressure, water (140 mL) was added, and the product extracted three times with hexane. The extracts were washed with brine, dried over MgSO$_4$, and concentrated. The product was isolated by SGC with gradient elution (30% AcOEt in hexane to 100% AcOEt) to give (R)-18 (58.9 g, 96%) as colourless oil. $^1$H NMR (400 MHz, CDCl$_3$) δ 0.97 (s, 9H), 1.55-1.73 (m, 1H), 2.00-2.13 (m, 1H), 2.45 (m, 2H), 3.44 (dd, J=10.3, 7.5 Hz, 1H), 3.54 (dd, J=10.3, 4.1 Hz, 1H), 3.73 (m, 1H), 6.00 (bs, 1H), 7.25-7.40 (m, 6H), 7.56 (m, 4H).

(R)-5-[(tert-Butyl)dimethylsilyloxy]methyl-2-thiopyrrolidinone; (R)-19

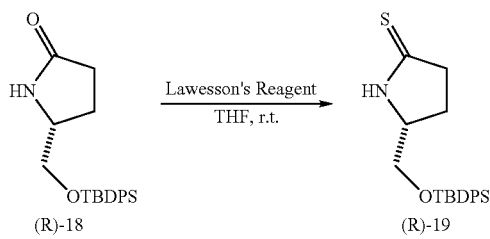

A mixture of (R)-18 (58.0 g, 164 mmol) and Lawesson's reagent (36.5 g, 90.2 mmol) in THF (188 mL) was stirred for 3 h at room temperature. The residue was concentrated and the product was isolated by SGC with gradient elution (10% AcOEt in hexane to 20% AcOEt in hexane, use toluene to load sample) to give (R)-19 (53.61 g, 88%) as a white solid. $^1$H NMR (400 MHz, CDCl$_3$) δ 1.06 (s, 9H), 1.75-1.90 (m, 1H), 2.13-2.30 (m, 1H), 2.80-3.05 (m, 2H), 3.57 (dd, J=10.6, 7.6 Hz, 1H), 3.68 (dd, J=10.6, 3.8 Hz, 1H), 4.19 (m, 1H), 7.50-7.65 (m, 6H), 7.78 (m, 4H), 7.95-8.15 (bs, NH); MS (ESP+) m/z 387 (M+H$_2$O)

(R)-2-(tert-Butyl-diphenyl-silanyloxymethyl)-5-methylsulfanyl-3,4-dihydro-2H-pyrrole; (R)-20

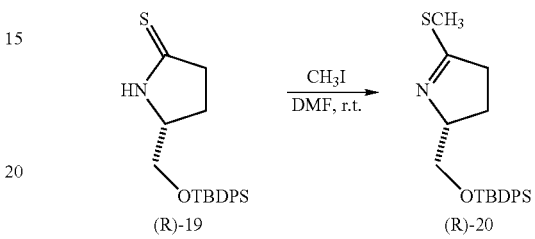

To a solution of (R)-19 (53.0 g, 143 mmol) in DMF (320 mL), cooled to 0° C., was added methyl iodide (9.82 mL, 158 mmol). After stirring at room temperature for 2 h 10 min under N$_2$ the reaction mixture was concentrated under reduced pressure. The product was added to ice-cold saturated aqueous NaHCO$_3$ (265 mL), extracted with hexane, washed with brine and dried over MgSO$_4$ to give of (R)-20 (53.44 g, 97%) as a colourless oil. $^1$H NMR (400 MHz, CDCl$_3$) δ 0.96 (s, 9H), 1.90-2.15 (m, 2H), 2.39 (s, 3H), 2.52 (m, 1H), 2.60-2.73 (m, 1H), 3.68 (dd, J=10.1, 5.0 Hz, 1H), 3.78 (dd, J=10.1, 3.6 Hz, 1H), 4.17 (m, 1H), 7.25-7.40 (m, 6H), 7.60 (m, 4H).

(R)-2-(tert-Butyl-diphenyl-silanyloxymethyl)-5-methylsulfanyl-3,4-dihydro-2H-pyrrole hydrochloride; (R)-21

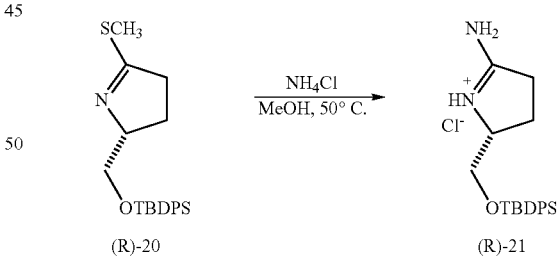

A mixture of (R)-20 (53.0 g, 138 mmol) and NH$_4$Cl (7.45 g, 138 mmol) in MeOH (320 mL) was heated at 50° C. for 3 h under N$_2$ then more NH$_4$Cl (150 mg) was added and the heating continued for 1 h. The solvent was evaporated and the residue was washed with diisopropyl ether to give (R)-21 as a white solid (50.0 g, 93%). $^1$H NMR (400 MHz, CDCl$_3$) δ 1.09 (s, 9H), 2.05-2.18 (m, 1H), 2.25-2.40 (m, 1H), 2.80-3.10 (m, 2H), 3.73 (dd, J=10.9, 3.9 Hz, 1H), 3.82 (dd, J=10.9, 3.2 Hz, 1H), 4.15 (m, 1H), 7.40-7.55 (m, 6H), 7.67 (m, 4H).

(R)-5-(tert-Butyl-diphenyl-silanyloxymethyl)-4,5-dihydro-3H-pyrrol-2-ylamine; (R)-22

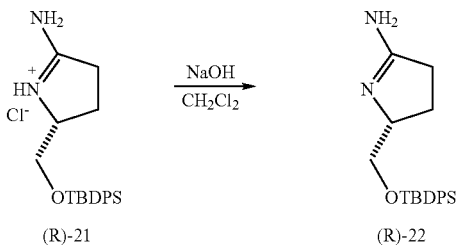

To a suspension of (R)-21 (49.5 g, 127 mmol) in CH$_2$Cl$_2$ (248 mL) was added 5 M aqueous solution of NaOH (50 mL, 250 mmol) dropwise. Reaction mixture was stirred for 0.5 h, the layers separated and the aqueous layer extracted with more CH$_2$Cl$_2$. The combined organic extracts were dried over K$_2$CO$_3$ and concentrated to give (R)-22 (46.25 g, 103%) as a clear oil. $^1$H NMR (400 MHz, CDCl$_3$) δ 0.98 (s, 9H), 0.73-1.85 (m, 1H), 0.95-2.10 (m, 1H), 2.25-2.50 (m, 2H), 3.46 (dd, J=9.9, 6.1 Hz, 1H), 3.69 (dd, J=9.9, 4.5 Hz, 1H), 3.89 (m, 1H), 4.20-4.60 (bs, NH$_2$), 7.20-7.40 (m, 6H), 7.60 (m, 4H); MS (ESP+) m/z 353.0 (M+H).

(R)-2-[2-Amino-5-(tert-butyl-diphenyl-silanyloxymethyl)-pyrrolidin-1-yl]-1-(4-fluoro-phenyl)-ethanone hydrobromide; (R)-23

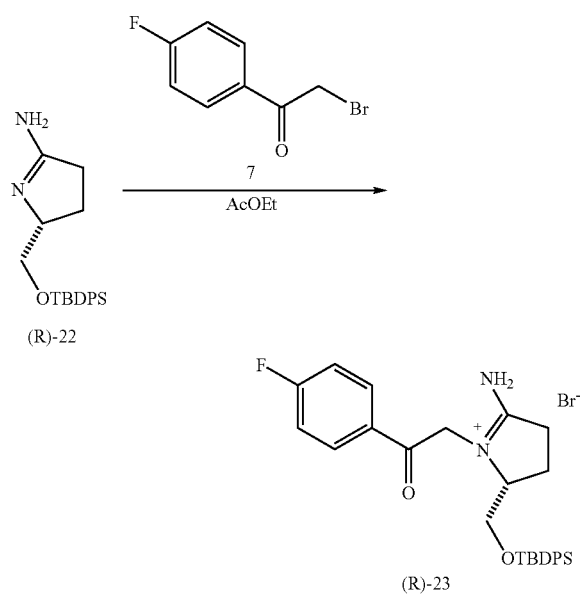

To a stirred solution of (R)-22 (44.9 g, 127 mmol) in AcOEt (410 mL) was added bromomethylketone 7 (34.6 g, 159 mmol) and the reaction mixture stirred for 18 h. The resulting precipitate was filtered and washed with AcOEt to give the hydrobromide salt of starting (R)-22 as a white solid (10.49 g). The mother liquor was evaporated and the residue was placed under high vacuum to give orange foam. The foam was washed with hexane (5×500 mL) with sonication to give (R)-23 as an orange solid (64.65 g, 89%). $^1$H NMR (400 MHz, CDCl$_3$) δ 0.68 (s, 9H), 1.58-1.72 (m, 1H), 2.00-2.15 (m, 1H), 2.94 (m, 2H), 3.40 (dd, J=11.9, 3.0 Hz, 1H), 3.50 (11.8, 6.1 Hz, 1H), 3.83 (m, 1H), 4.71 (d, J=18.5 Hz, 1H), 5.89 (d, J=18.5 Hz, 1H), 6.88 (t, J=8.7 Hz, 2H), 7.10-7.22 (m, 6H), 7.30 (m, 4H), 7.76 (dd, J=8.9, 5.3 Hz, 2H).

(R)-[2-(4-Fluoro-phenyl)-6,7-dihydro-5H-pyrrolo[1,2-a]imidazol-5-yl]-methanol; (R)-9

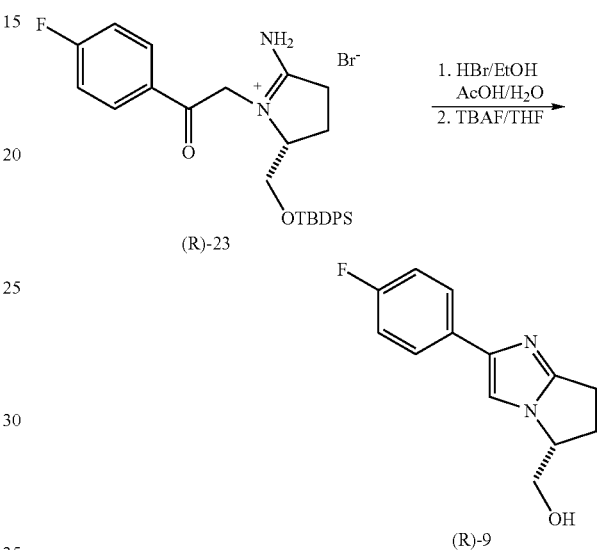

30% HBr in AcOH (0.3 mL) was added to a solution of amidinium salt (R)-23 (64.0 g, 112 mmol) in water (522 mL) and ethanol (260 mL) and the reaction mixture refluxed for 15 h. After cooling, the mixture was neutralized with sat. aq. NaHCO$_3$ (20 g) and extracted with AcOEt. The organic extracts were combined and washed with brine, dried over MgSO$_4$ then concentrated. The resulting oil placed under high vacuum to give (R)-9 (53.3 g, 101%, red foam) as a mixture of TBDPS-protected and unprotected alcohol. This mixture (53.0 g) was dissolved in THF (200 mL), cooled in an ice-bath, and treated rapidly with 1.0 M solution of TBAF in THF (69 mL, 69 mmol). After stirring at room temperature for 1 h the starting material was still present (TLC). The reaction mixture was cooled in an ice-bath and more 1.0 M solution of TBAF in THF (30 mL, 30 mmol) was added, and the stirring continued at r.t. for 40 min. Saturated aqueous NaHCO$_3$ was added and the reaction mixture extracted with AcOEt, and the combined organic extracts washed with water then brine. The organic phase was dried over MgSO$_4$, concentrated, and the residue purified by SGC with gradient elution (100% AcOEt to 10% MeOH in AcOEt) to give (R)-9 (12.0 g, 46%) as a light orange solid. $^1$H NMR (400 MHz, CDCl$_3$) δ 2.35-2.45 (m, 1H), 2.58-2.70 (m, 1H), 2.75-3.00 (m, 2H), 3.69 (dd, J=11.8, 5.9 Hz, 1H), 3.93 (dd, J=11.8, 3.1 Hz, 1H), 4.29 (m, 1H), 4.20-4.60 (bs, OH), 6.99 (s, 1H), 7.04 (t, 8.7 Hz, 2H), 7.57 (dd, J=9.0, 5.5 Hz, 2H); MS (ESP+) m/z 232.9.

(R)-2-(4-Fluoro-phenyl)-5-(4-methoxy-benzyloxymethyl)-6,7-dihydro-5H-pyrrolo[1,2-a]imidazole; (R)-10

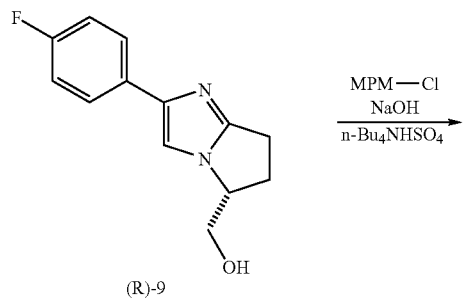

(R)-9

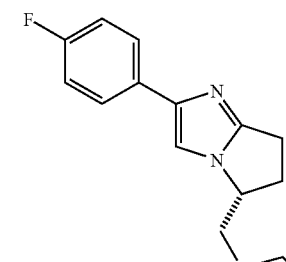

(R)-10

Compound (R)-10 was prepared from (R)-9 (12.0 g, 51.7 mmol), following the method used for (S)-10. Yield 17.84 g (98%) of pale yellow oil, which crystallised on standing in a refrigerator. $^1$H NMR (400 MHz, CDCl$_3$) δ 2.18-2.30 (m, 1H), 2.60-2.75 (m, 1H), 2.80-3.02 (m, 2H), 3.54 (dd, J=9.7, 7.8 Hz, 1H), 3.66 (dd, J=9.7, 3.9 Hz, 1H), 3.81 (s, 3H), 4.42 (m, 1H), 4.47 (d, J=11.6 Hz, 1H), 5.52 (d, J=11.6 Hz, 1H), 6.90 (d, J=8.7 Hz, 2H), 7.05 (t, J=6.7 Hz, 2H), 7.21 (s, 1H), 7.25 (d, J=8.7 Hz, 2H), 7.71 (dd, J=8.9, 5.5 Hz, 2H); MS (ESP+) m/z 353 (M+H).

Stannyl Derivative (R)-11

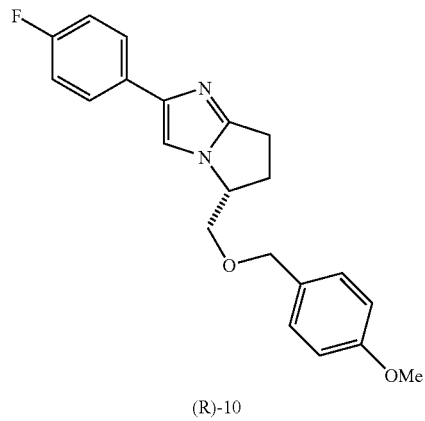

(R)-10

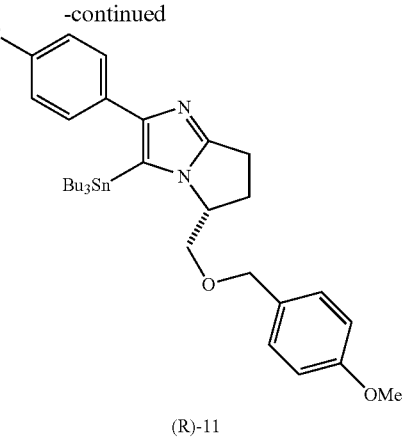

(R)-11

Compound (R)-11 was prepared from (R)-10 (9.0 g, 25.5 mmol) following the method used for preparation of (S)-11. Yield 18.5 g (113%) of crude (R)-11 as dark brown oil.

(R)-2-(4-Fluoro-phenyl)-5-(4-methoxy-benzyloxymethyl)-3-(2-methylsulfanyl-pyrimidin-4-yl)-6,7-dihydro-5H-pyrrolo[1,2-a]imidazole; (R)-12

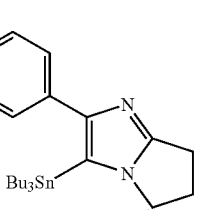

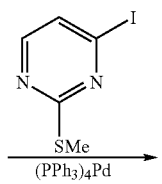

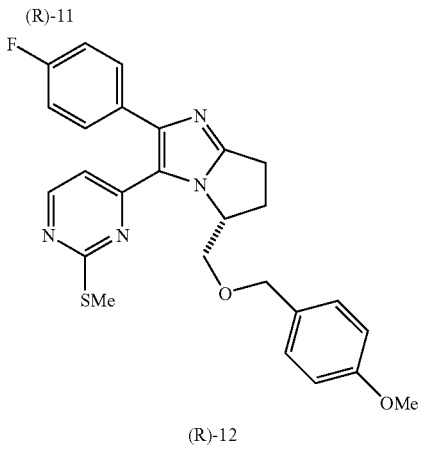

(R)-12

Compound (R)-12 was prepared from (R)-11 (16.38 g 25.5 mmol) following the method used for preparation of (S)-12. Yield 8.29 g (68%) of (R)-12. $^1$H NMR (400 MHz, CDCl$_3$) δ 2.40-2.60 (m, 4H), 2.62-2.85 (m, 3H), 2.90-3.05 (m, 1H), 3.45 (dd, J=9.8, 5.0 Hz, 1H), 3.58 (dd, J=9.8, 3.1

Hz, 1H), 4.17 (d, J=11.7 Hz, 1H), 4.30 (d, J=11.7 Hz, 1H), 5.08 (m, 1H), 6.66 (d, J=5.4 Hz, 1H), 7.01 (m, 4H), 7.45 (dd, J=8.9, 5.5 Hz, 2H), 8.10 (d, J=5.4 Hz, 1H).

(R)-[2-(4-Fluoro-phenyl)-3-(2-methylsulfanyl-pyrimidin-4-yl)-6,7-dihydro-5H-pyrrolo[1,2-a]imidazol-5-yl]-methanol; (R)-13

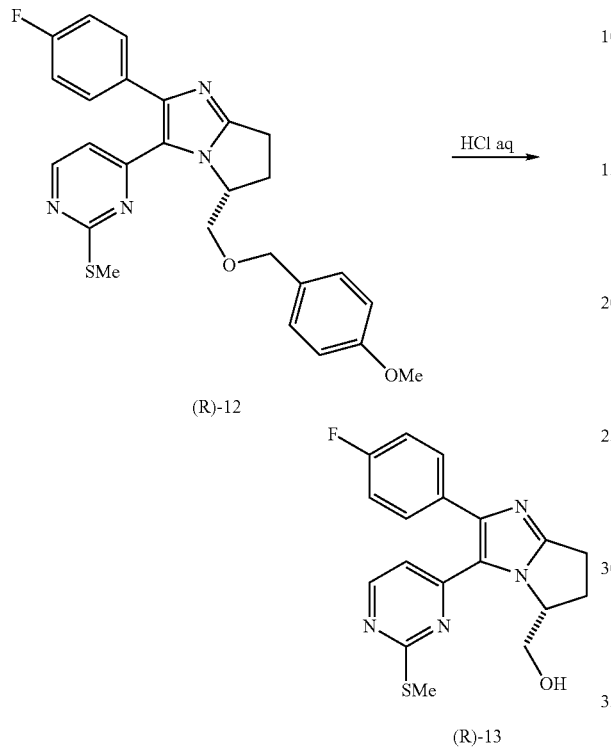

Compound (R)-13 was synthesized from (R)-12 (8.10 g, 17.0 mmol) using the method for preparation of (S)-13. Yield 4.85 g (80%) of (R)-13 as a light orange solid. $^1$H NMR (400 MHz, CDCl$_3$) δ 2.38-2.52 (m, 4H), 2.60-2.85 (m, 2H), 2.90-3.10(m, 1H), 3.49 (t, J=5.1 Hz, OH), 3.73 (m, 11H), 3.85 (m, 11H), 4.95 (m, 1H), 6.73 (d, J=5.4 Hz, 1H), 7.00 (t, J=8.7 Hz, 2H), 7.42 (dd, J=8.8, 5.4 Hz, 2H), 8.15 (d, J=5.4 Hz, 1H); MS (ESP+) m/z 356.9.

Preparation of Alcohol (S)-25

Scheme 5

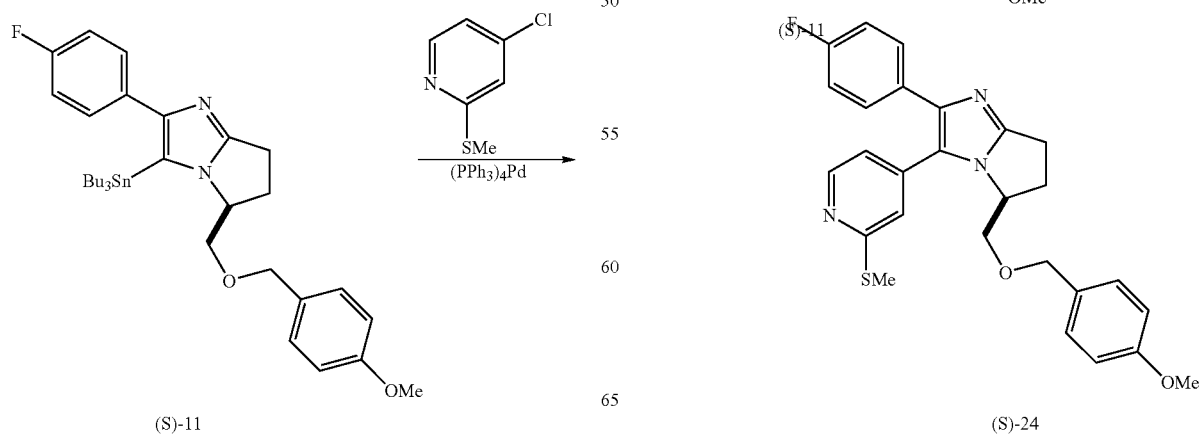

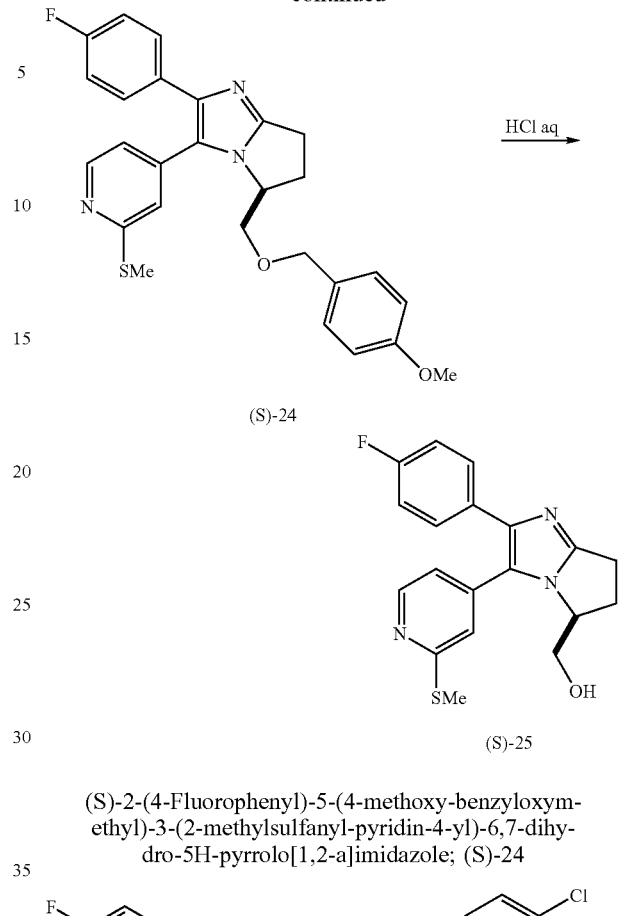

(S)-2-(4-Fluorophenyl)-5-(4-methoxy-benzyloxymethyl)-3-(2-methylsulfanyl-pyridin-4-yl)-6,7-dihydro-5H-pyrrolo[1,2-a]imidazole; (S)-24

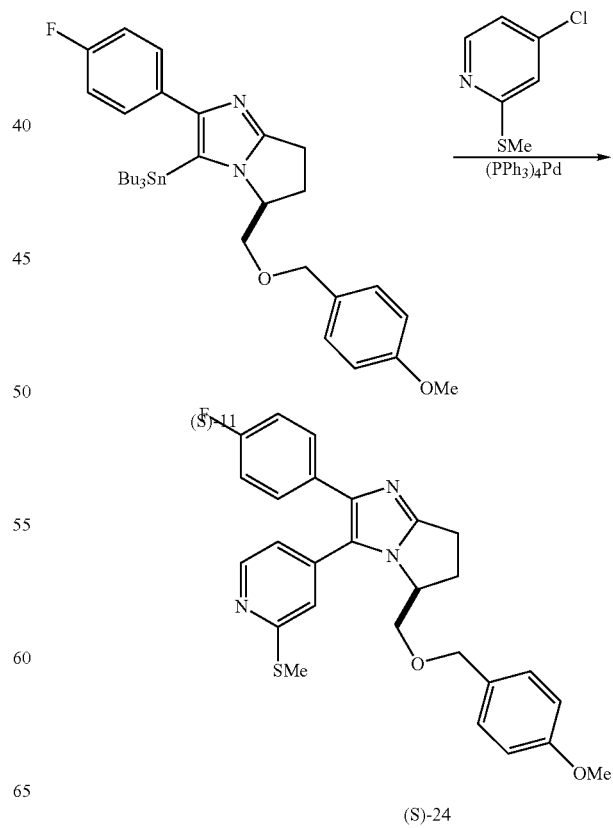

To a solution of the 4-chloro-2-thiomethylpyridine (5.03 g, 31.5 mmol; prepared according to Choppin, S. et al. *Eur. J. Org. Chem.* 2001, 3, 603-606) and stannane (S)-11 (12.62 g, 19.7 mmol) in dimethylformamide (150 mL) was added Pd(PPh$_3$)$_4$ (9.13 g, 7.9 mmol) in one portion, and the mixture was heated at 85° C. in darkness. After 2.5 days the solvent was removed in vacuum and the residue was azeotroped with p-xylene (2×). The resulting material was dissolved in ethyl acetate and washed with water (1×) and brine (1×). The organic layer was dried (MgSO$_4$), filtered and concentrated in vacuo. The crude residue was purified by SGC with hexanes-propan-2-ol (9:1) as eluent to afford a 1:1 (by $^1$H NMR) mixture of the Stille product (S)-24 and byproduct (S)-10; total of 3.98 g, as yellow oil.

(S)-[2-(4-Fluoro-phenyl)-3-(2-methylsulfanyl-pyridin-4-yl)-6,7-dihydro-5H-pyrrolo[1,2-a]imidazol-5-yl]-methanol; (S)-25

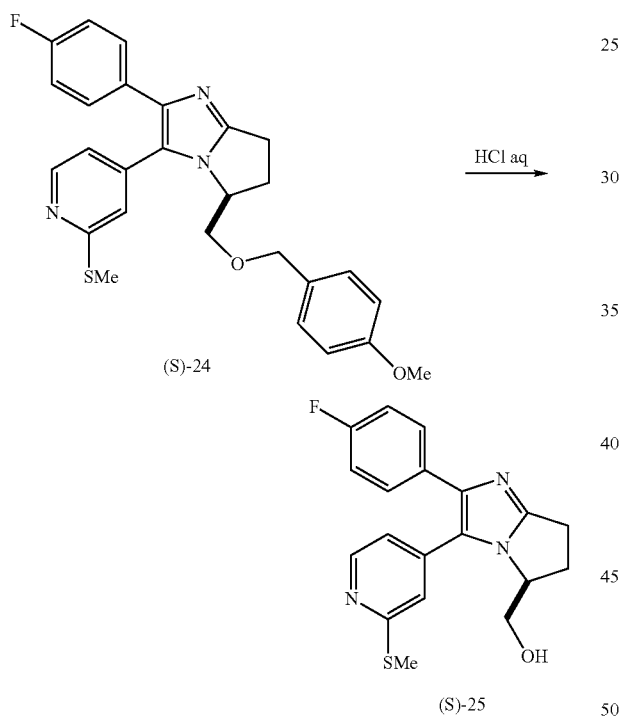

A 1:1 mixture of (S)-24 and (S)-10 prepared in the previous step (200 mg) in 6 M HCl (3.2 mL) and MeOH (0.8 mL) was refluxed for 45 min. The mixture was allowed to cool to r.t. and diluted with CH$_2$Cl$_2$. This solution was slowly transferred into a cooled (0° C.) and stirred 6 M NaOH solution. The mixture was separated and the aqueous layer extracted with CH$_2$Cl$_2$ (2×). The combined organic solutions were dried (MgSO$_4$), filtered and concentrated in vacuo. The crude residue was purified by SGC with AcOEt-MeOH as eluent (gradient elution 10:1 to 5:1) to afford a 10:1 (by UV absorbance in LC-MS) mixture of the alcohols (S)-9 and (S)-25; total yield of 107 mg as a pale yellow oil. This material was used directly in the preparation of alcohol (S)-27 (Method 1, Scheme 6)

Preparation of Alcohol (S)-27 (Method 1)

Scheme 6

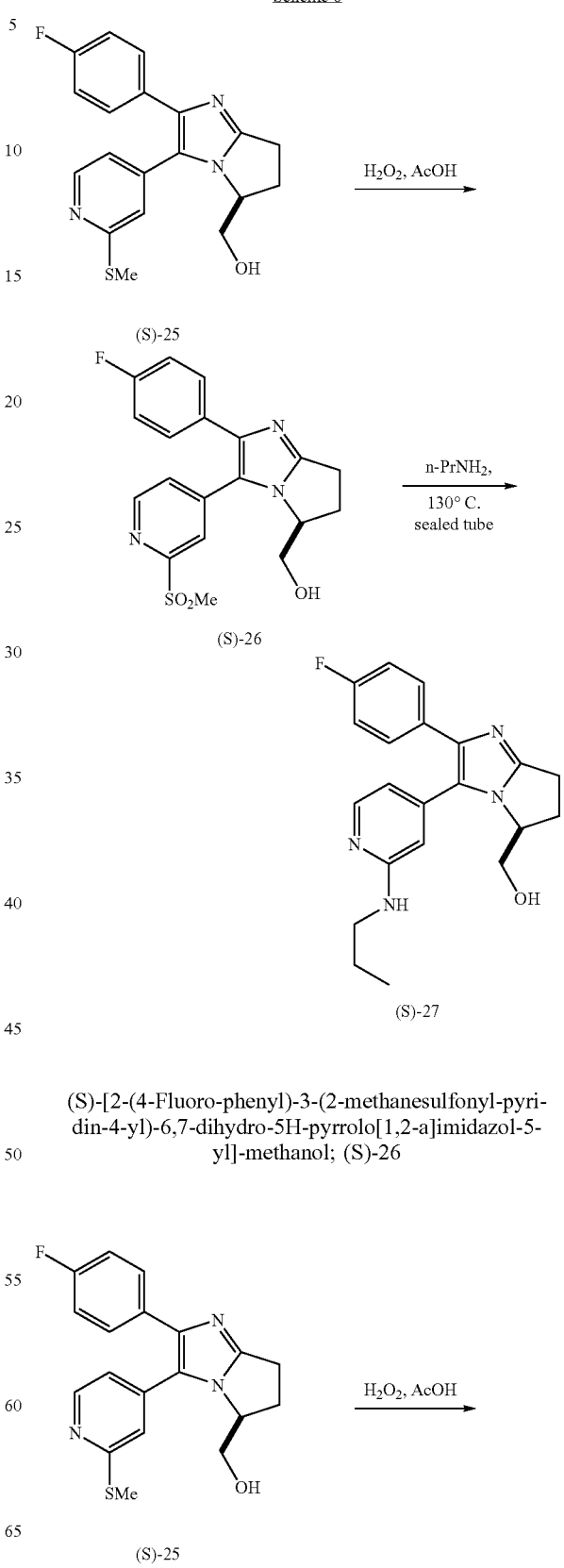

(S)-[2-(4-Fluoro-phenyl)-3-(2-methanesulfonyl-pyridin-4-yl)-6,7-dihydro-5H-pyrrolo[1,2-a]imidazol-5-yl]-methanol; (S)-26

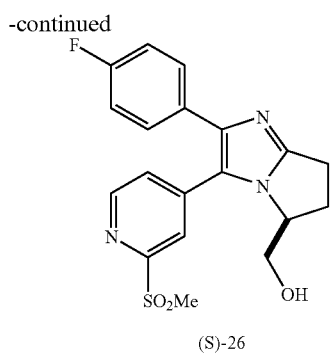

(S)-26

A mixture of the alcohols (S)-9 and (S)-25 obtained in the previous step (total of 90 mg) in 27.5% H₂O₂ (0.1 mL) and AcOH (1 mL) was stirred at r.t. for 3 days. The mixture was diluted with AcOEt and washed with saturated aqueous NaHCO₃. The aqueous layer was washed with AcOEt (3×) and the combined organic extracts dried (MgSO₄), filtered and concentrated in vacuo. The crude residue was purified by preparative thin layer chromatography (PTLC) with AcOEt as eluent (3-fold elution) and AcOEt-MeOH (10:1; 3-fold elution) to afford the methylsulfone (S)-26 (22 mg, 7% starting from (S)-11) as an oil. ¹H NMR (400 MHz; CDCl₃) δ 2.55 (m, 1H), 3.01-2.80 (m, 3H), 3.23 (s, 3H), 3.47 (tt, J=11.6, 4.2 Hz, 2H), 4.66 (m, 1H), 6.98 (t, J=8.7, Hz, 2H), 7.39-7.33 (m, 3H), 7.96 (s, 1H), 8.55 (d, J=5.5 Hz, 1H); MS (ESP+) m/e 388 (M+H).

(S)-[2-(4-Fluoro-phenyl)-3-(2-propylamino-pyridin-4-yl)-6,7-dihydro-5H-pyrrolo[1,2-a]imidazol-5-yl]-methanol; (S)-27

A solution of the methylsulfone (S)-26 (21 mg, 0.05 mmol) in n-PrNH₂ (1.0 mL, 12.2 mmol) was heated at 130° C. in a sealed tube. After 2.5 days the mixture was allowed to cool to r.t. and concentrated in vacuo. The residue was purified by PTLC with CHCl₃:MeOH=40:1 as eluent (8-fold elution) to afford the desired (S)-27 (12 mg, 66%) as a solid. ¹H NMR (400 MHz; CDCl₃) δ 0.94 (t, J=7.4 Hz, 3H), 1.56 (tq, J=7.2, 7.4 Hz, 2H), 2.61 (m, 1H), 2.75-3.13 (m, 6H), 3.53 (t, J=3.1 Hz, 2H), 4.53 (m, 1H), 4.61 (m, 1H), 6.26 (s, 1H), 6.49 (dd, J=5.2, 1.4 Hz, 1H), 6.95 (t, J=8.9 Hz, 2H), 7.48 (dd, J=8.9, 5.5 Hz, 2H), 8.04 (d, J=5.2 Hz, 1H); MS (ESP+) m/e 367 (M+H).

Preparation of Alcohol (S)-27 (Method 2)

Scheme 7

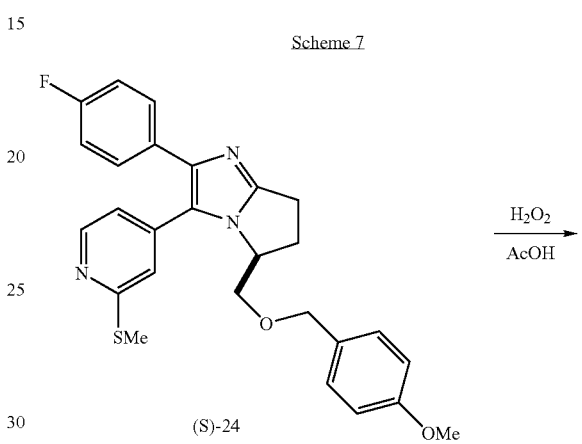

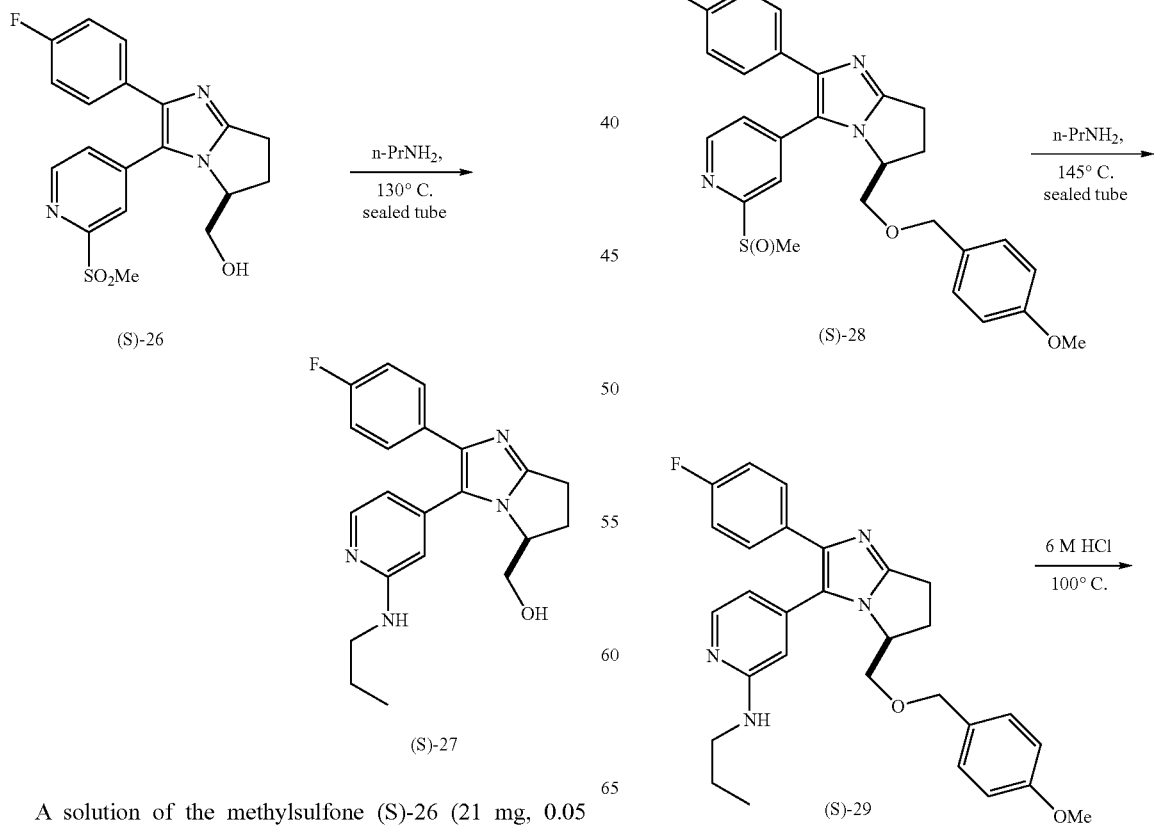

-continued

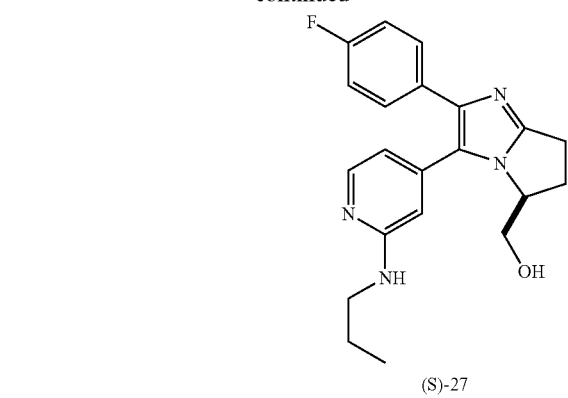

(S)-27

(S)-2-(4-Fluoro-phenyl)-3-(2-methanesulfinyl-pyridin-4-yl)-5-(4-methoxy-benzyloxymethyl)-6,7-dihydro-5H-pyrrolo[1,2-a]imidazole; (S)-28

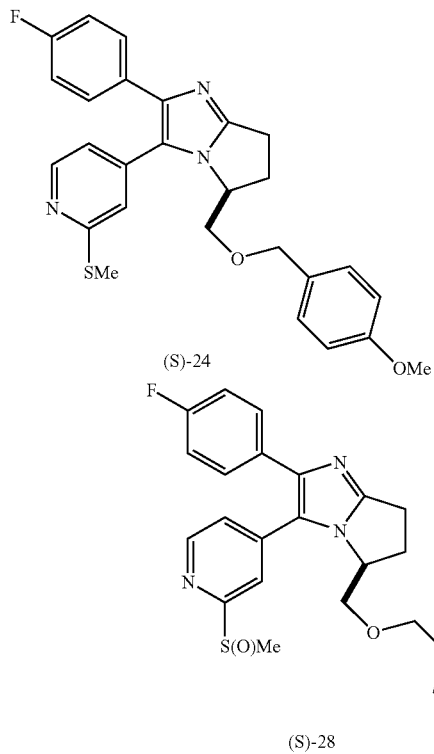

A mixture of the Stille product (S)-24 and imidazole (S)-10 (3.37 g) in 27.5% H$_2$O$_2$ (2 mL) and AcOH (20 mL) was stirred at r.t. for 7 h. The mixture was diluted with AcOEt, quenched with saturated NaHCO$_3$ and separated. The aqueous layer was extracted with AcOEt (3×) and the combined organic solutions dried (MgSO$_4$), filtered and concentrated in vacuo. The crude residue was partially purified by SGC with AcOEt to AcOEt-MeOH as eluent (gradient elution, 5:1 to 2:1) to afford a mixture of sulfoxide (S)-28 and imidazole (S)-10 (698 mg) in 6.3:1 ratio (based on UV absorbance in LC-MS). Further purification of this material by PTLC with AcOEt as eluent furnished sulfoxide (S)-28 (327 mg, 4% from (S)-11) as a solid containing less than 1% of imidazole (S)-10; MS (ESP+) m/e 492.8 (M+H).

(S)-{4-[2-(4-Fluoro-phenyl)-5-(4-methoxy-benzyloxymethyl)-6,7-dihydro-5H-pyrrolo[1,2-a]imidazol-3-yl]-pyridin-2-yl}-propyl-amine; (S)-29

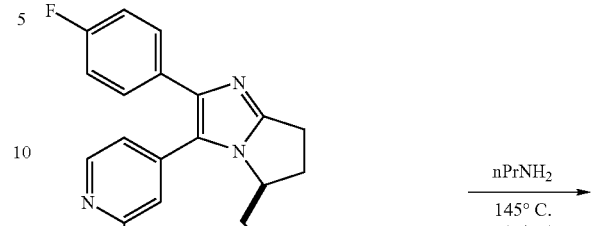

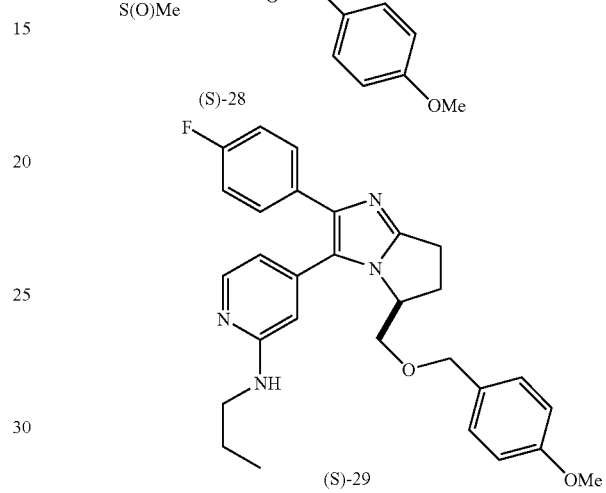

A solution of the sulfoxide (S)-28 (422 mg, 0.86 mmol) in n-PrNH$_2$ (12 mL, 145.9 mmol) was heated at 145° C. in a sealed tube for 6 days. The mixture was allowed to cool to r.t. and then concentrated in vacuo. The residue was purified by SGC with AcOEt:MeOH=50:1) as eluent to afford the desired (S)-29 (314 mg, 75%) as an oil. $^1$H NMR (400 MHz, CDCl$_3$) δ 0.93 (t, J=7.1 Hz, 3H), 1.54 (tq, J=7.4, 7.2 Hz, 2H), 2.76 (m, 1H), 2.56 (m, 1H), 2.91 (dt, J=9.6, 2.6 Hz, 1H), 3.07 (m, 3H), 3.21 (dd, J=9.9, 5.0 Hz, 1H), 3.36 (dd, J=9.9, 3.0 Hz, 1H), 3.74 (s, 3H), 4.13 (d, J=11.8 Hz, 1H), 4.27 (d, J=11.8 Hz, 1H), 6.15 (s, 1H), 4.55 (m, 1H), 6.43 (dd, J=5.2, 1.4 Hz, 1H), 6.78 (d, J=8.8 Hz, 2H), 6.95 (t, J=8.8 Hz, 2H), 7.00 (d, J=8.8 Hz, 2H), 7.51 (dd, J=8.9, 5.5 Hz, 2H), 8.03 (d, J=5.1 Hz, 1H); MS (ESP+) m/e 487.9 (M+H).

(S)-[2-(4-Fluoro-phenyl)-3-(2-propylamino-pyridin-4-yl)-6,7-dihydro-5H-pyrrolo[1,2-a]imidazol-5-yl]-methanol; (S)-27

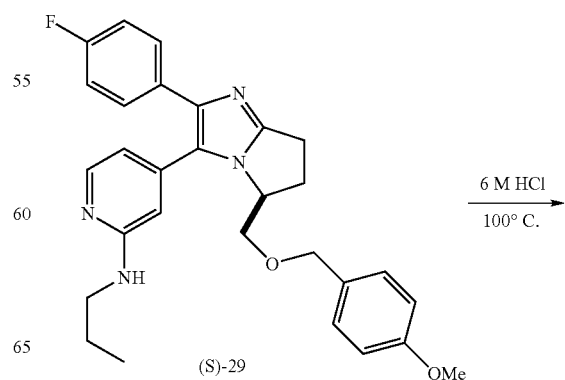

-continued

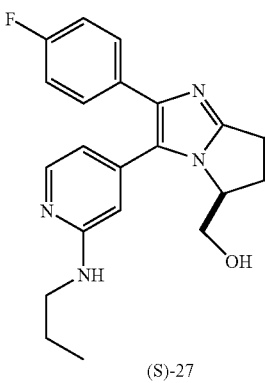

(S)-27

The ether (S)-29 (297 mg, 0.61 mmol) in 6 M HCl (5 mL) and MeOH (12 mL) was refluxed for 1.5 h. The mixture was allowed to cool to r.t. and diluted with AcOEt. The solution was basified to pH 9 by the dropwise addition of 50% aqueous NaOH. The mixture was partitioned and the aqueous layer extracted with AcOEt (3×). The combined organic extracts were washed with brine (1×), dried (MgSO$_4$), filtered and concentrated in vacuo. The crude residue was purified by PTLC with AcOEt, (2-fold elution) to afford the alcohol (S)-27 (129 mg, 58%) as a solid. $^1$H NMR (400 MHz, CDCl$_3$) 0.94 (t, J=7.4 Hz, 3H), 1.56 (tq, J=7.2, 7.4 Hz, 2H), 2.61 (m, 1H), 2.75-3.13 (m, 6H), 3.53 (t, J=3.1 Hz, 2H), 4.53 (m, 1H), 4.61 (m, 1H), 6.26 (s, 1H), 6.49 (dd, J=5.2, 1.4 Hz, 1H), 6.95 (t, J=8.9 Hz, 2H), 7.48 (dd, J=8.9, 5.5 Hz, 2H), 8.04 (d, J=5.2 Hz, 1H); MS (ESP+) m/e 367.0 (M+H).

Preparation of Alcohol (R)-27

Scheme 8

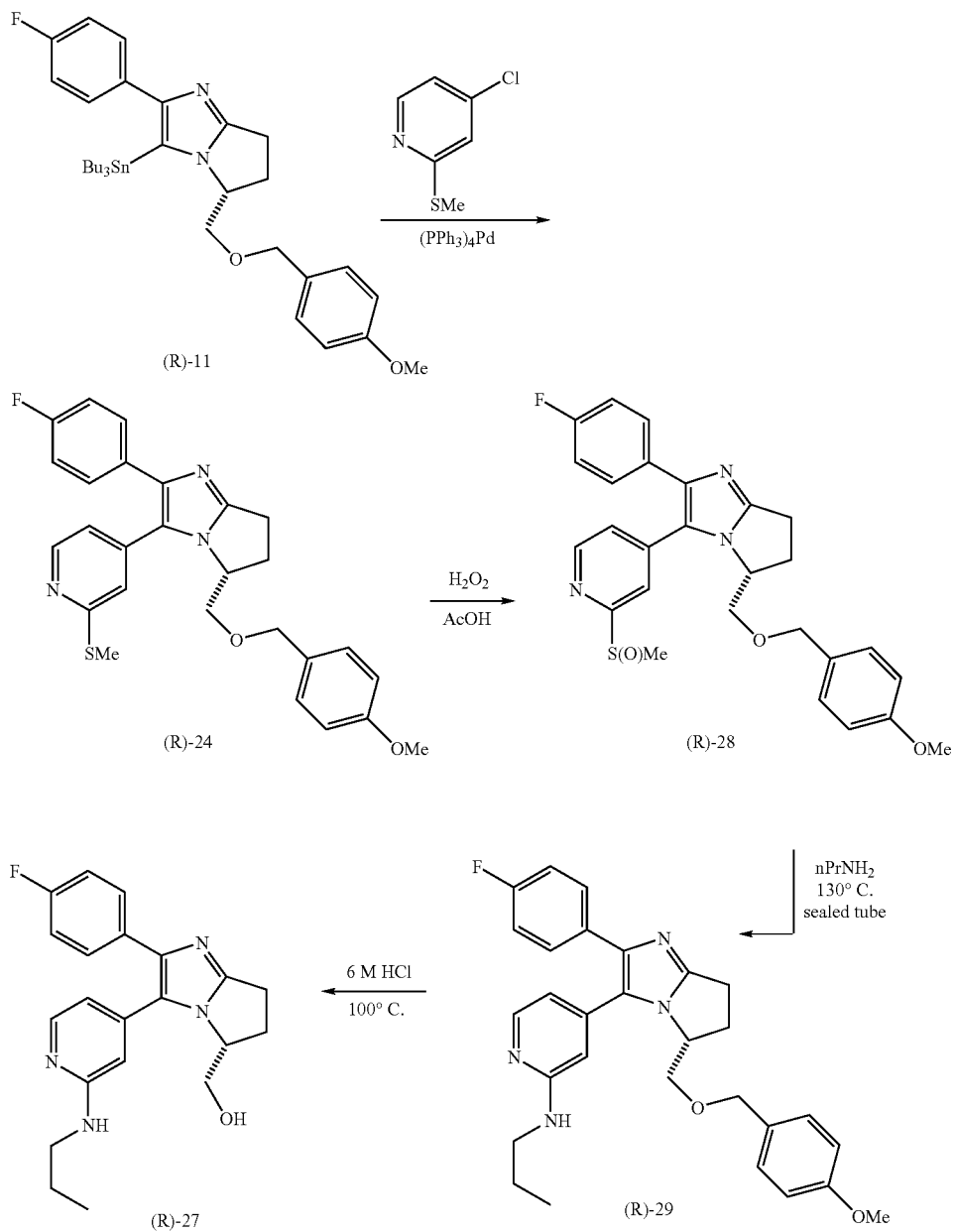

(R)-2-(4-Fluoro-phenyl)-5-(4-methoxy-benzyloxymethyl)-3-(2-methylsulfanyl-pyridin-4-yl)-6,7-dihydro-5H-pyrrolo[1,2-a]imidazole; (R)-24

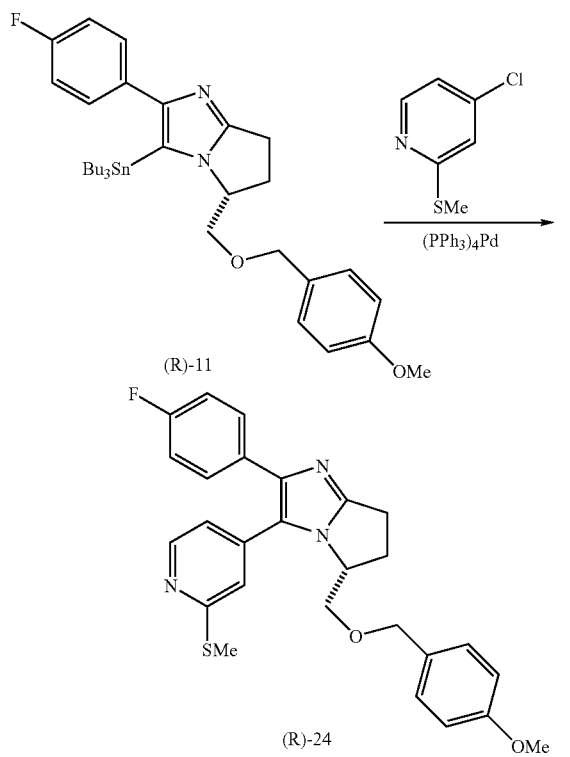

Compound (R)-24 was prepared from (R)-11 (9.69 g, 15.1 mmol) following a modified protocol used for preparation of (S)-24.

To a solution of the 4-chloro-2-thiomethylpyridine (3.86 g, 24.2 mmol) and stannane (R)-11 (9.69 g, 15.1 mmol) in DMF (80 mL) was added Pd(PPh$_3$)$_4$ (6.98 g, 6.0 mmol) in one portion, and the mixture was heated at 85° C. in darkness for 7 days. Solvent was removed in vacuum and the residue was azeotroped with p-xylene (2×). The crude residue was purified by SGC with hexanes:i-PrOH as eluent in gradient (from 9:1 to 1:1 v/v) to afford a 1:2 (by $^1$H NMR) mixture of the Stille product (R)-24 and byproduct (R)-10; total of 1.33 g, as yellow oil. MS (ESP+) m/e 475.9 (M+H) for (R)-24 and m/e 353.9 (M+H) for (R)-10.

(R)-2-(4-Fluoro-phenyl)-3-(2-methanesulfinyl-pyridin-4-yl)-5-(4-methoxy-benzyloxymethyl)-6,7-dihydro-5H-pyrrolo[1,2-a]imidazole; (R)-28

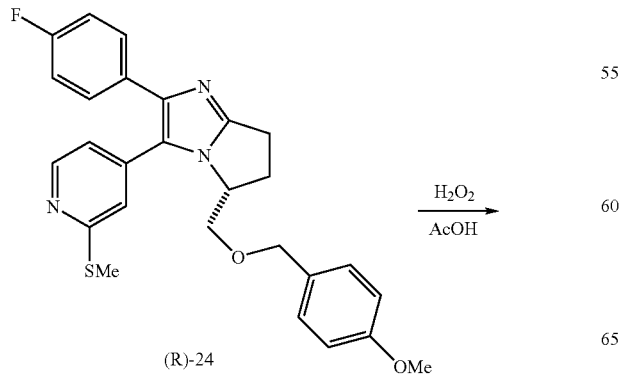

-continued

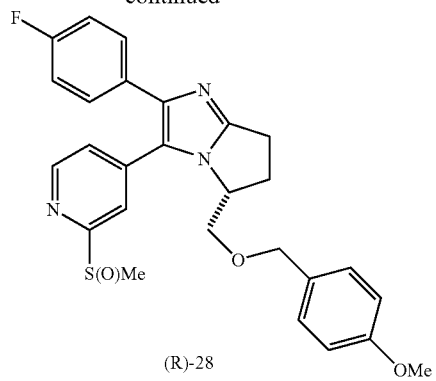

Compound (R)-28 was synthesized from a mixture of the Stille product (R)-24 and byproduct (R)-10 derived from the previous step (1.33 g) using the method for preparation of (S)-28. Yield 182 mg of (R)-28 (2.5% from (R)-11).

(R)-{4-[2-(4-Fluoro-phenyl)-5-(4-methoxy-benzyloxymethyl)-6,7-dihydro-5H-pyrrolo[1,2-a]imidazol-3-yl]-pyridin-2-yl}-propyl-amine; (R)-29

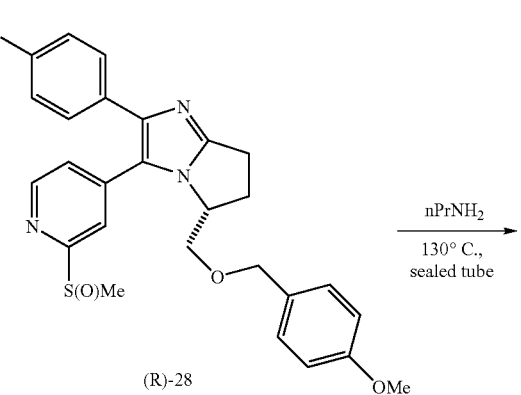

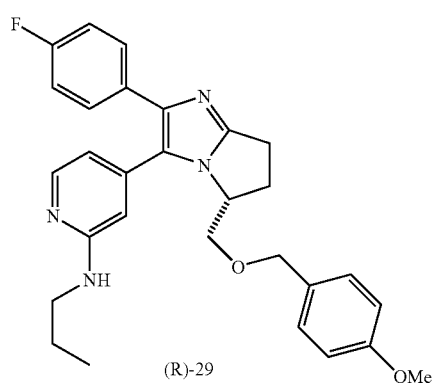

A solution of the sulfoxide (R)-28 (127 mg, 0.259 mmol) in n-PrNH₂ (3 mL) was heated at 130° C. in a sealed tube for 8 days. The mixture was allowed to cool to r.t. and then concentrated in vacuo. The residue was purified by PTLC with AcOEt as eluent (6-fold elution) to afford a 5:1 mixture of the desired (R)-29 and (R)-10 (58 mg) as an oil. This mixture was used in the next step without further purification.

(R)-[2-(4-Fluoro-phenyl)-3-(2-propylamino-pyridin-4-yl)-6,7-dihydro-5H-pyrrolo[1,2-a]imidazol-5-yl]-methanol; (R)-27

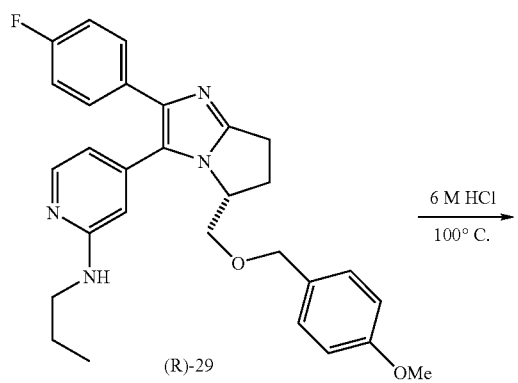

(R)-29

6 M HCl
100° C.

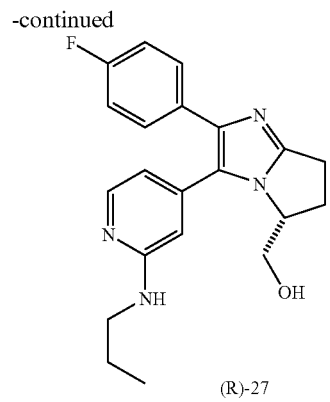

(R)-27

The aforementioned mixture of ether (R)-29 and (R)-10 (58 mg) was treated at 100° C. with 6 M HCl (2 mL) in methanol (4 mL). After 1.5 h the mixture was cooled to r.t., diluted with AcOEt and basified with 50% aqueous NaOH. The mixture was partitioned, and the aqueous layer was extracted with AcOEt (3×). The combined organic extracts were dried (MgSO₄), filtered and concentrated in vacuo. The residue was purified by PTLC with AcOEt:MeOH=10:1 as eluent (2-fold elution) to afford (R)-27 (13 mg, 14% from (R)-28) as an oil.

$^1$H NMR (400 MHz, CDCl₃) 0.94 (t, J=7.4 Hz, 3H), 1.56 (tq, J=7.2, 7.4 Hz, 2H), 2.61 (m, 1H), 3.13-2.75 (m, 6H), 3.53 (t, J=3.1 Hz, 2H), 4.53 (m, 1H), 4.61 (m, 1H), 6.26 (s, 1H), 6.49 (dd, J=5.2, 1.4 Hz, 1H), 6.95 (t, J=8.9 Hz, 2H), 7.48 (dd, J=8.9, 5.5 Hz, 2H), 8.04 (d, J=5.2 Hz, 1H); MS (ESP+) m/e 366.9 (M+H).

Preparation of Alcohol (S)-34.

Scheme 9

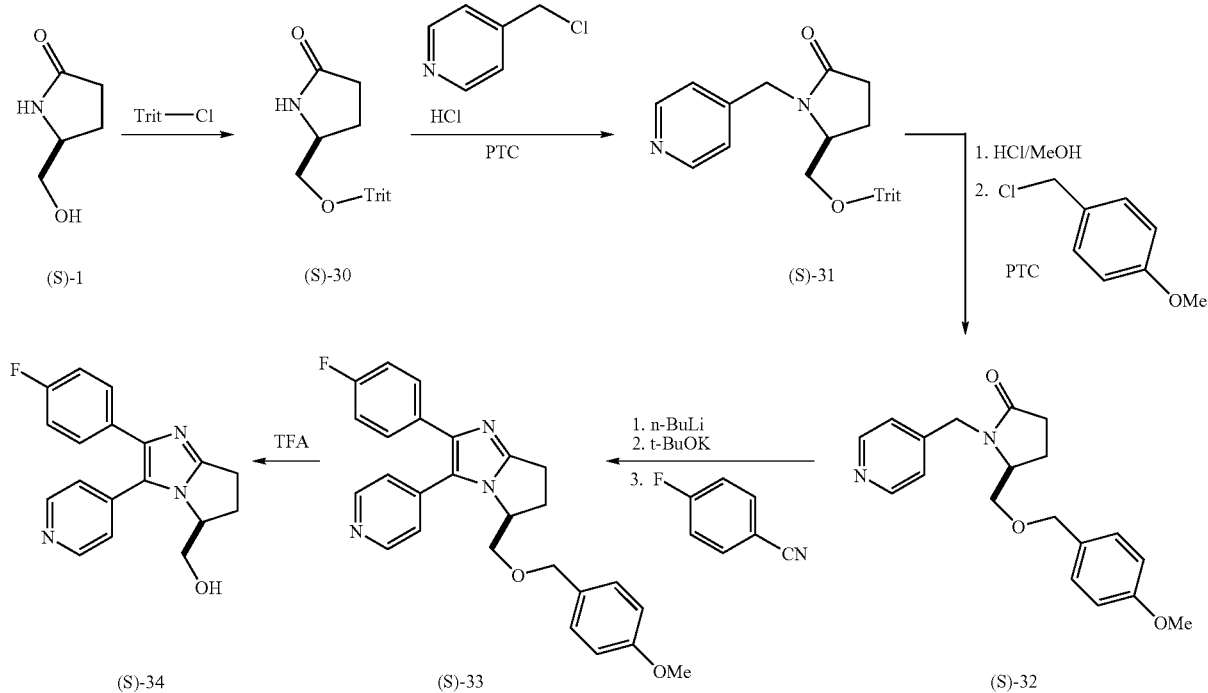

(S)-5-Trityloxymethyl-pyrrolidin-2-one; (S)-30

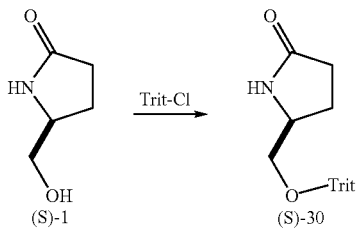

i-Pr₂NEt (160.46 g, 1.24 mol) was added to a stirred and cooled (0° C.) solution of (S)-1 (110.0 g, 0.955 mol), DMAP (11.67 g, 95.5 mmol) and trityl chloride (320 g, 1.24 mol) in DMF (200 mL). Cooling bath was removed and the mixture was stirred at r.t. overnight. Solvents were removed by evaporation in vacuum and the residue was separated between AcOEt-water. The aqueous layer was extracted with AcOEt (8×1 L). Combined organic solutions were washed with brine (3 L), concentrated and purified by means of SGC with CH₂Cl₂-AcOEt (in gradient up to 5% AcOEt) to give (S)-30 (300.0 g, 88%).

(S)-1-Pyridin-4-ylmethyl-5-trityloxymethyl-pyrrolidin-2-one; (S)-31

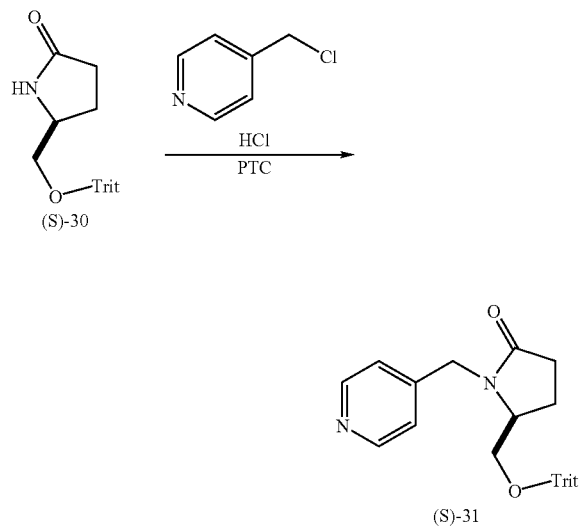

A 50% aqueous sodium hydroxide solution (198 mL, 3.8 mol) was added slowly to a stirred and cooled (8° C.; ice bath) mixture of (S)-30 (270.0 g, 755 mmol), picolyl chloride hydrochloride (136.28 g, 831 mmol), n-Bu₄NHSO₄ (25.65 g, 75.53 mmol) and benzene (1.5 L). An exothermic reaction occurred and the temperature of the mixture reached 15° C. Cooling bath was removed and the reaction mixture was stirred at r.t. overnight. The organic layer was decanted off. The aqueous layer was extracted with benzene (3×0.5 L). Organic solutions were combined and concentrated in vacuum. The residue was purified by SGC with hexane:CH₂Cl₂ as eluent in gradient (up to 100% CH₂Cl₂) and then with CH₂Cl₂:AcOEt in gradient (up to 100% AcOEt) to afford (S)-31 (312 g, 92%).

(S)-5-(4-Methoxy-benzyloxymethyl)-1-pyridin-4-ylmethyl-pyrrolidin-2-one; (S)-32

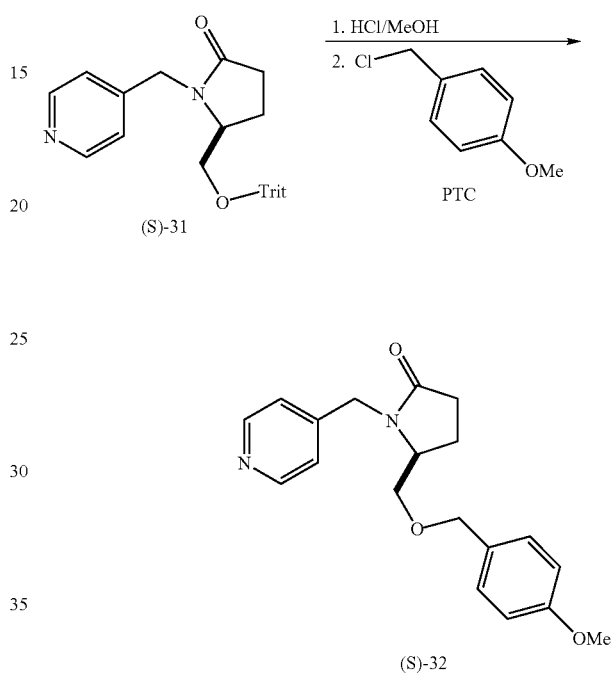

A 4.0 M solution of HCl in MeOH (450 mL, 1.8 mol) was added to (S)-31 (311.0 g, 693 mmol) and the mixture was stirred at r.t. overnight to form a suspension. The mixture was diluted with MeOH and washed with hexane (3×1 L). Hexane layer was discarded. Benzene was added to the methanolic layer, and the mixture was concentrated in vacuum. The residue was dried by repeated evaporation with toluene (2×1 L) and subsequently in vacuum to give 223 g of crude alcohol hydrochloride salt as yellow viscous oil. The salt (whole amount) and n-Bu₄NHSO₄ (23.54 g, 69.33 mmol) were dissolved in benzene (320 mL). The solution was cooled to 0° C. and 50% aqueous NaOH solution (277 mL, 5.26 mol) was added slowly followed by a solution of p-methoxybenzyl chloride (MPM-Cl; 130.29 g, 832 mmol) in benzene (1.6 L). Exothermic reaction occurred. The mixture was stirred overnight at r.t. More MPM-Cl (12.7 g, 81.1 mmol) and 50% aqueous NaOH (30 mL, 570 mmol) was added and stirring continued for 7 h. The organic layer was decanted off. The aqueous layer was extracted with benzene (3×0.5 L). The organic solutions were combined and concentrated in vacuum. The residue was purified by SGC with CH₂Cl₂:MeOH (in gradient) to afford (S)-32 (213 g, 94%).

177
(S)-2-(4-Fluoro-phenyl)-5-(4-methoxy-benzyloxym-ethyl)-3-pyridin-4-yl-6,7-dihydro-5H-pyrrolo[1,2-a]imidazole; (S)-33

178
(S)-[b 2-(4-Fluoro-phenyl)-3-pyridin-4-yl-6,7-dihy-dro-5H-pyrrolo[1,2-a]imidazol-5-yl]-methanol; (S)-34

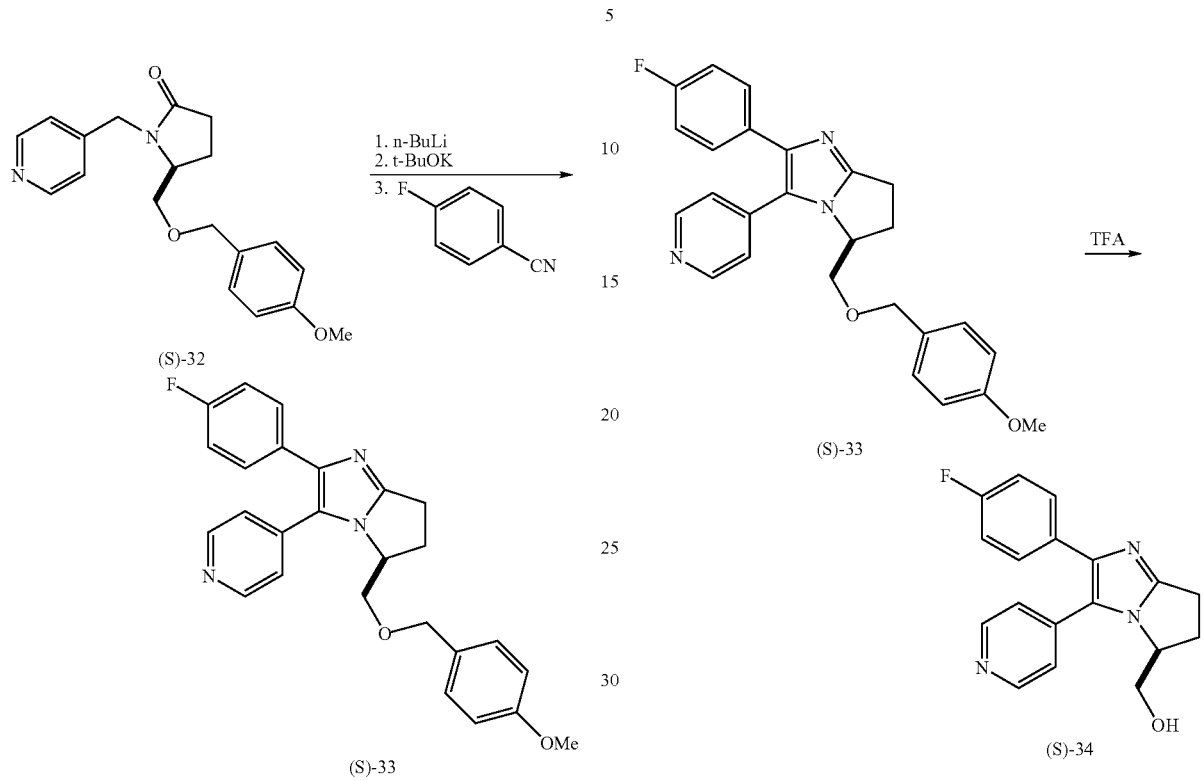

1.6 M n-BuLi in hexane (426 mL, 682 mmol) was added dropwise to a stirred and cooled (−48° C.) solution of (S)-32 (198.0 g, 606 mmol) in THF (2.0 L) and the yellow solution was stirred at −48° C. for 5 min. Then, 1.0 M solution of t-BuOK in THF (620 mL, 620 mmol) was added, the mixture was stirred at −48° C. for 10 rnin, and was treated with a solution of 4-fluorobenzonitrile (225 g, 1.86 mol) in THF (300 mL). Stirring was continued at −48° C. for 1 h and then overnight at r.t. The reaction was quenched with water (200 mL), and the mixture was separated between AcOEt and water. The aqueous layer was extracted with AcOEt (6×2 L). Combined organic solutions were washed with brine, dried (MgSO$_4$), concentrated and separated by means of SGC with AcOEt to afford (S)-33 (52.0 g, 20%) as yellow oil.

TFA (350 mL) was added to (S)-33 (33.13 g, 77.14 mmol) and the solution was stirred at r.t. overnight. The volatiles were removed under reduced pressure and the residue was dissolved in CH$_2$Cl$_2$ (100 mL). Saturated aqueous solution of NaHCO$_3$ was added slowly to raise pH of the mixture to 8.0. The organic layer was separated and the aqueous layer was extracted with CH$_2$Cl$_2$ (6×200 mL). Combined organic solutions were washed with brine, dried (MgSO$_4$), concentrated and purified by SGC with CH$_2$Cl$_2$:MeOH as eluent (in gradient, up to 10% MeOH) to give (S)-34 (17.93 g, 76%).
$^1$H NMR (250 MHz, CDCl$_3$) δ 1.93 (bs, 1H), 2.55-2.70 (m, 1H), 2.70-2.88 (m, 1H), 2.88-3.08 (m, 2H), 3.40-3.52 (m, 2H), 4.49-4.58 (m, 1H), 6.90-7.00 (m, 2H), 7.15-7.22 (m, 2H), 7.34-7.42 (m, 2H), 8.47-8.50 (m, 2H); MS (APCI+) m/e 310 (M+H).

Preparation of Alcohol (R)-34.

Scheme 10

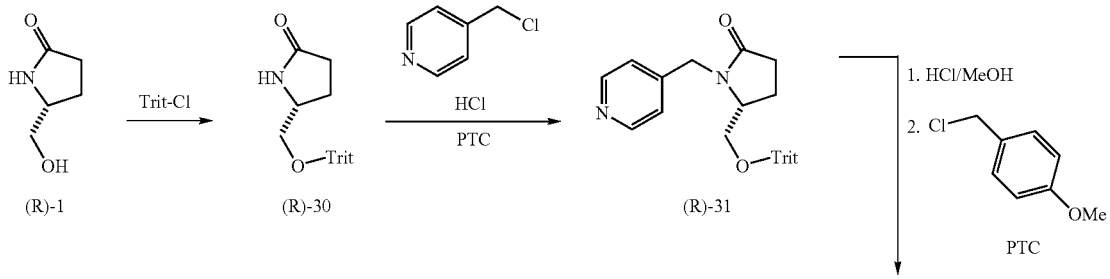

-continued

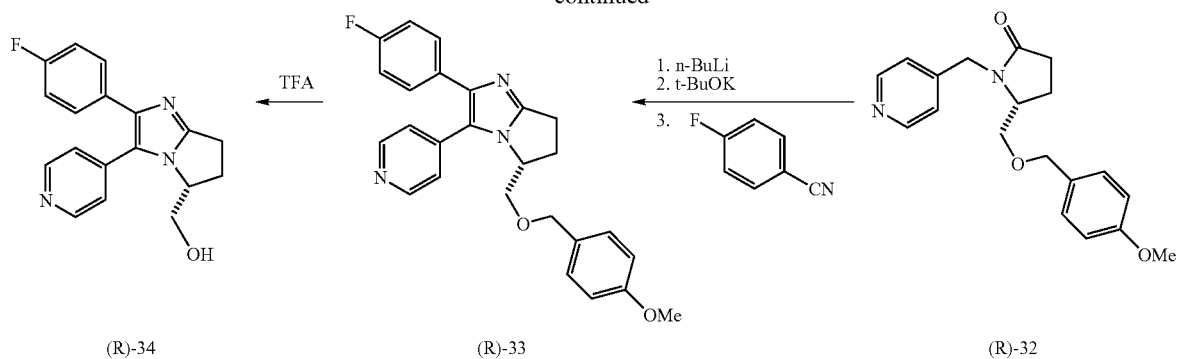

(R)-5-Trityloxymethyl-pyrrolidin-2-one; (R)-30

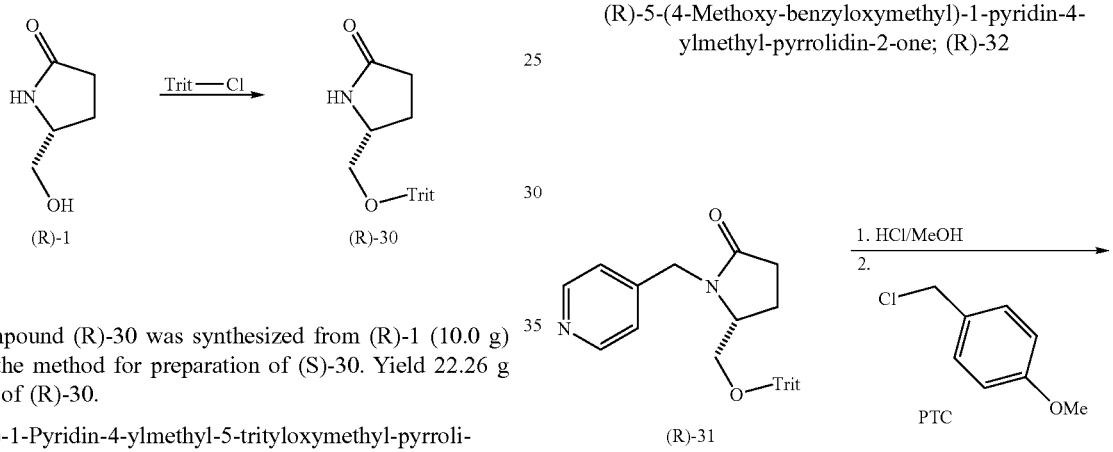

Compound (R)-30 was synthesized from (R)-1 (10.0 g) using the method for preparation of (S)-30. Yield 22.26 g (72%) of (R)-30.

(S)-1-Pyridin-4-ylmethyl-5-trityloxymethyl-pyrrolidin-2-one; (R)-31

Compound (R)-31 was synthesized from (R)-30 (22.26 g) using the method for preparation of (S)-31. Yield 19.79 g (70%) of (R)-31.

(R)-5-(4-Methoxy-benzyloxymethyl)-1-pyridin-4-ylmethyl-pyrrolidin-2-one; (R)-32

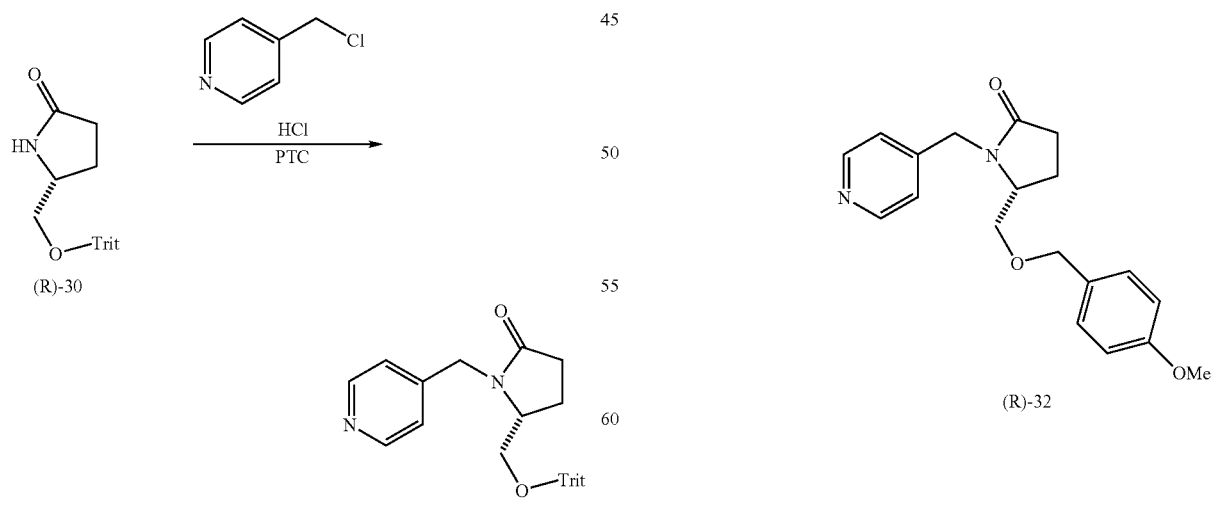

Compound (R)-32 was synthesized from (R)-31 (23.28 g) using the method for preparation of (S)-32. Yield 13.08 g (77%) of (R)-32.

(R)-2-(4-Fluoro-phenyl)-5-(4-methoxy-benzyloxymethyl)-3-pyridin-4-yl-6,7-dihydro-5H-pyrrolo[1,2-a]imidazole; (R)-33

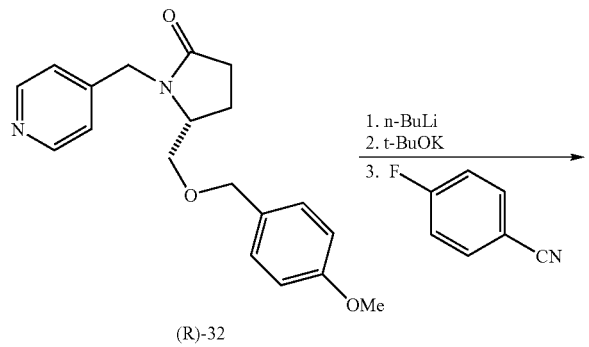

Compound (R)-33 was synthesized from (R)-32 (13.08 g) using the method for preparation of (S)-33. Yield 2.15 g (25%) of (R)-33.

(R)-[2-(4-Fluoro-phenyl)-3-pyridin-4-yl-6,7-dihydro-5H-pyrrolo[1,2-a]imidazol-5-yl]-methanol; (R)-34

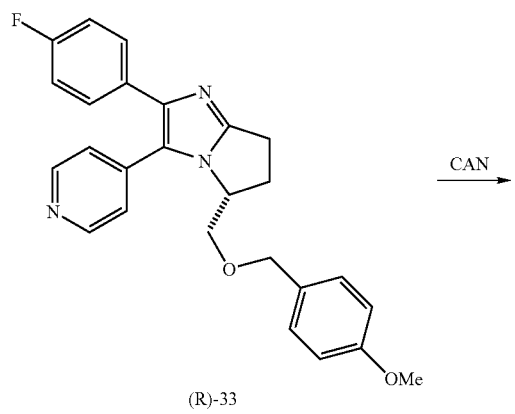

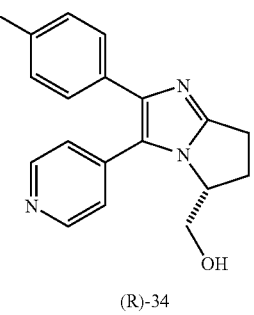

0.5 M aqueous solution of cerium (IV) ammonium nitrate (CAN; 8.6 mL, 4.3 mmol) was added to a solution of (R)-33 (1.00 g, 2.33 mmol) in $CH_2Cl_2$ (16 mL) and a mixture was stirred at r.t. Additional portions of aqueous 0.5 M CAN solution (2.9 and 2.5 mL, total of 2.7 mmol) were added after 0.5 and 1.5 h, respectively. The mixture was stirred for 4.5 h at r.t., and the reaction was quenched by the addition of aqueous $NaHCO_3$ solution. The mixture was extracted with AcOEt. Combined extracts were dried ($MgSO_4$), concentrated and separated by means of SGC with $CH_2Cl_2$:MeOH as eluent in gradient (from 0 to 5% of MeOH) to afford (R)-34 (300 mg, 42%) as a tan solid.

Synthesis of Example imidazo[1,2-a]pyridine (S)-44 (Scheme 11)

Scheme 11

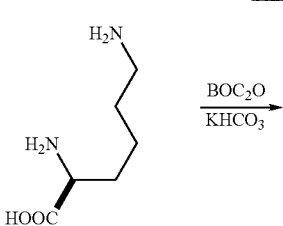

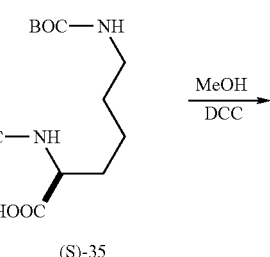

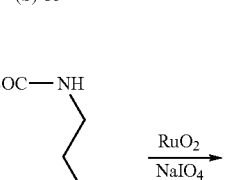

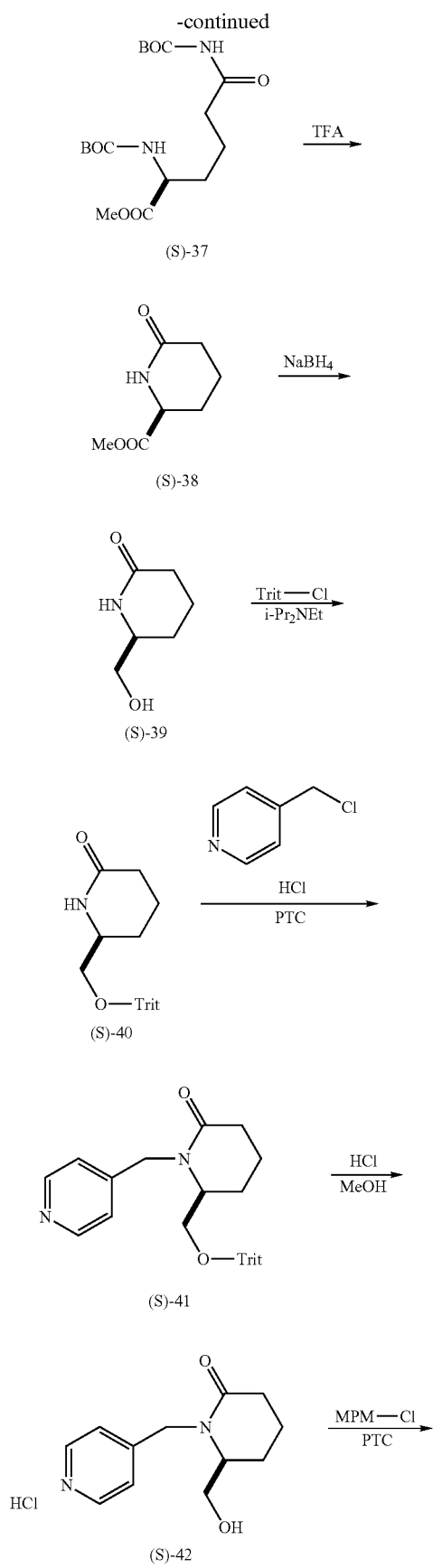
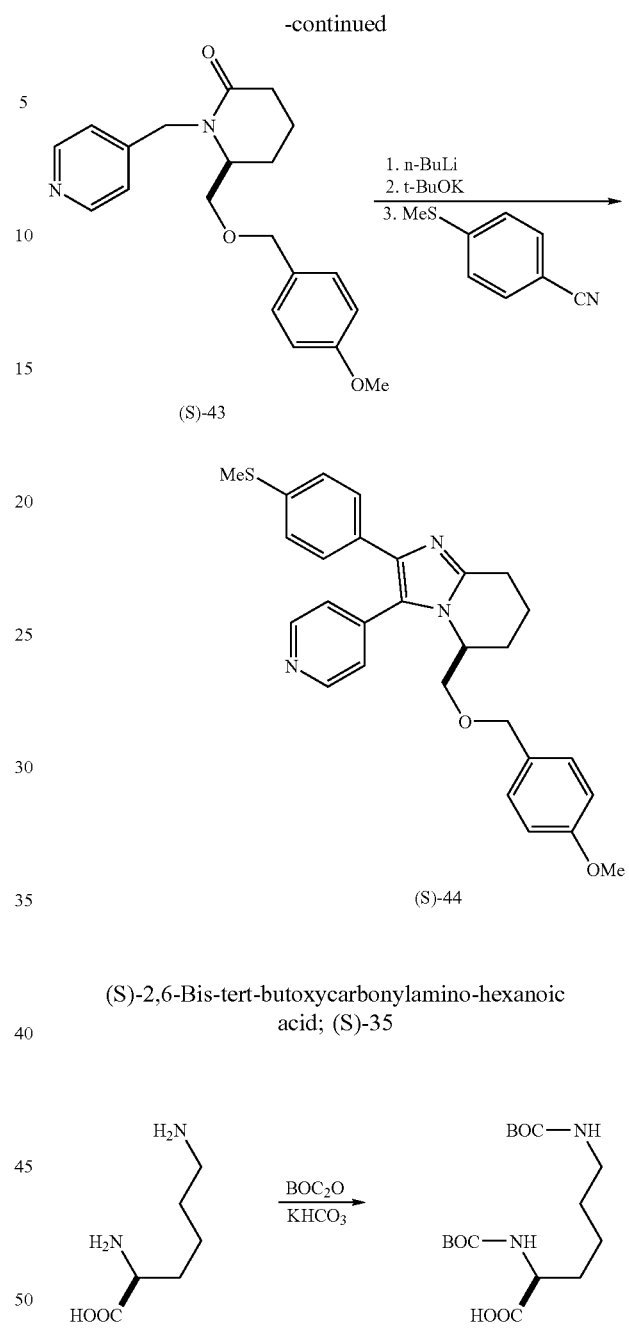

(S)-2,6-Bis-tert-butoxycarbonylamino-hexanoic acid; (S)-35

A mixture of l-lysine (2.012 g, 13.76 mmol), di-tert-butyl dicarbonate (BOC$_2$O; 7.21 g, 33.0 mmol) and KHCO$_3$ (7.008 g, 70.0 mmol) in methanol (50 mL) was stirred at r.t. for 3 days. The mixture was concentrated in vacuum, acidified to pH 4 with 10% aqueous citric acid, and extracted with AcOEt (3×30 mL). Combined organic solutions were washed with brine, dried MgSO$_4$, and concentrated to give (S)-35 (5.05 g, 106%) as a white foam. $^1$H NMR (400 MHz, DMSO-d$_6$) δ 1.20-1.63 (m, 6H), 1.35 (s, 9H), 1.36 (s, 9H), 2.82-2.90 (m, 2H), 3.79 (td, J=8.6, 4.5 Hz, 1H), 6.75 (t, J=5.4 Hz, 1H), 6.99 (t, J=7.9 Hz, 1H), 12.4 (bs, 1H).

(S)-2,6-Bis-tert-butoxycarbonylamino-hexanoic acid methyl ester; (S)-36

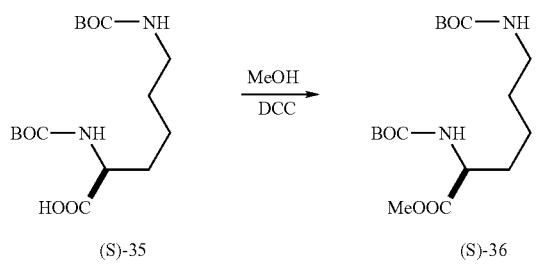

MeOH (3.4 mL, 84 mmol) was added at r.t. to a stirred mixture of (S)-35 (26.23 g, 75.86 mmol), DCC (17.2 g, 83.4 mmol) and DMAP (8.35 mmol) in dry $CH_2Cl_2$ (220 mL). After overnight stirring at r.t. the mixture was filtered and concentrated. The residue was purified by SGC with hexane-AcOEt as eluent to afford (S)-36 (27.28 g, quant.) as colourless glass. $^1$H NMR (250 MHz, $CDCl_3$) δ 1.23-1.88 (m, 6H), 1.43 (s, 18H), 3.10 (q, J=6.3 Hz, 2H), 3.73 (s, 3H), 4.22-4.33 (m, 1H), 4.59 (bs, 1H), 5.10 (d, J=7.7 Hz, 1H).

(S)-2,6-Bis-tert-butoxycarbonylamino-6-oxo-hexanoic acid methyl ester; (S)-37

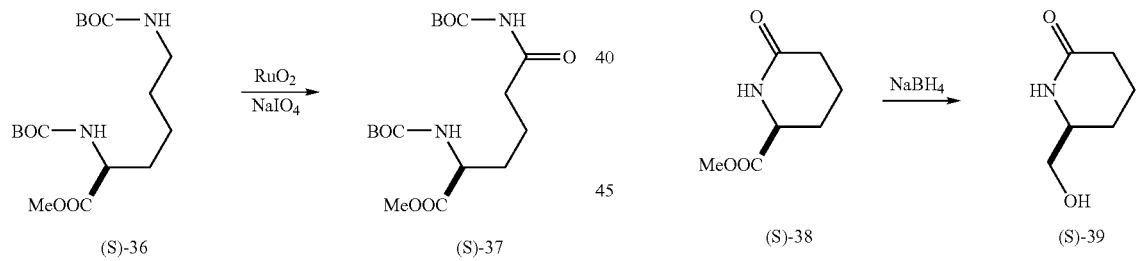

A solution of (S)-36 (26.42 g, 73.3 mmol) in AcOEt (210 mL) was added to a solution of $NaIO_4$ (36.6 g, 171.1 mmol) and $RuO_2$ hydrate (496 mg, 3.73 mmol) in water (300 mL). The mixture was then stirred at r.t. in a closed flask in darkness for 7 h. Organic phase was separated and the aqueous layer was extracted with AcOEt (3×70 mL). Combined organic yellow solutions were treated with propan-2-ol (25 mL, 326 mmol). Black precipitate appeared. The black suspension was stirred at r.t. overnight, filtered, and concentrated to give (S)-37 (27.20 g, 99%) as a brown foam, which was directly used for preparation of (S)-38. Analytical sample of (S)-37 was isolated by means of PTLC with hexane:AcOEt=2:1 as eluent; $^1$H NMR (250 MHz, $CDCl_3$) δ 1.43 (s, 9H), 1.48 (s, 9H), 1.63-1.78 (m, 4H), 2.67-2.77 (m, 2H), 3.73 (s, 3H), 4.25-4.35 (m, 1H), 5.14 (d, J=8.3 Hz, 1H), 7.46 (bs, 1H).

(S)-6-Oxo-piperidine-2-carboxylic acid methyl ester; (S)-38

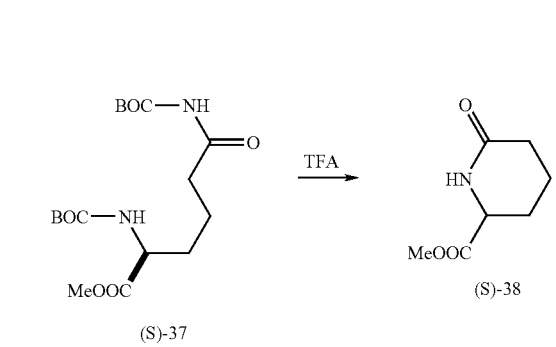

A solution of (S)-37 (27.20 g, 72.6 mmol) in TFA (160 mL) was stirred at 85° C. for 4 h. The reaction mixture was concentrated in vacuum and purified by SGC using as eluent hexane:$CH_2Cl_2$ (in gradient) followed by $CH_2Cl_2$ and $CH_2Cl_2$:MeOH, to afford (S)-38 (12.885 g, 113%). $^1$H NMR (250 MHz, $CDCl_3$) δ 1.70-2.00 (m, 3H), 2.12-2.32 (m, 1H), 2.41-2.55 (m, 2H), 3.80 (s, 3H), 4.10-4.22 (m, 1H), 7.32 (bs, 1H).

(S)-6-Hydroxymethyl-piperidin-2-one; (S)-39

To a cooled (ice bath) solution of (S)-38 (12,885 g, 82.03 mmol) in MeOH (65 mL), was added $NaBH_4$ (total of 11 g, 0.29 mol) in small portions at such a rate that the temperature of the reaction mixture was maintained below 10° C. The formed thick suspension was left in a refrigerator overnight. Then, MeOH (100 mL) was added followed by silicagel (Kieselgel 60, 230-400 mesh, 100 g) and benzene (250 mL). Solvents were removed by evaporation under reduced pressure. The residue was applied on a silicagel column, and the product was eluted with $CH_2Cl_2$:MeOH (in gradient) to afford (S)-39 (7.20 g, 68%) as colourless oil. $^1$H NMR (250 MHz, $CDCl_3$) δ 1.20-1.43 (m, 1H), 1.57-1.94 (m, 3H), 2.12-2.42 (m, 2H), 3.33-3.56 (m, 2H), 3.62 (d, J=8.6 Hz, 1H), 4.63 (s, 1H), 7.34 (s, 1H). $^{13}$C NMR (62.9 MHz, $CDCl_3$)) δ 19.48, 24.31, 31.21, 54.84, 66.00, 173.28.

(S)-6-Trityloxymethyl-piperidin-2-one; (S)-40

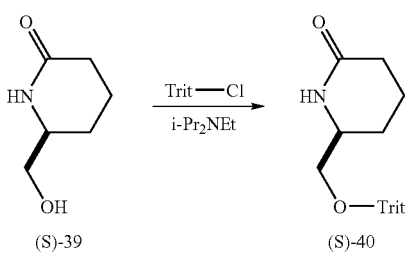

A mixture of (S)-39 (5.85 g, 45.3 mmol), trityl chloride (16.04 g, 57.5 mmol), i-Pr$_2$NEt (11.6 mL, 66.6 mmol) and DMAP (0.527 g, 4.31 mmol) in DMF (21 mL) was stirred at r.t for 3 days. Reaction mixture was separated between brine (80 mL) and water (80 mL). The aqueous layer was extracted with AcOEt (4×80 mL). Combined organic solutions were washed with brine, dried (MgSO$_4$), concentrated and separated by SGC with hexane:AcOEt (in gradient, up to 40% AcOEt) to afford (S)-40 as a foam; yield 12.20 g (73%). $^1$H NMR (250 MHz, CDCl$_3$) δ 1.16-1.34 (m, 1H), 1.58-1.90 (m, 3H), 2.17-2.31 (m, 1H), 2.33-2.47 (m, 1H), 2.94 (t, J=9.1 Hz, 1H), 3.23 (dd, J=9.1, 3.1 Hz, 1H), 3.56-3.68 (m, 1H), 6.21 (s, 1H), 7.21-7.45 (m, 15H).

(S)-1-Pyridin-4-ylmethyl-6-trityloxymethyl-piperidin-2-one; (S)-41

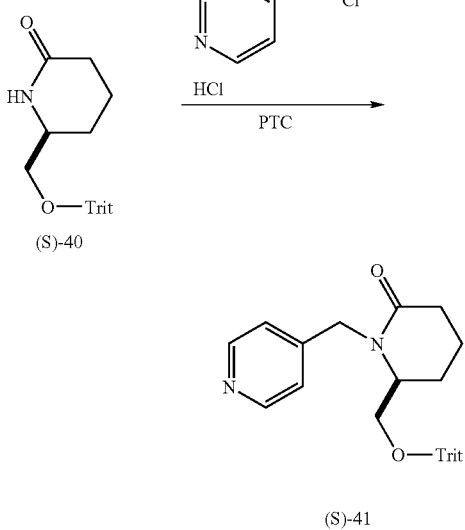

A mixture of (S)-40 (14.57 g, 39.22 mmol), picolyl chloride hydrochloride (6.42 g, 39.1 mmol), n-Bu$_4$NHSO$_4$ (1.45 g, 4.27 mmol) and 50% aqueous NaOH (10.2 mL, ca 195 mmol) in benzene (78 mL) was stirred at r.t for 3 days. The organic layer was separated and the residue was extracted with benzene (3×50 mL). Combined organic solutions were concentrated and separated by SGC with CH$_2$Cl$_2$:MeOH as eluent (gradient up to 5% MeOH) to afford (S)-41 (12.20 g, 67%) as white foam. $^1$H NMR (250 MHz, CDCl$_3$) δ 1.70-1.93 (m, 3H), 2.04-2.17 (m, 1H), 2.46 (t, J=6.3 Hz, 2H), 3.11 (dd, J=9.8, 7.3 Hz, 1H), 3.21 (dd, J=9.8, 4.3 Hz, 1H), 3.40-3.50 (m, 1H), 3.97 (d, J=15.9 Hz, 1H), 5.00 (d, J=15.9 Hz, 1H), 6.92 (d, J=6.0 Hz, 2H), 7.20-7.40 (m, 15H), 8.46 (d, J=6.0 Hz, 2H).

(S)-6-(4-Methoxy-benzyloxymethyl)-1-pyridin-4-ylmethyl-piperidin-2-one; (S)-43

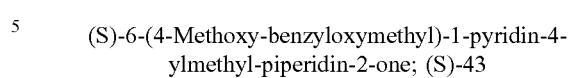

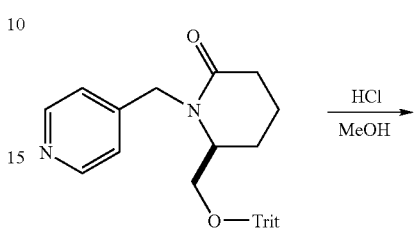

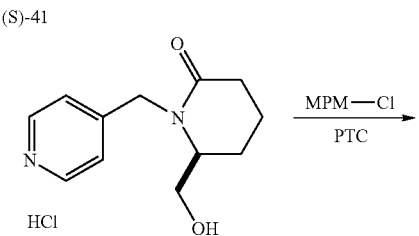

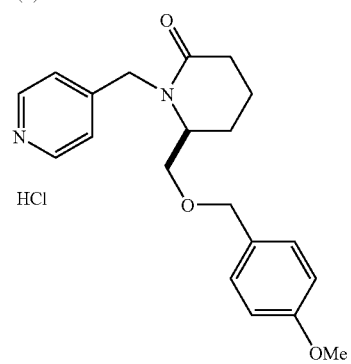

A mixture of (S)-41 (1.20 g, 2.60 mmol) and 4.2 M HCl in MeOH (1.5 mL, 6.3 mmol) was stirred at r.t. overnight. Then, the two-phase system was washed with hexane (3×5 mL). The residual methanolic solution was concentrated to dryness in vacuum and azeotroped with benzene (3×2 mL) to afford (S)-42 as a foam. To this foam were added 4-methoxybenzyl chloride (0.51 mL, 3.76 mmol), n-Bu$_4$NHSO$_4$ (168 mg, 0.49 mmol) and 50% aqueous NaOH (1.6 mL, ca 30 mmol) in benzene (7 mL), and the mixture was stirred overnight at r.t. The organic layer was separated and the residue was extracted with benzene (3×5 mL). Combined organic solutions were concentrated and separated by SGC with CH$_2$Cl$_2$:MeOH as eluent (gradient up to 5% MeOH) to afford (S)-43 (879.5 mg, 99%) as yellowish oil. $^1$H NMR (250 MHz, CDCl$_3$) δ 1.70-2.00 (m, 4H), 2.46 (t, J=6.1 Hz, 2H), 3.42-3.56 (m, 3H), 3.82 (s, 3H), 4.27-4.38 (m, 3H), 5.04 (d, J=15.9 Hz, 1H), 6.88 (d, J=8.7 Hz, 2H), 7.08 (d, J=6.0 Hz, 2H), 7.17 (d, J=8.7 Hz, 2H), 8.51 (d, J=6.0 Hz, 2H).

189

(S)-5-(4-Methoxy-benzyloxymethyl)-2-(4-methyl-sulfanyl-phenyl)-3-pyridin-4-yl-5,6,7,8-tetrahydro-imidazo[1,2-a]pyridine; (S)-44

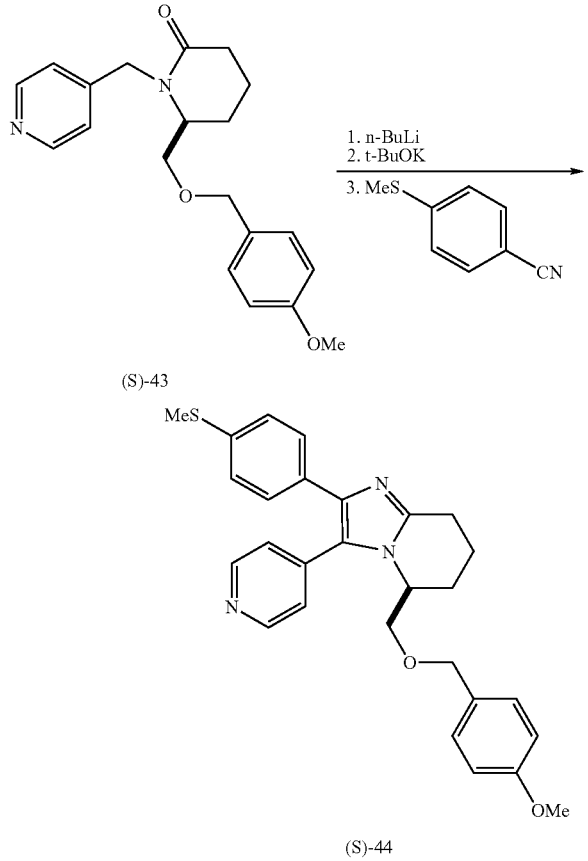

(S)-43

(S)-44

1.6 M n-BuLi in hexane (1.9 mL, 3.0 mmol) was added dropwise to a stirred and cooled (−45° C.) solution of (S)-43 (934.4 mg, 2.745 mmol) in THF (14 mL) and the yellow solution was stirred at −45° C. for 5 min. Then, 1.0 M solution of t-BuOK in THF (2.8 mL, 2.8 mmol) was added, the mixture was stirred at −45° C. for 10 min, and was treated with a solution of 4-(methylthio)benzonitrile (1.02 g, 6.84 mmol) in THF (2.8 mL). Stirring was continued at −45° C. for 1 h and then overnight at r.t. The reaction was quenched with water (2 mL), and the mixture was separated between AcOEt and saturated aqueous NaHCO$_3$ solution. The aqueous layer was extracted with AcOEt (4×15 mL). Combined organic solutions were washed with brine, dried MgSO$_4$, concentrated and separated by means of SGC with hexane:AcOEt (gradient, up to 100% AcOEt) to afford (S)-44 (731.8 mg, 56%) as colourless foam. $^1$H NMR (250 MHz, CDCl$_3$) δ 1.88-2.10 (m, 3H), 2.20-2.37 (m, 1H), 2.44 (s, 3H), 2.80-2.94 (m, 1H), 3.01-3.13 (m, 1H), 3.07 (dd, J=9.5, 3.9 Hz, 1H), 3.22 (dd, J=9.5, 8.6 Hz, 1H), 3.78 (s, 3H), 4.11 (d, J=11.8 Hz, 1H), 4.18 (d, J=11.8 Hz, 1H), 4.34-4.43 (m, 1H), 6.79 (d, J=8.8 Hz, 2H), 6.97 (d, J=8.8 Hz, 2H), 7.09 (d, J=8.7 Hz, 2H), 7.15 (d, J=6.1 Hz, 2H), 7.28 (d, J=8.7 Hz, 2H), 8.61 (d, J=6.1 Hz, 2H); MS (APCI+) m/e 472 (M+H).

190

Synthesis of Example imidazo[1,2-a]imidazol-2-one (R)-49 (Scheme 12)

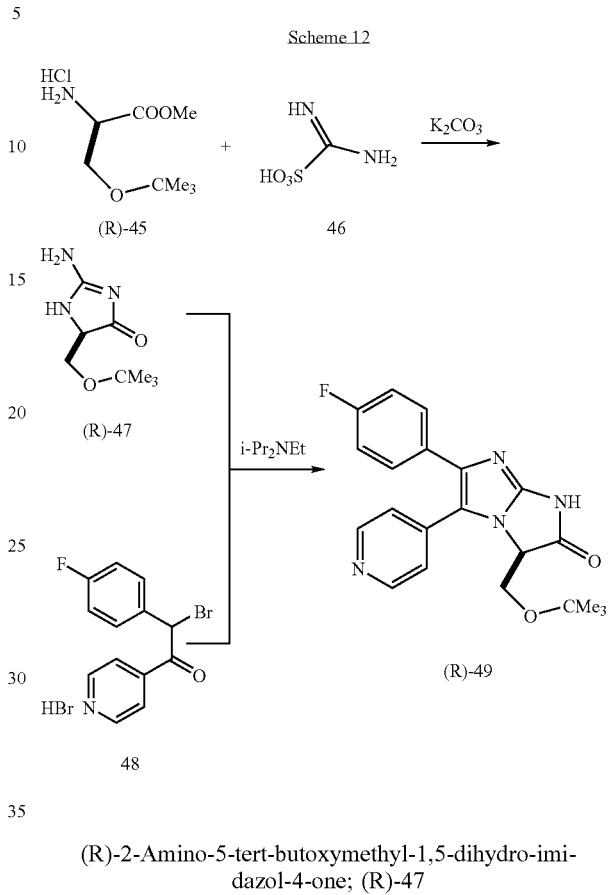

(R)-2-Amino-5-tert-butoxymethyl-1,5-dihydro-imidazol-4-one; (R)-47

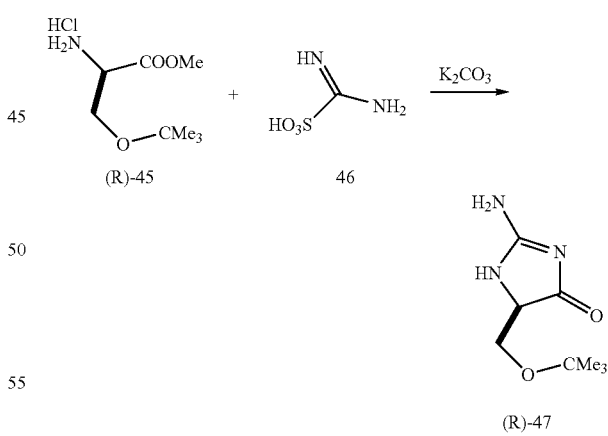

Anhydrous K$_2$CO$_3$ (6.66 g, 48.3 mmol) was added to a solution of (R)-H-Ser(tBu)-OMeHCl [(R)-45] (10.21 g, 48.3 mmol) in water (30 mL). Then, sulfonic acid 46 (5.99 g, 48.3 mmol; prepared according to Miller Synthesis 1986, 777) was added in small portions over a period of 20 min. A suspension, which formed after 30 min, was stirred at r.t. for 3 days. The solid was filtered off, washed with small amount of water and dried in vacuum to afford (R)-47 (5.05 g, 56%) as white powder. $^1$H NMR (250 MHz, DMSO-d$_6$) δ 1.10 (s, 9H), 3.24 (dd, J=9.5, 7.4 Hz, 1H), 3.53 (dd, J=9.5, 3.0 Hz, 1H), 3.76 (dd, J=7.4, 3.0 Hz, 1H), 7.0 (bs, 2H), 7.63 (bs, 1H).

(R)-3-tert-Butoxymethyl-6-(4-fluoro-phenyl)-5-pyridin-4-yl-1H-imidazo[1,2-a]imidazol-2-one; (R)-49

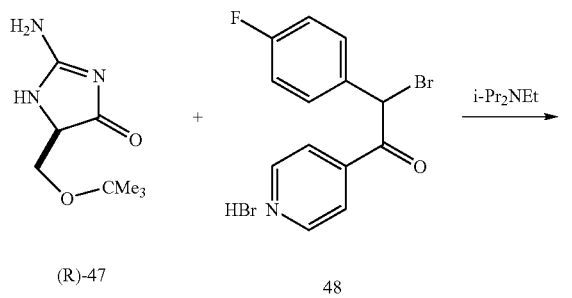

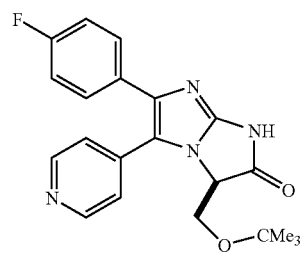

(R)-49 i-Pr₂NEt (785 µl, 4.51 mmol) was added dropwise to stirred suspension of 48 (1.691 g, 4.51 mmol) in DMF (12.5 mL). A yellow solution was formed. Then, guanidine (R)-47 (835.1 mg, 4.51 mmol) was added in one portion. The mixture was sonicated at r.t. for 5 min. and dark red-brown solution, which was formed, was stirred at r.t. overnight and concentrated in vacuum. The residue was evaporated with p-xylene (4×20 mL). Purification by means of SGC with AcOEt:MeOH as eluent in gradient (up to 7% MeOH) afforded 604.5 mg of pre-purified material. Further purification by PTLC with CHCl₃:MeOH=9:1 as eluent, and then with AcOEt as eluent afforded (R)-49 (42.8 mg, 3%) as colourless oil. ¹H NMR (250 MHz, CDCl₃) δ 1.18 (s, 9H), 3.66 (dd, J=9.4, 7.2 Hz, 1H), 3.85 (dd, J=9.4, 3.2 Hz, 1H), 4.55 (dd, J=7.2, 3.2 Hz, 1H), 7.10 (t, J=8.7 Hz, 2H), 7.39 (d, J=6.2 Hz, 2H), 7.40 (bs, 1H), 7.44 (dd, J=8.7, 5.3 Hz, 2H), 8.49 (d, J=6.2 Hz, 2H).

Synthesis of Example imidazo[1,2-a]imidazol-2-one (S)-49 (Scheme 13)

Scheme 13

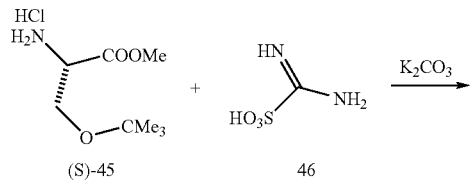

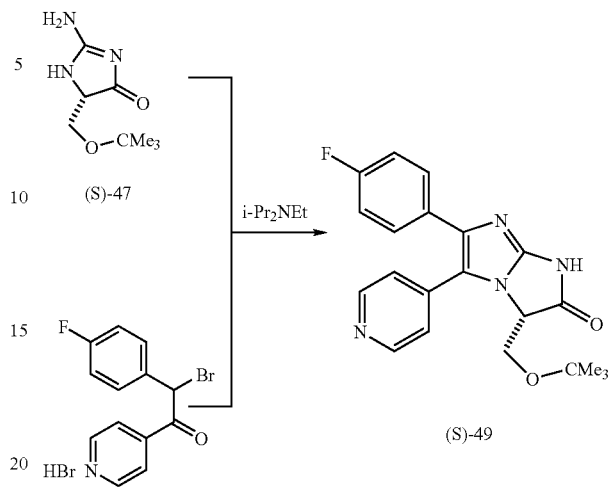

(S)-2-Amino-5-tert-butoxymethyl-1,5-dihydro-imidazol-4-one; (S)-47

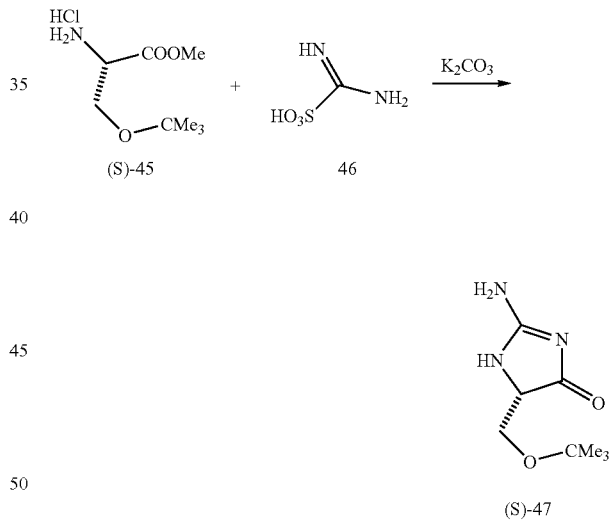

Anhydrous K₂CO₃ (1.38 g, 10.0 mmol) was added to a solution of (S)-H-Ser(tBu)-OMe HCl [(S)-45] (2.117 g, 10.0 mmol) in water (10 mL). Then, sulfonic acid 46 (1.241 g, 10.0 mmol) was added in small portions over a period of 10 min. A suspension, which formed after 1 h, was stirred overnight at RT. The solid was filtered off, washed with small amount of water and dried in vacuum to afford (S)-47 (652.4 mg, 35%) as white powder. ¹H NMR (250 MHz, DMSO-d₆) δ 1.10 (s, 9H), 3.24 (dd, J=9.4, 7.5 Hz, 1H), 3.54 (dd, J=9.4, 3.0 Hz, 1H), 3.76 (dd, J=7.5, 3.0 Hz, 1H), 7.0 (bs, 2H), 7.67 (bs, 1H).

(S)-3-tert-Butoxymethyl-6-(4-fluoro-phenyl)-5-pyridin-4-yl-1H-imidazo[1,2-a]imidazol-2-one; (S)-49

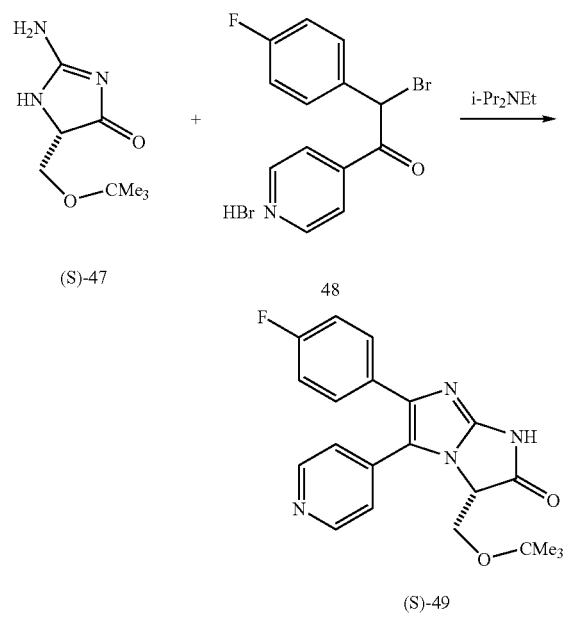

i-Pr$_2$NEt (94 μl, 0.54 mmol) was added dropwise to stirred suspension of 48 (202.5 mg, 0.54 mmol) in DMF (1.5 mL). A yellow solution was formed. Then, guanidine (S)-47 (100.0 mg, 0.54 mmol) was added in one portion. The dark red-brown solution, which was formed, was stirred at r.t. overnight and concentrated in vacuum. The residue was evaporated with p-xylene (2×5 mL), dissolved in CH$_2$Cl$_2$ (20 mL), and washed with water. The organic solution was concentrated and separated by PTLC with AcOEt as eluent and then again by PTLC with CH$_2$Cl$_2$:MeOH=19:1 as eluent to afford (S)-49 (8.2 mg, 4%) as colourless oil. $^1$H NMR (250 MHz, CDCl$_3$) δ 1.19 (s, 9H), 3.67 (dd, J=9.2, 7.6 Hz, 1H), 3.86 (dd, J=9.2, 3.0 Hz, 1H), 4.56 (dd, J=7.6, 3.0 Hz, 1H), 7.11 (t, J=8.7 Hz, 2H), 7.35-7.49 (m, 4H), ), 8.43 (bs, 1H), 8.49 (d, J=5.0 Hz, 2H); MS (APCI+) m/e 381 (M+H).

Synthesis of Example Indole Derivative (S)-54 (Scheme 14)

Scheme 14

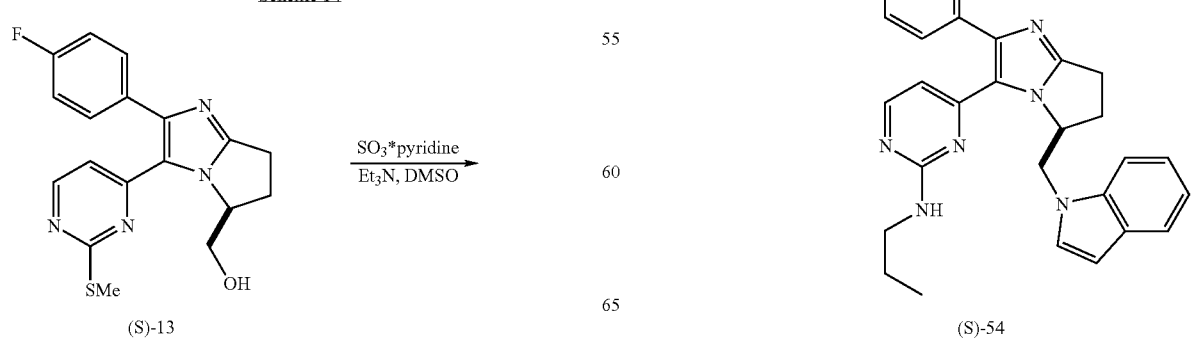

(S)-2-(4-Fluoro-phenyl)-3-(2-methylsulfanyl-pyrimidin-4-yl)-6,7-dihydro-5H-pyrrolo[1,2-a]imidazole-5-carbaldehyde; (S)-50

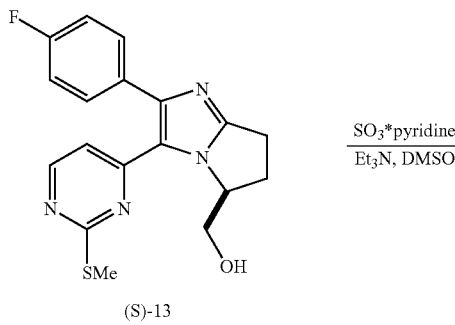

(S)-13

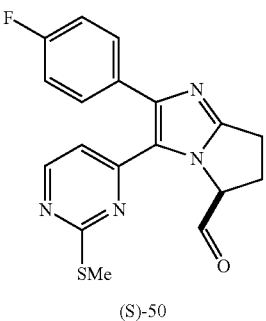

(S)-50

A mixture of SO₃ pyridine complex (2.59 g, 16.3 mmol) in DMSO was stirred at r.t. for 10 min until a clear solution was formed. This solution was added in one portion to a mixture of alcohol (S)-13 (1.874 g, 5.26 mmol) and Et₃N (2.16 mL, 15.5 mmol) in CH₂Cl₂ (90 mL). The reaction mixture was then stirred at r.t. for 3.5 h until complete conversion of (S)-13 into (S)-50 was achieved (TLC control). The reaction was quenched by the addition of saturated aqueous NaHCO₃. The mixture was diluted with AcOEt. The aqueous layer was extracted with AcOEt (3×200 mL). Combined organic solutions were washed with brine, dried (MgSO₄) and concentrated. The residual oil (S)-50 (1.87 g, quant.) was evaporated with p-xylene (2×100 mL) and used in the next step without additional purification.

(S)-1-[2-(4-Fluoro-phenyl)-3-(2-methylsulfanyl-pyrimidin-4-yl)-6,7-dihydro-5H-pyrrolo[1,2-a]imidazol-5-ylmethyl]-2,3-dihydro-1H-indole; (S)-51

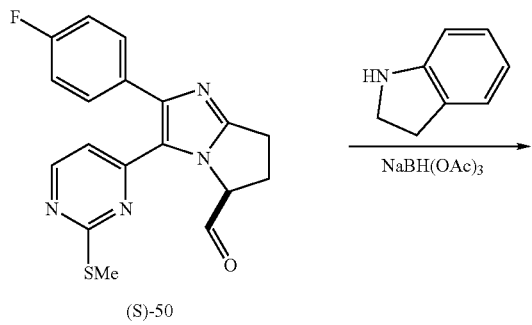

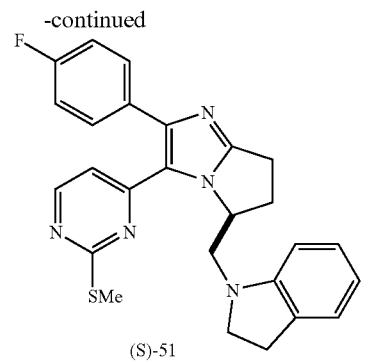

(S)-51

Sodium triacetoxyborohydride (1.70 g, 8.02 mmol) was added to a solution of (S)-50 (1.87 g, 5.26 mmol) and indoline (1.5 mL, 13.4 mmol) in 1,2-dichloroethane (8.7 mL) and the mixture was stirred overnight. The mixture was separated between AcOEt-saturated aqueous NaHCO₃. The aqueous layer was extracted with AcOEt (3×).

Combined organic solutions were washed with brine, dried (MgSO₄), and concentrated. Purification by means of SGC afforded (S)-51 (0.66 g, 27%) as an yellowish foam.

(S)-1-[2-(4-Fluoro-phenyl)-3-(2-methylsulfanyl-pyrimidin-4-yl)-6,7-dihydro-5H-pyrrolo[1,2-a]imidazol-5-ylmethyl]-1H-indole; (S)-52

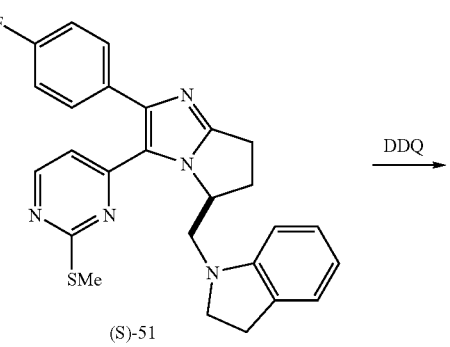

(S)-51

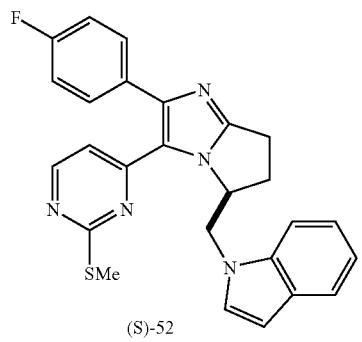

(S)-52

DDQ (335 mg, 1.48 mmol) was added in small portions over a period of 10 min into a stirred solution of (S)-51 (0.66 g, 1.4 mmol) in CH₂Cl₂ (80 mL) and aqueous phosphate buffer pH 7.0 (0.87 mL). Then, the dark mixture was stirred at r.t. for 30 min and saturated aqueous NaHCO₃ (20 mL) was added. Stirring was continued for 30 min. The organic layer was separated and the aqueous phase was extracted with CH₂Cl₂ (3×20 mL). Combined organic solutions were washed with brine, dried (MgSO₄), concentrated, and purified by means of SGC with CH₂Cl₂:AcOEt as eluent (in gradient) to afford (S)-52 (629 mg, 95%) as white foam. ¹H NMR (400 MHz, CDCl₃) δ 2.37-2.47 (m, 2H), 2.61 (s, 3H), 2.68-2.78 (m, 2H), 4.41 (dd, J=14.8, 5.6 Hz, 1H), 4.48 (dd, J=14.8, 4.8 Hz, 1H), 5.48 (m, 1H), 6.43 (d, J=3.2 Hz, 1H), 6.67 (d, J=5.4 Hz, 1H), 6.82 (d, J=3.2 Hz, 1H), 7.05-7.13 (m, 1H), 7.10 (t, J=8.7 Hz, 2H), 7.16-7.20 (m, 2H), 7.50 (dd, J=8.7, 5.4 Hz, 2H), 7.55 (d, J=7.8 Hz, 1H), 8.20 (d, J=5.4 Hz, 1H).

(S)-1-[2-(4-Fluoro-phenyl)-3-(2-methanesulfinyl-pyrimidin-4-yl)-6,7-dihydro-5H-pyrrolo [1,2-a]imidazol-5-ylmethyl]-1H-indole; (S)-53

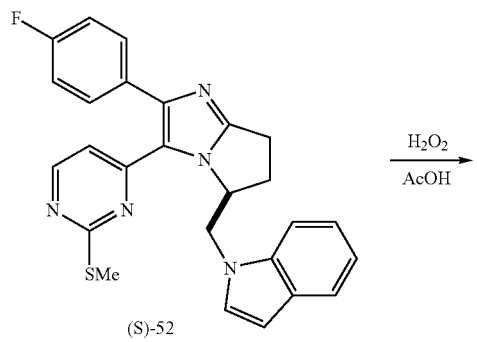

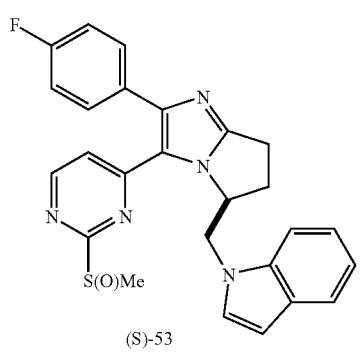

To a solution of (S)-52 (650 mg, 1.43 mmol) in glacial acetic acid (40 mL), was added 30% aqueous solution of H₂O₂ (800 µL, about 7.7 mmol). The mixture was stirred at r.t. for 2 days and concentrated at r.t. under high vacuum. The residue was separated between AcOEt (100 mL) and saturated aqueous NaHCO₃ (100 mL). The aqueous layer was extracted with AcOEt (3×100 mL). Combined organic solutions were washed with brine, dried (MgSO₄), concentrated, and evaporated with p-xylene (2×10 mL) to afford crude (S)-53 (0.62 g, 92%), which was used in the preparation of (S)-54 without additional purification.

(S)-{4-[2-(4-Fluoro-phenyl)-5-indol-1-ylmethyl-6,7-dihydro-5H-pyrrolo[1,2-a]imidazol-3-yl]-pyrimidin-2-yl}-propyl-amine; (S)-54

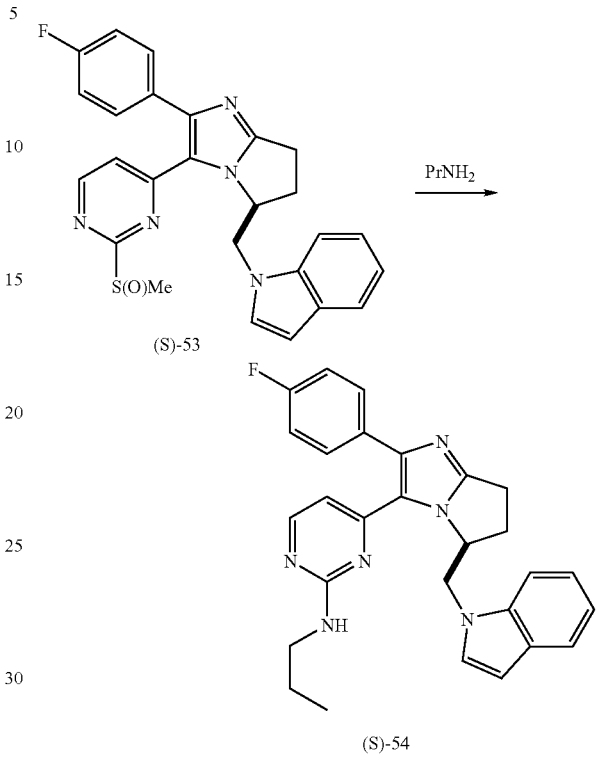

Neat n-PrNH₂ (2.16 mL, 26.3 mmol) was added to (S)-53 (0.62 g, 1.32 mmol) and the mixture was stirred at r.t. overnight. The excess of n-PrNH₂ was evaporated in vacuum and the residue was separated by means of SGC with hexane-AcOEt as eluent (in gradient) to afford inhibitor (S)-54 (418.8 mg, 68%) as white foam. ¹H NMR (400 MHz, CDCl₃) δ 1.04 (t, J=7.4 Hz, 3H), 1.69 (qt, J=7.4, 7.0 Hz, 2H), 2.17 (bs, 1H), 2.43 (dd, J=13.0, 8.9 Hz, 1H), 2.60-2.78 (m, 2H), 3.43 (td, J=7.0, 5.9 Hz, 2H), 4.46 (bs, 2H), 5.13 (bs, 1H), 5.44 (dt, J=7.8, 4.5 Hz, 1H), 6.41-6.45 (m, 2H), 6.63 (bs, 1H), 7.05-7.12 (m, 1H), 7.08 (t, J=8.6 Hz, 2H), 7.16 (dd, J=8.1, 6.4 Hz, 1H), 7.21 (d, J=8.1 Hz, 1H), 7.55 (dd, J=8.6, 5.5 Hz, 2H), 7.58 (d, J=8.5 Hz, 1H), 8.06 (d, J=5.3 Hz, 1H); MS (FAB+) m/e 467 (M+H).

Synthesis of Example Quinoline Derivative (S)-57 (Scheme 15)

Scheme 15

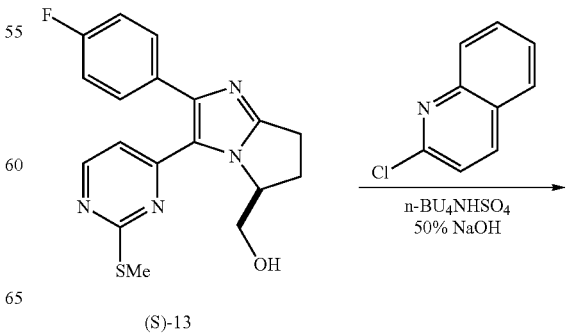

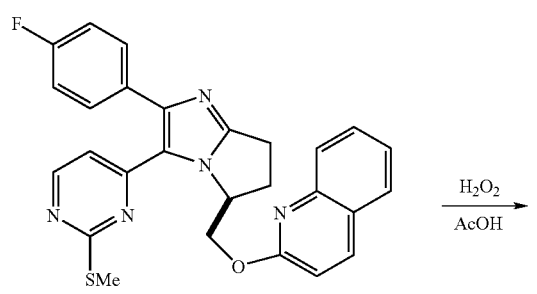

(S)-55

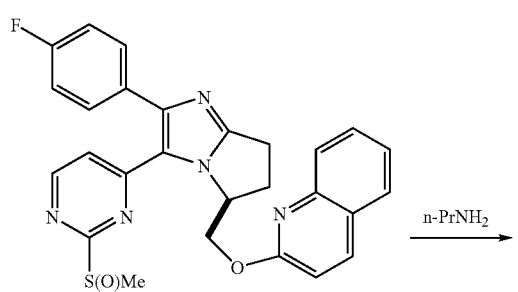

(S)-56

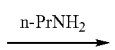

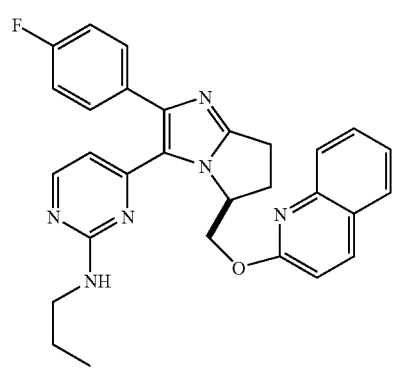

(S)-57

(S)-2-[2-(4-Fluoro-phenyl)-3-(2-methylsulfanyl-pyrimidin-4-yl)-6,7-dihydro-5H-pyrrolo [1,2-a]imidazol-5-ylmethoxy]-quinoline; (S)-55

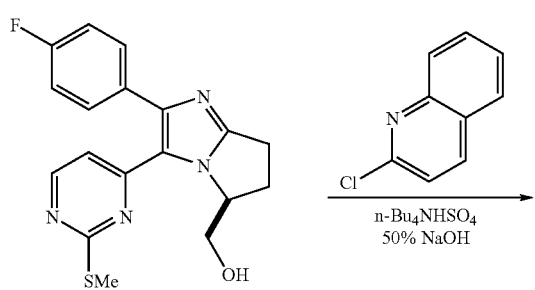

(S)-13

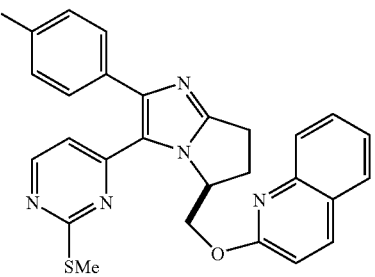

(S)-55

A mixture of alcohol (S)-13 (1.769 g, 4.97 mmol), 2-chloroquinoline (1.134 g, 6.93 mmol), n-Bu₄NHSO₄ (0.585 g, 1.72 mmol) and 50% aqueous NaOH (3.6 mL, ca 68 mmol) in benzene (52 mL) was stirred at r.t. overnight. The mixture was separated between water-benzene (50:50 mL). The aqueous phase was extracted with benzene (4×10 mL). Combined organic solutions were washed with brine, concentrated, and separated by means of SGC with hexane-AcOEt as eluent (in gradient) to afford (S)-55 (1.22 g, 51%) as white foam. $^1$H NMR (400 MHz, CDCl$_3$) δ 2.51 (s, 3H), 2.66-2.74 (m, 1H), 2.89-3.01 (m, 2H), 3.07-3.20 (m, 1H), 4.58 (dd, J=11.4, 4.3 Hz, 1H), 4.92 (dd, J=11.4, 4.3 Hz, 1H), 5.50 (dt, J=7.8, 4.3 Hz), 6.64 (d, J=8.7 Hz, 1H), 6.74 (d, J=5.4 Hz, 1H), 7.04 (t, J=8.7 Hz, 2H), 7.34-7.39 (m, 1H), 7.37 (dd, J=8.7, 5.5 Hz, 2H), 7.57 (ddd, J=8.4, 6.9, 1.4 Hz, 1H), 7.66 (d, J=8.4 Hz, 1H), 7.69 (dd, J=8.1, 1.4 Hz, 1H), 7.93 (d, J=8.7 Hz, 1H), 8.21 (d, J=5.4 Hz, 1H).

(S)-2-[2-(4-Fluoro-phenyl)-3-(2-methanesulfinyl-pyrimidin-4-yl)-6,7-dihydro-5H-pyrrolo [1,2-a]imidazol-5-ylmethoxy]-quinoline; (S)-56

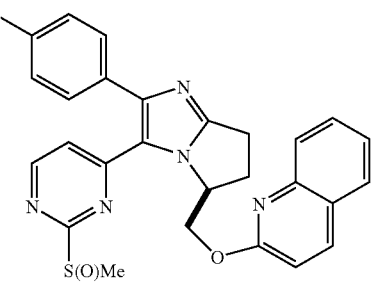

(S)-55

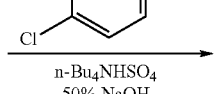

(S)-56

This compound was prepared from (S)-55 and H₂O₂/AcOH in 86% yield following the method used for the synthesis of (S)-53.

(S)-{4-[2-(4-Fluoro-phenyl)-5-(quinolin-2-yloxymethyl)-6,7-dihydro-5H-pyrrolo [1,2-a]imidazol-3-yl]-pyrimidin-2-yl}-propyl-amine; (S)-57

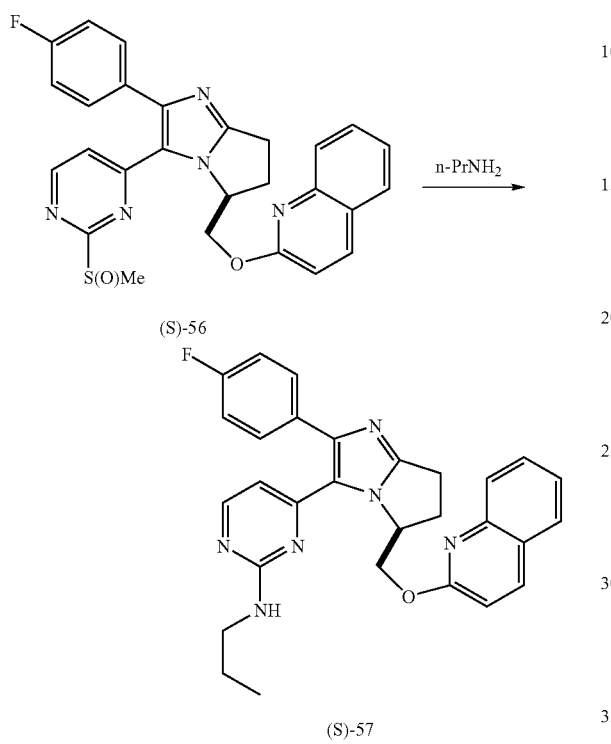

This compound was synthesised from (S)-56 and n-PrNH₂ using the general method described for inhibitor (S)-54. Yield 59% of (S)-57 as white foam. ¹H NMR (400 MHz, CDCl₃) δ 0.91 (t, J=7.4 Hz, 3H), 1.51 (qt, J=7.4, 6.5 Hz, 2H), 2.68 (m, 1H), 2.85-2.98 (m, 2H), 3.05-3.16 (m, 1H), 3.20-3.30 (m, 2H), 4.66 (dd, J=11.1, 4.5 Hz, 1H), 4.85 (dd, J=11.1, 5.1 Hz, 1H), 4.99 (bs, 1H), 5.45 (m, 1H), 6.39 (d, J=5.3 Hz, 1H), 6.69 (d, J=8.8 Hz, 1H), 7.03 (t, J=8.8 2H), 7.37 (ddd, J=7.9, 7.1, 1.2 Hz, 1H), 7.45 (dd, J=8.8, 5.5 Hz, 2H), 7.59 (ddd, J=8.3, 7.1, 1.5 Hz, 1H), 7.69 (dd, J=8.3, 1.2 Hz, 1H), 7.72 (d, J=7.9 Hz, 1H), 7.94 (d, J=8.8 Hz, 1H), 8.01 (d, J=5.3 Hz, 1H); MS (ESP+) m/e 495 (M+H).

Synthesis of Amine (S)-61

Scheme 16

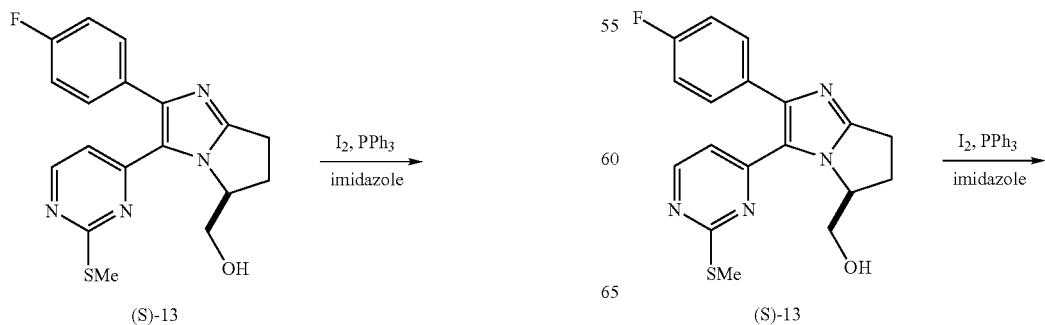

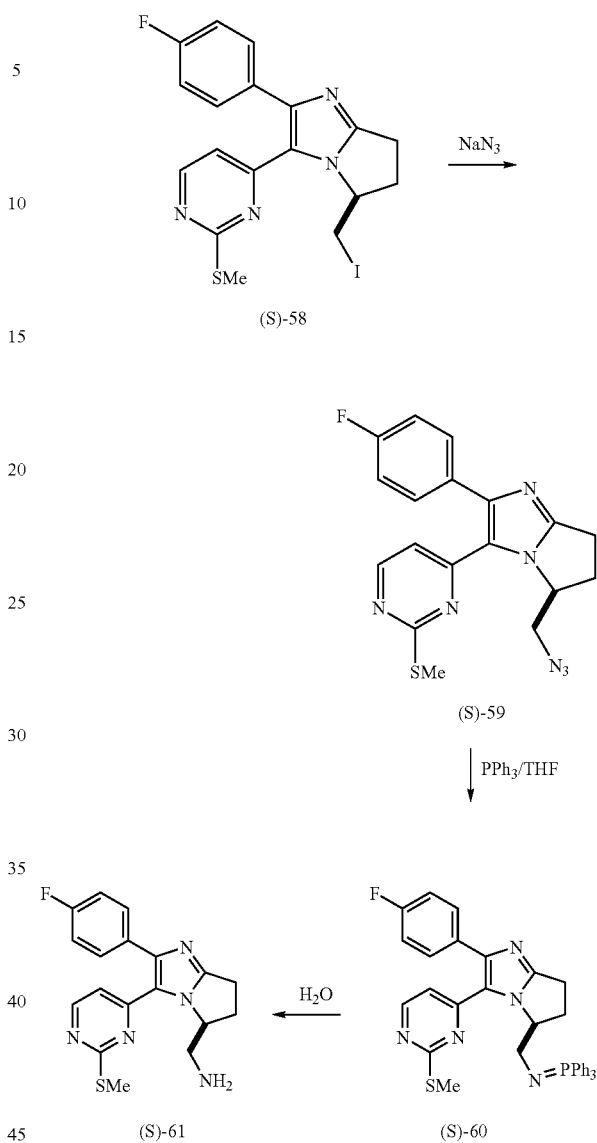

(S)-2-(4-Fluoro-phenyl)-5-iodomethyl-3-(2-methylsulfanyl-pyrimidin-4-yl)-6,7-dihydro-5H-pyrrolo[1,2-a]imidazole; (S)-58

-continued

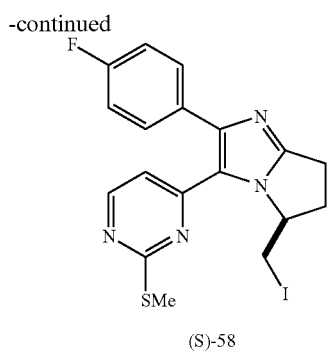

(S)-58

To the alcohol (S)-13 (1.00 g, 2.81 mmol) in anhydrous diethyl ether (110 mL) and anhydrous acetonitrile (36 mL) was added imidazole (0.76 g, 11.2 mmol), triphenylphosphine (2.95 g, 11.2 mmol) then iodine (2.14 g, 8.42 mmol) and the mixture stirred for 6 h. Saturated aqueous NaHCO$_3$ was added then extracted with AcOEt (3×70 mL) and the combined organic extracts wash with brine (70 mL), dried (MgSO$_4$) and concentrated. The residue was purified by SGC using 20% AcOEt:hexane (gradient) as the eluent to afford the iodide (S)-58 (1.29 g, 98%) as orange foam.

(S)-5-Azidomethyl-2-(4-fluoro-phenyl)-3-(2-methyl-sulfanyl-pyrimidin-4-yl)-6,7-dihydro-5H-pyrrolo [1,2-a]imidazole; (S)-59

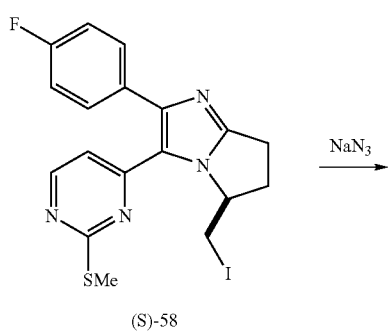

To a solution of the iodide (S)-58 (1.29 g, 2.77 mmol) in anhydrous DMF (11.0 mL) was added NaN$_3$ (0.90 g, 13.8 mmol) and the reaction mixture stirred for 3 days. The solvent was evaporated and the product purified by SGC using 40% AcOEt:hexane (gradient) as eluent to give the azide (S)-59 (961 mg, 91%) as a white foam.

(S)-C-[2-(4-Fluoro-phenyl)-3-(2-methylsulfanyl-pyrimidin-4-yl)-6,7-dihydro-5H-pyrrolo [1,2-a]imidazol-5-yl]-methylamine; (S)-61

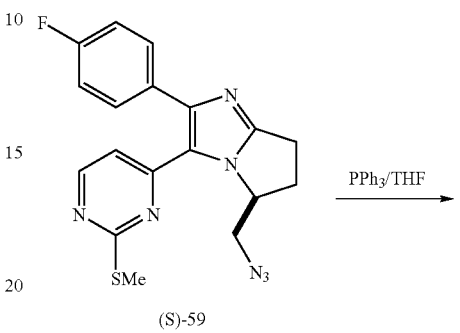

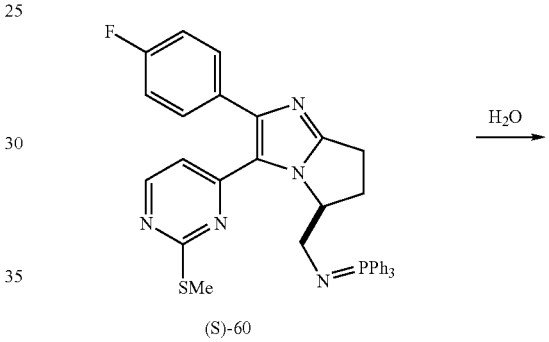

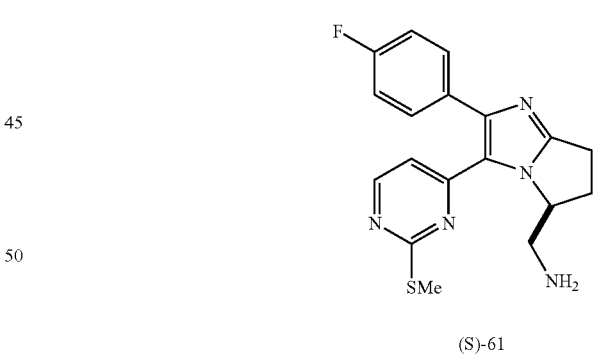

To the azide (S)-59 (0.90 g, 2.36 mmol) in anhydrous THF (18 mL) was added Ph$_3$P (1.24 g, 4.72 mmol) and the reaction mixture stirred for 5 h at r.t. and then heated at reflux for 2 h. Water (1.8 mL) was added and the reaction mixture stirred at r.t. for 20 h and then refluxed for 45 min. The mixture was concentrated and the residue was evaporated with toluene (150 mL). The resulting crude oil was purified by SGC using AcOEt and subsequently CH$_2$Cl$_2$: MeOH as eluent in gradient (up to 10% MeOH) to give (S)-61 as a colourless oil which formed a white foam (775 mg, 92%) on drying in high vacuum.

Synthesis of Amide (S)-63

Scheme 17

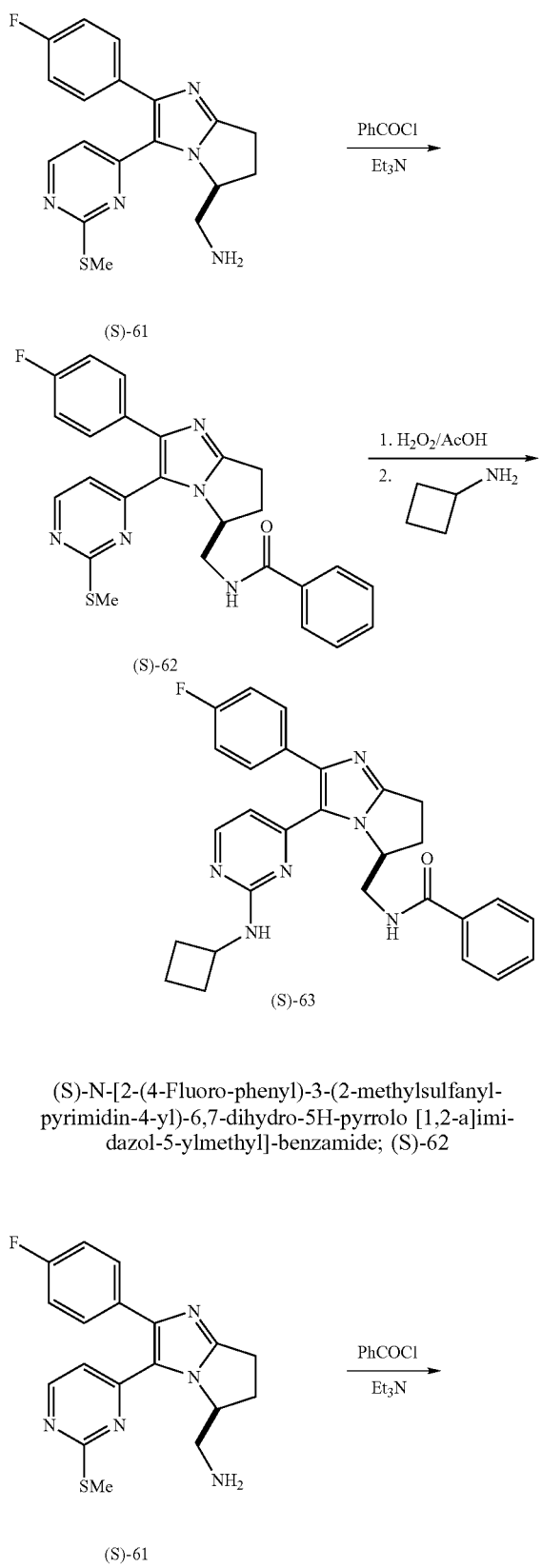

(S)-N-[2-(4-Fluoro-phenyl)-3-(2-methylsulfanyl-pyrimidin-4-yl)-6,7-dihydro-5H-pyrrolo [1,2-a]imidazol-5-ylmethyl]-benzamide; (S)-62

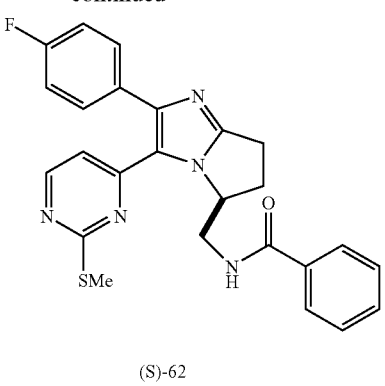

To a solution of the amine (S)-62 (135 mg, 0.38 mmol) in THF (2.0 mL) was added $Et_3N$ (79 μL, 0.57 mmol) followed by dropwise addition of benzoyl chloride (66 μL, 0.57 mmol). The reaction mixture was stirred at room temperature for 0.5 h, poured onto saturated $NaHCO_3$ (50 mL) and extracted with AcOEt (3×50 mL). The combined organic extracts were washed with brine, dried ($MgSO_4$) and concentrated. The residue was purified by SGC with AcOEt: hexane=1:1 as to give the amnide (S)-62 as a white solid (133 mg, 76%).

(S)-N-[3-(2-Cyclobutylamino-pyrimidin-4-yl)-2-(4-fluoro-phenyl)-6,7-dihydro-5H-pyrrolo [1,2-a]imidazol-5-ylmethyl]-benzamide; (S)-63

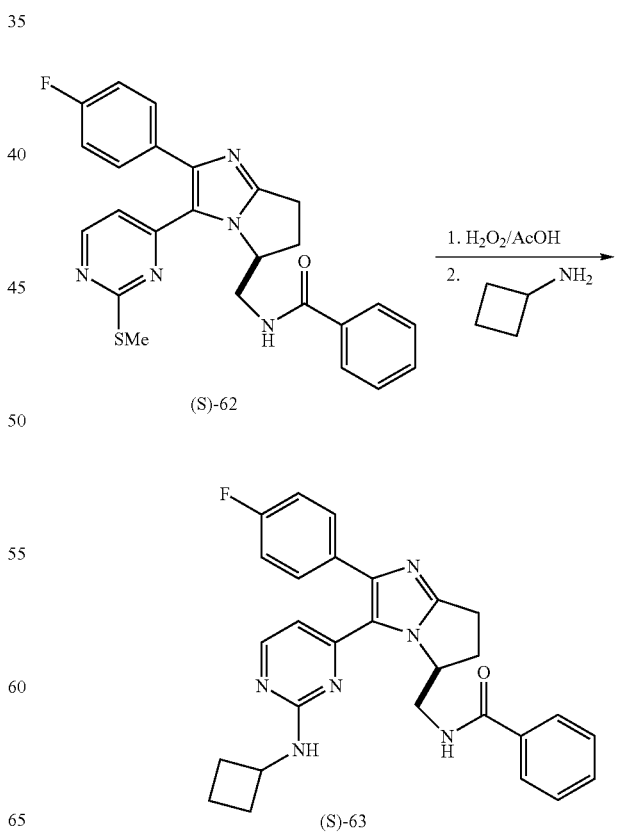

Following the methods used for the synthesis of (S)-53 and (S)-54, sulphide (S)-62 was converted into (S)-63 (24% overall yield); light orange oil. ¹H NMR (400 MHz, CDCl₃) δ 1.55-2.00 (m, 4H), 2.20-2.55 (m, 3H), 2.65-3.05 (m, 3H), 4.33 (sextet, J=8.2 Hz, 1H), 5.17 (m, 1H), 6.32 (d, J=5.3 Hz, 1H), 7.00 (m, 2H), 7.34 (t, J=7.6 Hz, 2H), 7.34 (t, J=7.6 Hz, 2H), 7.45 (m, 3H), 7.50-7.65 (bs, 2H), (m, 5H), 7.98 (d, J=9.1 Hz, 1H); MS (ESP+) m/z 483.4.

Synthesis of 2-aminopyridine Derivative (S)-65

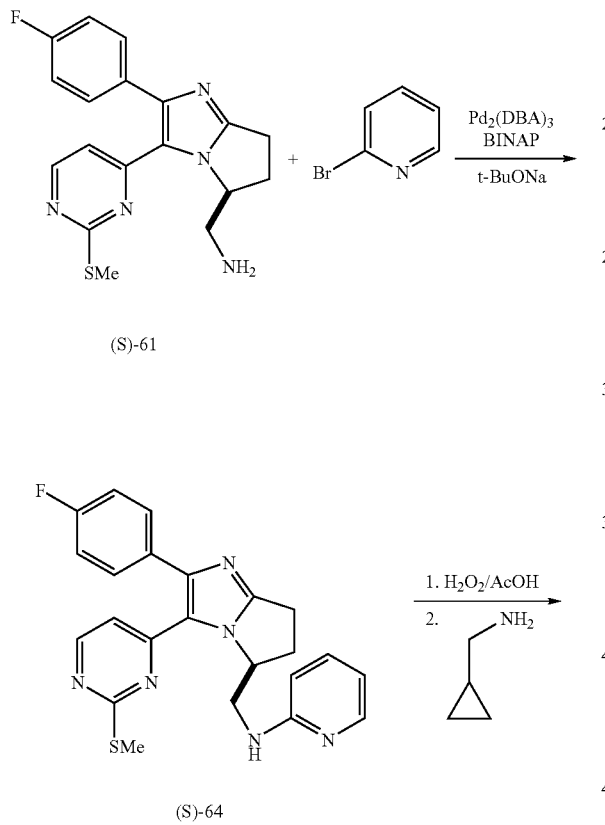

(S)-[2-(4-Fluoro-phenyl)-3-(2-methylsulfanyl-pyrimidin-4-yl)-6,7-dihydro-5H-pyrrolo [1,2-a]imidazol-5-ylmethyl]-pyridin-2-yl-amine; (S)-64

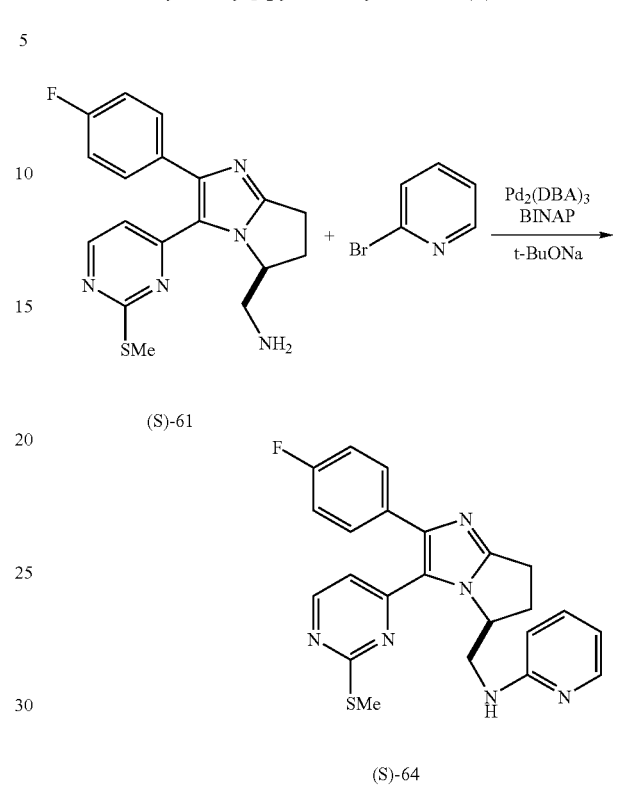

To a solution of the amine (S)-61 (579 mg, 1.63 mmol) in anhydrous toluene (5.8 mL) was added 2-bromopyridine (51.7 µL, 0.54 mmol), tris(dibenzylideneacetone)dipalladium (0) (13.4 mg, 14.6 µmol), (±)-BINAP (13.5 mg, 21.7 µmol) and t-BuONa (78.4 mg, 0.82 mmol). The reaction mixture was stirred at r.t. for 13 h, heated at 70° C. for 1.5 h, and then at 80° C. for 2 h. After cooling the mixture was separated by SGC with AcOEt:MeOH as eluent in gradient (up to 10% MeOH) to afford (S)-64 (192 mg, 27%) as a white foam. Further elution with 5% of MeOH in CH₂Cl₂ gave recovered unreacted amine (S)-61 (403 mg, 70%).

(S)-Cyclopropylmethyl-{4-[2-(4-fluoro-phenyl)-5-(pyridin-2-ylaminomethyl)-6,7-dihydro-5H-pyrrolo[1,2-a]imidazol-3-yl]-pyrimidin-2-yl}-amine; (S)-65

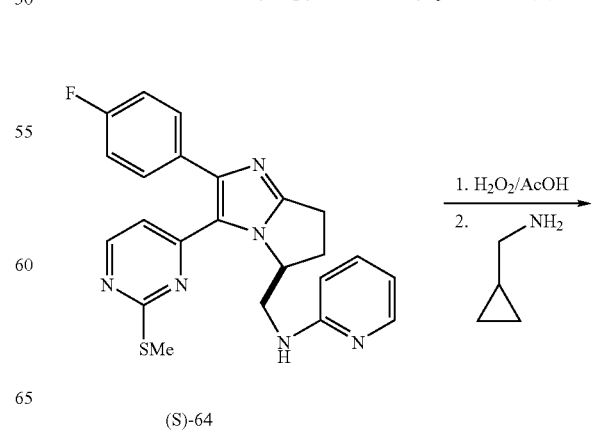

-continued

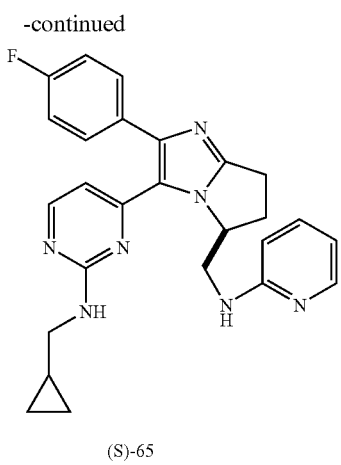

(S)-65

Following the methods used for the synthesis of (S)-53 and (S)-54, sulphide (S)-64 was converted into (S)-65 (20% overall yield); light orange foam. ¹H NMR (400 MHz, CDCl₃) δ 0.15-0.35 (m, 2H), 0.45-0.65 (m, 2H), 1.09 (m, 1H), 1.70-2.00 (bs, NH), 2.51 (m, 1H), 2.70-3.40 (m, 5H), 3.45-3.65 (bs, NH), 3.78 (m, 1H), 5.15 (bs, 1H), 6.19 (d, J=8.1 Hz, 1H), 6.39 (d, J=5.2 Hz, 1H), 6.56 (m, 1H), 7.04 (t, J=8.8 Hz, 2H), 7.35 (t, J=6.8 Hz, 1H), 7.52 (dd, J=8.8, 5.5 Hz, 2H), 8.05 (m, 1H+NH); MS (ESP+) m/z 456.3 (M+H).

Synthesis of Pyrrole Derivative (S)-67

Scheme 19

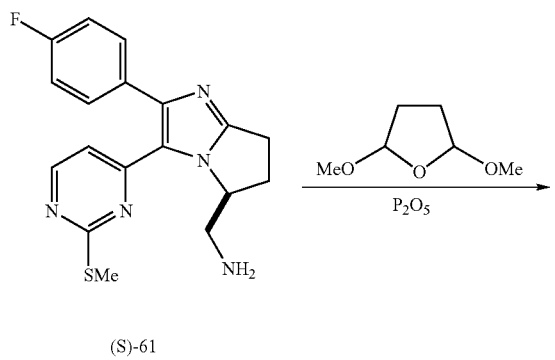

(S)-61

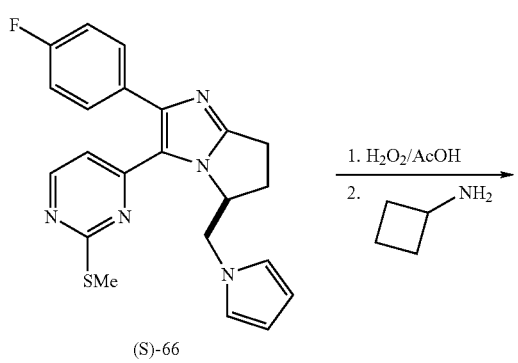

(S)-66

-continued

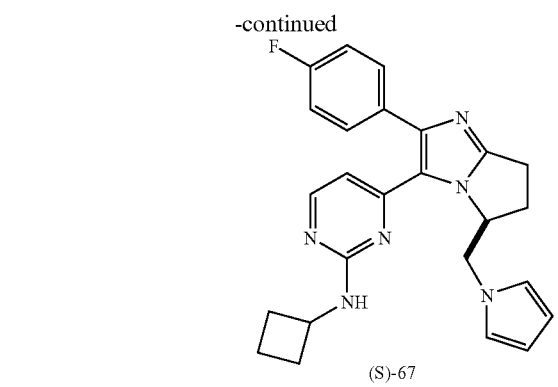

(S)-67

(S)-2-(4-Fluoro-phenyl)-3-(2-methylsulfanyl-pyrimidin-4-yl)-5-pyrrol-1-ylmethyl-6,7-dihydro-5H-pyrrolo[1,2-a]imidazole; (S)-66

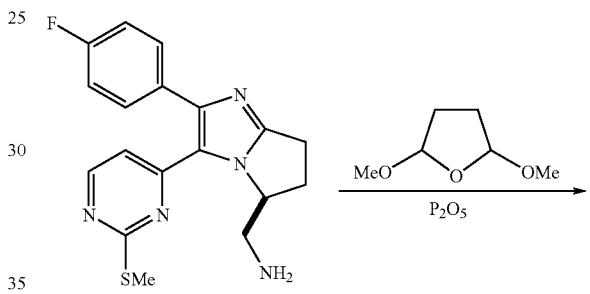

To a suspension of phosphorus pentoxide (20.0 mg, 0.14 mmol) in anhydrous toluene (2.0 mL) was added the amine (S)-61 (50 mg, 0.14 mmol) followed by 2,5-dimethoxytetrahydrofuran (27.4 μL, 0.21 mmol), and the reaction mixture heated at 110° C. for 3 h. More 2,5-dimethoxytetrahydrofuran (1.00 mL, 7.66 mmol) was added and the heating continued for further 2 h. Purification by PTLC with AcOEt as eluent and evaporation with toluene (2×50 mL) gave (S)-66 (35 mg, 61%) as a white foam.

(S)-Cyclobutyl-[4-[2-(4-fluoro-phenyl)-5-pyrrol-1-ylmethyl-6,7-dihydro-5H-pyrrolo [1,2-a]imidazol-3-yl]-pyrimidin-2-yl]-amine; (S)-67

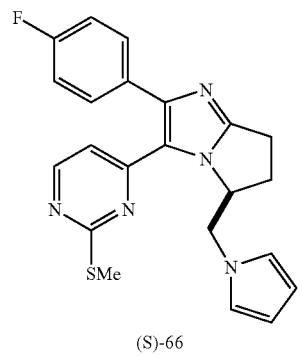

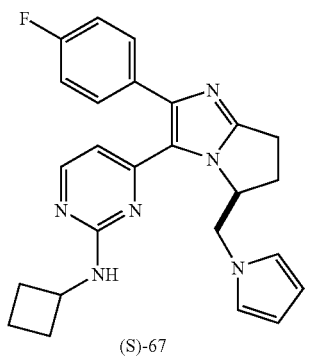

Following the methods used for the synthesis of (S)-53 and (S)-54, sulphide (S)-66 was converted into (S)-67 (23% overall yield); light orange foam. $^1$H NMR (400 MHz, CDCl$_3$) δ 1.5-2.2 (m, 5H), 2.25-2.48 (m, 3H), 2.50-2.80 (m, 2H), 4.06 (m, 1H), 4.26 (d, J=14.5 Hz, 1H), 4.41 (sextet, J=8.0 Hz, 1H), 5.21 (m, 1H+NH), 6.03 (m, 2H), 6.23 (bs, 2H), 6.44 (m, J=5.3 Hz, 1H), 7.01 (t, J=10.7 Hz, 2H), 7.48 (dd, J=8.8, 5.5 Hz, 2H), 7.99 (m, J=5.2 Hz, 1H); MS (ESP+) m/z 429.3 (M+H).

Synthesis of Cyclopentane Derivative (S)-71

Scheme 20

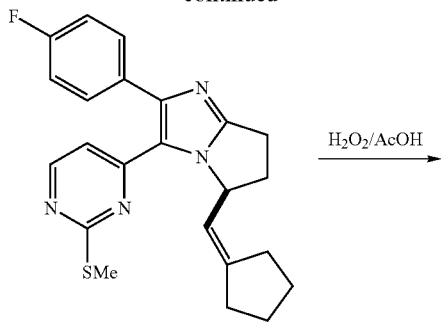

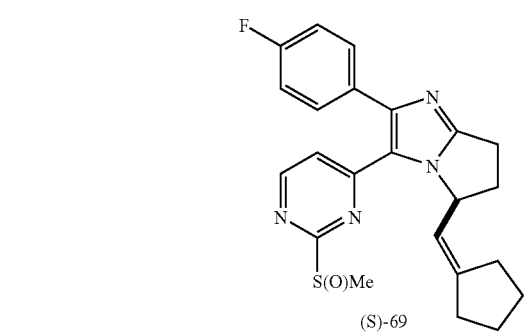

(S)-5-Cyclopentylidenemethyl-2-(4-fluoro-phenyl)-3-(2-methylsulfanyl-pyrimidin-4-yl)-6,7-dihydro-5H-pyrrolo[1,2-a]imidazole; (S)-68

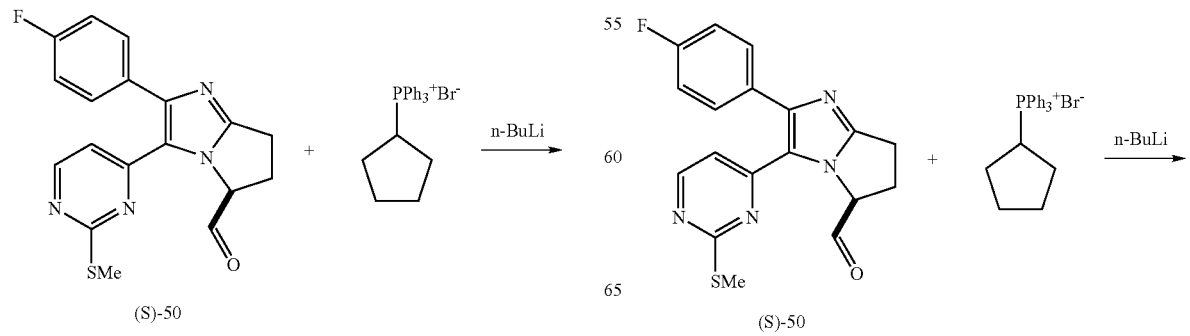

-continued

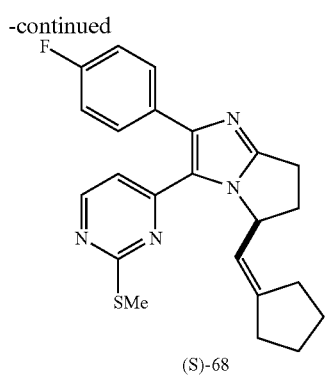

(S)-68

A solution of cyclopentyltriphenylphosphonium bromide (639 mg, 1.55 mmol) in THF (20 mL) was cooled to −78° C. and treated dropwise with 1.6 M solution of n-BuLi in THF (0.97 mL, 1.55 mmol). When the addition was complete the solution was stirred at r.t. for 2 h to give a dark solution. This was cooled to −78° C. and treated dropwise with a solution of (S)-50 (500 mg, 1.41 mmol) in THF (10 mL). When the addition was complete the solution was stirred at r.t. for 48 h, poured into saturated aqueous NH$_4$Cl (20 mL) and extracted with diethyl ether (3×20 mL). The combined organic extracts were dried (MgSO$_4$) and concentrated to give an orange oil which was purified by SGC using AcOEt:hexane as eluent in gradient (up to 40% AcOEt) to give the alkene (S)-68 (401 mg, 70%) as a light orange oil.

(S)-5-Cyclopentylidenemethyl-2-(4-fluoro-phenyl)-3-(2-methanesulfinyl-pyrimidin-4-yl)-6,7-dihydro-5H-pyrrolo[1,2-a]imidazole; (S)-69

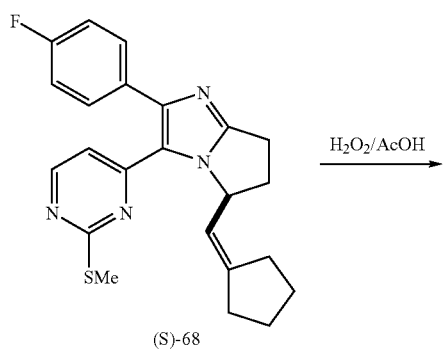

(S)-68

Following the method used for (S)-53, compound (S)-68 (392 mg, 0.96 mmol) was converted into (S)-69 (347 mg, 85%), light orange foam.

(S)-{4-[5-Cyclopentylidenemethyl-2-(4-fluoro-phenyl)-6,7-dihydro-5H-pyrrolo [1,2-a]imidazol-3-yl]-pyrimidin-2-yl}-ethyl-amine; (S)-70

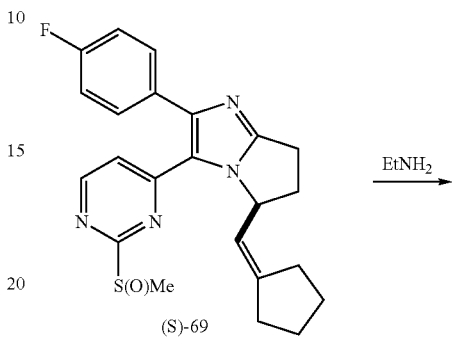

(S)-69

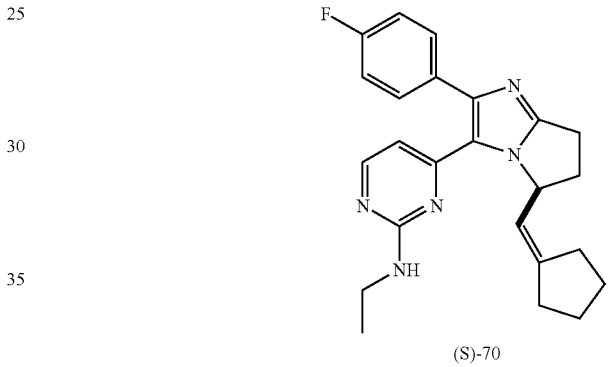

(S)-70

Product (S)-69 (87.0 mg, 206 μmol) was dissolved in 2.0 M solution of ethylamine in THF (2.0 mL, 4.0 mmol) and the solution was kept at r.t. for 18 h. The volatiles were removed in vacuum and the residue was separated by PTLC with CH$_2$Cl$_2$:MeOH=19: 1 as eluent to give (S)-70 as a white foam (33.0 mg, 40%).

(S)-{4-[5-Cyclopentylmethyl-2-(4-fluoro-phenyl)-6,7-dihydro-5H-pyrrolo [1,2-a]imidazol-3-yl]-pyrimidin-2-yl}-ethyl-amine; (S)-71

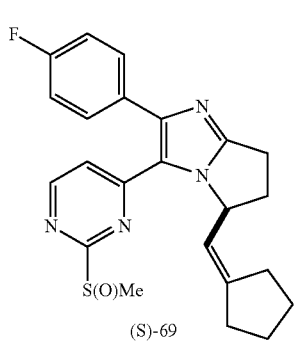

(S)-69

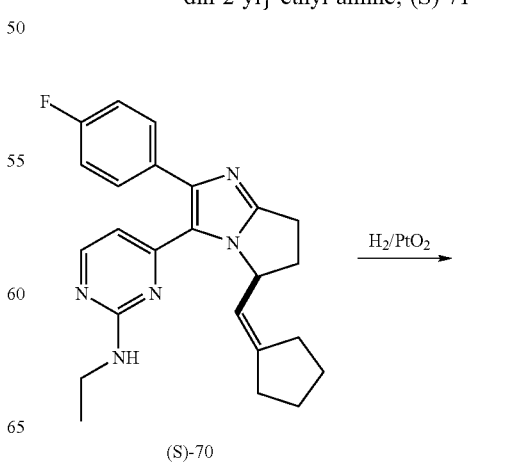

(S)-70

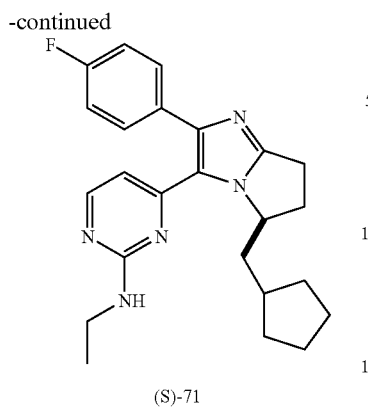

(S)-71

To a solution of the alkene (S)-70 (20 mg, 49.6 gmol) in AcOEt (15 mL) was added platinum (IV) oxide catalyst (1.14 mg, 5.0 gmol) and the reaction mixture was de-aerated by placing under vacuum and purging with hydrogen (5×). It was then stirred overnight under hydrogen, the old catalyst filtered and fresh catalyst added (1.14 mg, 5.0 μmol) and the reaction mixture stirred again overnight. This procedure was repeated once more with stirring overnight then the catalyst was filtered off and the solvent evaporated. The residual orange oil was purified by PTLC (60% AcOEt in hexane) to give (S)-71 as a clear oil (16 mg, 80%) which turned into a white foam on placing under high vacuum. $^1$H NMR (400 MHz, CDCl$_3$) δ 0.7-1.10 (m, 2H), 1.17 (t, J=7.2 Hz, 3H), 1.30-1.80 (m, 9H), 2.33 (m, 1H), 2.60-3.00 (m, 3H), 3.30-3.60 (m, 2H), 4.93 (m, 1H), 4.97 (bs, NH), 6.35 (d, J=5.2 Hz, 1H), 6.96 (t, J=8.8 Hz, 2H), 7.46 (dd, J=8.8, 5.5 Hz, 2H), 8.00 (d, J=5.2 Hz, 1H); MS (ESP+) m/z 406.1 (M+H).

Synthesis of Imidazol-1-yl Derivative (S)-75

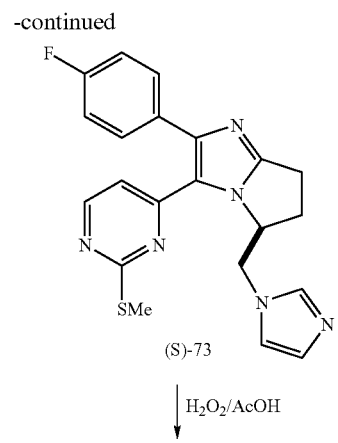

(S)-Methanesulfonic acid 2-(4-fluoro-phenyl)-3-(2-methylsulfanyl-pyrimidin-4-yl)-6,7-dihydro-5H-pyrrolo[1,2-a]imidazol-5-ylmethyl ester; (S)-72

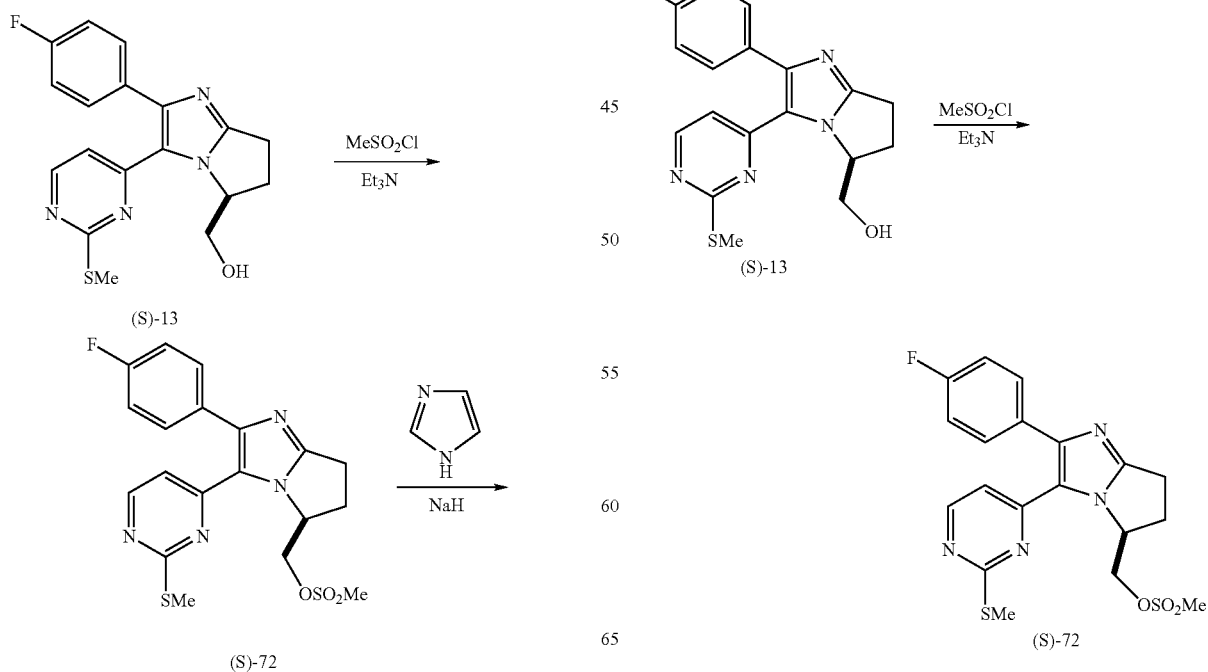

Scheme 21

To a mixture of alcohol (S)-13 (0.50 g, 1.40 mmol) and triethylamine (431 µL, 3.09 mmol) in THF (10 mL) was added methanesulfonyl chloride (431 µL, 3.09 mmol) dropwise. When the addition was complete the reaction mixture stirred for 40 min then poured onto saturated aqueous NaHCO₃ (50 mL). Extraction with AcOEt (3×30 mL), drying (MgSO₄) and concentrating gave (S)-72 (640 mg, 105%) as a white foam which was used in the next step without further purification.

(S)-2-(4-Fluoro-phenyl)-5-imidazol-1-ylmethyl-3-(2-methylsulfanyl-pyrimidin-4-yl)-6,7-dihydro-5H-pyrrolo[1,2-a]imidazole; (S)-73

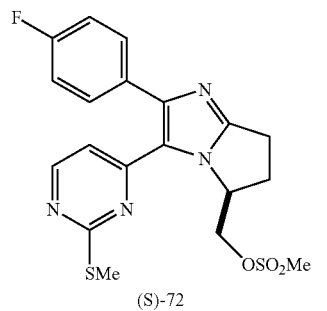

(S)-72

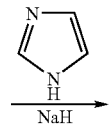

NaH

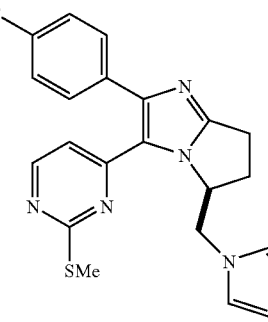

(S)-73

A suspension of sodium hydride (176 mg, 4.60 mmol, 60% in mineral oil) in THF (10 mL) was cooled to 0° C. and treated dropwise with a solution of imidazole (352 mg, 5.18 mmol) in THF (5 mL). When the addition was complete the reaction mixture was stirred at r.t. for 1 h, cooled to −78° C. and treated dropwise with a solution of the mesylate (S)-72 (500 mg, 1.15 mmol) in THF (5 mL). The reaction mixture was then stirred at r.t. overnight then heated at reflux for 24 h. TLC still showed the presence of starting material so more sodium salt of imidazole (4 mole equivalents) was added while cooling to 0° C., and the reaction mixture heated at reflux for a further 5.5 h. The mixture was cooled to r.t., poured onto saturated aqueous NaHCO₃ (100 mL) and extracted with AcOEt (4×50 mL). The combined organic extracts were washed with brine (70 mL), dried (MgSO₄) and concentrated. The residue was purified by SGC using AcOEt:MeOH in gradient (up to 5% MeOH) and then CH₂Cl₂:MeOH in gradient (up to 5% MeOH) to give desired (S)-73 (386 mg, 82%) as a white foam.

(S)-2-(4-Fluoro-phenyl)-5-imidazol-1-ylmethyl-3-(2-methanesulfinyl-pyrimidin-4-yl)-6,7-dihydro-5H-pyrrolo[1,2-a]imidazole; (S)-74

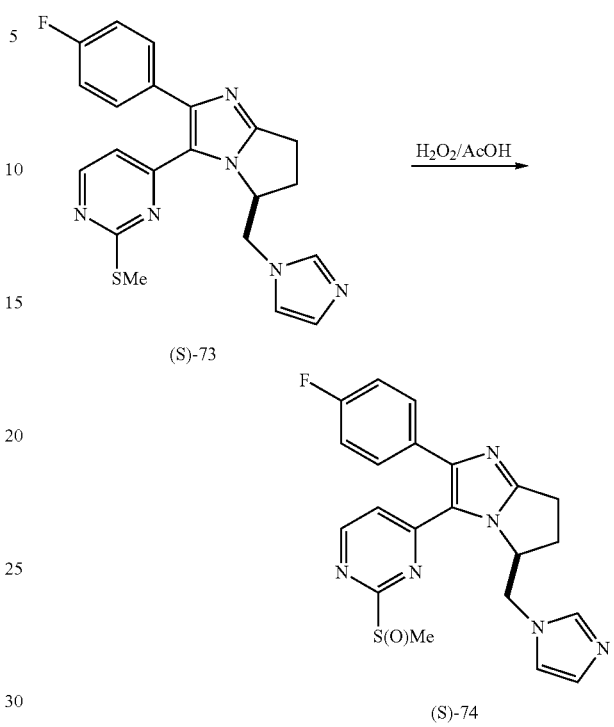

Following the method used for (S)-53, compound (S)-73 (380 mg, 0.93 mmol) was converted into (S)-74 (205 mg, 52%), light orange foam.

(S)-{4-[2-(4-Fluoro-phenyl)-5-imidazol-1-ylmethyl-6,7-dihydro-5H-pyrrolo [1,2-a]imidazol-3-yl]-pyrimidin-2-yl}-propyl-amine; (S)-75

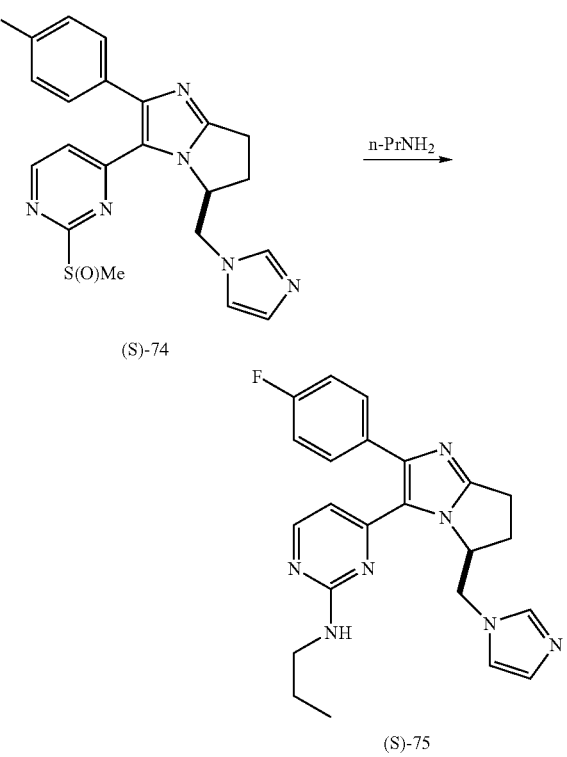

Following the method used for (S)-54, compound (S)-74 (51.3 mg, 121 µmol) was converted into (S)-75 (10.0 mg, 20%), light orange foam.
Synthesis of Sulphone (S)-79
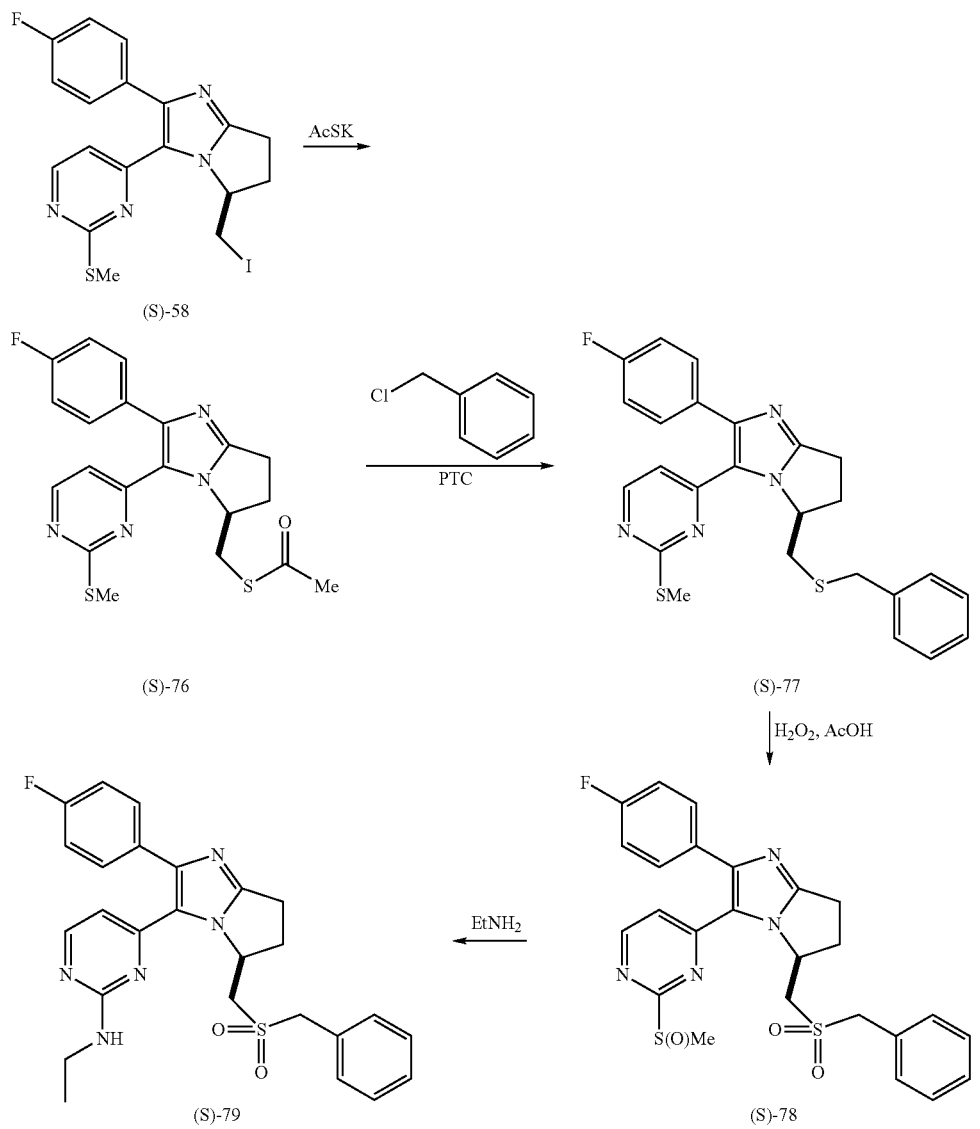
(S)-Thioacetic acid S-[2-(4-fluoro-phenyl)-3-(2-methylsulfanyl-pyrimidin-4-yl)-6,7-dihydro-5H-pyrrolo[1,2-a]imidazol-5-ylmethyl] ester; (S)-76
-continued
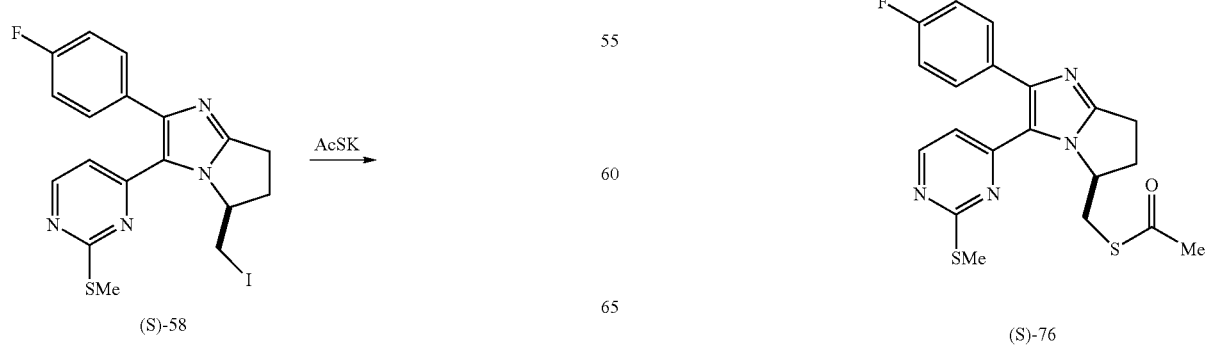

A mixture of iodide (S)-58 (362 mg, 1.21 mmol) and potassium thioacetate (688 mg, 6.03 mmol) in dry DMF (5.5 mnL) was stirred at r.t. overnight. Then, it was separated between AcOEt and brine. The organic solution was dried over MgSO₄, and concentrated in vacuo. Separation by means of SGC with AcOEt/hexane as eluent afforded (S)-76 (244 mg, 76%) as a pink foam.

(S)-5-Benzylsulfanylmethyl-2-(4-fluoro-phenyl)-3-(2-methylsulfanyl-pyrimidin-4-yl)-6,7-dihydro-5H-pyrrolo[1,2-a]imidazole; (S)-77

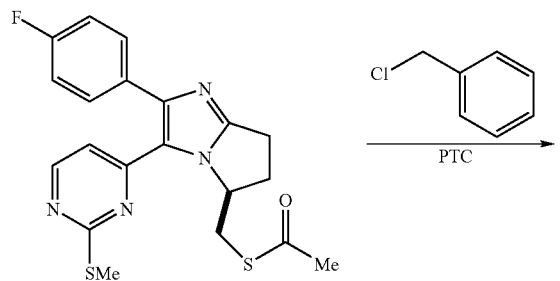

A mixture of thioacetate (S)-76 (25 mg, 60.3 µmol), benzyl chloride (17 µL, 0.15 mmol), 40% aqueous solution of tetra-n-butylammonium hydroxide (20 µL, 30 µmol) and 50% sodium hydroxide solution (10 µL, 190 µmol) in benzene (0.1 mL) was stirred at r.t. overnight. The organic layer was separated by PTLC with AcOEt as eluent to afford (S)-77 (27.0 mg, 97%) as yellowish oil.

(S)-2-(4-Fluoro-phenyl)-3-(2-methanesulfinyl-pyrimidin-4-yl)-5-phenylmethanesulfonylmethyl-6,7-dihydro-5H-pyrrolo[1,2-a]imidazole; (S)-78

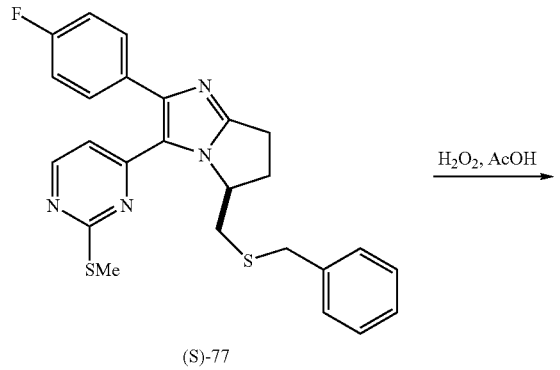

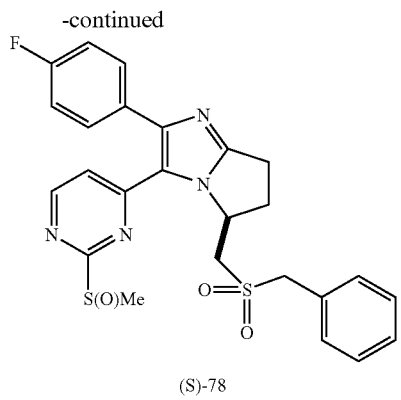

Sulfide (S)-77 (26.95 mg, 58.27 µmol) and 30% hydrogen peroxide solution (13 µL, 0.1165 mmol) in glacial acetic acid (195 µL) was stirred at r.t. overnight. The mixture was concentrated in vacuum and evaporated with toluene. The residual white solid was used directly for preparation of (S)-78.

(S)-Ethyl-{4-[2-(4-fluoro-phenyl)-5-phenylmethane-sulfonylmethyl-6,7-dihydro-5H-pyrrolo [1,2-a]imidazol-3-yl]-pyrimidin-2-yl}-amine; (S)-79

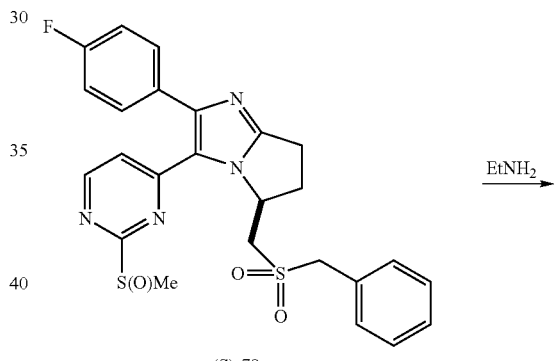

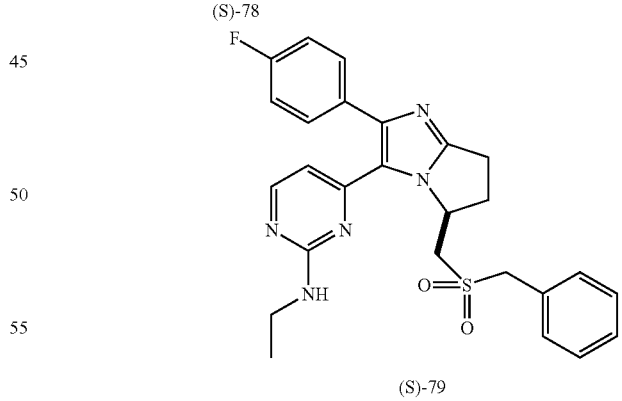

Following the method used for (S)-70, compound (S)-78 (9.28 mg, 19.4 µmol) was converted into (S)-79 (8.8 mg, 98%); white solid. $^1$H NMR (400 MHz, CDCl₃) δ 2.79-2.97 (m, 3H), 3.02-3.21 (m, 2H), 3.39 (bs, 2H), 3.69 (t, J=7.1 Hz, 1H), 4.23-4.39 (m, 4H), 5.30 (s, 1H), 5.47-5.50 (m, 1H), 6.34 (d, J=5.5 Hz, 1H), 6.70 (d, J=9.8 Hz, 1H), 6.93 (t, J=8.7 Hz, 1H), 7.05-7.11 (m, 2H), 7.39-7.43 (m, 2H), 7.50-7.54 (m, 2H), 7.99 (bs, 1H), 8.04 (d, J=9.7 Hz, 1H).

Synthesis of Sulphide (S)-80

Scheme 23

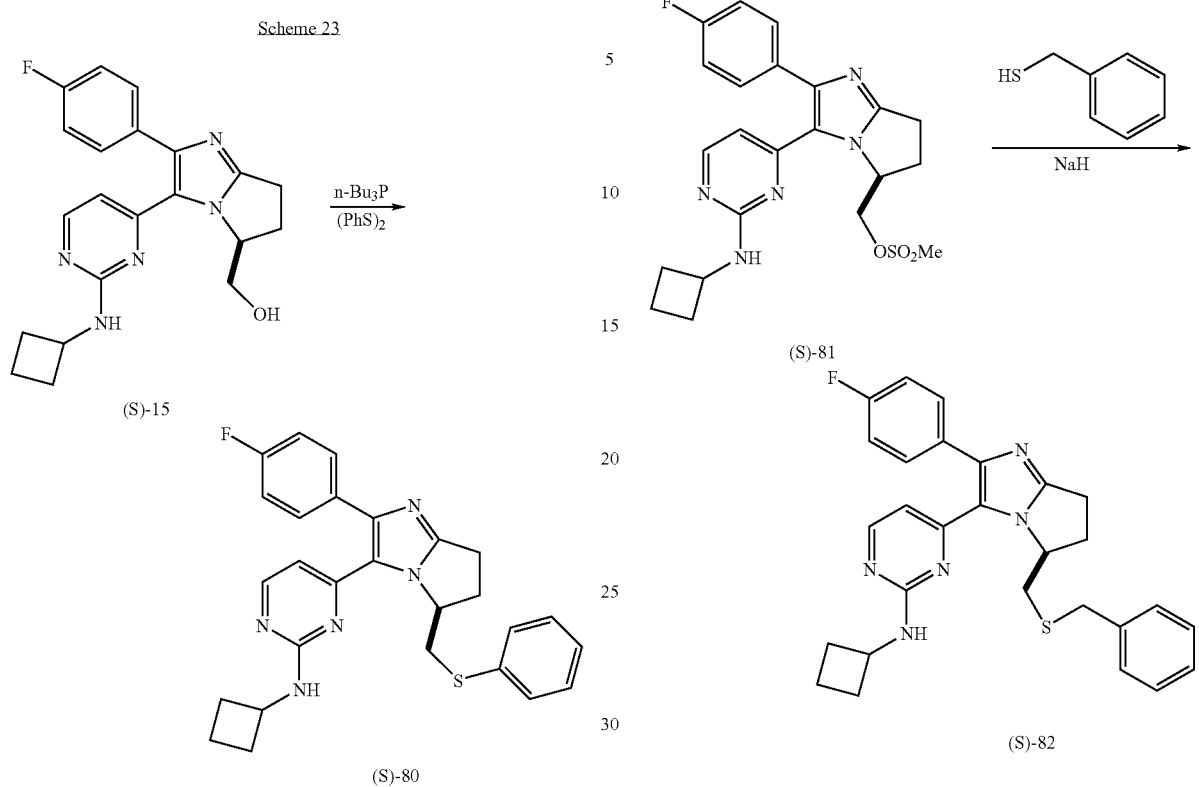

Phenyldisulphide (26 mg, 0.119 mmol) and tri-n-butylphosphine (30 μL, 0.119 mmol) were added to a solution of (S)-15 (41.37 mg, 0.109 mmol) in dry DMF (0.2 mL). The reaction was left to stir at r.t. overnight and separated between AcOEt and saturated aqueous NaHCO$_3$. Organic solutions were dried over MgSO$_4$, concentrated and separated by PTLC with AcOEt as eluent to afford sulphide (S)-80 (11.02 mg, 21%) as a white solid. $^1$H NMR (400 MHz, CDCl$_3$) δ 5.25-5.46 (m, 3H), 2.54-2.64 (m, 1H), 2.83-2.90 (m, 2H), 2.92 (s, 3H), 3.19-3.3.18 (m, 1H), 3.25 (bs, 1H), 3.34-3.41 (m, 1H), 5.22 (bs, 1H), 5.29 (s, 1H), 6.19 (d, J=5.3 Hz, 1H), 7.02 (t, J=8.7 Hz, 2H), 7.20-7.22 (m, 1H), 7.22 (s, 1H), 7.41-7.45 (m, 2H), 7.28-7.32 (m, 1H), 7.41-7.45 (m, 2H), 7.95 (d, J=5.0 Hz, 1H).

Synthesis of Sulphide (S)-82

Scheme 24

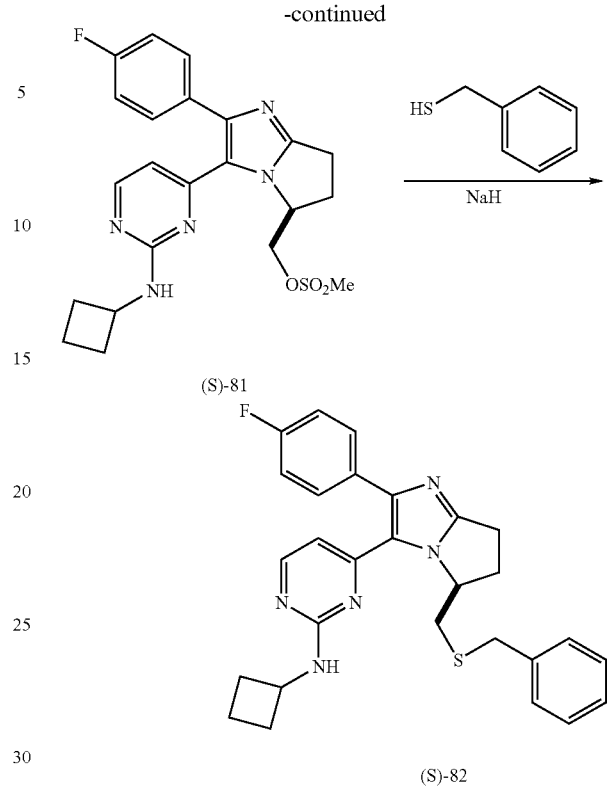

(S)-Methanesulfonic acid 3-(2-cyclobutylamino-pyrimidin-4-yl)-2-(4-fluoro-phenyl)-6,7-dihydro-5H-pyrrolo[1,2-a]imidazol-5-ylmethyl ester; (S)-81

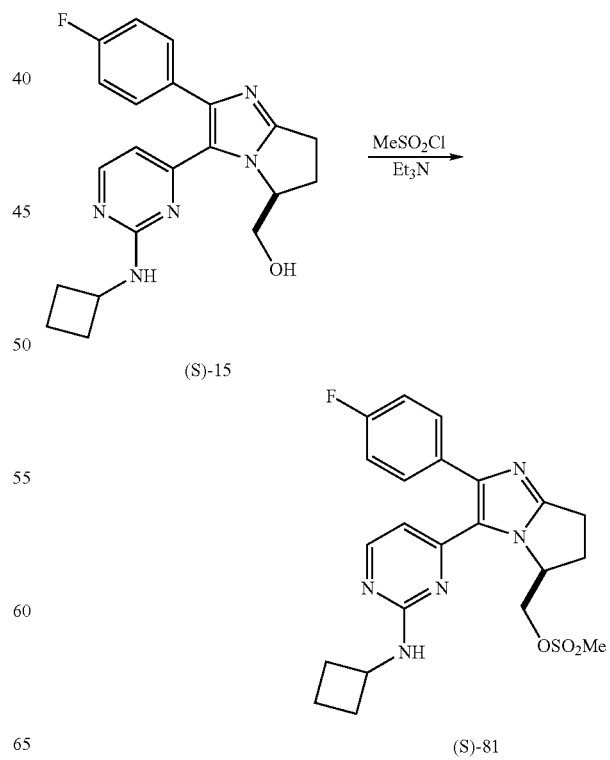

Triethylamine (141 µL, 1.014 mmol) and methanesulfonyl chloride (71 µL, 0.922 mmol) were added to a solution of alcohol (S)-15 (175 mg, 0.461 mmol; dried by evaporation with benzene) in dry THF (4.0 mL). The reaction was stirred at r.t. for 40 min. and separated between AcOEt and saturated aqueous NaHCO₃. The aqueous layer was extracted with AcOEt (2×10 mL). Combined organic solutions were washed with brine, dried MgSO₄, concentrated and separated by SGC with AcOEt:hexane as eluent to afford mesylate (S)-81 (120.07 mg, 60%) as a yellow oil.

(S)-{4-[5-Benzylsulfanylmethyl-2-(4-fluoro-phenyl)-6,7-dihydro-5H-pyrrolo[1,2-a]imidazol-3-yl]-pyrimidin-2-yl}-cyclobutyl-amine; (S)-82

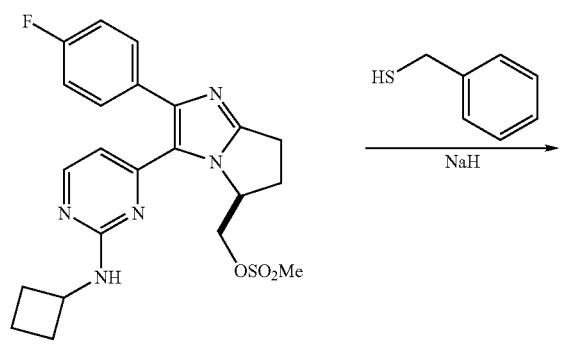

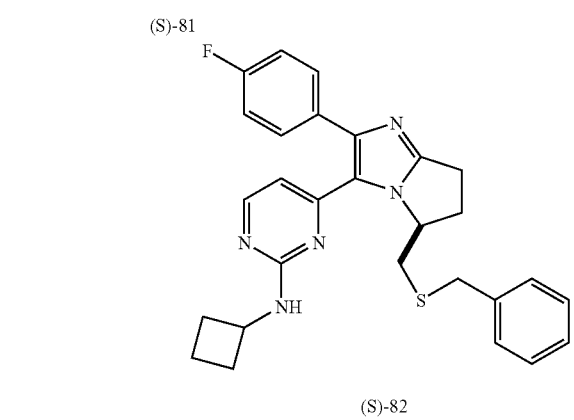

Benzyl mercaptan (14 µL, 0.1167 mmol) was added dropwise to a stirred and cooled (0° C.) suspension of sodium hydride (2.6 mg of 60% suspension in mineral oil, 0.0642 mmol) in dry DMF (0.2 mL). Cooling bath was removed and the mixture was stirred for a further 10 min. at r.t. A solution of (S)-81 (26.7 mg, 58.3 µmol) in dry DMF (0.6 mL) was added dropwise at 0° C. and mixture allowed to warm to r.t. After overnight stirring the mixture was separated between AcOEt and saturated aqueous solution of NaHCO₃. The organic layer was dried over MgSO₄, concentrated and the residue was purified by PTLC with AcOEt as eluent to afford sulphide (S)-82 (27.44 mg, 97%) as a white solid.

$^1$H NMR (400 MHz, CDCl₃) δ 2.36-2.49 (m, 4H), 2.67-2.72 (m, 1H), 2.75-2.92 (m, 4H), 2.99-3.10 (m, 1H), 3.47 (s, 1H), 3.51 (d, J=3.59 Hz, 1H0, 3.59 (s, 1H), 4.42-4.4.50 (m, 1H), 5.14 (bs, 1H), 6.39 (d, J=5.3 Hz, 1H), 7.04 (t, J=6.7 Hz, 1H), 7.11-7.18 (m, 2H), 7.22 (s, 1H), 7.23 (s, 1H), 7.28-7.32 (m, 1H), 7.36 (s, 1H), 7.50-7.53 (m, 2H), 8.01 (d, J=5.0 Hz, 1H).

Synthesis of Quinoline Derivative (S)-85

Scheme 25

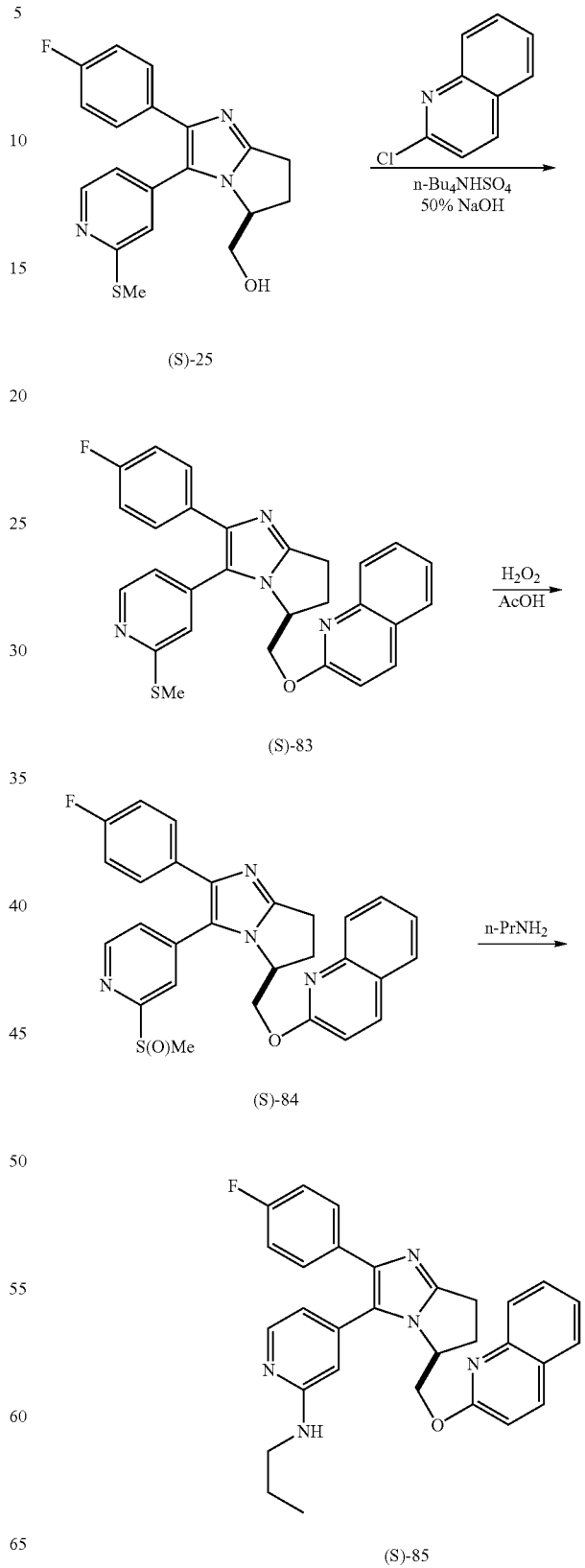

(S)-2-[2-(4-Fluoro-phenyl)-3-(2-methanesulfinyl-pyridin-4-yl)-6,7-dihydro-5H-pyrrolo [1,2-a]imidazol-5-ylmethoxy]-quinoline; (S)-84

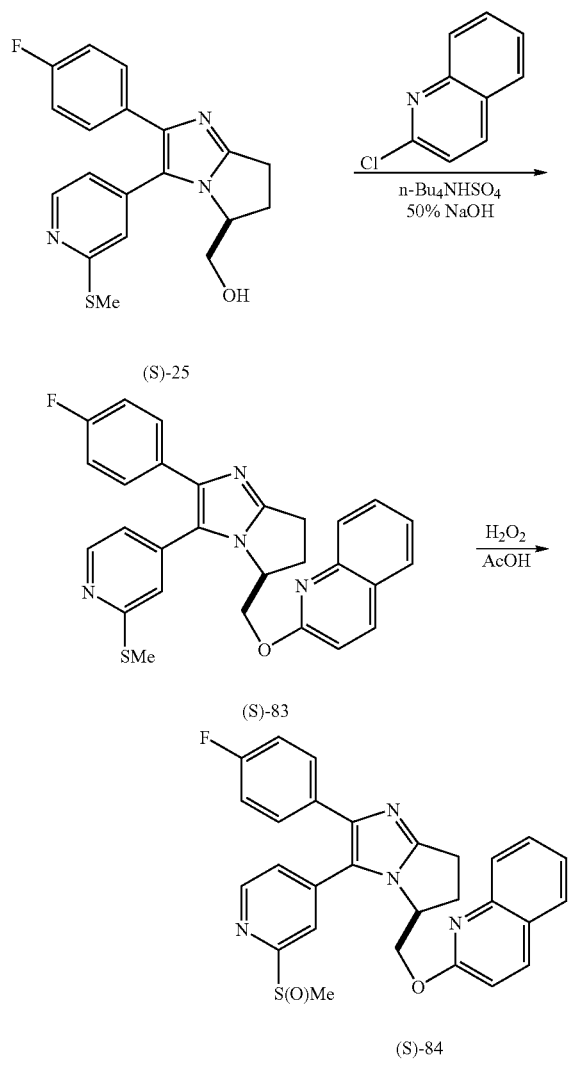

(S)-84

A mixture of the alcohols (S)-9 and (S)-25 (106.6 g; about 10:1 ratio by UV; prepared as in Scheme 5) was converted into sulphoxide (S-)-84 following the method for (S-)-55 and (S-)-56. Yield 45 mg. MS (ESP+) m/e 499.9 (M+H).

(S)-{⁴-[2-(4-Fluoro-phenyl)-5-(quinolin-2-yloxymethyl)-6,7-dihydro-5H-pyrrolo[1,2-a]imidazol-3-yl]-pyridin-2-yl}-propyl-amine; (S)-85

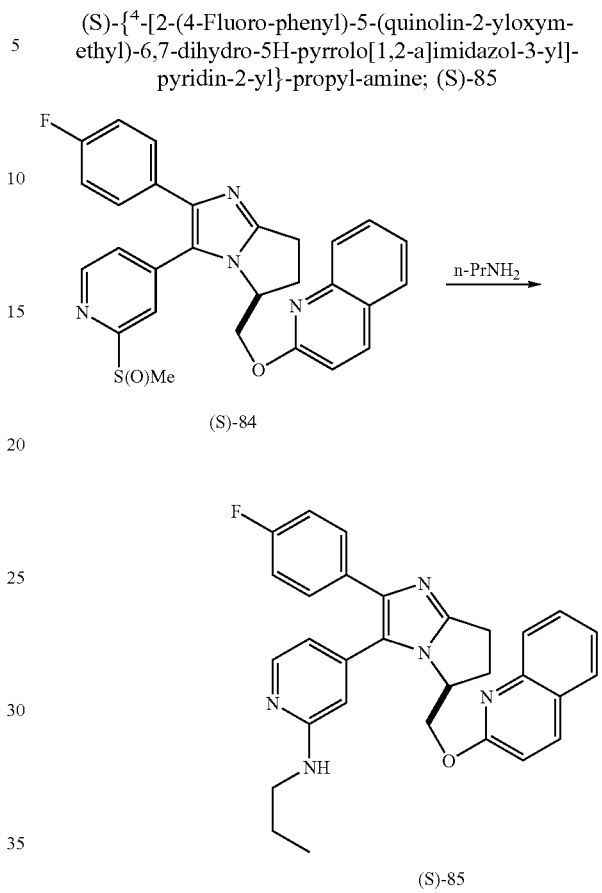

(S)-85

A mixture of the sulphoxide (S)-84 (45 mg, 0.09 mmol) in n-propylamine (0.4 mL) was heated at 120° C. in an oil bath. After 6 days the mixture was cooled to room temperature and purified by PTLC with AcOEt and then hexane-i-PrOH=9: 1 (3-fold elution) to afford the quinoline (S)-85 (6 mg, 13%) as an oil. MS (ESP+) m/e 494.0 (M+H)

Synthesis of Iodide (S)-86 and its Further Transformations (Scheme 26).

Scheme 26

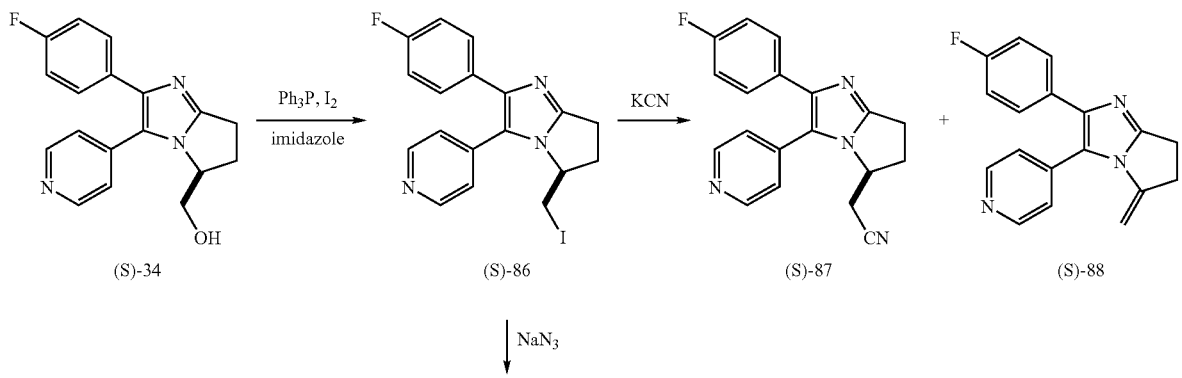

-continued

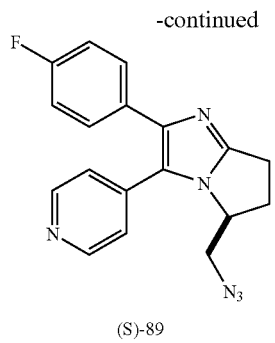

(S)-89

(S)-2-(4-Fluoro-phenyl)-5-iodomethyl-3-pyridin-4-yl-6,7-dihydro-5H-pyrrolo[1,2-a]imidazole; (S)-86

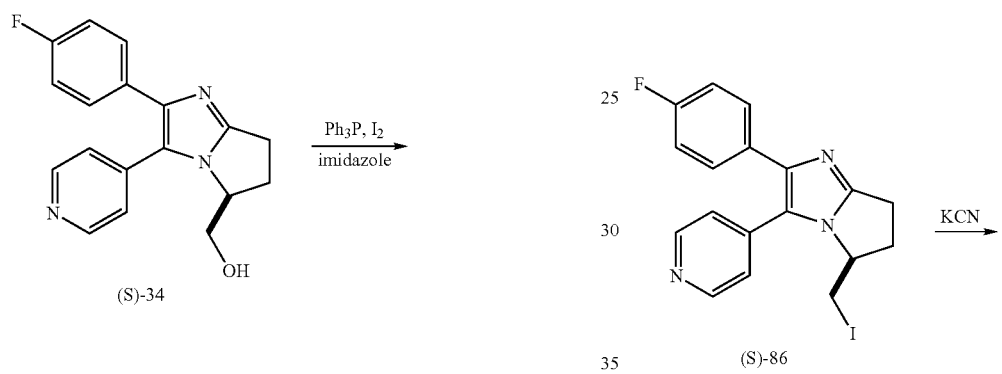

Iodine (50.4 mg, 199 μmol) was added to a mixture of alcohol (S)-34 (20.0 mg, 64.7 μmol), Ph$_3$P (69.3 mg, 264 mol) and imidazole (17.6 mg, 259 μmol) in Et$_2$O (2.5 mL) —hexane (0.84 mL). The mixture was stirred at r.t. for 2 h and separated between AcOEt—saturated aqueous NaHCO$_3$. The aqueous layer was extracted with AcOEt (4×2 mL). Combined organic solutions were washed with brine, dried MgSO$_4$, concentrated and separated by PTLC with AcOEt as eluent to afford (S)-86 (25.7 mg, 95%) as white solid. $^1$H NMR (250 MHz, CDCl$_3$) δ [ppm] 2.40-2.54 (m, 1H), 2.85-3.20 (m, 5H), 4.57-4.66 (m, 1H), 6.97 (t, J=8.8 Hz, 2H), 7.26 (d, J=6.1 Hz, 2H), 7.41-7.50 (m, 2H), 8.64 (d, J=6.1 Hz, 2H).

(S)-[2-(4-Fluoro-phenyl)-3-pyridin-4-yl-6,7-dihydro-5H-pyrrolo[1,2-a]imidazol-5-yl]-acetonitrile (S)-87 and (S)-2-(4-Fluoro-phenyl)-5-methylene-3-pyridin-4-yl-6,7-dihydro-5H-pyrrolo [1,2-a]imidazole (S)-88

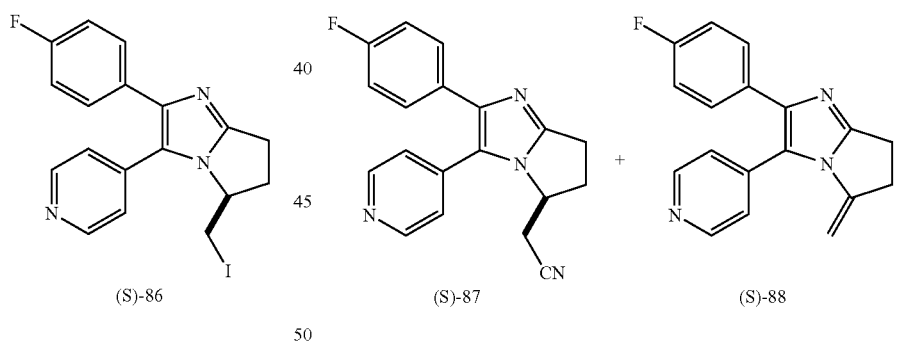

A mixture of (S)-86 (21.1 mg, 50.3 μmol), KCN (16.6 mg, 255 μmol), and DMAP (cat. amount) in DMF (0.5 mL) was stirred at r.t. overnight. Solvent was removed in vacuum and the residual DMF was removed by evaporation with p-xylene (2×10 mL). The crude product was separated by PTLC with CH$_2$Cl$_2$:MeOH=19:1 as eluent to afford lower R$_f$ nitrile (S)-87 (2.0 mg, 12%) and higher Rf alkene (S)-88 (12.3 mg, 84%). (S)-87: $^1$H NMR (250 MHz, CDCl$_3$) δ 2.37 (dd, J=16.9, 7.0 Hz, 1H), 2.47 (dd, J=16.9, 3.8 Hz, 1H), 2.54-2.69 (m, 1H), 3.00-3.28 (m, 3H), 4.75-4.86 (m, 1H), 6.98 (t, J=8.8 Hz, 2H), 7.25 (d, J=6.1 Hz, 2H), 7.43 (dd, J=9.0, 5.4 Hz, 2H), 8.67 (d, J=6.1 Hz, 2H); MS (APCI+) m/e 319 (M+H).

(S)-88: $^1$H NMR (250 MHz, CDCl$_3$) δ 2.98-3.10 (m, 2H), 3.15-3.26 (m, 2H), 4.34 (q, J=1.9 Hz, 1H), 4.44 (q, J=1.9 Hz, 1H), 6.93 (t, J=8.8 Hz, 2H), 7.33-7.42 (m, 4H), 8.67 (d, J=6.1 Hz, 2H); MS (APCI+) m/e 292 (M+H).

(S)-5-Azidomethyl-2-(4-fluoro-phenyl)-3-pyridin-4-yl-6,7-dihydro-5H-pyrrolo[1,2-a]imidazole; (S)-89

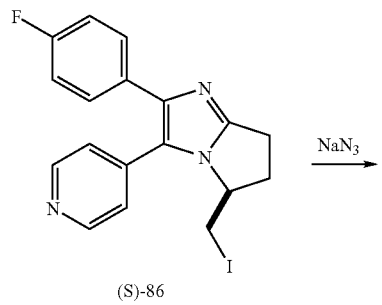

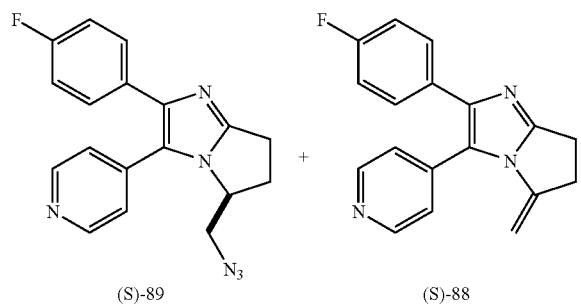

A mixture of (S)-86 (174.5 mg, 416 μmol), NaN$_3$ (135.2 mg, 2.08 mmol) in DMF (1.7 mL) was stirred at r.t. overnight. Solvent was removed in vacuum and the residual DMF was removed by evaporation with p-xylene (3×10 mL). The crude product was separated by PTLC with AcOEt as eluent to afford lower Rf azide (S)-89 (71.2 mg, 51%) and higher Rf alkene (S)-88 (23.4 mg, 19%).

(S)-89: $^1$H NMR (250 MHz, CDCl$_3$) δ 2.43-2.57 (m, 1H), 2.81-3.16 (m, 3H), 3.20 (d, J=4.0 Hz, 2H), 6.97 (t, J=8.9 Hz, 2H), 7.25 (d, J=7.1 Hz, 2H), 7.45 (dd, J=8.9, 5.4 Hz, 2H), 8.64 (d, J=7.1 Hz, 2H); MS (FAB+) m/e 335 (M+H).

Assays for Measuring Activity of Compounds

JNK1, JNK2, JNK3—SPA Assay

1. Compound is dissolved in DMSO to a convenient concentration and this is diluted in 10% DMSO to a five times concentrate of the desired starting concentration (frequently 1: 100).
2. 10 μl of 500 mM EDTA is added to alternative wells of the Opti-plate row, which will receive kinase reaction plus DMSO. This creates the negative control.
3. For the JNK2 and JNK3 assay, compounds are prepared in six 2-fold dilutions with water and each concentration is tested in duplicate. For the JNK1 assay compounds are prepared in four 5-fold dilutions with water which are tested in triplicate. Controls are treated identically.
4. 20 μl per well of each compound concentration is transferred to an Opti-plate, in duplicate.
5. 30 μl (JNK2/3 SPA) or 50 μl (JNK1 SPA) of substrate solution (25 mM HEPES pH 7.5, 10 mM magnesium acetate with 3.33 μM ATP (JNK2/3) or 2 μM ATP (JNK1), approximately 7.5 kBq [γ-$^{33}$P] ATP, GST-c-Jun, in water) is added to each well.
6. 50 μl (JNK2/3 SPA) or 30 gl (JNK1 SPA) of kinase solution (JNK in 25 mM HEPES pH 7.5, 10 mM Mg Acetate) is added to each well.

| Kinase | Kinase per well (μg) | GST-c-Jun per well (μg) |
|---|---|---|
| JNK1 | 0.25 | 1 |
| JNK2 | 0.2 | 1.2 |
| JNK3 | 0.16 | 1.2 |

7. The plate is incubated for 30 minutes at room temperature.
8. 100 μl of bead/stop solution is added to each well (5 mg/ml glutathione-PVT-SPA beads, 40 mM ATP in PBS).
9. Plates are sealed and incubated for 30 minutes at room temperature, centrifuged for 10 minutes at 2500 g and counted.
10. The IC$_{50}$ values are calculated as the concentration of the compound being tested at which the phosphorylation of c-Jun is decreased to 50% of the control value. Example IC$_{50}$ values for the compounds of this invention are given in Table 1.

p38 ELISA

Active p38 kinase (100 ng; Upstate) was added to 2 μg GST-ATF2 substrate (NEB) in 250 mM Hepes pH 7.5/100 mM MgAc/50 μM ATP (final) in the presence or absence of compounds in 50 μl. The mixture was incubated at 30° C. for 1 hour, and then diluted with 200 μl PBS-Tween (0.05%). From this, duplicate volumes of 100 μl were added to a Reacti-Bind glutathione coated plate (Pierce) and incubated for 1 hour. After washing 3 times with PBS-Tween (0.05%), rabbit anti-phospho-ATF2 (Thr71) antibody (NEB) was added at 1:500, and incubated for another hour at room temperature. After 3 additional washes with PBS-Tween (0.05%), 100 μl of anti-rabbit IgG alkaline phosphatase-conjugated secondary antibody (Sigma) was added at 1:1000, the reaction was incubated for a further hour, washed 3 times, and then phosphatase substrate (Sigma) was added (100 μl per well; 3 tablets in 5 ml water). After incubation in the dark at 37° C. for 1 hour, the reaction mixture was transferred to a clear 96 well plate, and the absorbance at 405 nm was read. The IC$_{50}$ values are calculated as the concentration of the compound being tested at which the phosphorylation of ATF2 is decreased to 50% of the control value. Example IC$_{50}$ values for the compounds of this invention are given in Table 1 (last column).

TABLE 1

IC$_{50}$ values for selected compounds against JNK1, JNK2, JNK3, and p38 MAP kinase

| Compound | JNK3 IC$_{50}$ (nM) | JNK2 IC$_{50}$ (nM) | JNK1 IC$_{50}$ (nM) | p38 IC$_{50}$ (nM) |
|---|---|---|---|---|
| [structure] | 88 | 52 | 183 | 270 |
| [structure] | 295 | | | |
| [structure] | 91 | 250 | 636 | 619 |
| [structure] | 150 | | | |

TABLE 1-continued

IC$_{50}$ values for selected compounds against JNK1, JNK2, JNK3, and p38 MAP kinase

| Compound | JNK3 IC$_{50}$ (nM) | JNK2 IC$_{50}$ (nM) | JNK1 IC$_{50}$ (nM) | p38 IC$_{50}$ (nM) |
|---|---|---|---|---|
| (structure) | 61 | 125 | 125 | 696 |
| (structure) | 29 | 125 | 313 | 185 |
| (structure) | 54 | 83 | 412 | |
| (structure) | 71 | 114 | 249 | |

TABLE 1-continued
IC$_{50}$ values for selected compounds against JNK1, JNK2, JNK3, and p38 MAP kinase
| Compound | JNK3 IC$_{50}$ (nM) | JNK2 IC$_{50}$ (nM) | JNK1 IC$_{50}$ (nM) | p38 IC$_{50}$ (nM) |
|---|---|---|---|---|
| 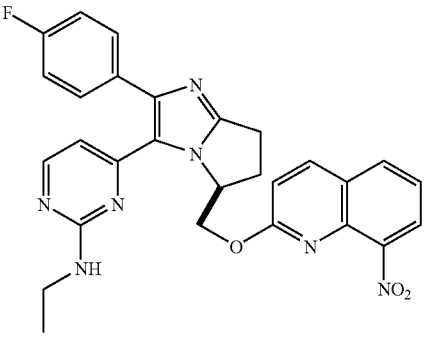 | 86 | 38 | 137 | |
| 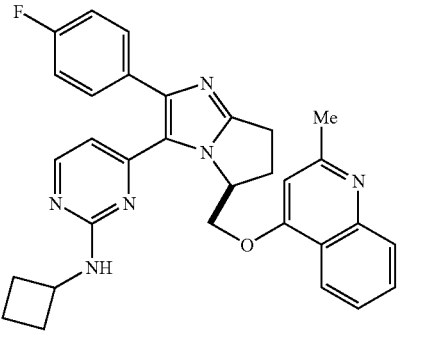 | 25 | 30 | 78 | |
| 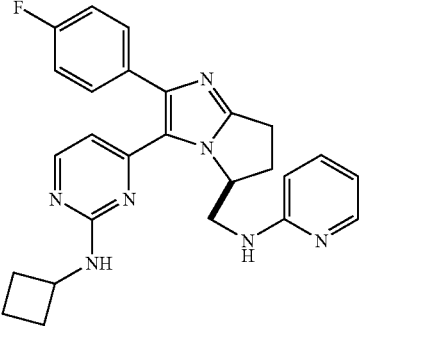 | 38 | 126 | 524 | |
| 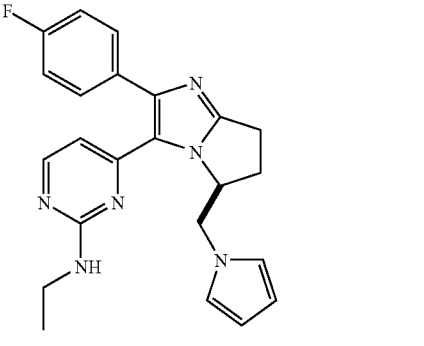 | 14 | 13 | 27 | 59 |

TABLE 1-continued
IC$_{50}$ values for selected compounds against JNK1, JNK2, JNK3, and p38 MAP kinase
| Compound | JNK3 IC$_{50}$ (nM) | JNK2 IC$_{50}$ (nM) | JNK1 IC$_{50}$ (nM) | p38 IC$_{50}$ (nM) |
|---|---|---|---|---|
| 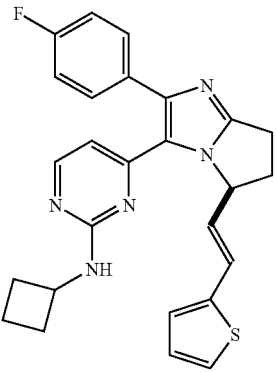 | | 53 | | 248 |
| 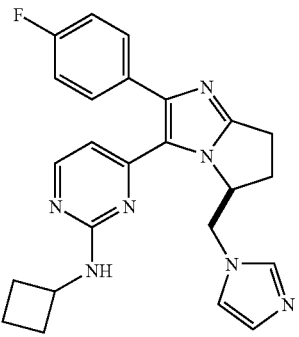 | | 7 | | 22 |
| 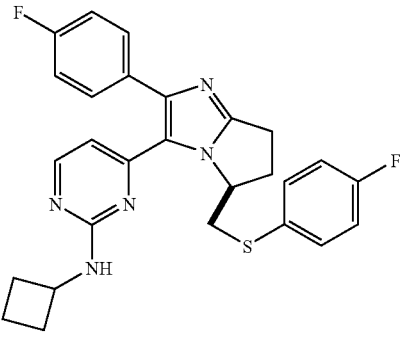 | | 8 | | 92 |
| 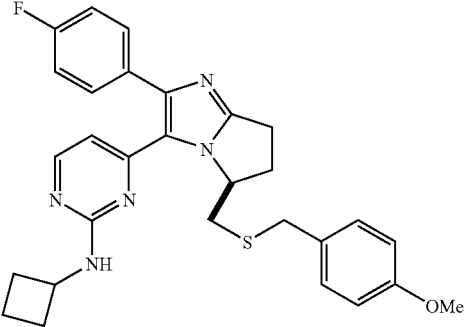 | | 30 | | 94 | 148 |

TABLE 1-continued
IC$_{50}$ values for selected compounds against JNK1, JNK2, JNK3, and p38 MAP kinase
| Compound | JNK3 IC$_{50}$ (nM) | JNK2 IC$_{50}$ (nM) | JNK1 IC$_{50}$ (nM) | p38 IC$_{50}$ (nM) |
|---|---|---|---|---|
| 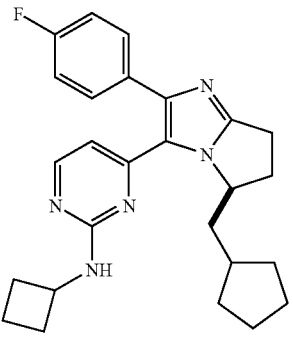 | 10 | | | |
| 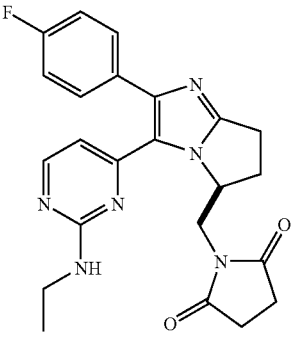 | 17 | | | |
| 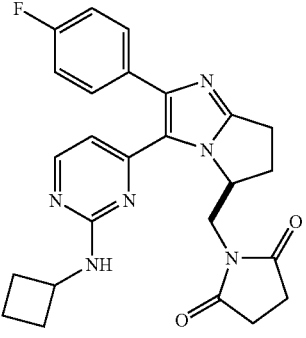 | 6 | | 60 | |
| 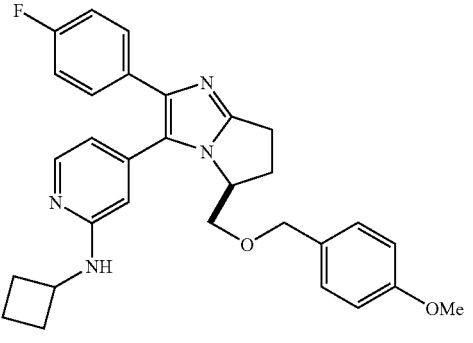 | 23 | | | |

TABLE 1-continued

IC$_{50}$ values for selected compounds against JNK1, JNK2, JNK3, and p38 MAP kinase

| Compound | JNK3 IC$_{50}$ (nM) | JNK2 IC$_{50}$ (nM) | JNK1 IC$_{50}$ (nM) | p38 IC$_{50}$ (nM) |
| --- | --- | --- | --- | --- |
| 301 | | | | |

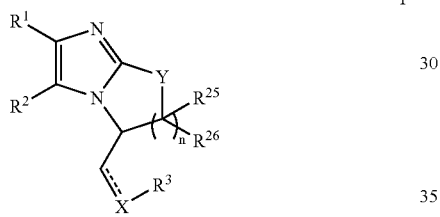

What is claimed is:

1. A compound of formula I, or a pharmaceutically acceptable salt thereof:

I wherein Y is CH$_2$,

R$^{25}$ and R$^{26}$ are both hydrogen or R$^{25}$ and R$^{26}$ together are carbonyl;

n is 1;

the bond C⋯X is a single or double bond;

R$^1$ is aryl or substituted aryl, wherein the aryl or substituted aryl is optionally fused to a partially unsaturated or fully saturated five to seven membered carbocyclic ring, and each substitutable carbon atom in R$^1$, including the optional fused ring, is optionally and independently substituted by one or more of halogen C$_{1-4}$ alkyl, haloalkyl, OR, SR, OH, NO$_2$, CN, NH$_2$, NHR, NR$_2$, NHCOR, NHCONHR, NHCONR$_2$, NRCOR, NHCO$_2$R, CO$_2$R, CO$_2$H, COR, CONHR, CONR$_2$, S(O)$_2$R, SONH$_2$, S(O)R, SO$_2$NHR, or NHS(O)$_2$R; and each saturated carbon in the optional fused ring is further optionally and independently substituted by =O, =S, =NNHR, =NNR$_2$, =N—OR, =NNHCOR, NNHCO$_2$R, =NNSO$_2$R, or =NR; wherein R is H, C$_{1-4}$ alkyl or haloalkyl;

R$^2$ is an optionally substituted pyridine;

X is CHR$^{16}$, CR$^{16}$, NR$^{16}$, C=O, NR$^{16}$CO, O or S, SO or SO$_2$, wherein R$^{16}$ is hydrogen. C$_{1-4}$ alkyl optionally substituted with one or more of OR$^{20}$, NR$^{20}$R$^{21}$ or aryl, where R$^{20}$ and R$^{21}$ are independently H, aryl or C$_{1-4}$ alkyl;

R$^3$ is H, optionally substituted C$_{1-10}$ alkyl, optionally substituted alkylaryl, aryl, substituted aryl, optionally substituted alkylheterocyclyl, heterocyclyl or substituted heterocyclyl wherein the optionally substituted aryl or heterocyclyl group is optionally fused to one or more partially unsaturated or fully saturated five to seven membered ring containing zero to three heteroatoms and wherein each substitutable carbon atom including the optional fused ring, is optionally and independently substituted by one or more of H, C$_{1-4}$ alkyl, aryl, heterocyclyl, alkylaryl, halogen, haloalkyl, OR$^{15}$, SR$^{15}$, OH, NO$_2$, CN, NH$_2$, NHR$^{15}$, NR$^{15}_2$, NHCOR$^{15}$, NHCONHR$^{15}$, NHCONR$^{15}_2$, NRCOR$^{15}$, NHCO$_2$R$^{15}$, CO$_2$R$^{15}$, CO$_2$H, COR$^{15}$, CONHR$^{15}$, CONR$^{15}_2$, S(O)$_2$R$^{15}$, SONH$_2$, S(O)R$^{15}$, SO$_2$NHR$^{15}$, or NHS(O)$_2$R$^{15}$ and wherein each saturated carbon in the fused ring is further optionally and independently substituted by =O, =S, =NNHR$^{15}$, NNR$^{15}_2$, =N—OR$^{15}$, =NNHCOR$^{15}$, =NNSO$_2$R$^{15}$, =NNSO$_2$R$^{15}$, or =NR$^{15}$ wherein each substitutable nitrogen atom is optionally substituted by H, or C$_{1-4}$ alkyl, COR$^{15}$, SO$_2$R$^{15}$ or CO$_2$R$^{15}$, wherein R$^{15}$ is H, C$_{1-4}$ alkyl, haloalkyl, or optionally substituted alkylaryl;

wherein if X is NR$^{16}$, R$^{16}$ and R$^3$ together optionally form a fully saturated, partially unsaturated and unsaturated four to seven membered heterocyclyl or substituted heterocyclyl ring containing up to three heteroatoms, wherein the ring is optionally fused to a partially unsaturated or fully saturated five to seven membered ring containing zero to three heteroatoms, and wherein each substitutable carbon atom in the ring including the optional fused ring, is optionally and independently substituted by C$_{1-4}$ alkyl, aryl, alkylaryl, halogen, OR$^{22}$, SR$^{22}$, OH, NO$_2$, CN, NH$_2$, NHR$^{22}$, NR$^{22}_2$, NHCOR$^{22}$, NHCONHR$^{22}$, NHCONR$^{22}_2$, NRCOR$^{22}$, NHCO$_2$R$^{22}$, CO$_2$R$^{22}$, CO$_2$H, COR$^{22}$, CONHR$^{22}$, CONR$^{22}_2$, S(O)$_2$R$^{22}$, SONH$_2$, S(O)R$^{22}$, SO$_2$NHR$^{22}$, or NHS(O)$_2$R$^{22}$ and wherein each saturated carbon in the fused ring is further optionally and independently substituted by =O, =S, =NNHR$^{22}$, NNR$^{22}_2$, =N—OR$^{22}$, =NNHCOR$^{22}$, =NNHCO$_2$R$^{22}$, =NNSO$_2$R$^{22}$, or =NR$^{22}$; wherein each substitutable nitrogen atom in the ring structure is optionally substituted by R$^{22}$, COR$^{22}$, SO$_2$R$^{22}$ or CO$_2$R$^{22}$, where R$^{22}$ is hydrogen or C$_{1-4}$ alkyl, provided that when the bond C⋯X is a single bond, X is CHR$^{16}$ and R$^3$ is hydrogen or an unsubstituted C$_{1-10}$ alkyl, then R$^{16}$ is not hydrogen or an unsubstituted C$_{1-4}$ alkyl.

2. A compound of formula I or a pharmaceutically acceptable salt thereof:

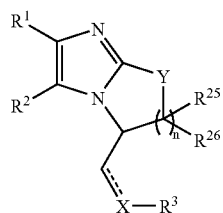

wherein Y is $CH_2$;
$R^{25}$ and $R^{26}$ are both hydrogen or $R^{25}$ and $R^{26}$ together are carbonyl;
n is 1;
the bond C⋯X is a single or double bond;
$R^1$ is aryl or substituted aryl, wherein the aryl or substituted aryl is optionally fused to a partially unsaturated or fully saturated five to seven membered carbocyclic ring, and each substitutable carbon atom in $R^1$, including the optional fused ring, is optionally and independently substituted by one or more of halogen $C_{1-4}$ alkyl, haloalkyl, OR, SR, OH, $NO_2$, CN, $NH_2$, NHR, $NR_2$, NHCOR, NHCONHR, NHCONR₂, NRCOR, $NHCO_2R$, $CO_2R$, $CO_2H$, COR, CONHR, $CONR^2$, $S(O)_2R$, $SONH_2$, S(O)R, $SO_2NHR$, or $NHS(O)_2R$; and each saturated carbon in the optional fused ring is further optionally and independently substituted by =O, =S, =NNHR, NNR₂, =N—OR, =NNHCOR, $NNHCO_2R$, $=NNSO_2R$, or =NR; wherein R is H, $C_{1-4}$ alkyl or haloalkyl;
$R^2$ is an optionally substituted pyridine;
X is $CHR^{16}$, $CR^{16}$, $NR^{16}$, C=O, $NR^{16}CO$, O or S, SO or $SO_2$, wherein $R^{16}$ is hydrogen, $C_{1-4}$ alkyl optionally substituted with one or more of $OR^{20}$, $NR^{20}R^{21}$ or aryl, where $R^{20}$ and $R^{21}$ are independently H, aryl or $C_{1-4}$ alkyl;
$R^3$ is H, optionally substituted $C_{1-10}$ alkyl, optionally substituted alkylaryl, aryl, substituted aryl, optionally substituted alkylheterocyclyl, heterocyclyl or substituted heterocyclyl wherein the optionally substituted aryl or heterocyclyl group is optionally fused to one or more partially unsaturated or fully saturated five to seven membered ring containing zero to three heteroatoms and wherein each substitutable carbon atom including the optional fused ring, is optionally and independently substituted by one or more of H, $C_{1-4}$ alkyl, aryl, heterocyclyl, alkylaryl, halogen, haloalkyl, $OR^{15}$, $SR^{15}$, OH, $NO_2$, CN, $NH_2$, $NHR^{15}$, $NR^{15}_2$, $NHCOR^{15}$, $NHCONHR^{15}$, $NHCONR^{15}_2$, $NRCOR^{15}$, $NHCO_2R^{15}$, $CO_2R^{15}$, $CO_2H$, $COR^{15}$, $CONHR^{15}CONR^{15}_2$, $S(O)_2R^{15}$, $SONH_2$, $S(O)R^{15}$, $SO_2NHR^{15}$, or $NHS(O)_2R^{15}$ and wherein each s carbon in the fused ring is further optionally and independently substituted by =O, =S, $=NNHR^{15}$, $NNR^{15}_2$, $=N—OR^{15}$, $=NNHCOR^{15}$, $=NNHCO_2R^{15}$, $=NNSO_2R^{15}$, or $=NR^{15}$; wherein each substitutable nitrogen atom is optionally substituted by H, or $C_{1-4}$ alkyl, $COR^{15}$, $SO_2R^{15}$ or $CO_2R^{15}$, wherein $R^{15}$ is H, $C_{1-4}$ alkyl, haloalkyl, or optionally substituted alkylaryl;
wherein if X is $CHR^{16}$ or $CR^{16}$, $R^{16}$ and $R^3$ can together form a fully saturated, partially unsaturated and unsaturated four to seven membered ring, aryl, substituted aryl, heterocyclyl or substituted heterocyclyl ring containing up to three heteroatoms, wherein the ring structure is optionally fused to a partially unsaturated or fully saturated five to seven membered ring containing zero to three heteroatoms, and wherein each substitutable carbon atom in the ring including the optional fused ring, is optionally and independently substituted by $C_{1-4}$ alkyl, aryl, alkylaryl, halogen, $OR^{22}$, $SR^{22}$, OH, $NO_2$, CN, $NH_2$, $NHR^{22}$, $NR^{22}_2$, $NHCOR^{22}$, $NHCONHR^{22}$, $NHCONR^{22}_2$, $NRCOR^{22}$, $NHCO_2R^{22}$, $CO_2R^{22}$, $CO_2H$, $COR^{22}$, $CONHR^{22}CONR^{22}_2$, $S(O)_2R^{22}$, $SONH_2$, $S(O)R^{22}$, $SO_2NHR^{22}$, or $NHS(O)_2R^{22}$ and wherein each saturated carbon in the fused ring is further optionally and independently substituted by =O, =S, $=NNHR^{22}$, $NNR^{22}_2$, $=N—OR^{22}$, $=NNHCOR^{22}$, $=NNHCO_2R^{22}$, $=NNSO_2R^{22}$, or $=NR^{22}$; wherein each substitutable nitrogen atom in the ring structure is optionally substituted by $R^{22}$, $COR^{22}$, $SO^2R^{22}$ or $C_{02}R^{22}$, where $R^{22}$ is hydrogen or $C_{1-4}$ alkyl, provided that when the bond C⋯X is a single bond, X is $CHR^{16}$ and $R^3$ is hydrogen or an unsubstituted $C_{1-10}$ alkyl, then $R^{16}$ is not hydrogen or an unsubstituted $C_{1-4}$ alkyl.

3. A compound as claimed in claim 1, wherein where X is O, $R^3$ is $C_{1-8}$ alkyl, alkylaryl, alkylheterocyclyl, aryl, heterocyclyl or cycloalkyl optionally substituted with one or more of $C_{1-4}$ alkyl, halogen, haloalkyl, aryl, alkylaryl, $NO_2$, $NH_2$, or $OR^{15}$; wherein aryl is phenyl or napthyl; alkylaryl is methyl or ethyl carrying one or more phenyl groups wherein the aryl group may be substituted by $C_{1-4}$ alkyl, halogen, haloalkyl, aryl, alkylaryl, $NO_2$, $NH_2$, or $OR^{15}$; heterocyclyl is preferably 2-pyridyl, 4-pyridyl, 2-quinolinyl, 2-pyrimidinyl, pyrazinyl, 2-quinoxalinyl, pyridazinyl, 1-isoquinolinyl, or 4-quinolinyl, more preferably 2-pyridyl or 4-pyridyl, the cycloalkyl group is a 3, 4, 5, 6 or 7 membered ring and can be fused to one or more aryl, heterocyclyl or cycloalkyl group.

4. A compound as claimed in claim 3, wherein the one or more phenyl groups are substituted with halogen, alkyl, haloalkyl, aryl, alkylaryl, $NO_2$, $NH_2$ or $OR^{15}$; naphthyl groups are optionally substituted with alkyl more preferably with methyl; and heterocyclyl groups are optionally substituted with halogen, haloalkyl, alkyl, aryl, $NO_2$, CN or $OR^{15}$.

5. A compound as claimed in claim 4 wherein the halogen is F, Cl or Br; alkyl is methyl, ethyl, propyl or butyl; haloalkyl is $CF_3$; and $R^{15}$ is methyl.

6. A compound as claimed in claim 1, wherein where X is $NR^{16}$ $R^{16}$ is hydrogen, or $C_{1-4}$ alkyl optionally substituted with $OR^{20}$ or $NR^{20}R^{21}$, wherein alkyl is methyl, ethyl, n-propyl, i-propyl or butyl, $R^{20}$ and $R^{21}$ are independently hydrogen, aryl, preferably phenyl, or $C_{1-4}$ alkyl, preferably methyl, heterocyclyl is pyridinyl, quinolinyl or isoquinolinyl.

7. A compound as claimed in claim 1, wherein $R^3$ is alkylaryl optionally substituted with $OR^{15}$, alkyl or halogen, wherein the alkyl group is methyl, ethyl, propyl or butyl more preferably methyl or ethyl, halogen is F, Cl or Br, $R^{15}$ is alkyl preferably methyl or ethyl and aryl is phenyl.

8. A compound as claimed in claim 1, wherein when X is $NR^{16}$, $R^{16}$ and $R^3$ form a heterocyclyl or substituted heterocyclyl ring selected from the group consisting of morpholinyl, tetrahydroquinolinyl, tetrahydroisoquinolinyl, indolinyl and indolyl, each of which is optionally substituted with one or more of aryl, alkylaryl, halogen or $OR^{22}$ where R is $C_{1-4}$ alkyl, preferably methyl or ethyl, aryl is phenyl, and halogen is F, Cl or Br.

9. A compound as claimed in claim 2 wherein X is $CR^{16}$ or $CHR^{16}$ $R^{16}$ and $R^3$ form a fully saturated or unsaturated five to seven membered ring selected from the group consisting of cyclopentyl, phenyl, and cyclohexyl, each of which is optionally substituted with one or more of aryl, alkylaryl, halogen or $OR^{22}$ wherein $R^{22}$ is $C_{1-4}$ alkyl preferably methyl or ethyl, aryl is preferably phenyl, halogen is preferably F, Cl or Br.

10. A compound selected from the group consisting of:

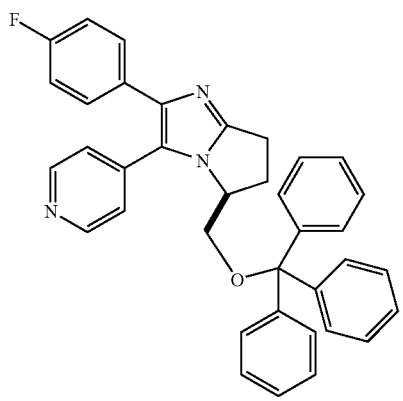

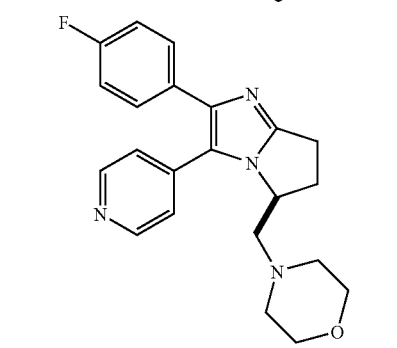

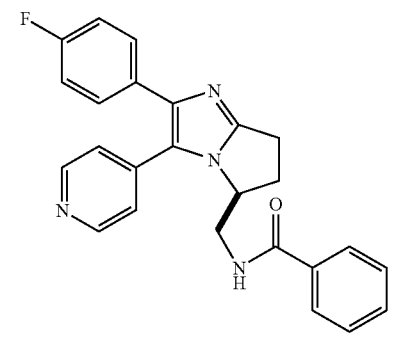

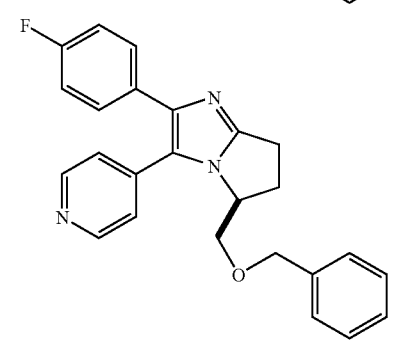

-continued

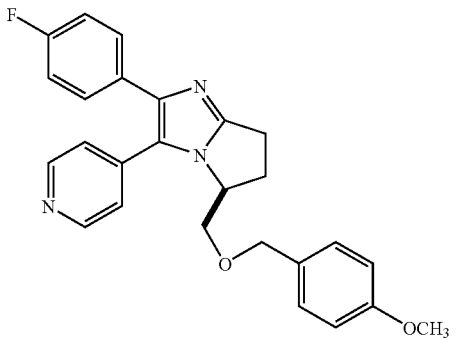

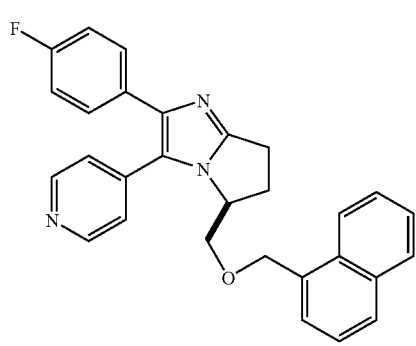

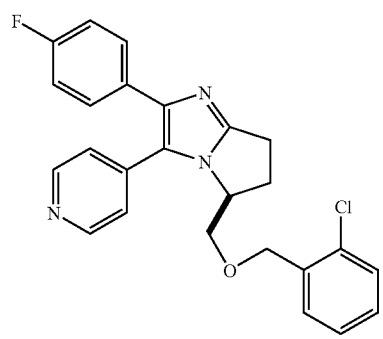

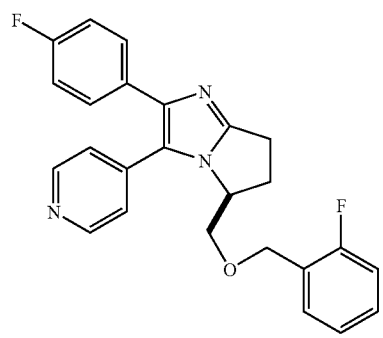

249
-continued
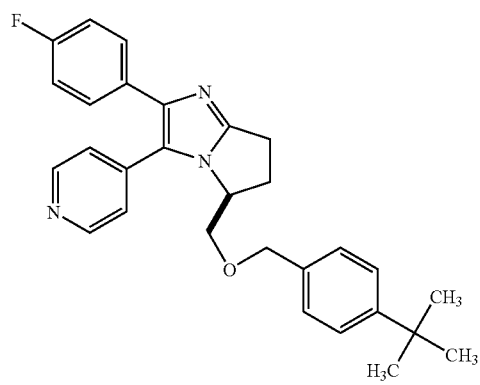
250
-continued
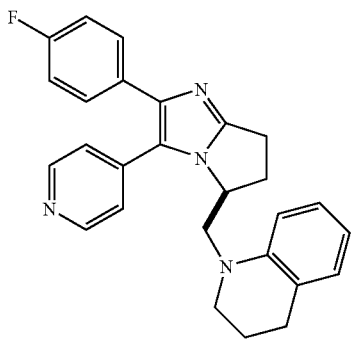
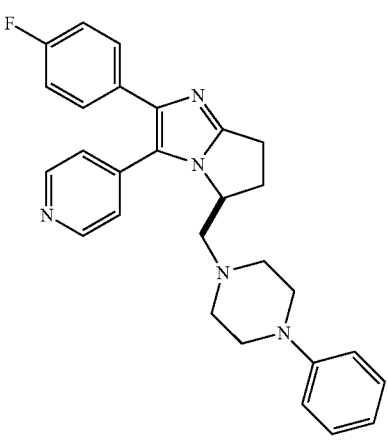
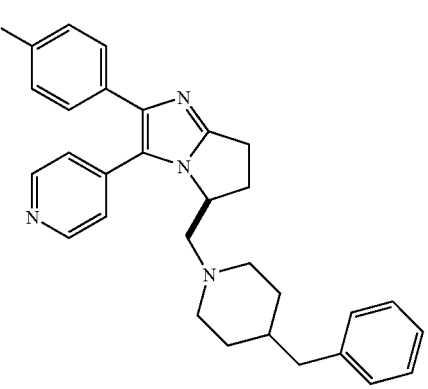
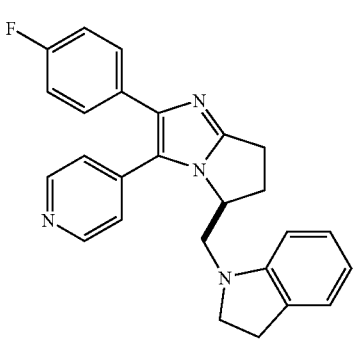

251
-continued
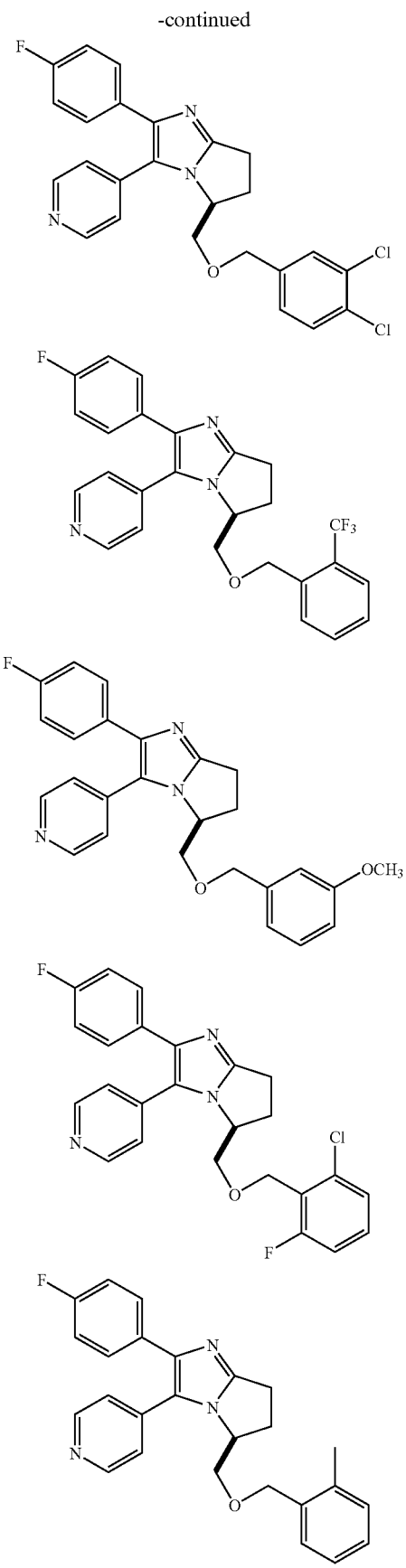
252
-continued
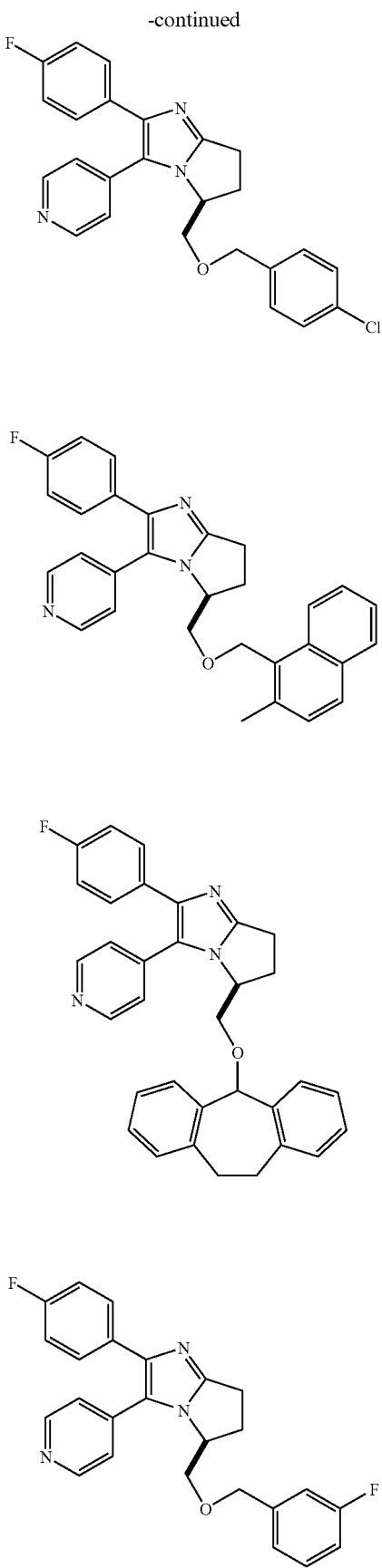

253
-continued
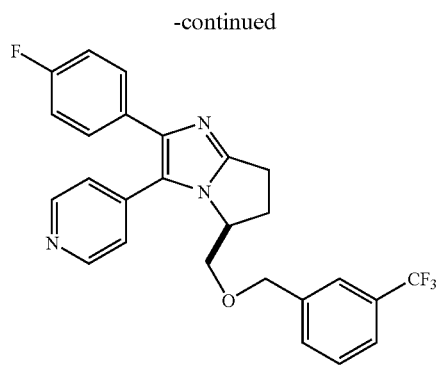
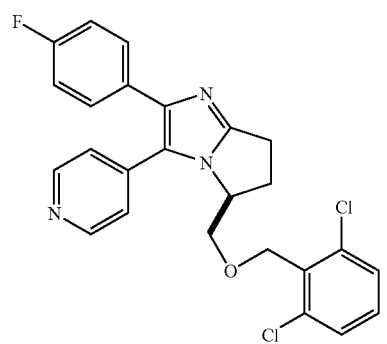
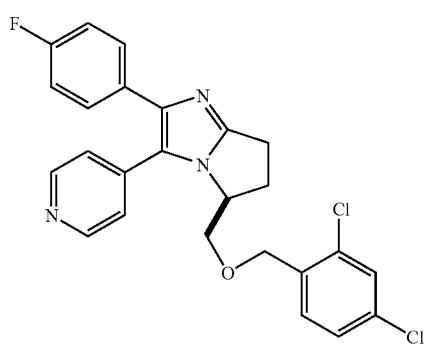
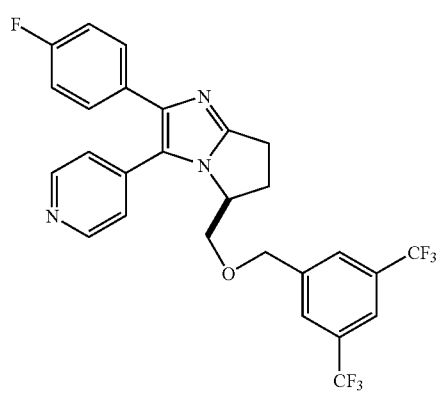
254
-continued
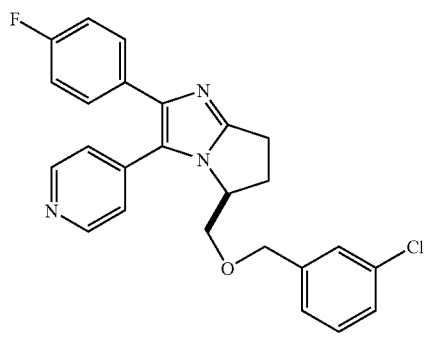
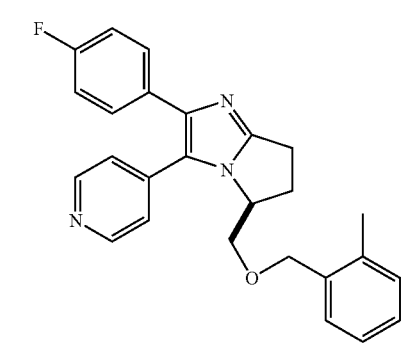
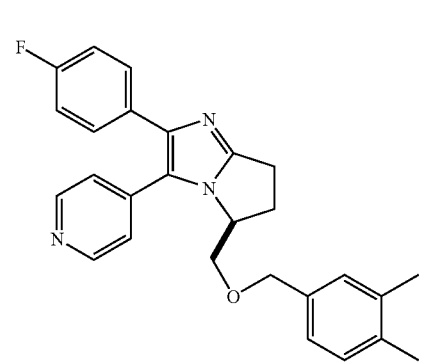
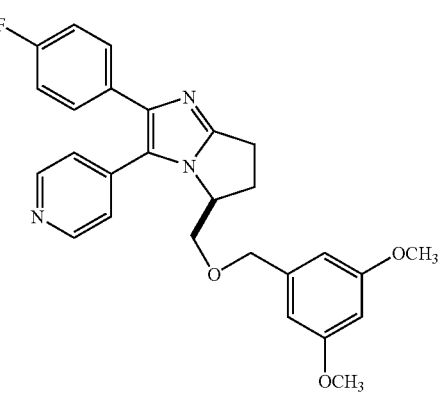

255
-continued
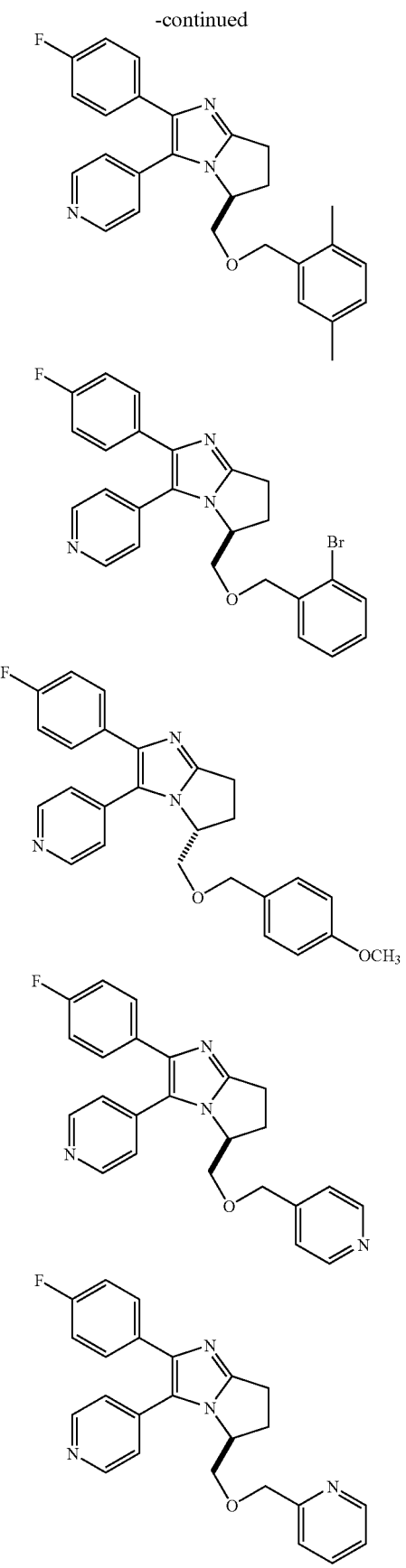
256
-continued
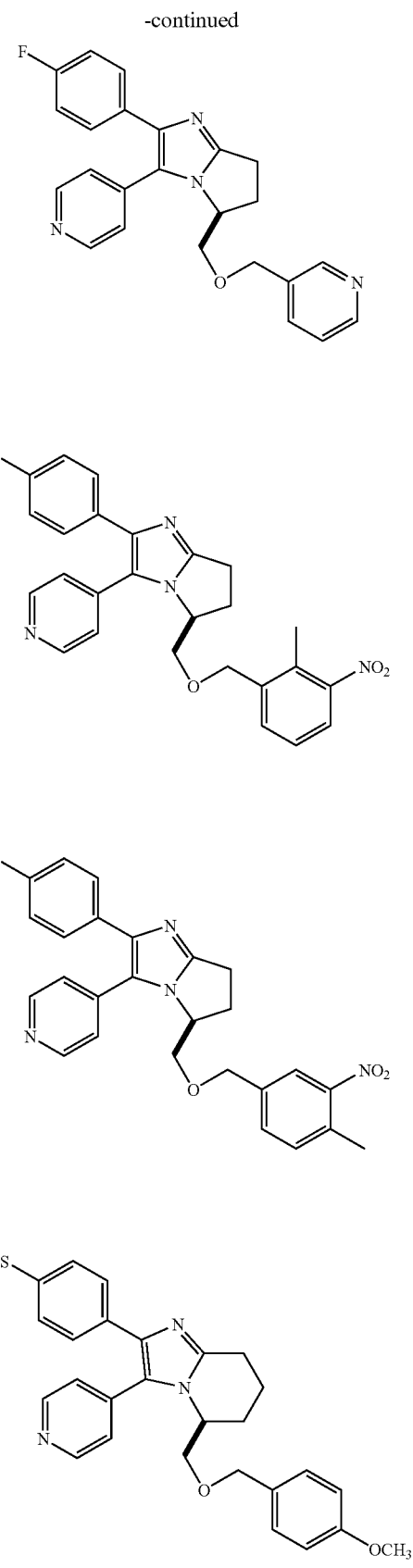

257
-continued
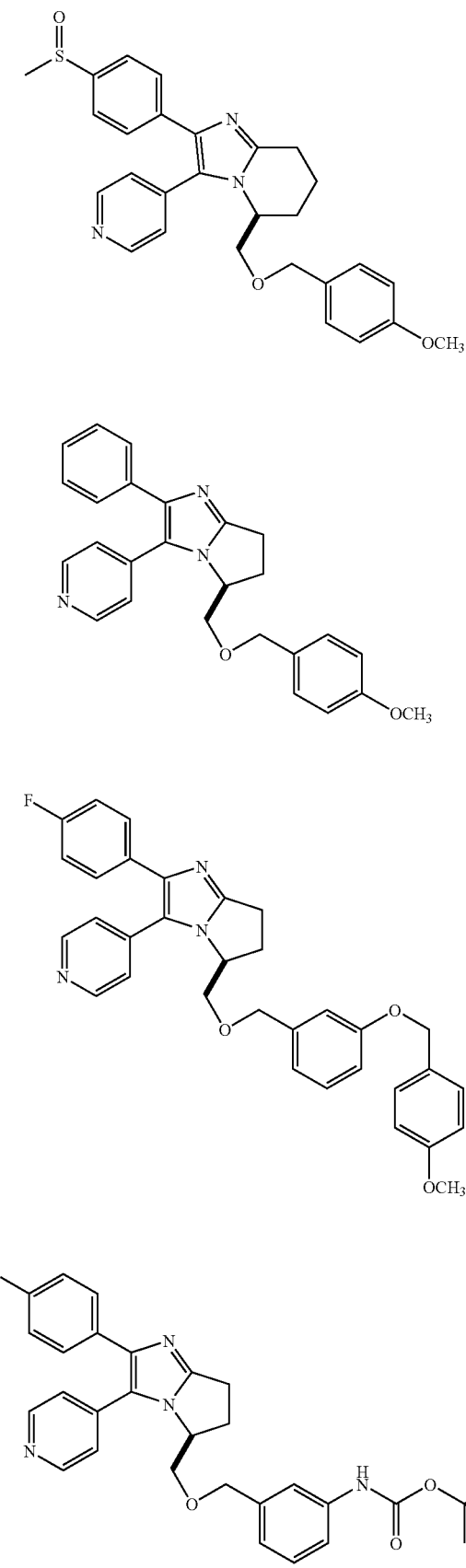
258
-continued
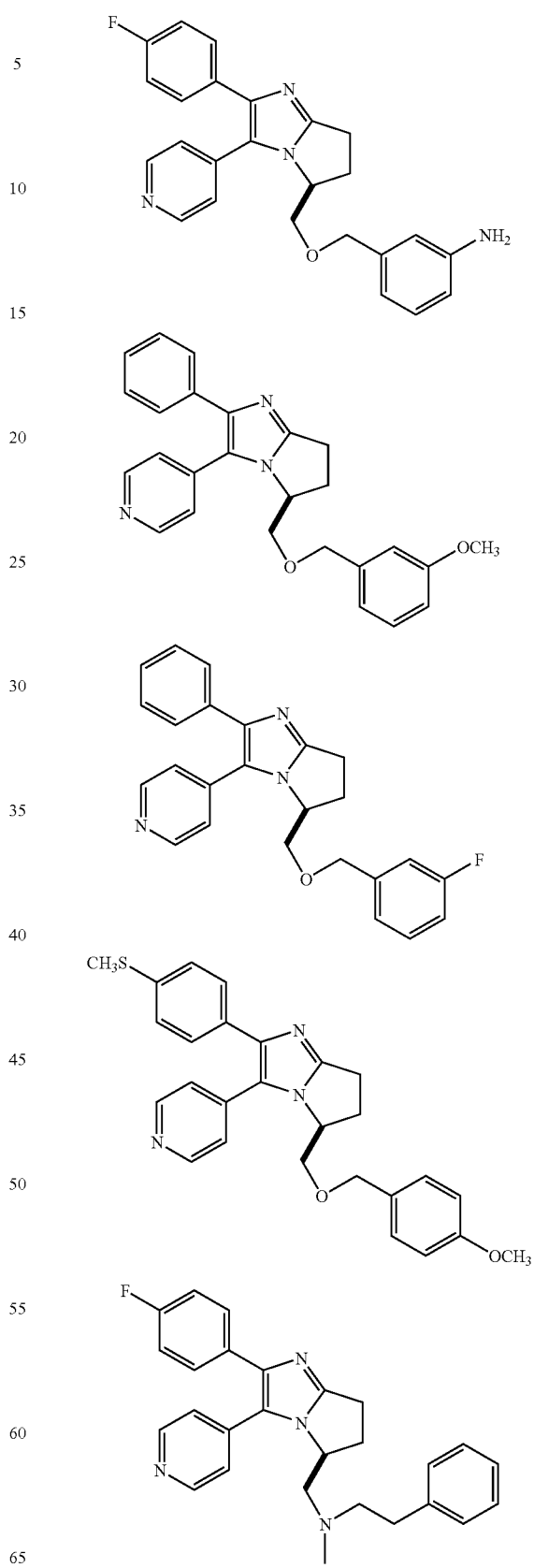

259
-continued
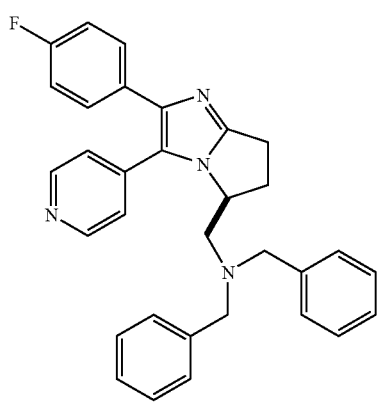
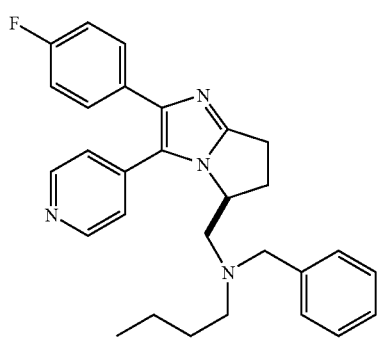
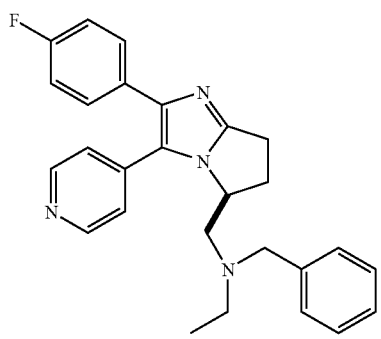
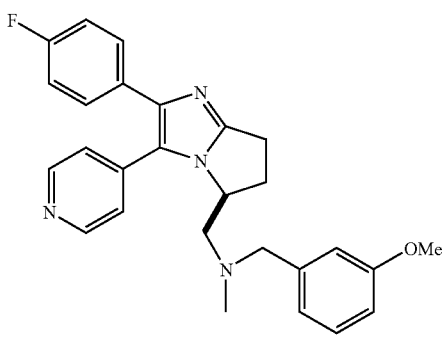
260
-continued
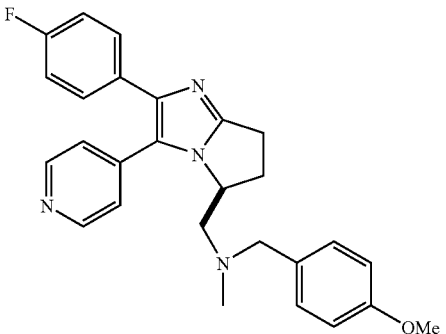
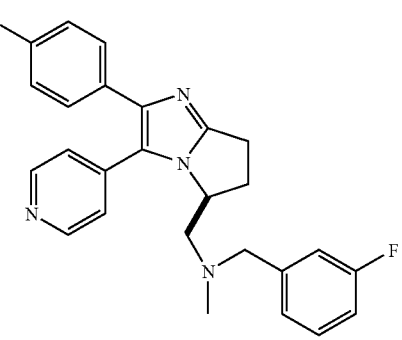

261
-continued
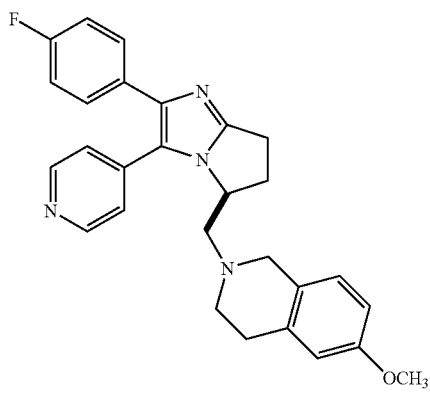
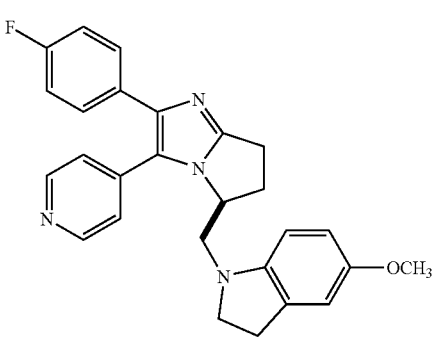
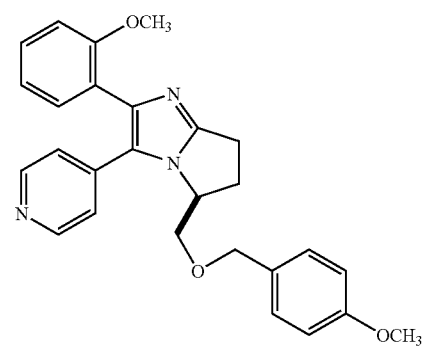
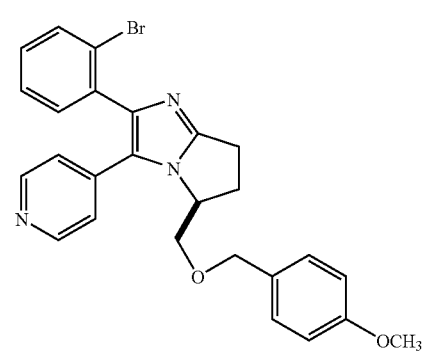
262
-continued
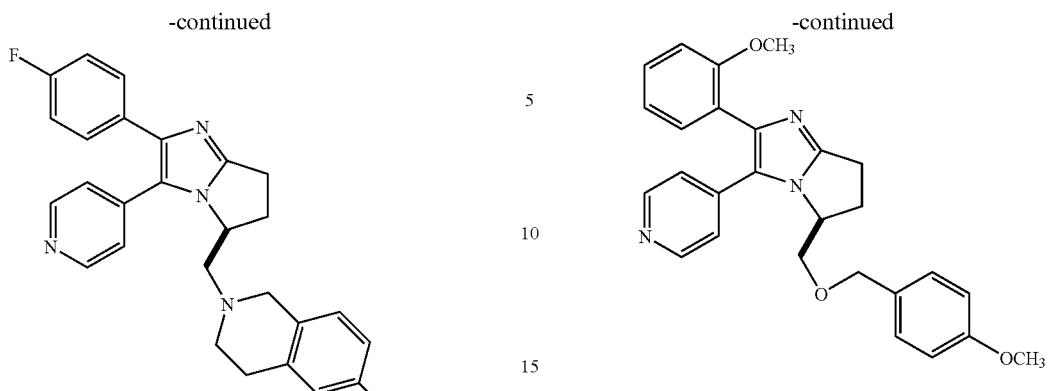
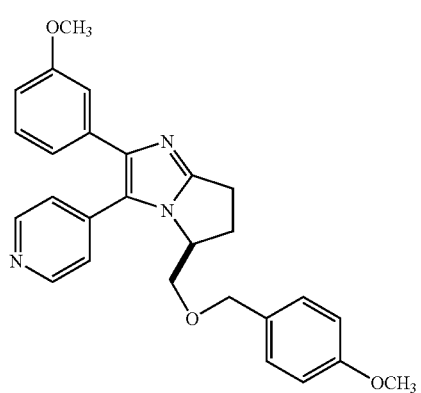
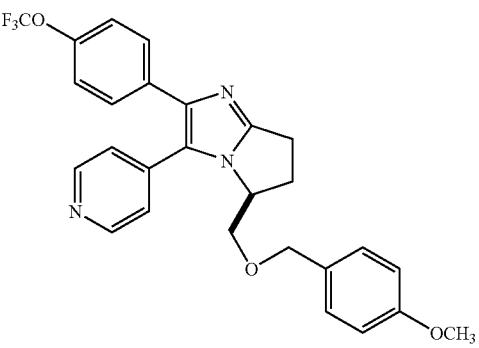
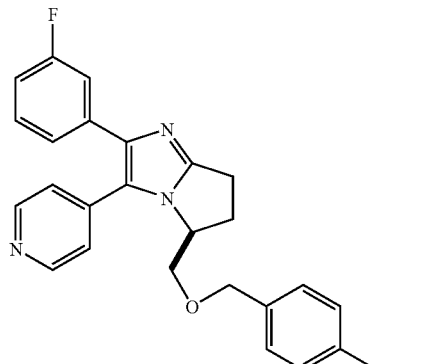

263
-continued
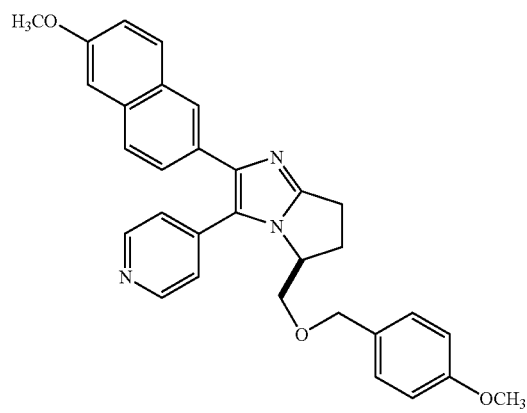
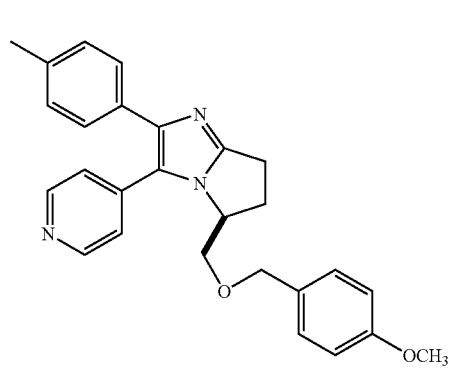
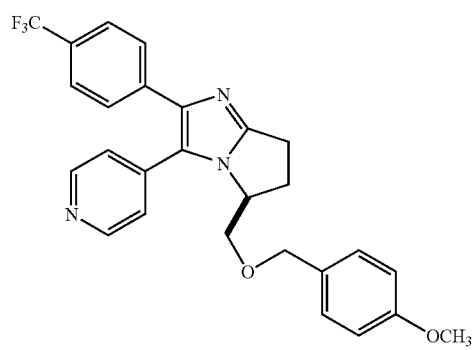
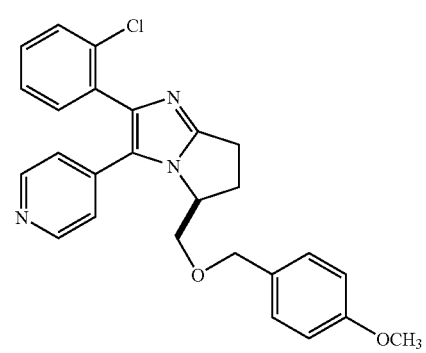
264
-continued
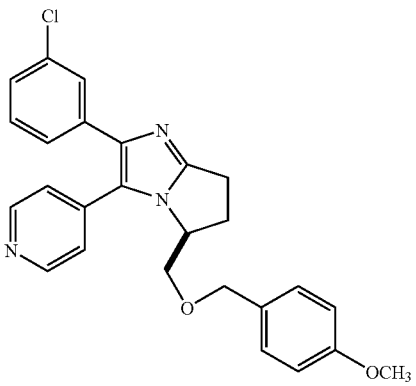
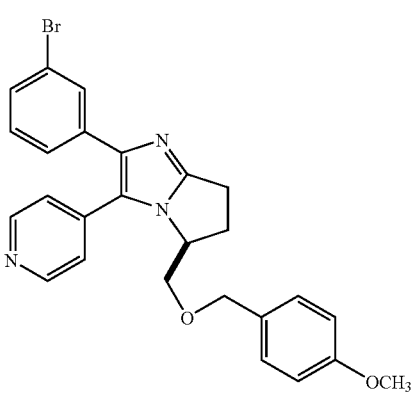
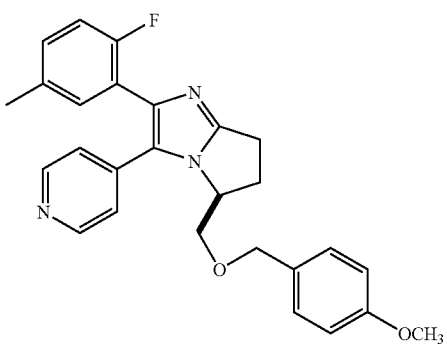
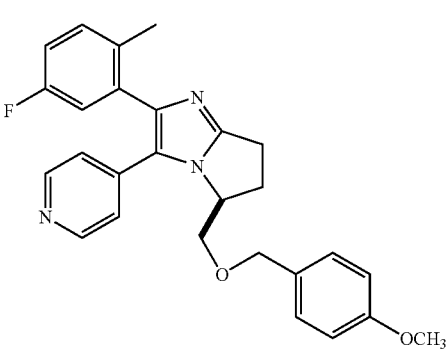

-continued
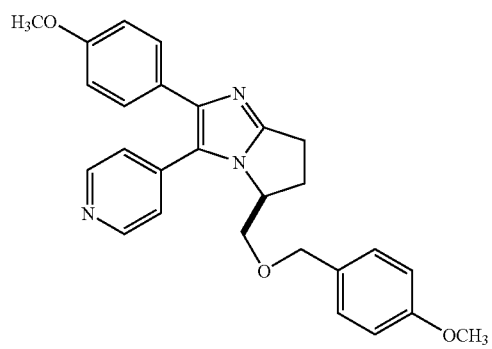
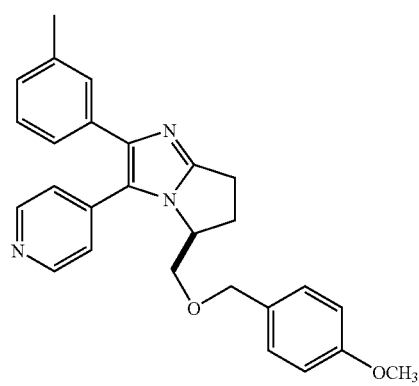
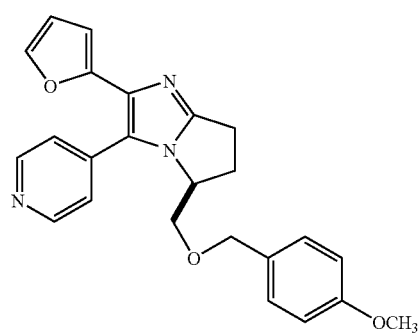
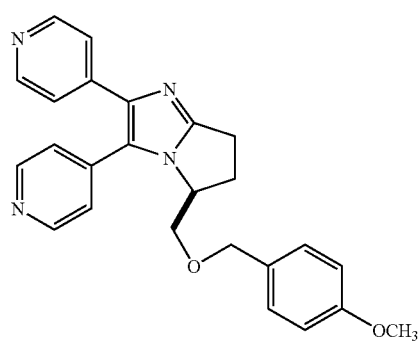
-continued
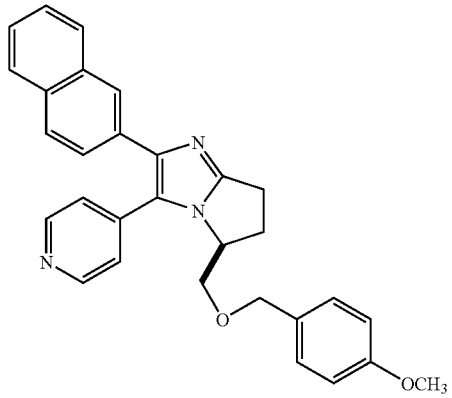
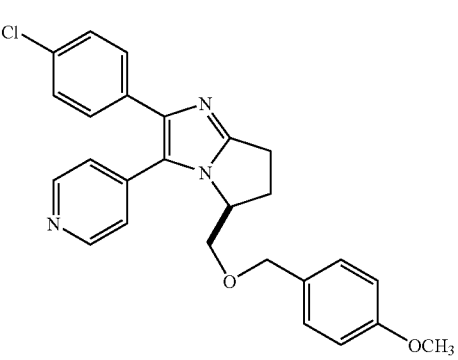
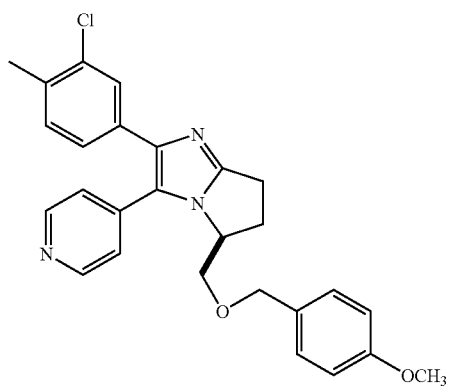
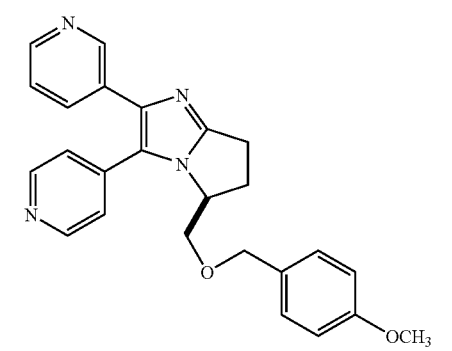

267
-continued
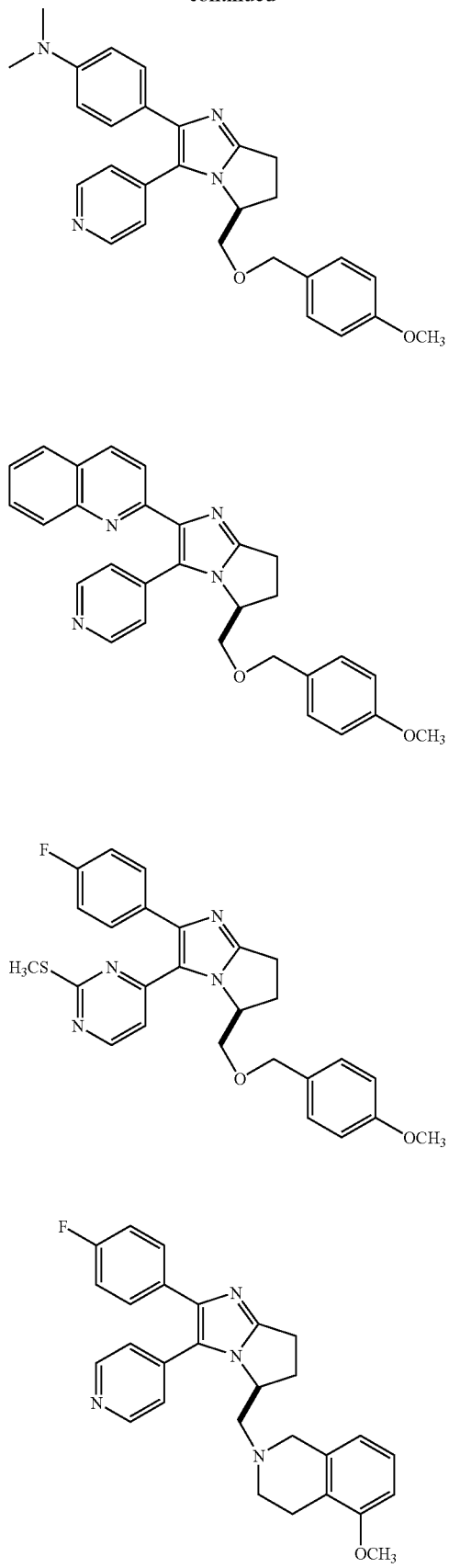
268
-continued
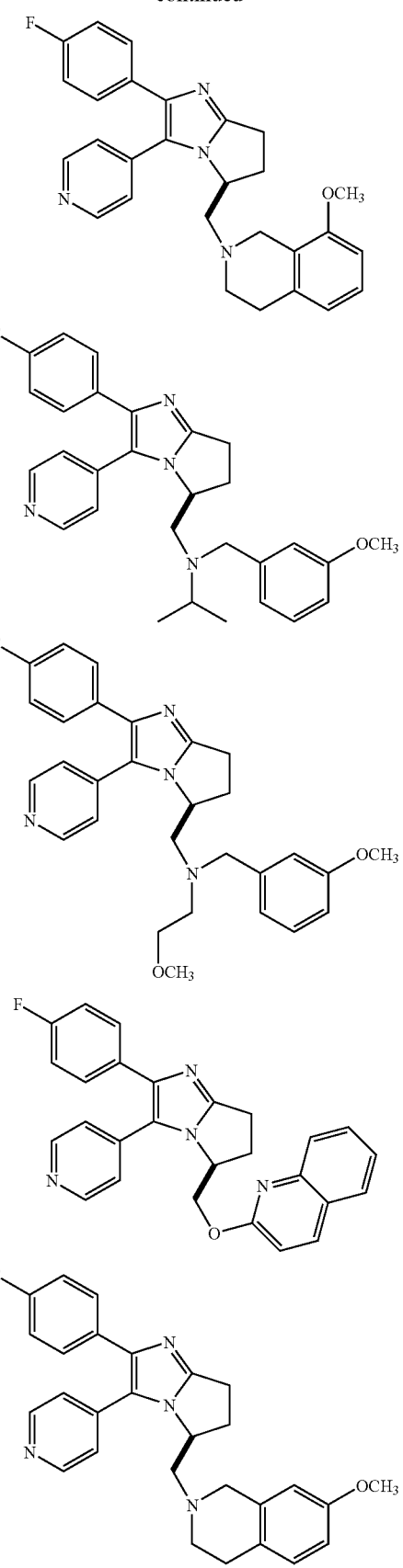

269
-continued
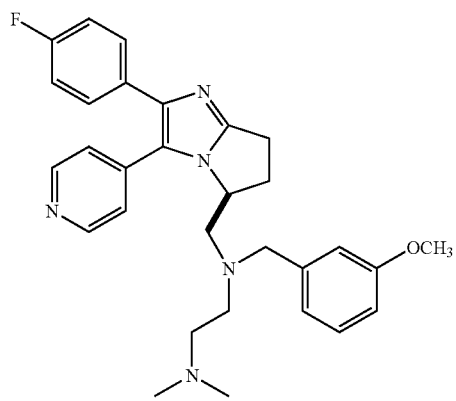
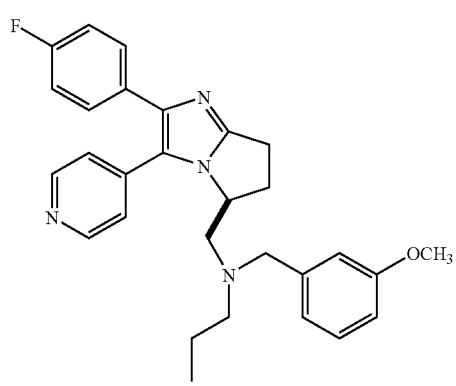
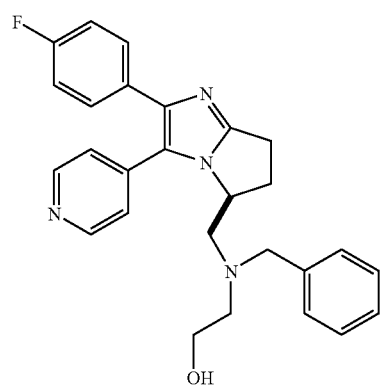
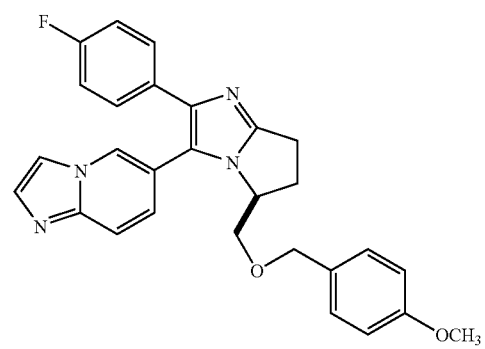
270
-continued
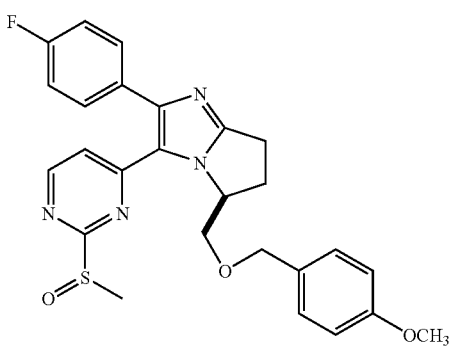
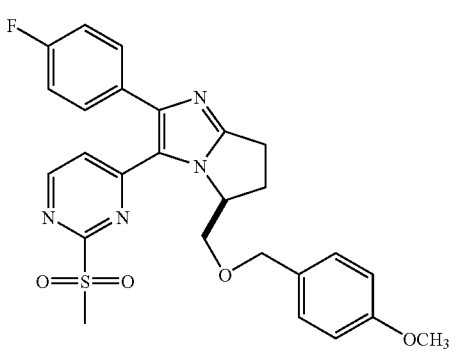
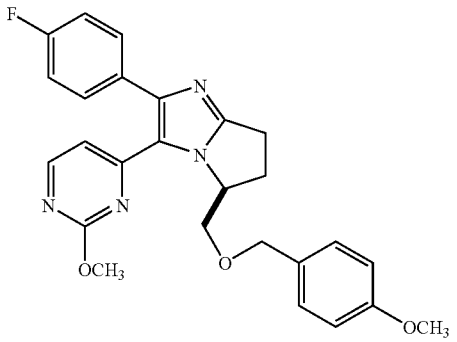
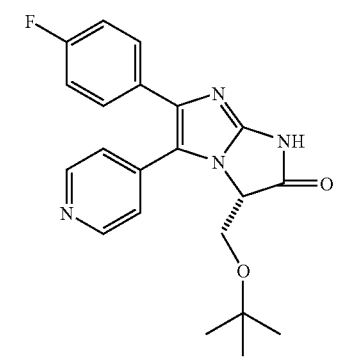

271
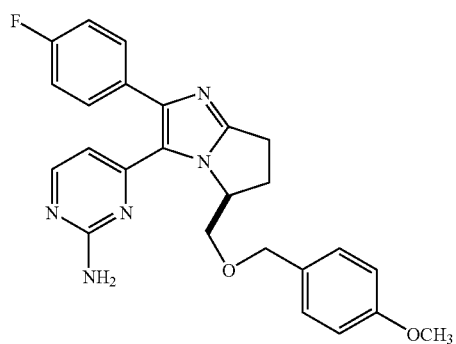
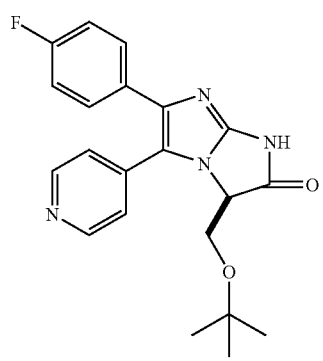
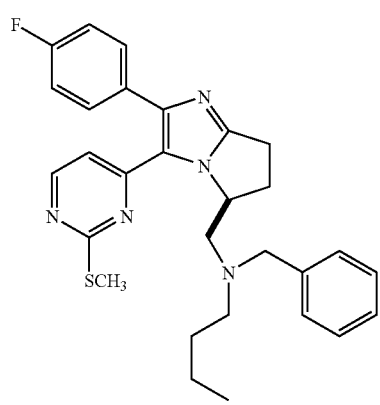
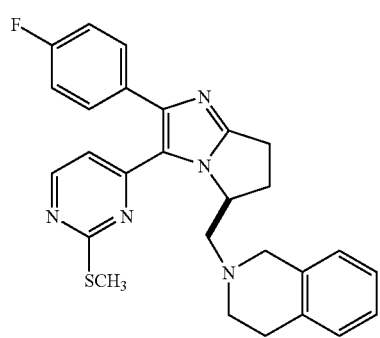
272
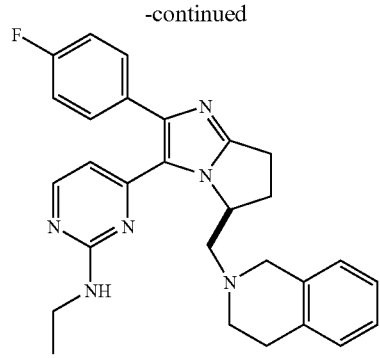
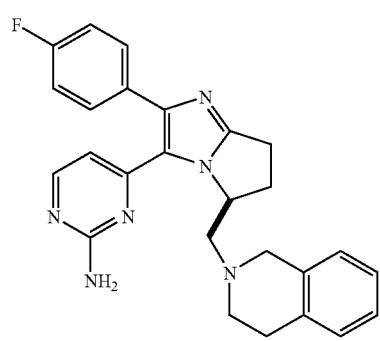
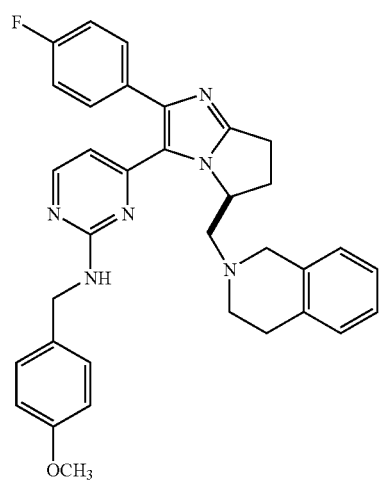
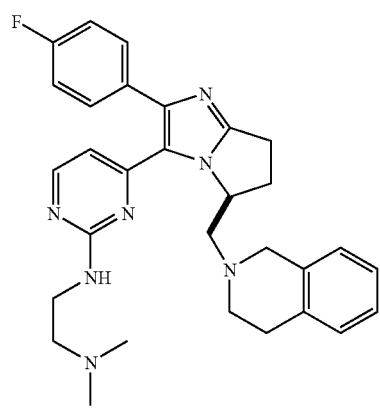

-continued
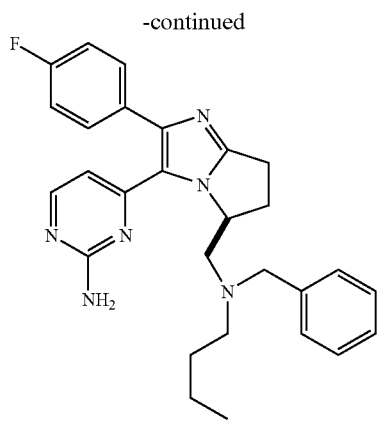
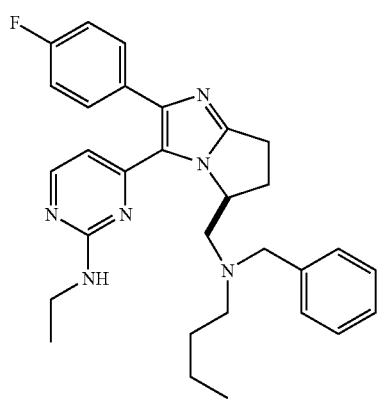
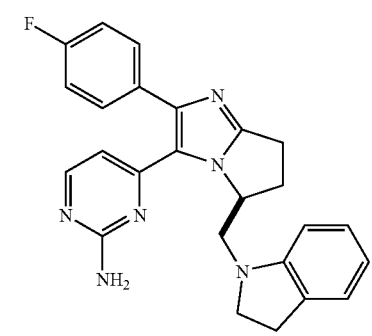
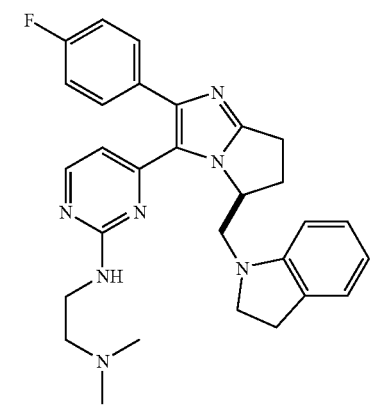
-continued
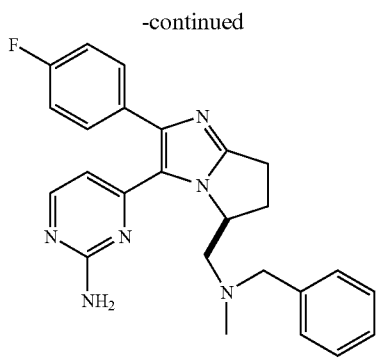
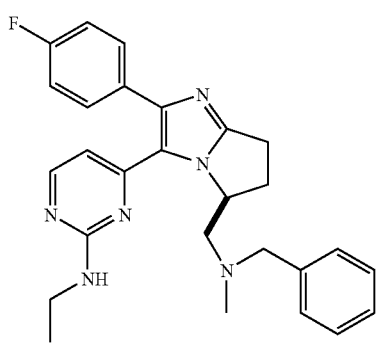
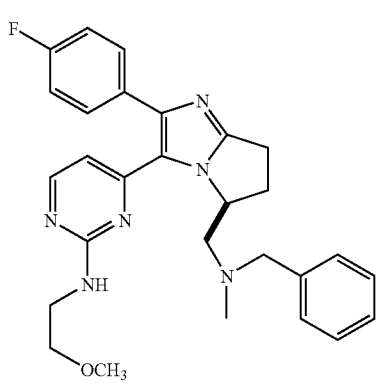
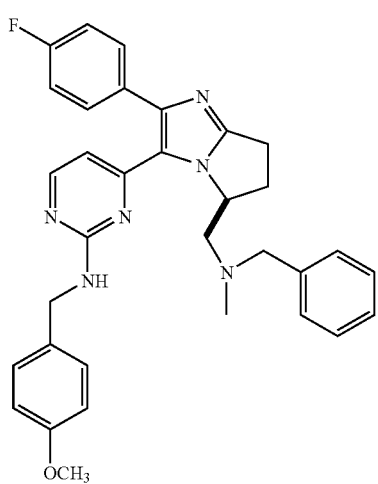

275
-continued
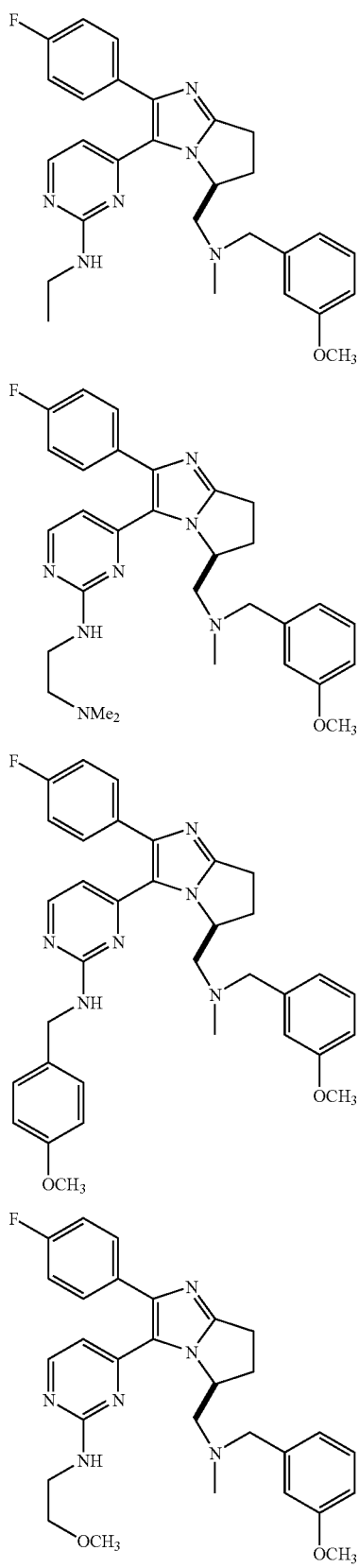
276
-continued
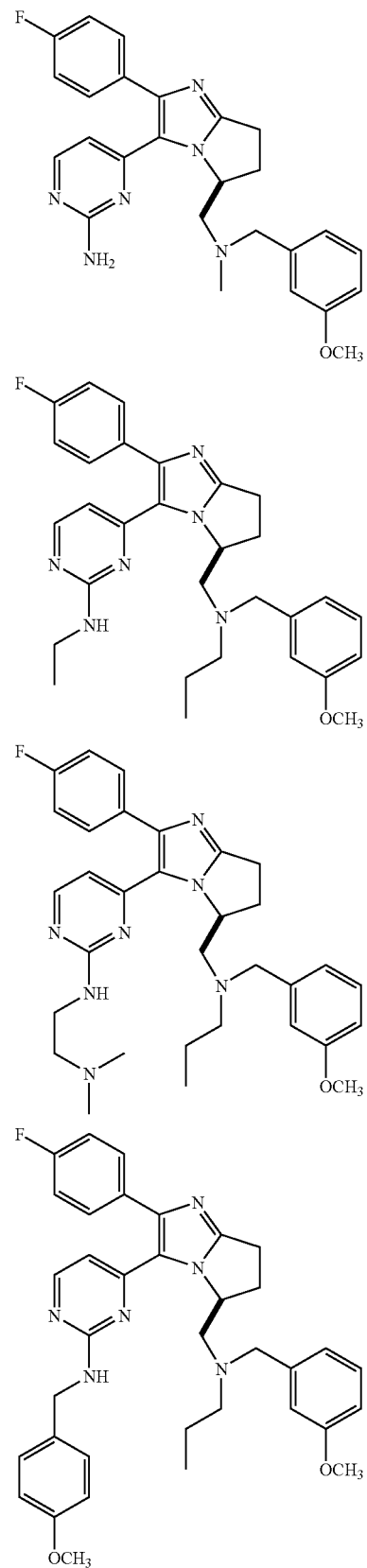

277
-continued
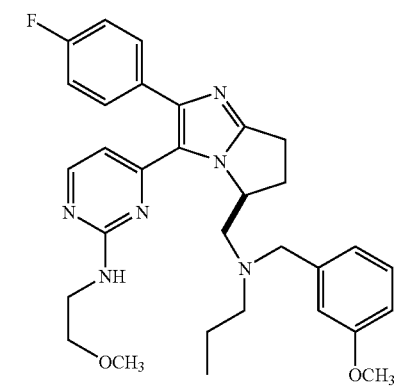
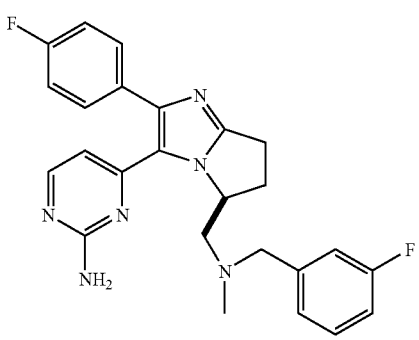
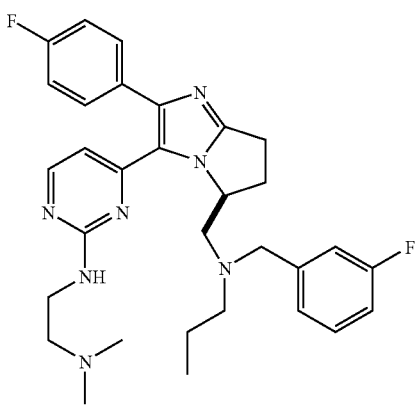
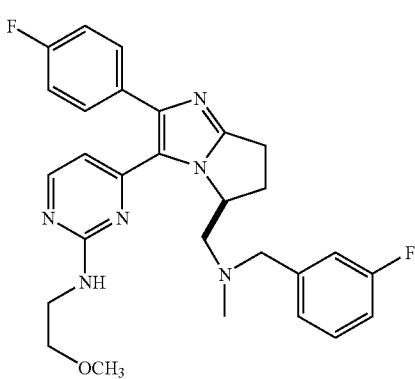
278
-continued
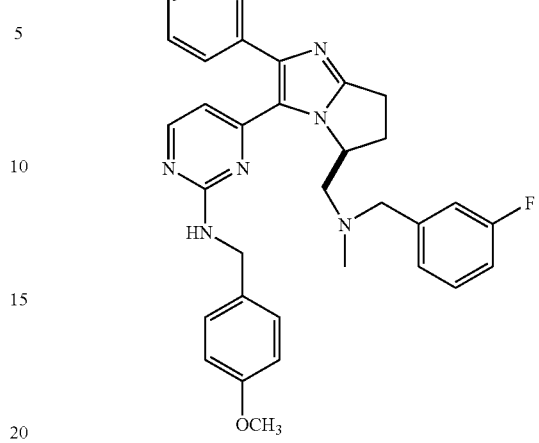
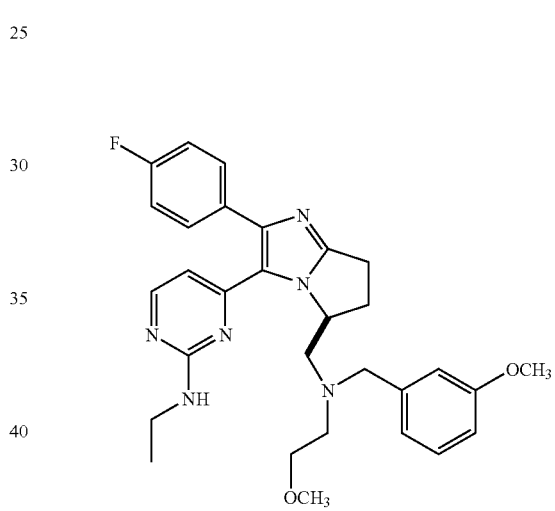
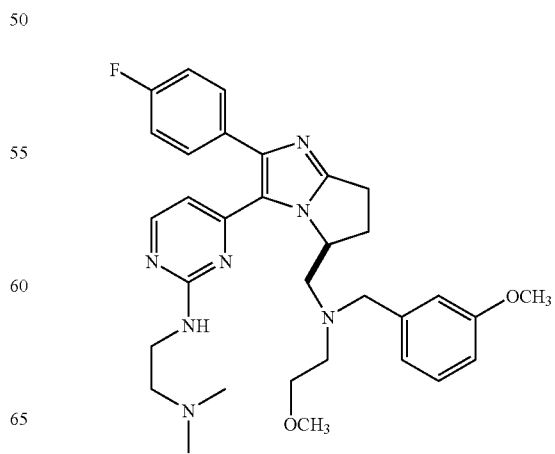

279
-continued
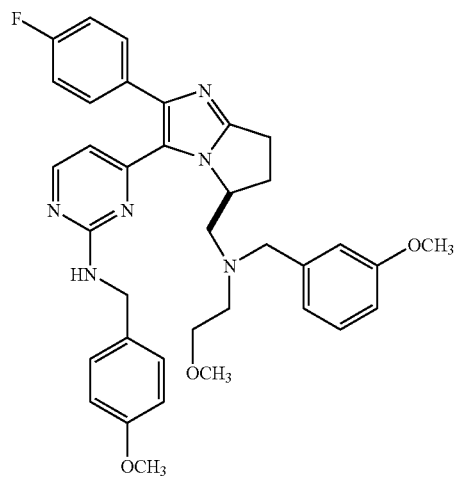
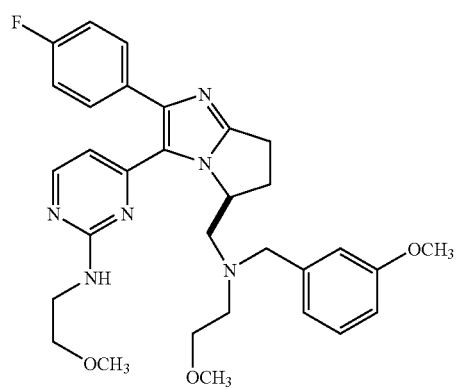
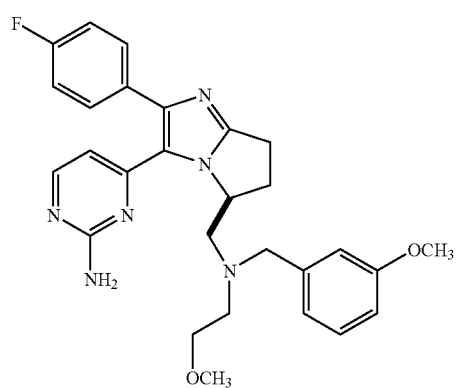
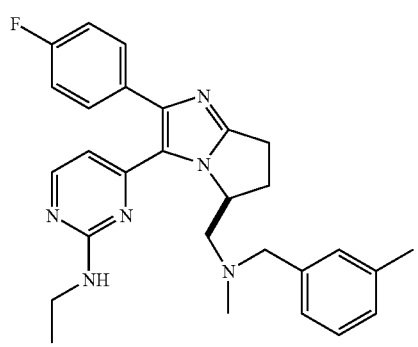
280
-continued
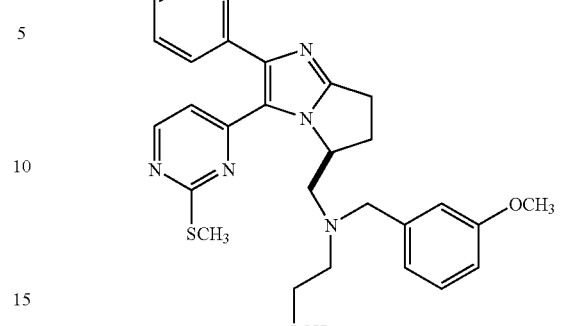
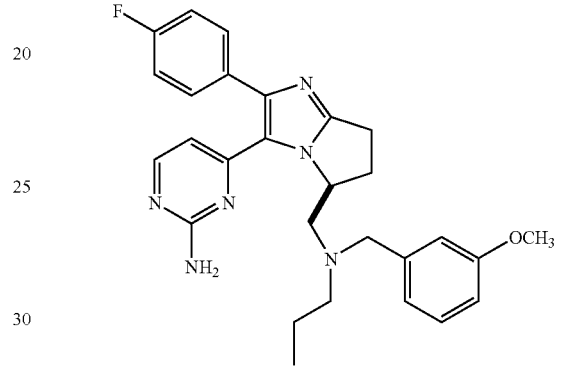
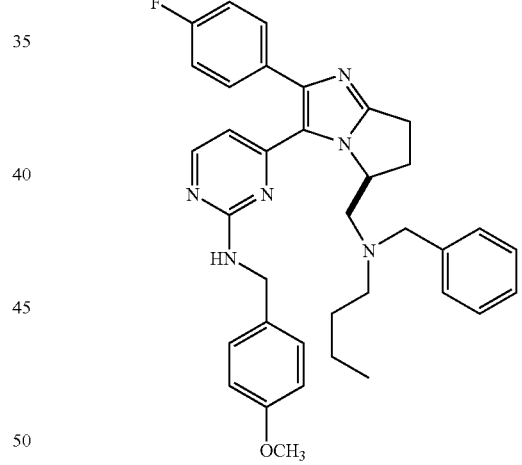
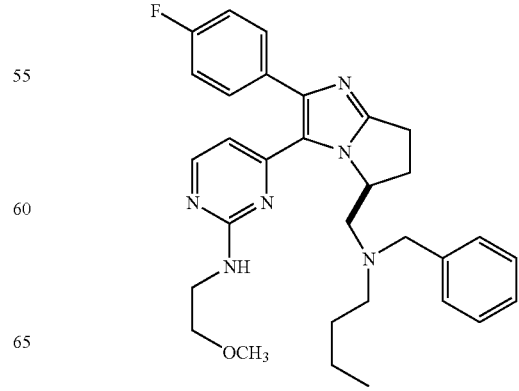

-continued
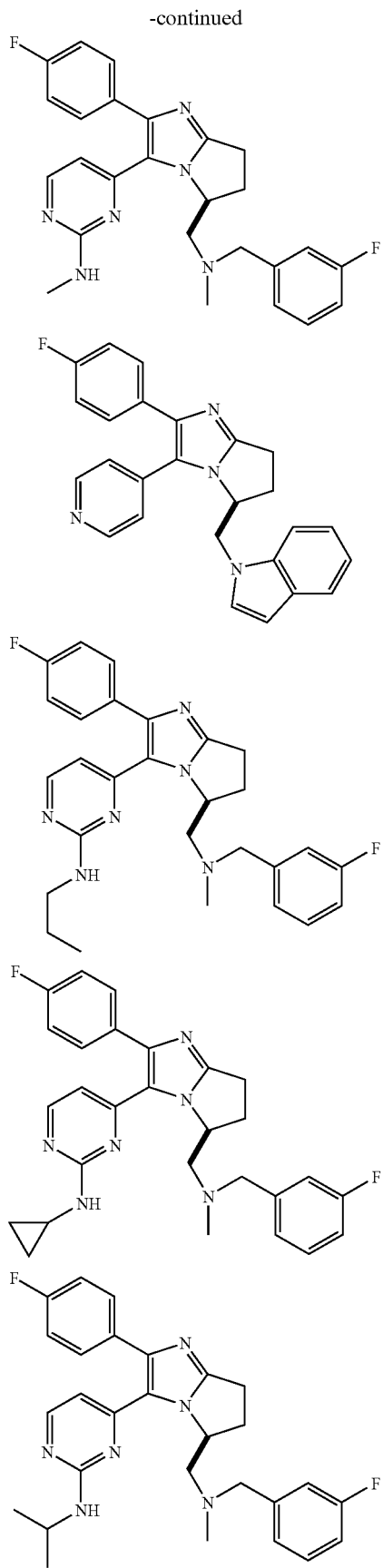
-continued
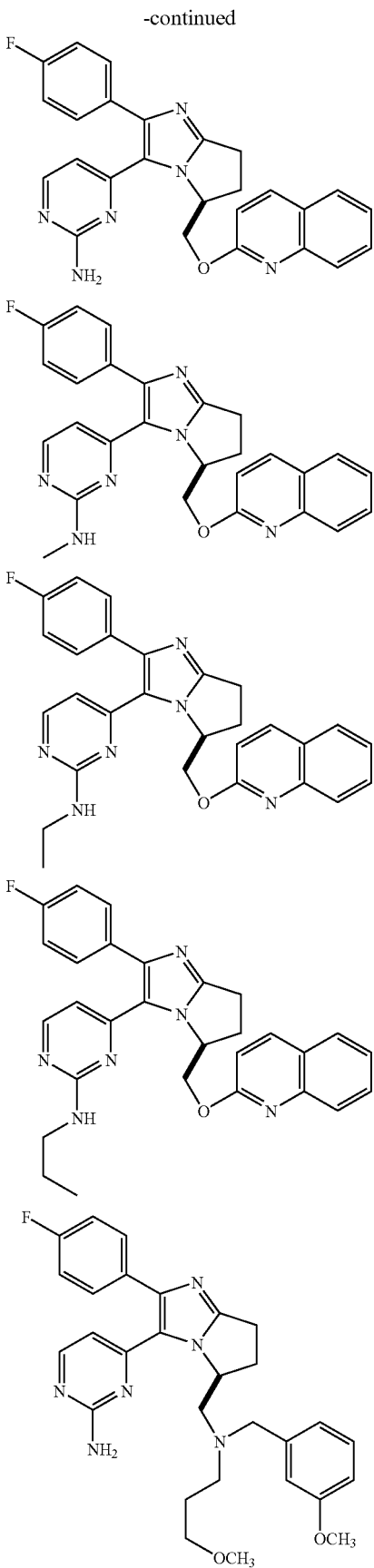

-continued
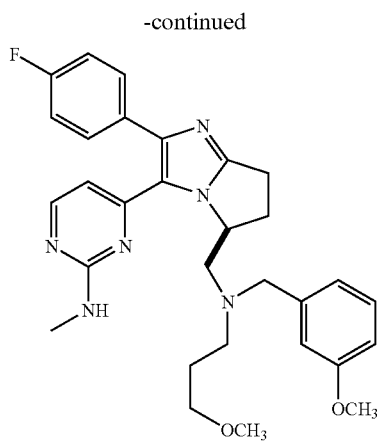
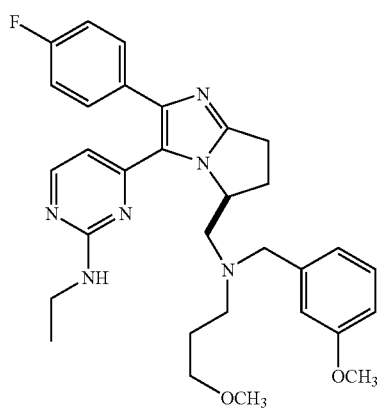
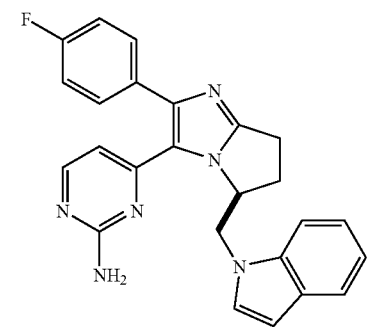
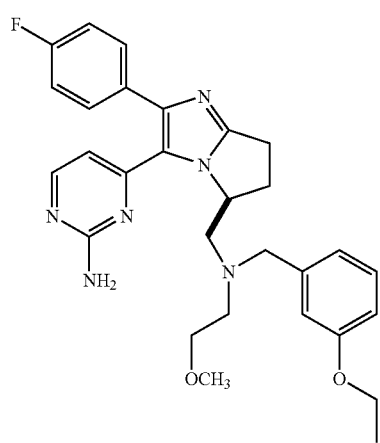
-continued
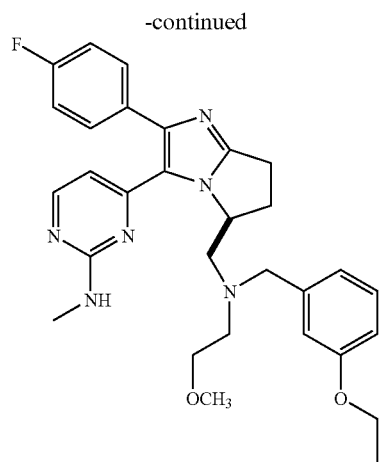
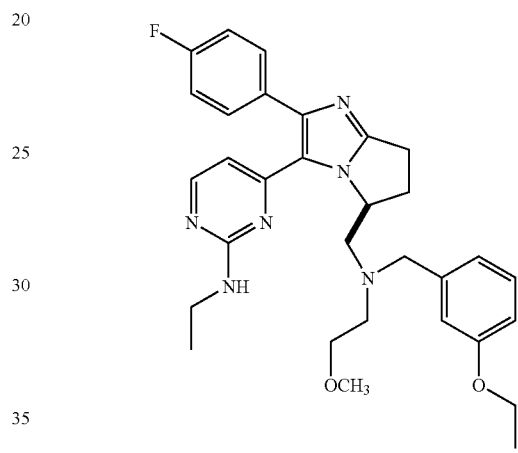
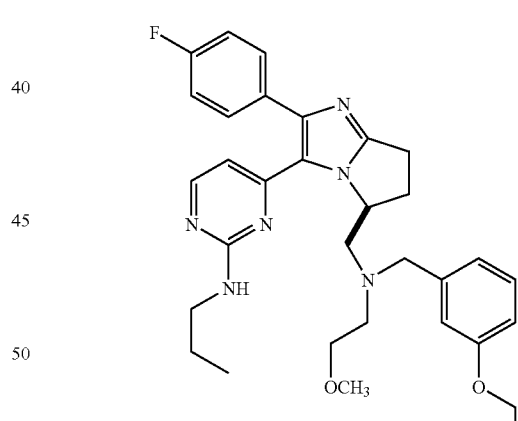
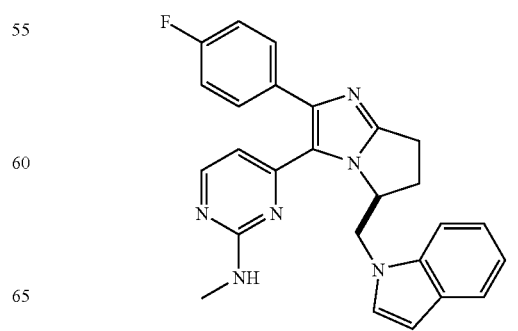

-continued
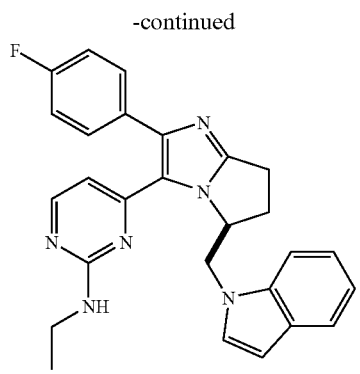
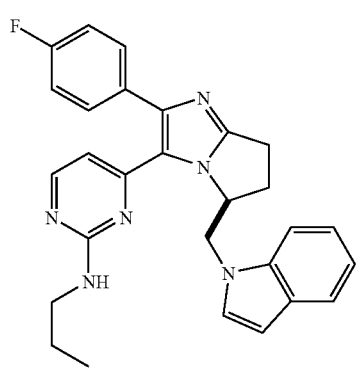
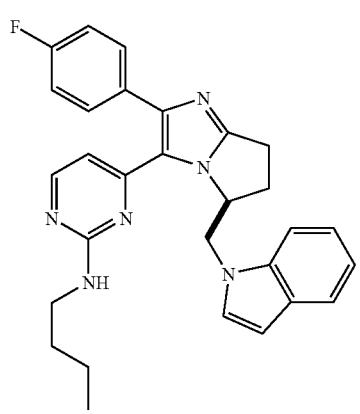
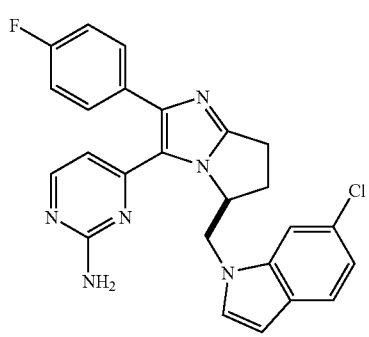
-continued
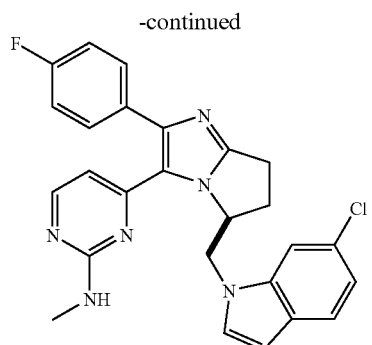
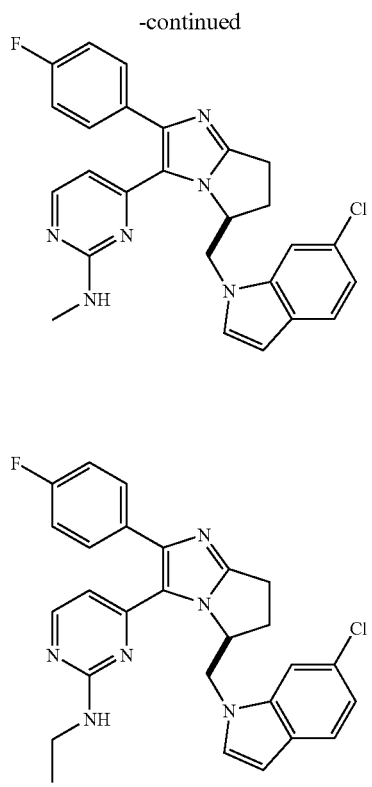
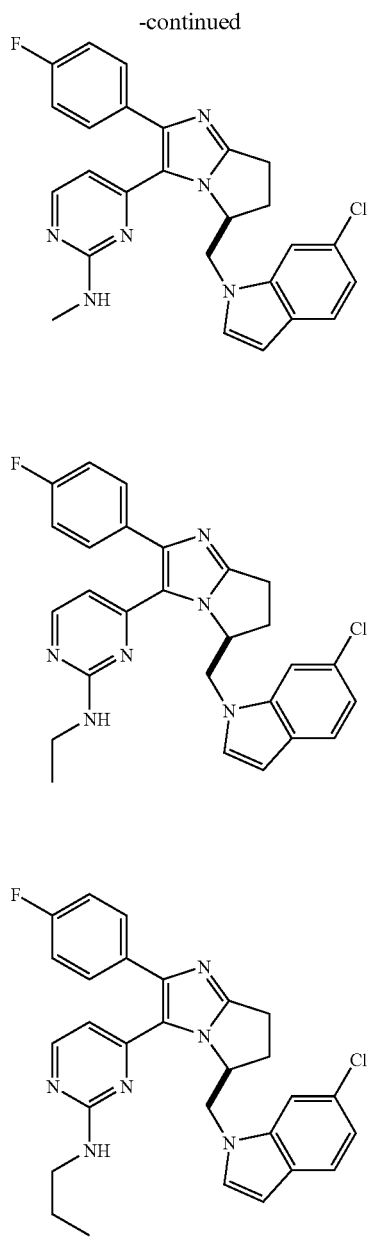
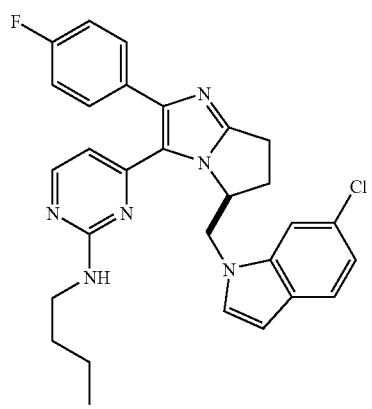

-continued
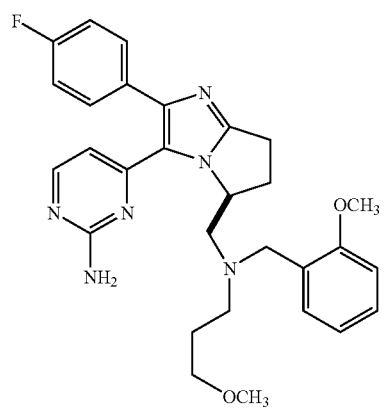
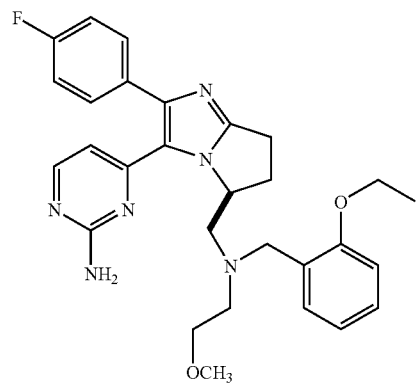
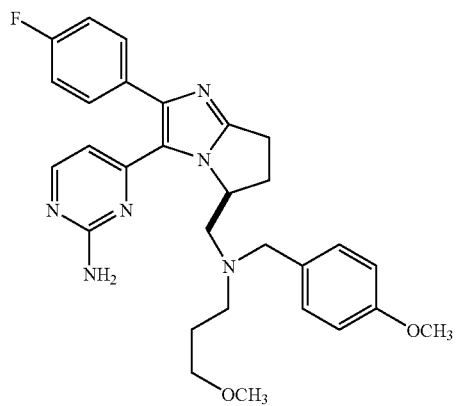
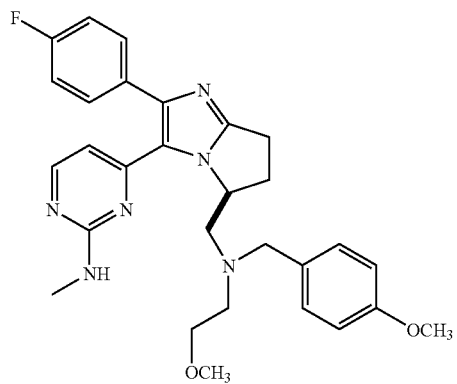
-continued
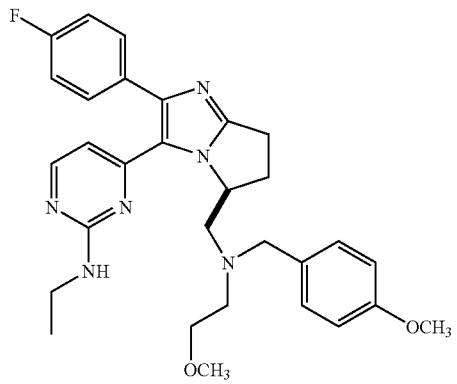
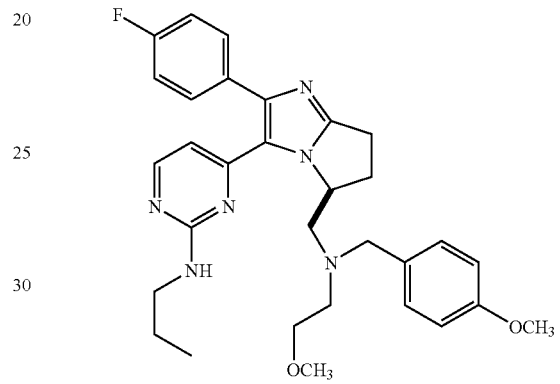
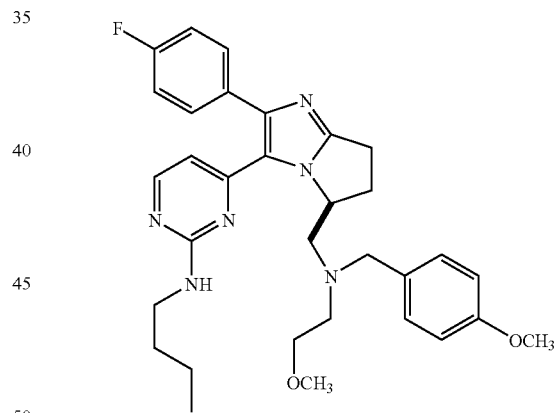
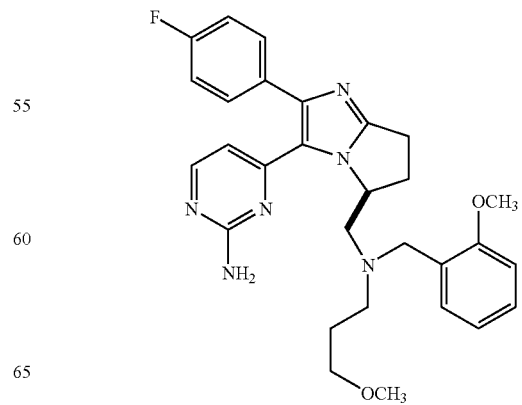

-continued
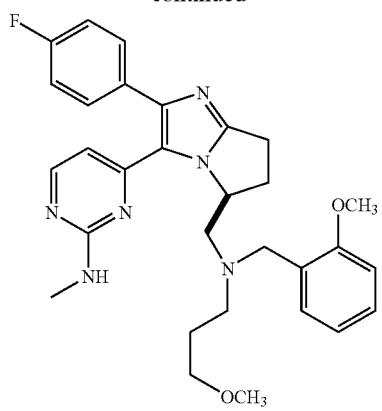
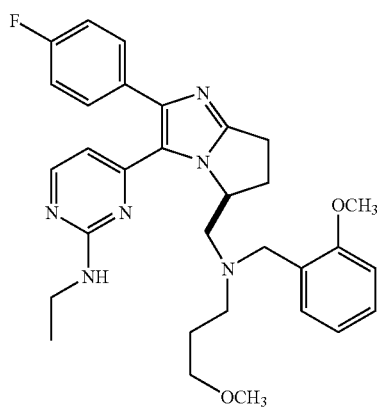
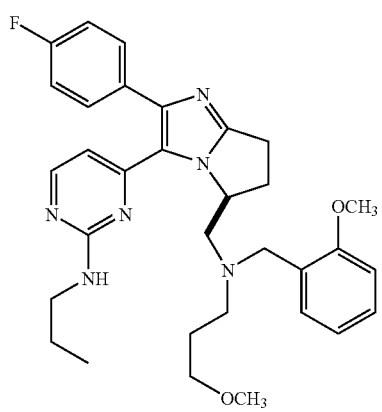
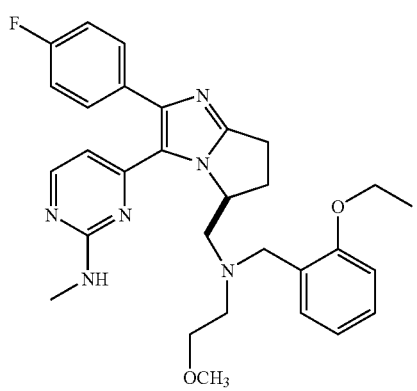
-continued
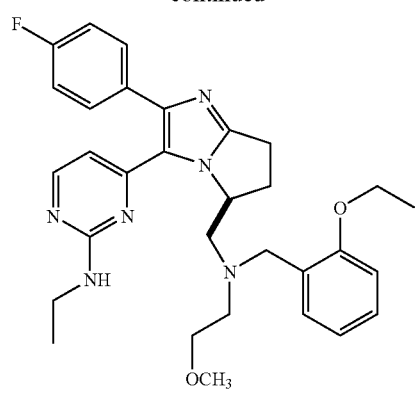
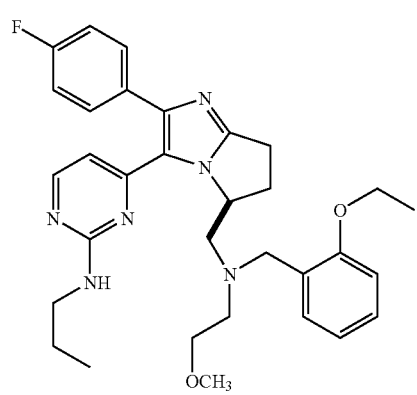
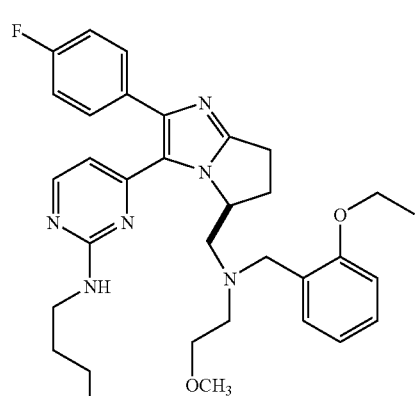
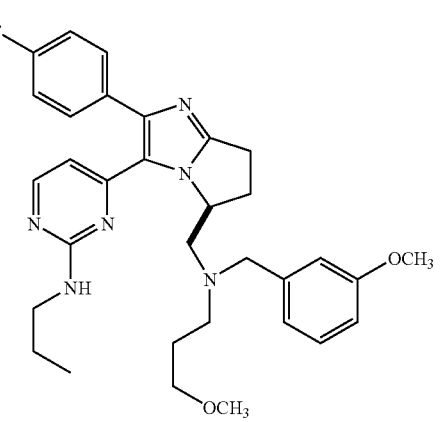

291
-continued
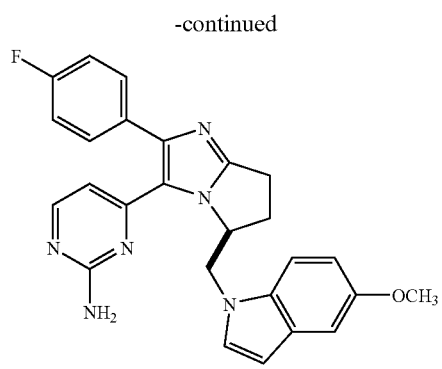
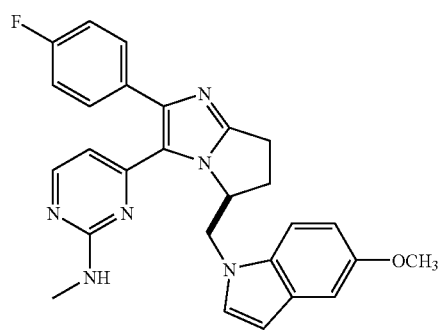
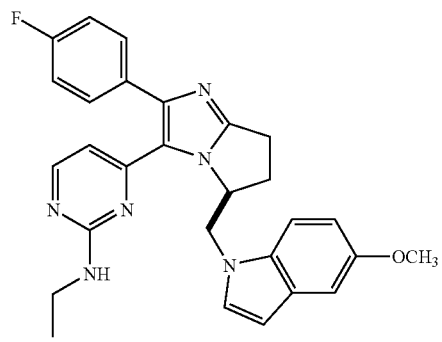
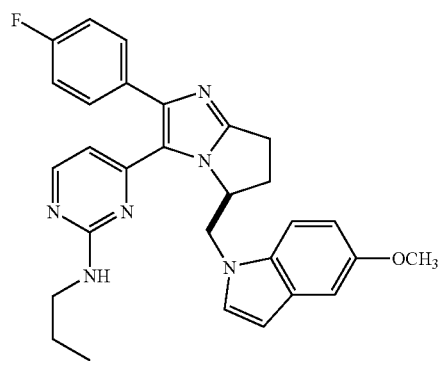
292
-continued
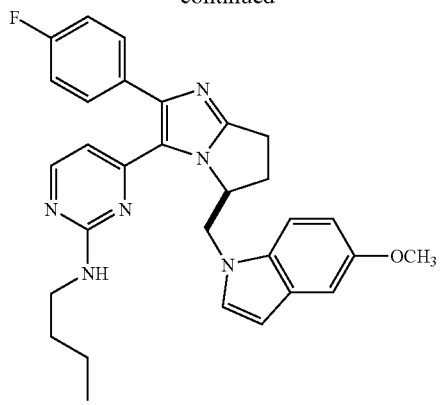
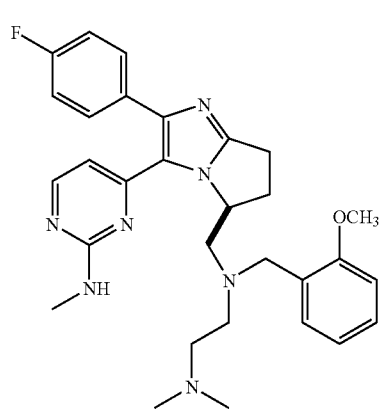
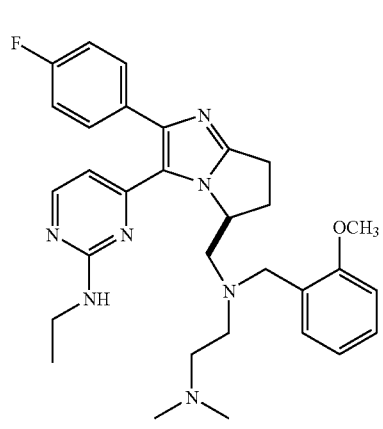
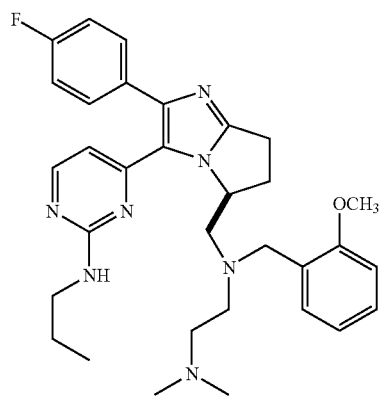

-continued
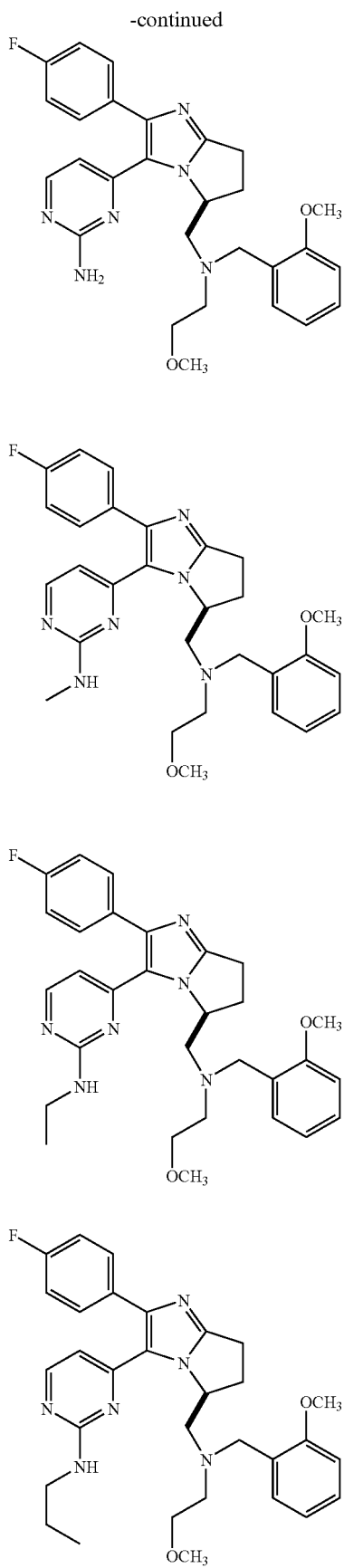
-continued
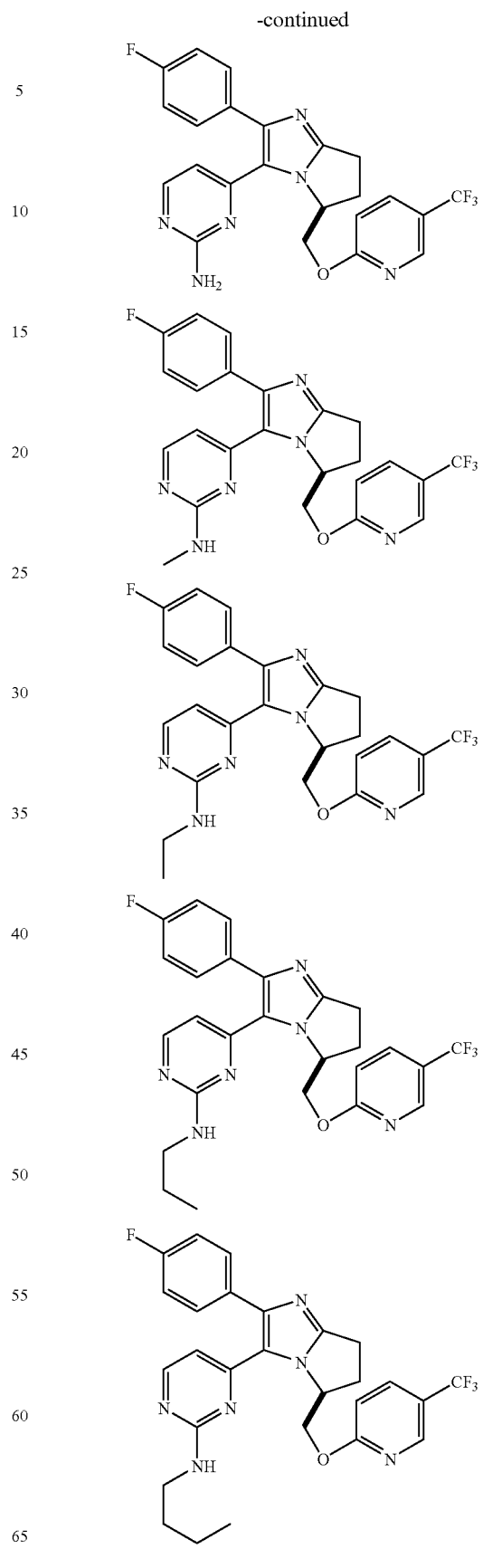

295
-continued
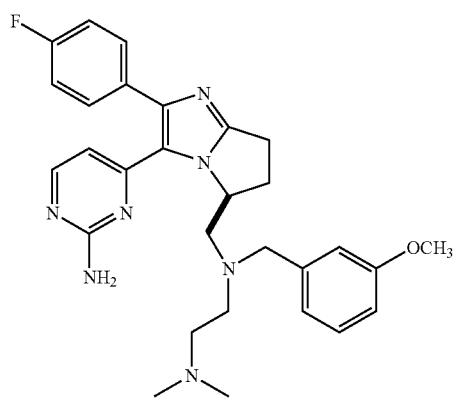
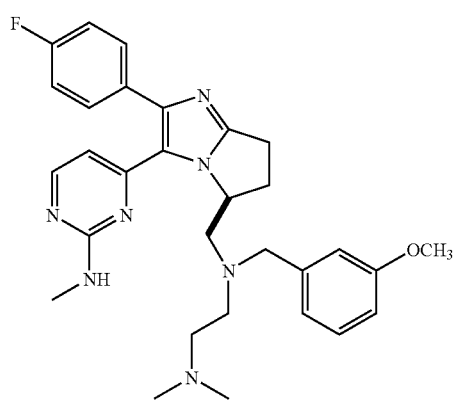
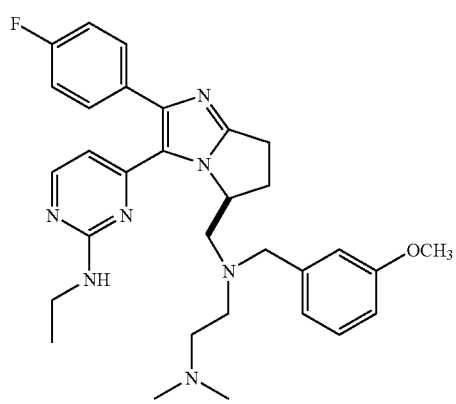
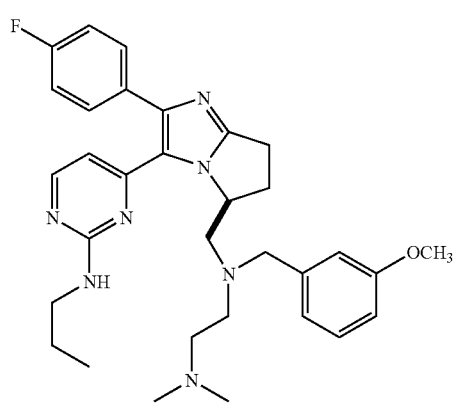
296
-continued
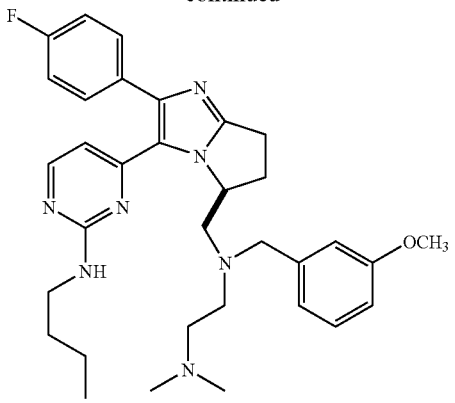
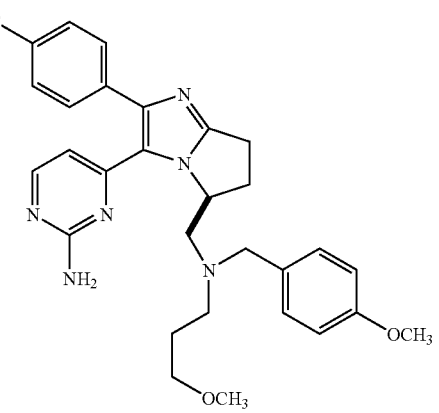
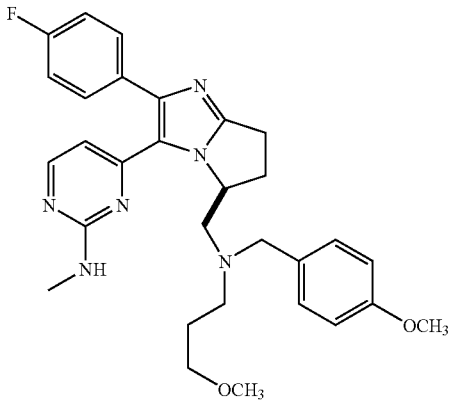
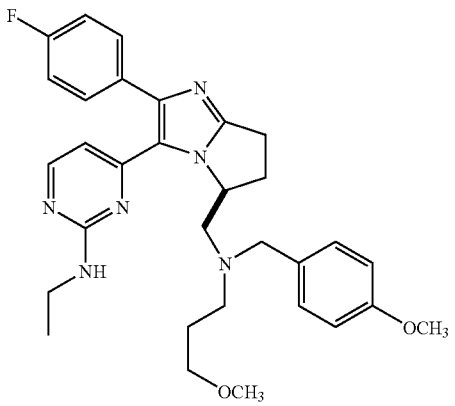

-continued
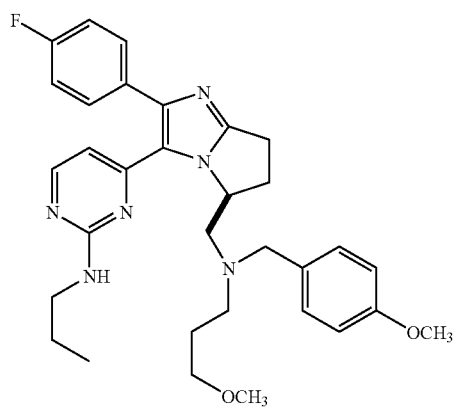
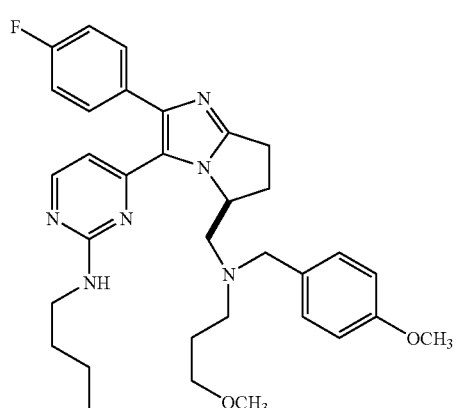
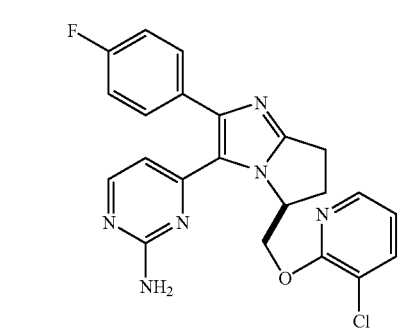
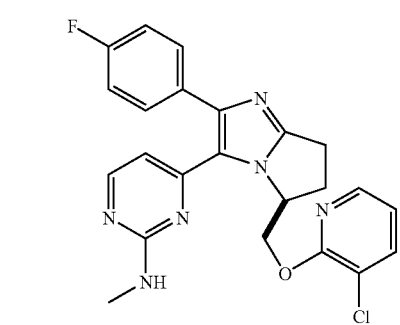
-continued
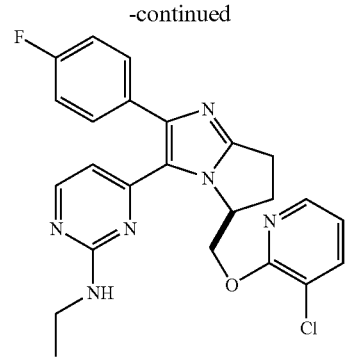
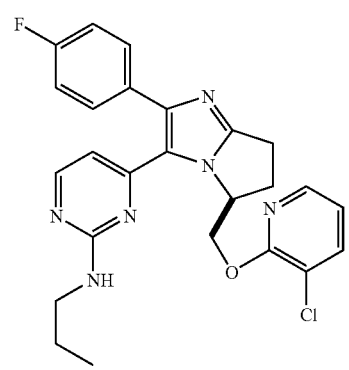
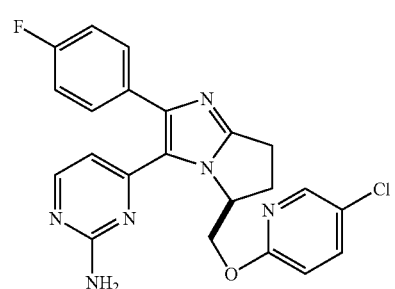
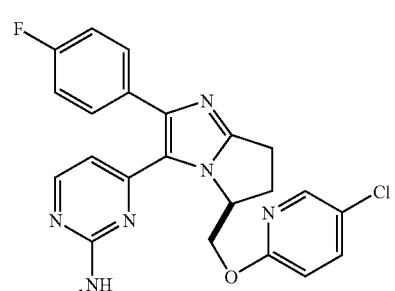
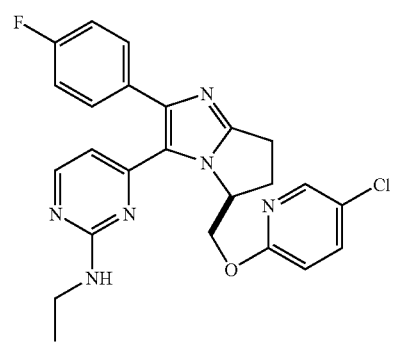

-continued

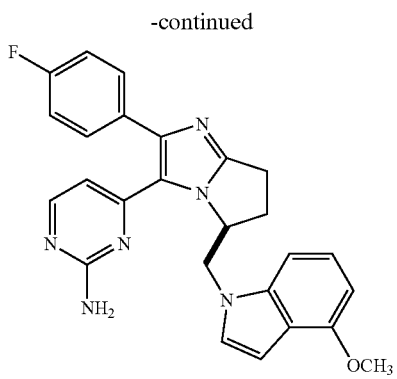

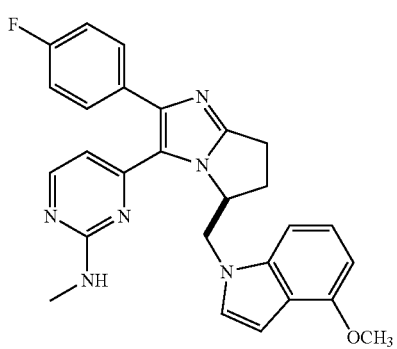

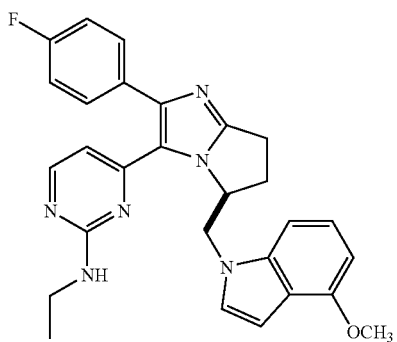

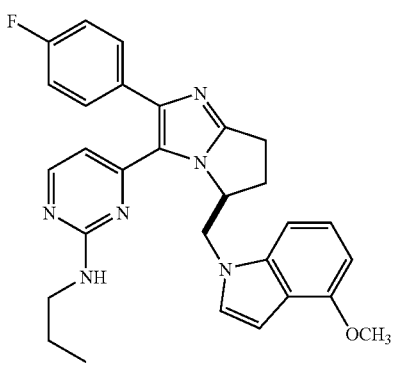

-continued

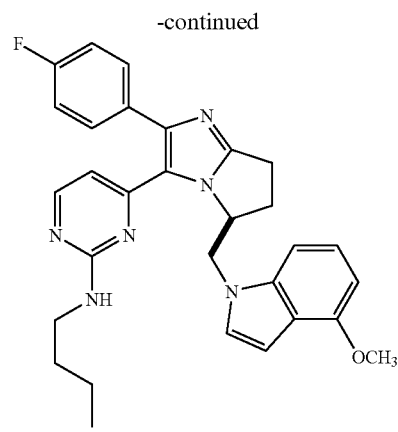

11. A compound of formula IV with the structure:

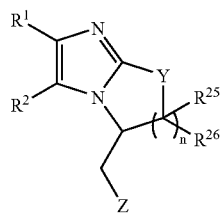

IV wherein $R^1$ is aryl or substituted aryl, wherein the aryl or substituted aryl is optionally fused to a partially unsaturated or fully saturated five to seven membered carbocyclic ring, and each substitutable carbon atom in $R^1$, including the optional fused ring, is optionally and independently substituted by one or more of halogen, $C_{1-4}$ alkyl, haloalkyl, OR, SR, OH, $NO_2$, CN, $NH_2$, NHR, $NR^2$, NHCOR, NHCONHR, $NHCONR_2$, NRCOR, $NHCO_2R$, $CO_2R$, $CO_2H$, COR, CONHR, $CONR_2$, $S(O)_2R$, $SONH_2$, $S(O)R$, $SO_2NHR$, or $NHS(O)_2R$; and each saturated carbon in the optional fused ring is further optionally and independently substituted by =O, =S, =NNHR, $NNR_2$, =N—OR, =NNH-COR, $=NNHCO_2R$, $=NNSO_2R$, or =NR; wherein R is H, $C_{1-4}$ alkyl or haloalkyl;

$R^2$ is an optionally substituted pyridine;

$R^{25}$ and $R^{26}$ are both hydrogen or $R^{25}$ and $R^{26}$ together are carbonyl;

n is 1; and

Z is selected from the group consisting of OH, =O, $N_3$, $NH_2$, $OSO_2R^{30}$, $SCOR^{30}$ CN and I wherein $R^{30}$ is $C_{1-4}$ alkyl.

12. A compound as claimed in claim 11, selected from the group consisting of:

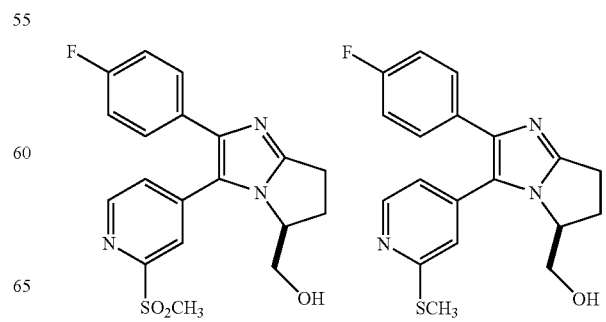

-continued
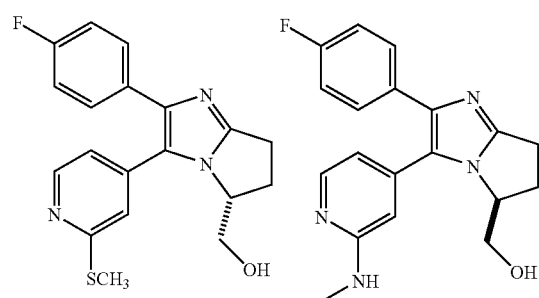
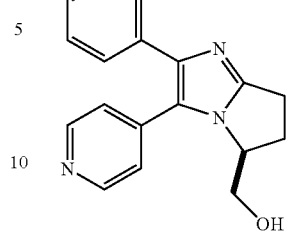
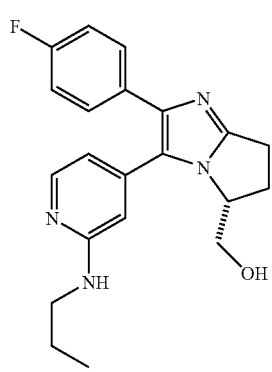
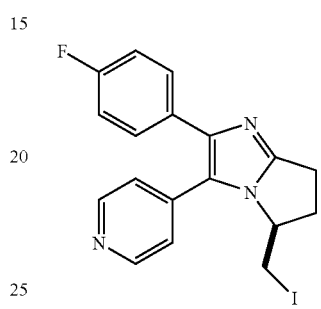
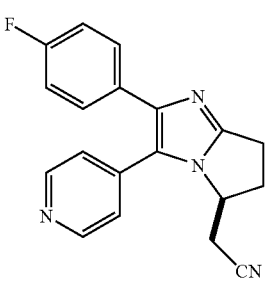
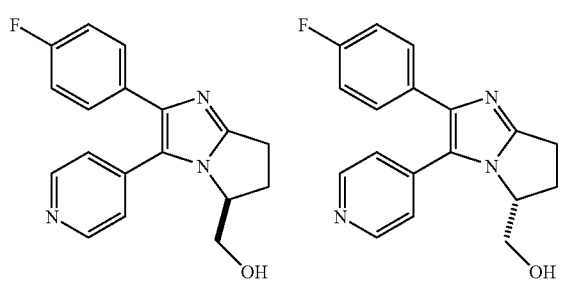
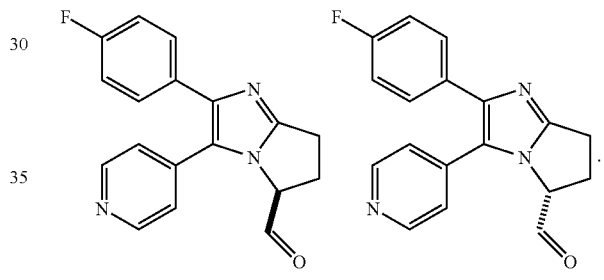
* * * * *